United States Patent
McGrath et al.

(10) Patent No.: US 11,692,038 B2
(45) Date of Patent: Jul. 4, 2023

(54) ANTIBODIES THAT BIND CHEMOKINE (C-C MOTIF) RECEPTOR 8 (CCR8)

(71) Applicant: Gilead Sciences, Inc., Foster City, CA (US)

(72) Inventors: Lara Lewis McGrath, Arlington, VA (US); Fabien Dépis, Brookline, MA (US); Changyun Hu, Belmont, MA (US); Leonard G. Presta, San Francisco, CA (US); Joshua Adam Buggé, Arlington, MA (US)

(73) Assignee: Gilead Sciences, Inc., Foster City, CA (US)

( * ) Notice: Subject to any disclaimer, the term of this patent is extended or adjusted under 35 U.S.C. 154(b) by 57 days.

(21) Appl. No.: 17/171,866

(22) Filed: Feb. 9, 2021

(65) Prior Publication Data

US 2021/0277129 A1   Sep. 9, 2021

Related U.S. Application Data

(60) Provisional application No. 63/130,157, filed on Dec. 23, 2020, provisional application No. 62/976,869, filed on Feb. 14, 2020.

(51) Int. Cl.
*C07K 16/28* (2006.01)
*A61P 35/00* (2006.01)
*A61K 39/00* (2006.01)

(52) U.S. Cl.
CPC .......... *C07K 16/2866* (2013.01); *A61P 35/00* (2018.01); *A61K 2039/505* (2013.01); *C07K 2317/24* (2013.01); *C07K 2317/41* (2013.01); *C07K 2317/565* (2013.01); *C07K 2317/732* (2013.01); *C07K 2317/734* (2013.01); *C07K 2317/76* (2013.01); *C07K 2317/92* (2013.01)

(58) Field of Classification Search
CPC ............ C07K 16/2866; C07K 2317/24; C07K 2317/41; C07K 2317/565; C07K 2317/732; C07K 2317/734; C07K 2317/76; C07K 2317/92; A61P 35/00; A61K 2039/505
See application file for complete search history.

(56) References Cited

U.S. PATENT DOCUMENTS

| | | | |
|---|---|---|---|
| 4,816,567 A | 3/1989 | Cabilly et al. |
| 4,943,593 A | 7/1990 | Palfreyman et al. |
| 4,965,288 A | 10/1990 | Palfreyman et al. |
| 4,997,854 A | 3/1991 | Kagan et al. |
| 5,021,456 A | 6/1991 | Palfreyman et al. |
| 5,059,714 A | 10/1991 | Palfreyman et al. |
| 5,120,764 A | 6/1992 | McCarthy et al. |
| 5,182,297 A | 1/1993 | Palfreyman et al. |
| 5,252,608 A | 10/1993 | Palfreyman et al. |
| 5,500,362 A | 3/1996 | Robinson et al. |
| 5,750,373 A | 5/1998 | Garrard et al. |
| 5,770,429 A | 6/1998 | Lonberg et al. |
| 5,821,337 A | 10/1998 | Carter et al. |
| 6,075,181 A | 6/2000 | Kucherlapati et al. |
| 6,150,584 A | 11/2000 | Kucherlapati et al. |
| 6,194,551 B1 | 2/2001 | Idusogie et al. |
| 6,319,494 B1 | 11/2001 | Capon et al. |
| 6,602,684 B1 | 8/2003 | Umaña et al. |
| 6,737,056 B1 | 5/2004 | Presta |
| 6,982,321 B2 | 1/2006 | Winter |
| 7,041,870 B2 | 5/2006 | Tomizuka et al. |
| 7,087,409 B2 | 8/2006 | Barbas |
| 7,189,826 B2 | 3/2007 | Rodman |
| 7,527,791 B2 | 5/2009 | Adams et al. |
| 7,741,465 B1 | 6/2010 | Eshhar et al. |
| 7,923,538 B2 | 4/2011 | Shitara et al. |
| 7,994,290 B2 | 8/2011 | Shitara et al. |
| 8,450,321 B2 | 5/2013 | Mitchell et al. |
| 9,089,520 B2 | 7/2015 | Brenner |
| 10,087,259 B1 | 10/2018 | Rudensky et al. |
| 10,550,191 B2 | 2/2020 | Yoshida et al. |
| 2002/0164328 A1 | 11/2002 | Shinkawa et al. |
| 2003/0115614 A1 | 6/2003 | Kanda et al. |
| 2003/0157108 A1 | 8/2003 | Presta |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2004/0248871 A1 | 12/2004 | Farjanel et al. |
| 2005/0079574 A1 | 4/2005 | Bond |
| 2005/0119455 A1 | 6/2005 | Fuh et al. |

(Continued)

FOREIGN PATENT DOCUMENTS

| | | |
|---|---|---|
| EP | 3431105 A1 | 1/2019 |
| EP | 3616720 | 2/2021 |

(Continued)

OTHER PUBLICATIONS

Paul, We (1993) Fundamental Immunology, 3rd ed. Raven Press, NY, Chap. 9, pp. 292-295.*
Rudikoff, S et al. (1982) Proc. Natl. Acad. Sci. USA, 79:1979-1983 (doi: 10.1073/pnas.79.6.1979).*
Colman, PM (1994) Research in Immunology, Elsevier, NY, 145(1):33-36.*
Bendig M. M. (1995) Methods: A Companion to Methods in Enzymology, 8:83-93.*
MacCallum et al. (Oct. 11, 1996) J. Mol. Biol., 262(5):732-745. (doi: 10.1006/jmbi.1996.0548).*
Casset et al (2003) Biochemical and Biophysical Research Communications, 307:198-205. (doi:10.1016/S0006-291X(03)01131-8).*
Chen et al. (1995) EMBO J., 14(12):2784-2794. (doi: 10.1002/j.1460-2075.1995.tb07278.x).*

(Continued)

*Primary Examiner* — Robert S Landsman
(74) *Attorney, Agent, or Firm* — Greenberg Traurig, LLP

(57) ABSTRACT

Provided herein are various embodiments relating to antibodies and fusion proteins and uses thereof. Some of the embodiments include antibodies that bind CCR8. Some of the embodiments include fusion proteins that bind CCR8. Such antibodies and fusion proteins can be used in methods to treat, for example, cancer.

29 Claims, 11 Drawing Sheets

Specification includes a Sequence Listing.

(56) References Cited

U.S. PATENT DOCUMENTS

| | | |
|---|---|---|
| 2005/0123546 A1 | 6/2005 | Umana et al. |
| 2005/0266000 A1 | 12/2005 | Bond et al. |
| 2006/0270045 A1 | 11/2006 | Cregg et al. |
| 2007/0061900 A1 | 3/2007 | Murphy |
| 2007/0117126 A1 | 5/2007 | Sidhu et al. |
| 2007/0160598 A1 | 7/2007 | Dennis et al. |
| 2007/0237764 A1 | 10/2007 | Birtalan et al. |
| 2007/0292936 A1 | 12/2007 | Barthelemy et al. |
| 2008/0234251 A1 | 9/2008 | Doherty et al. |
| 2008/0306050 A1 | 12/2008 | Doherty et al. |
| 2009/0002360 A1 | 1/2009 | Chen et al. |
| 2009/0047249 A1 | 2/2009 | Graupe et al. |
| 2009/0142345 A1 | 6/2009 | Satou et al. |
| 2009/0214533 A1 | 8/2009 | Clynes |
| 2010/0029585 A1 | 2/2010 | Howbert et al. |
| 2010/0143301 A1 | 6/2010 | Desai et al. |
| 2011/0092485 A1 | 4/2011 | Howbert et al. |
| 2011/0098248 A1 | 4/2011 | Halcomb et al. |
| 2011/0118235 A1 | 5/2011 | Howbert et al. |
| 2011/0287011 A1 | 11/2011 | Gurney et al. |
| 2012/0082658 A1 | 4/2012 | Hershberg |
| 2012/0219615 A1 | 8/2012 | Hershberg et al. |
| 2013/0251673 A1 | 9/2013 | Hartman et al. |
| 2014/0045849 A1 | 2/2014 | McGowan et al. |
| 2014/0066432 A1 | 3/2014 | Howbert et al. |
| 2014/0073642 A1 | 3/2014 | McGowan et al. |
| 2014/0088085 A1 | 3/2014 | Burgess et al. |
| 2014/0275167 A1 | 9/2014 | Hartman |
| 2014/0350031 A1 | 11/2014 | McGowan et al. |
| 2015/0175616 A1 | 6/2015 | Blomgren et al. |
| 2015/0352206 A1 | 12/2015 | Gajewski et al. |
| 2016/0060237 A1 | 3/2016 | Balog et al. |
| 2016/0303196 A1 | 10/2016 | Karin et al. |

FOREIGN PATENT DOCUMENTS

| | | | |
|---|---|---|---|
| WO | WO 1987/004462 A1 | 7/1987 |
| WO | WO 1992/003459 A1 | 3/1992 |
| WO | WO 1992/021766 A1 | 12/1992 |
| WO | WO 1997/027873 A1 | 8/1997 |
| WO | WO 1997/030087 A1 | 8/1997 |
| WO | WO 1998/058964 A1 | 12/1998 |
| WO | WO 1999/010494 A2 | 3/1999 |
| WO | WO 1999/022764 A1 | 5/1999 |
| WO | WO 1999/025734 A2 | 5/1999 |
| WO | WO 1999/040940 A1 | 8/1999 |
| WO | WO 1999/051642 A1 | 10/1999 |
| WO | WO 2000/061739 A1 | 10/2000 |
| WO | WO 2001/029246 A1 | 4/2001 |
| WO | WO 2001/040307 A1 | 6/2001 |
| WO | WO 2002/031140 A1 | 4/2002 |
| WO | WO 2002/092784 A2 | 11/2002 |
| WO | WO 2003/011878 A2 | 2/2003 |
| WO | WO 2003/084570 A1 | 10/2003 |
| WO | WO 2003/085107 A1 | 10/2003 |
| WO | WO 2003/085119 A1 | 10/2003 |
| WO | WO 2004/056312 A2 | 7/2004 |
| WO | WO 2004/080462 A1 | 9/2004 |
| WO | WO 2004/092219 A2 | 10/2004 |
| WO | WO 2005/020921 A2 | 3/2005 |
| WO | WO 2005/035586 A1 | 4/2005 |
| WO | WO 2005/035778 A1 | 4/2005 |
| WO | WO 2005/044857 A1 | 5/2005 |
| WO | WO 2005/053742 A1 | 6/2005 |
| WO | WO 2005/113556 A1 | 12/2005 |
| WO | WO 2005/113595 A2 | 12/2005 |
| WO | WO 2006/009755 A2 | 1/2006 |
| WO | WO 2006/031221 A1 | 3/2006 |
| WO | WO 2006/063466 A1 | 6/2006 |
| WO | WO 2006/081430 A2 | 8/2006 |
| WO | WO 2006/124692 A2 | 11/2006 |
| WO | WO 2006/124944 A1 | 11/2006 |
| WO | WO 2007/032255 A1 | 3/2007 |
| WO | 2007044756 A2 | 4/2007 |
| WO | WO 2007/059610 A1 | 5/2007 |
| WO | WO 2007/078034 A1 | 7/2007 |
| WO | WO 2007/092403 A1 | 8/2007 |
| WO | WO 2007/124589 A1 | 11/2007 |
| WO | WO 2007/127317 A2 | 11/2007 |
| WO | WO 2007/133811 A2 | 11/2007 |
| WO | WO 2007/137767 A1 | 12/2007 |
| WO | WO 2007/139791 A2 | 12/2007 |
| WO | WO 2008/005877 A2 | 1/2008 |
| WO | WO 2008/071173 A1 | 6/2008 |
| WO | WO 2008/077546 A1 | 7/2008 |
| WO | WO 2009/017833 A2 | 2/2009 |
| WO | WO 2009/035791 A1 | 3/2009 |
| WO | WO 2009/046541 A1 | 4/2009 |
| WO | WO 2009/064250 A1 | 5/2009 |
| WO | WO 2009/064251 A1 | 5/2009 |
| WO | WO 2009/082347 A1 | 7/2009 |
| WO | WO 2009/103778 A1 | 8/2009 |
| WO | WO 2009/117985 A1 | 10/2009 |
| WO | WO 2009/117987 A2 | 10/2009 |
| WO | WO 2009/130242 A1 | 10/2009 |
| WO | WO 2009/138376 A1 | 11/2009 |
| WO | WO 2009/146696 A1 | 12/2009 |
| WO | WO 2010/034796 A1 | 4/2010 |
| WO | WO 2010/034797 A1 | 4/2010 |
| WO | WO 2010/034798 A1 | 4/2010 |
| WO | WO 2010/034799 A1 | 4/2010 |
| WO | WO 2010/070047 A1 | 6/2010 |
| WO | WO 2010/083253 A2 | 7/2010 |
| WO | WO 2010/100249 A1 | 9/2010 |
| WO | WO 2010/106431 A2 | 9/2010 |
| WO | WO 2011/008709 A1 | 1/2011 |
| WO | WO 2011/023812 A1 | 3/2011 |
| WO | WO 2011/048004 A1 | 4/2011 |
| WO | WO 2011/062634 A2 | 5/2011 |
| WO | WO 2011/076781 A1 | 6/2011 |
| WO | WO 2011/097513 A1 | 8/2011 |
| WO | WO 2011/143624 A2 | 11/2011 |
| WO | WO 2012/022792 A1 | 2/2012 |
| WO | WO 2012/022793 A1 | 2/2012 |
| WO | WO 2012/027721 A2 | 3/2012 |
| WO | WO 2012/054825 A1 | 4/2012 |
| WO | WO 2012/076672 A1 | 6/2012 |
| WO | WO 2012/076673 A1 | 6/2012 |
| WO | WO 2012/079000 A1 | 6/2012 |
| WO | WO 2012/082647 A2 | 6/2012 |
| WO | WO 2012/087771 A1 | 6/2012 |
| WO | WO 2012/110860 A1 | 8/2012 |
| WO | WO 2012/154480 A1 | 11/2012 |
| WO | WO 2012/161965 A1 | 11/2012 |
| WO | WO 2012/170250 A1 | 12/2012 |
| WO | WO 2012/172341 A2 | 12/2012 |
| WO | WO 2013/024898 A1 | 2/2013 |
| WO | WO 2013/027802 A1 | 2/2013 |
| WO | WO 2013/034933 A1 | 3/2013 |
| WO | WO 2013/039889 A1 | 3/2013 |
| WO | WO 2013/041865 A1 | 3/2013 |
| WO | WO 2013/052699 A2 | 4/2013 |
| WO | WO 2013/056352 A1 | 4/2013 |
| WO | WO 2013/072825 A1 | 5/2013 |
| WO | WO 2013/109752 A1 | 7/2013 |
| WO | WO 2013/112741 A1 | 8/2013 |
| WO | WO 2013/116562 A1 | 8/2013 |
| WO | WO 2013/118071 A1 | 8/2013 |
| WO | WO 2013/119714 A1 | 8/2013 |
| WO | WO 2013/131010 A2 | 9/2013 |
| WO | WO 2013/153535 A1 | 10/2013 |
| WO | WO 2013/186692 A1 | 12/2013 |
| WO | WO 2014/023813 A1 | 2/2014 |
| WO | WO 2014/039714 A2 | 3/2014 |
| WO | WO 2014/047624 A1 | 3/2014 |
| WO | WO 2014/056953 A1 | 4/2014 |
| WO | WO 2014/064215 A1 | 5/2014 |
| WO | WO 2014/076221 A1 | 5/2014 |
| WO | WO 2014/087248 A2 | 6/2014 |
| WO | WO 2014/100620 A2 | 6/2014 |
| WO | WO 2014/100765 A1 | 6/2014 |
| WO | WO 2014/100767 A1 | 6/2014 |
| WO | WO 2014/107171 A1 | 7/2014 |
| WO | WO 2014/118236 A2 | 8/2014 |

(56) References Cited

FOREIGN PATENT DOCUMENTS

| | | |
|---|---|---|
| WO | WO 2014/128189 A1 | 8/2014 |
| WO | WO 2014/167444 A1 | 10/2014 |
| WO | WO 2014/201409 A1 | 12/2014 |
| WO | WO 2015/011450 A1 | 1/2015 |
| WO | WO 2015/059618 A1 | 4/2015 |
| WO | WO 2015/13 8600 A2 | 9/2015 |
| WO | WO 2015/134536 A1 | 9/2015 |
| WO | WO 2015/15 8204 A1 | 10/2015 |
| WO | WO 2015/148954 A1 | 10/2015 |
| WO | WO 2015/157386 A1 | 10/2015 |
| WO | WO 2015/191861 A1 | 12/2015 |
| WO | WO 2016/022971 A1 | 2/2016 |
| WO | WO 2016/023040 A1 | 2/2016 |
| WO | WO 2016/024021 A1 | 2/2016 |
| WO | WO 2016/033486 A1 | 3/2016 |
| WO | WO 2016/033570 A1 | 3/2016 |
| WO | WO 2016/055785 A1 | 4/2016 |
| WO | WO 2016/069374 A1 | 5/2016 |
| WO | WO 2016/069376 A1 | 5/2016 |
| WO | WO 2016/081423 A1 | 5/2016 |
| WO | WO 2016/090300 A1 | 6/2016 |
| WO | WO 2016/100236 A2 | 6/2016 |
| WO | WO 2016/109415 A1 | 7/2016 |
| WO | WO 2016/141328 A2 | 9/2016 |
| WO | WO 2016/142783 A2 | 9/2016 |
| WO | WO 2016/149562 A2 | 9/2016 |
| WO | WO 2016/177339 A1 | 11/2016 |
| WO | WO 2016/179399 A1 | 11/2016 |
| WO | WO 2016/179517 A1 | 11/2016 |
| WO | WO 2016/188449 A1 | 12/2016 |
| WO | WO 2016/191246 A2 | 12/2016 |
| WO | WO 2016/196388 A1 | 12/2016 |
| WO | WO 2016/205042 A1 | 12/2016 |
| WO | WO 2016/205942 A1 | 12/2016 |
| WO | WO 2016/210365 A2 | 12/2016 |
| WO | WO 2017/027422 A1 | 2/2017 |
| WO | WO 2017/044661 A1 | 3/2017 |
| WO | WO 2017/049166 A1 | 3/2017 |
| WO | WO 2017/049251 A2 | 3/2017 |
| WO | WO 2017/053423 A1 | 3/2017 |
| WO | WO 2017/076308 A1 | 5/2017 |
| WO | WO 2017/096179 A1 | 6/2017 |
| WO | WO 2017/096182 A1 | 6/2017 |
| WO | WO 2017/096189 A1 | 6/2017 |
| WO | WO 2017/096276 A1 | 6/2017 |
| WO | WO 2017/096281 A1 | 6/2017 |
| WO | WO 2017/109496 A1 | 6/2017 |
| WO | WO 2017/121771 A1 | 7/2017 |
| WO | WO 2017/147410 A1 | 8/2017 |
| WO | WO 2018/172984 A1 | 8/2017 |
| WO | WO 2017/160861 A1 | 9/2017 |
| WO | WO 2017/167182 A1 | 10/2017 |
| WO | WO 2017/174822 A1 | 10/2017 |
| WO | WO 2017/174823 A1 | 10/2017 |
| WO | WO 2017/174824 A1 | 10/2017 |
| WO | WO 2017/175006 A1 | 10/2017 |
| WO | WO 2017/178653 A2 | 10/2017 |
| WO | WO 2017/189254 A1 | 11/2017 |
| WO | WO 2017/194634 A1 | 11/2017 |
| WO | WO 2017/196793 A1 | 11/2017 |
| WO | WO 2017/211303 A1 | 12/2017 |
| WO | WO 2017/215585 A1 | 12/2017 |
| WO | WO 2018/005435 A1 | 1/2018 |
| WO | WO 2018/026600 A1 | 2/2018 |
| WO | WO 2018/049152 A1 | 3/2018 |
| WO | WO 2018/049191 A1 | 3/2018 |
| WO | WO 2018/049200 A1 | 3/2018 |
| WO | WO 2018/049214 A1 | 3/2018 |
| WO | WO 2018/057669 A1 | 3/2018 |
| WO | WO 2018/075857 A1 | 4/2018 |
| WO | WO 2018/075960 A1 | 4/2018 |
| WO | WO 2018/089508 A2 | 5/2018 |
| WO | WO 2018/089628 A1 | 5/2018 |
| WO | WO 2018/095428 A1 | 5/2018 |
| WO | WO 2018/097951 A1 | 5/2018 |
| WO | WO 2018/098280 A1 | 5/2018 |
| WO | 2018112032 A1 | 6/2018 |
| WO | WO 2018/102366 A1 | 6/2018 |
| WO | WO 2018/107058 A1 | 6/2018 |
| WO | WO 2018/112136 A1 | 6/2018 |
| WO | WO 2018/112140 A1 | 6/2018 |
| WO | WO 2018/119448 A1 | 6/2018 |
| WO | WO 2018/132739 A2 | 7/2018 |
| WO | WO 2018/137705 A1 | 8/2018 |
| WO | WO 2018/144649 A1 | 8/2018 |
| WO | WO 2018/170338 A2 | 9/2018 |
| WO | WO 2018/172533 A2 | 9/2018 |
| WO | WO 2018/167147 A1 | 10/2018 |
| WO | WO 2018/181425 A1 | 10/2018 |
| WO | WO 2018/183418 A1 | 10/2018 |
| WO | WO 2018/183956 A1 | 10/2018 |
| WO | WO 2018/183964 A1 | 10/2018 |
| WO | WO 2018/190719 A2 | 10/2018 |
| WO | WO 2018/195321 A1 | 10/2018 |
| WO | WO 2018/210793 A2 | 11/2018 |
| WO | WO 2018/223909 A1 | 12/2018 |
| WO | WO 2018/225732 A1 | 12/2018 |
| WO | WO 2018/226542 A1 | 12/2018 |
| WO | WO 2018/233575 A1 | 12/2018 |
| WO | WO 2018/234319 A1 | 12/2018 |
| WO | WO 2018/237026 A1 | 12/2018 |
| WO | WO 2019/023347 A1 | 1/2019 |
| WO | WO 2019/027903 A1 | 2/2019 |
| WO | WO 2019/034895 A1 | 2/2019 |
| WO | WO 2019/042119 A1 | 3/2019 |
| WO | WO 2019/042285 A1 | 3/2019 |
| WO | WO 2019/042470 A1 | 3/2019 |
| WO | WO 2019/043208 A1 | 3/2019 |
| WO | WO 2019/043217 A1 | 3/2019 |
| WO | WO 2019/067733 A1 | 4/2019 |
| WO | WO 2019/079701 A1 | 4/2019 |
| WO | WO 2019/084026 A1 | 5/2019 |
| WO | WO 2019/084030 A1 | 5/2019 |
| WO | WO 2019/084538 A1 | 5/2019 |
| WO | WO 2019/086573 A1 | 5/2019 |
| WO | WO 2019/099926 A1 | 5/2019 |
| WO | WO 2019/103203 A1 | 5/2019 |
| WO | WO 2019/108733 A2 | 6/2019 |
| WO | WO 2019/109821 A1 | 6/2019 |
| WO | WO 2019/138367 A1 | 7/2019 |
| WO | WO 2019/144895 A1 | 8/2019 |
| WO | WO 2019/155067 A1 | 8/2019 |
| WO | WO 2019/157843 A1 | 8/2019 |
| WO | WO 2019/160882 A1 | 8/2019 |
| WO | WO 2019/162043 A1 | 8/2019 |
| WO | WO 2019/173692 A2 | 9/2019 |
| WO | WO 2019/175218 A1 | 9/2019 |
| WO | WO 2019/179366 A1 | 9/2019 |
| WO | WO 2019/183266 A1 | 9/2019 |
| WO | WO 2019/184912 A1 | 10/2019 |
| WO | WO 2019/185717 A1 | 10/2019 |
| WO | WO 2019/201236 A1 | 10/2019 |
| WO | WO 2019/204683 A1 | 10/2019 |
| WO | WO 2019/238012 A1 | 12/2019 |
| WO | WO 2019/241732 A1 | 12/2019 |
| WO | WO 2020/009725 A1 | 1/2020 |
| WO | WO 2020/013170 A1 | 1/2020 |
| WO | WO 2020/014643 A1 | 1/2020 |
| WO | WO 2020/019135 A1 | 1/2020 |
| WO | WO 2020/036977 A1 | 2/2020 |
| WO | WO 2020/043188 A1 | 3/2020 |
| WO | WO 2020/063488 A1 | 4/2020 |
| WO | WO 2020/068752 A1 | 4/2020 |
| WO | WO 2020/076105 A1 | 4/2020 |
| WO | WO 2020/086158 A2 | 4/2020 |
| WO | WO 2020/086647 A1 | 4/2020 |
| WO | WO 2020/092528 A1 | 5/2020 |
| WO | WO 2020/092621 A1 | 5/2020 |
| WO | WO 2020/112687 A2 | 6/2020 |
| WO | WO 2020/138489 A1 | 7/2020 |
| WO | WO 2020/263830 A1 | 12/2020 |
| WO | 2021152186 A2 | 8/2021 |
| WO | 2021163064 A2 | 8/2021 |
| WO | 2021178749 A2 | 9/2021 |

(56) References Cited

FOREIGN PATENT DOCUMENTS

| | | |
|---|---|---|
| WO | WO 2021/194942 A1 | 9/2021 |
| WO | 2022003156 A1 | 1/2022 |
| WO | 2022004760 A1 | 1/2022 |
| WO | WO 2022/000443 A1 | 1/2022 |
| WO | 2022042690 A1 | 3/2022 |
| WO | WO 2022/078277 A1 | 4/2022 |
| WO | WO 2022/081718 A1 | 4/2022 |
| WO | 2022117569 A1 | 6/2022 |
| WO | 2022136647 A1 | 6/2022 |
| WO | 2022136649 A1 | 6/2022 |
| WO | 2022136650 A1 | 6/2022 |
| WO | 2022/200303 A1 | 9/2022 |
| WO | 2022/216965 A1 | 10/2022 |
| WO | WO 2022/241034 A1 | 11/2022 |
| WO | WO 2023/288241 A1 | 1/2023 |
| WO | WO 2023/010054 A1 | 2/2023 |
| WO | WO 2023/020621 A1 | 2/2023 |

OTHER PUBLICATIONS

International Search Report and Written Opinion for PCT Patent Application No. PCT/US2021/017268, dated Sep. 1, 2021, 31 pages.

Finotello et al. (Jan. 27, 2017) "New Strategies for Cancer Immunotherapy: Targeting Regulatory T Cells", Genome Medicine, 9(10):3 Pages.

Plitas et al. (Feb. 15, 2016) "Abstract P4-04-11: Preferential Expression of the Chemokine Receptor 8 (CCR8) on Regulatory T Cells (Treg) Infiltrating Human Breast Cancers Represents a Novel Immunotherapeutic Target", Cancer Research, 76(4): P4-04-11.

Monocclonal anti-human CCR8 antibody (Jul. 8, 2003), XP002430338, Retrieved from the Internet: URL:http://www.rndsystems.com [retrieved on Apr. 19, 2007] p. I, paragraph 7-paragraph 8 p. 2; figure 2.

Abdiche et al., "Determining kinetics and affinities of protein interactions using a parallel real-time label-free biosensor, the Octet," *Anal. Biochem.*, 377: 209-217 (2008).

Almagro et al., "Humanization of antibodies," *Front. Biosci.*, 13:1619-1633 (2008).

Baca et al., "Antibody humanization using monovalent phage display," *J. Biol. Chem.*, 272:10678-10684 (1997).

Bagger et al., "BloodSpot: a database of gene expression profiles and transcriptional programs for healthy and malignant haematopoiesis," *Nucleic Acids Res.*, 44(D1):D917-D924 (2016).

BioLegend Datasheet, "Purified anti-mouse CD198 (CCR8) Antibody," pp. 1-2 (2015).

Boerner et al., "Production of antigen-specific human monoclonal antibodies from in vitro-primed human splenocytes," *J. Immunol.*, 147:86-95 (1991).

Booth et al., "The levels of mutant K-RAS and mutant N-RAS are rapidly reduced in a Beclin1 / ATG5-dependent fashion by the irreversible ERBB1/2/4 inhibitor neratinib," *Cancer Biol Ther.*, 19(2): 132-137 (2018).

Brodeur et al., "Mouse-Human Myeloma Partners for the Production of Heterohybridomas," *Monoclonal Antibody Production Techniques and Applications*, Marcel Dekker, Inc., New York, pp. 51-63 (1987).

Capel et al., "Heterogeneity of human IgG Fc receptors," *Immunomethods*, 4:25-34 (1994).

Carreno et al., "Cancer immunotherapy. A dendritic cell vaccine increases the breadth and diversity of melanoma neoantigen-specific T cells," *Science*, 348:803-808 (2015).

Carter et al., "Humanization of an anti-p185HER2 antibody for human cancer therapy," *Proc. Natl. Acad. Sci. USA*, 89:4285-4289 (1992).

Chen et al., "Selection and analysis of an optimized anti-VEGF antibody: crystal structure of an affinity-matured Fab in complex with antigen," *J. Mol. Biol.*, 293:865-881 (1999).

Chiossone et al., "Natural killer cells and other innate lymphoid cells in cancer," *Nat Rev Immunol.*, 18(11):671-688 (2018).

Choo et al., "SPdb—a signal peptide database," *BMC Bioinformatics*, 6: 249 (2005).

Chothia et al., "Canonical structures for the hypervariable regions of immunoglobulins," *J. Mol. Biol.*, 196:901-917 (1987).

Clackson et al., "Making antibody fragments using phage display libraries," *Nature*, 352:624-628 (1991).

Clynes et al., "Fc receptors are required in passive and active immunity to melanoma," *Proc. Natl. Acad. Sci. USA*, 95:652-656 (1998).

Collado-Torres et al., "Reproducible RNA-seq analysis using recount2," *Nat. Biotechnol.*, 35(4):319-321 (2017).

Daeron, "Fc receptor biology," *Annu. Rev. Immunol.*, 15:203-234 (1997).

Dai et al., "Chimeric Antigen Receptors Modified T-Cells for Cancer Therapy," *J Natl Cancer Inst*, 108(7):djv439 (2016). doi: 10.1093/jnci/djv439.

Dall'Acqua et al., "Antibody humanization by framework shuffling," *Methods*, 36:43-60 (2005).

Davis et al., "Natural killer cells unleashed: Checkpoint receptor blockade and BiKE/TriKE utilization in NK-mediated anti-tumor immunotherapy," *Semin Immunol.*, 31:64-75 (2017).

De Goeij et al., "New developments for antibody-drug conjugate-based therapeutic approaches," *Curr. Opin. Immunol.*, 40:14-23 (2016).

De Haas et al., "Fc gamma receptors of phagocytes," *J. Lab. Clin. Med.*, 126:330-341 (1995).

De Simone et al., "Transcriptional Landscape of Human Tissue Lymphocytes Unveils Uniqueness of Tumor-Infiltrating T Regulatory Cells," *Immunity*, 45:1135-1147 (2016).

Emens, "Cancer vaccines: on the threshold of success," *Expert Opin Emerg Drugs*, 13(2):295-308 (2008).

Endo et al., "High-throughput, genome-scale protein production method based on the wheat germ cell-free expression system," *Biotechnol. Adv.*, 21:695-713 (2003).

Fang et al., "NK cell-based immunotherapy for cancer," *Semin Immunol.*, 31:37-54 (2017).

Felices et al., "Generation of BiKEs and TriKEs to Improve NK Cell-Mediated Targeting of Tumor Cells," *Methods Mol Biol.*, 1441:333 346 (2016).

Fellouse et al., "Synthetic antibodies from a four-amino-acid code: a dominant role for tyrosine in antigen recognition," *Proc. Natl. Acad. Sci. USA*, 101(34):12467-12472 (2004).

Gangwal et al., "p38 Mitogen-activated protein kinase inhibitors: a review on pharmacophore mapping and QSAR studies," *Curr. Top. Med. Chem.*, 13(9): 1015-1035 (2013).

Gariepy et al., "A powerful ICOS agonist that enhances anti-tumor immune responses restored by immune checkpoint inhibitors," *106th Annu Meet Am Assoc Immunologists (AAI)*, May 9-13, San Diego, Abst 71.5 (2019).

Gazzano-Santoro et al., "A non-radioactive complement-dependent cytotoxicity assay for anti-CD20 monoclonal antibody," *J. Immunol. Methods*, 202:163-171 (1997).

Ghetie et al., "FcRn: the MHC class I-related receptor that is more than an IgG transporter," *Immunol. Today*, 18(12):592-598 (1997).

Ghetie et al., "Increasing the serum persistence of an IgG fragment by random mutagenesis," *Nat. Biotechnol.*, 15(7):637-640 (1997).

Gibbs et al., "Emerging Contributions of Cancer/Testis Antigens to Neoplastic Behaviors," *Trends Cancer*, 4(10):701-712 (2018).

Gill et al., "Chimeric antigen receptor T cell therapy: 25 years in the making," *Blood Rev.*, 30(3): 157-167 (2015), doi: 10.1016/j.blre. 2015.10.003.

Gill et al., "Going viral: chimeric antigen receptor T-cell therapy for hematological malignancies," *Immunol. Rev.*, 263(1):68-89 (2015). doi: 10.1111/imr.12243.

Gohil et al., "An ROR1 bi-specific T-cell engager provides effective targeting and cytotoxicity against a range of solid tumors," *Oncoimmunology*, 6(7):e1326437 (2017).

Griffiths et al., "Human anti-self antibodies with high specificity from phage display libraries," *EMBO J*, 12(2):725-734 (1993).

Guyer et al., "Immunoglobulin binding by mouse intestinal epithelial cell receptors," *J. Immunol.*, 117:587-593 (1976).

(56) References Cited

OTHER PUBLICATIONS

Haferlach et al., "Clinical utility of microarray-based gene expression profiling in the diagnosis and subclassification of leukemia: report from the International Microarray Innovations in Leukemia Study Group," *J. Clin. Oncol.*, 28(15):2529-2537 (2010).
Hinton et al., "Engineered human IgG antibodies with longer serum half-lives in primates," *J. Biol. Chem.*, 279(8):6213-6216 (2004).
Hoogenboom et al., "By-passing immunisation. Human antibodies from synthetic repertoires of germline VH gene segments rearranged in vitro," *J. Mol. Biol.*, 227:381-388 (1992).
Hoogenboom, "Overview of antibody phage-display technology and its applications," *Methods Mol. Biol.*, 178: 1-37 (2002).
Horn et al., "CD3xPDL1 bi-specific T cell engager (BiTE) simultaneously activates T cells and NKT cells, kills PDL1+ tumor cells, and extends the survival of tumor-bearing humanized mice," *Oncotarget.*, 8(35):57964-57980 (2017).
Hu et al., "Discovery of indazoles as inhibitors of Tpl2 kinase," *Bioorg. Med. Chem. Lett.*, 21(16):475 8-4761 (2011).
Idusogie et al., "Mapping of the C1q binding site on rituxan, a chimeric antibody with a human IgG1 Fc," *J. Immunol.*, 164: 4178-4184 (2000).
Islam et al., "Mouse CCL8, a CCR8 agonist, promotes atopic dermatitis by recruiting IL-5+ TH2 cells," *Nat. Immunol.*, 12(2):1-23 (2011).
Kaila et al., "Identification of a novel class of selective Tpl2 kinase inhibitors: 4-Alkylamino-[1,7]naphthyridine-3-carbonitriles," *Bioorg. Med. Chem.*, 15(19):6425-6442 (2007).
Kanda et al., "Comparison of cell lines for stable production of fucose-negative antibodies with enhanced ADCC," *Biotechnol. Bioeng.*, 94(4):680-688 (2006).
Kantoff et al., "Sipuleucel-T immunotherapy for castration-resistant prostate cancer," *N. Engl. J. Med.*, 363:411-422 (2010).
Kashmiri et al., "SDR grafting—a new approach to antibody humanization," *Methods*, 36:25-34 (2005).
Kim et al., "Identifying amino acid residues that influence plasma clearance of murine IgG1 fragments by site-directed mutagenesis," *Eur. J. Immunol.*, 24:542-548 (1994).
Klimka et al., "Human anti-CD30 recombinant antibodies by guided phage antibody selection using cell panning," *Br. J. Cancer*, 83:252-260 (2000).
Kohler et al., "Continuous cultures of fused cells secreting antibody of predefined specificity," *Nature*, 256:495-497 (1975).
Kohlmann et al., "An international standardization programme towards the application of gene expression profiling in routine leukaemia diagnostics: the Microarray Innovations in LEukemia study prephase," *Br. J. Haematol.*, 142:802-807 (2008).
Kozbor et al., "A human hybrid myeloma for production of human monoclonal antibodies," *J Immunol,*, 133:3001-3005 (1984).
Lambert et al., "Antibody-Drug Conjugates (ADCs) for Personalized Treatment of Solid Tumors: A Review," *Adv. Ther.*, 34:1015-1035 (2017).
Lazar et al., "Engineered antibody Fc variants with enhanced effector function," *Proc. Natl. Acad. Sci. USA*, 103:4005-4010 (2006).
Lee et al., "Bivalent antibody phage display mimics natural immunoglobulin," *J. Immunol. Methods*, 284(1-2):119-132 (2004).
Lee et al., "High-affinity human antibodies from phage-displayed synthetic Fab libraries with a single framework scaffold," *J. Mol. Biol.*, 340(5):1073-1093 (2004).
Li et al., "Human antibodies for immunotherapy development generated via a human B cell hybridoma technology," *Proc. Natl. Acad. Sci. USA*, 103:3557-3562 (2006).
Liu et al., "Metformin represses bladder cancer progression by inhibiting stem cell repopulation via COX2/PGE2/STAT3 axis," *Oncotarget.*, 7(19):28235-28246 (2016).
Liu et al., "Targeting regulatory T cells in tumors," *FEBS J.*, 283(14):2731-2748 (2016). doi: 10.1111/febs.13656.
Lonberg, "Fully human antibodies from transgenic mouse and phage display platforms," *Curr. Opin. Immunol.*, 20:450-459 (2008).
Lonberg, "Human antibodies from transgenic animals," *Nat. Biotech.*, 23:1117-1125 (2005).
Marks et al., "By-passing immunization. Human antibodies from V-gene libraries displayed on phage," *J. Mol. Biol.*, 222:581-597 (1991).
Marks et al., "Selection of human antibodies from phage display libraries," *Methods Mol. Biol.*, 248:161-175 (2004).
McCafferty et al., "Phage antibodies: filamentous phage displaying antibody variable domains," *Nature*, 348:552-554 (1990).
Mimoto et al., "Novel asymmetrically engineered antibody Fc variant with superior FcγR binding affinity and specificity compared with afucosylated Fc variant," *MAbs*, 5:229-236 (2013).
Mitson-Salazar et al., "Hematopoietic prostaglandin D synthase defines a proeosinophilic pathogenic effector human T(H)2 cell subpopulation with enhanced function," *J. Allergy Clin. Immunol.*, 137:907-918 (2016).
Miyara et al., "Functional delineation and differentiation dynamics of human CD4+ T cells expressing the FoxP3 transcription factor," *Immunity*, 30:899-911 (2009).
Morrison et al., "Chimeric human antibody molecules: mouse antigen-binding domains with human constant region domains," *Proc. Natl. Acad. Sci. USA*, 81:6851-6855 (1984).
Mutalithas et al., "Expression of CCR8 is increased in asthma," *Clin. Exp. Allergy*, 40:1175-1185 (2010).
Nemunaitis, "Vaccines in cancer: GVAX, a GM-CSF gene vaccine," *Expert Rev Vaccines*, 4:259-274 (2005).
Okazaki et al., "Fucose depletion from human IgG1 oligosaccharide enhances binding enthalpy and association rate between IgG1 and FcgammaRIIIa," *J. Mol. Biol.*, 336:1239-1249 (2004).
Osbourn et al., "From rodent reagents to human therapeutics using antibody guided selection," *Methods*, 36:61-68 (2005).
Padlan, "A possible procedure for reducing the immunogenicity of antibody variable domains while preserving their ligand-binding properties," *Mol. Immunol.*, 28:489-498 (1991).
Petkova et al., "Enhanced half-life of genetically engineered human IgG1 antibodies in a humanized FcRn mouse model: potential application in humorally mediated autoimmune disease," *Int. Immunol.*, 18(12):1759-1769 (2006).
Plitas et al., "Regulatory T Cells Exhibit Distinct Features in Human Breast Cancer," *Immunity*, 45:1122-1134 (2016).
Presta et al., "Humanization of an antibody directed against IgE," *J. Immunol.*, 151:2623-2632 (1993).
Queen et al., "A humanized antibody that binds to the interleukin 2 receptor," *Proc. Natl Acad. Sci. USA*, 86: 10029-10033 (1989).
Ra Vetch et al., "Fc receptors," *Annu. Rev. Immunol.*, 9:457-492 (1991).
Riechmann et al., "Reshaping human antibodies for therapy," *Nature*, 332:323-329 (1988).
Ripka et al., "Two Chinese hamster ovary glycosylation mutants affected in the conversion of GDP-mannose to GDP-fucose," *Arch. Biochem. Biophys.*, 249:533-545 (1986).
Rosok et al., "A combinatorial library strategy for the rapid humanization of anticarcinoma BR96 Fab," *J. Biol. Chem.*, 271:22611-22618 (1996).
Running Deer et al., "High-level expression of proteins in mammalian cells using transcription regulatory sequences from the Chinese hamster EF-1alpha gene," *Biotechnol. Prog.*, 20:880-889 (2004).
Sheets et al., "Efficient construction of a large nonimmune phage antibody library: the production of high-affinity human single-chain antibodies to protein antigens," *Proc. Natl. Acad. Sci. USA*, 95:6157-6162 (1998).
Shields et al.,"High resolution mapping of the binding site on human IgG1 for Fc gamma RI, Fc gamma RII, Fc gamma RII, and FcRn and design of IgG1 variants with improved binding to the Fc gamma R," *J. Biol. Chem.*, 276(9):6591-6604 (2001).
Sidhu et al., "Phage-displayed antibody libraries of synthetic heavy chain complementarity determining regions," *J. Mol. Biol.*, 338(2):299-310 (2004).
Sims et al., "A humanized CD18 antibody can block function without cell destruction," *J. Immunol.* 151:2296-2308 (1993).
Sitaraman et al., "High-throughput protein expression using cell-free system," *Methods Mol. Biol.*, 498:229-244 (2009).
Spirin, "High-throughput cell-free systems for synthesis of functionally active proteins," *Trends Biotechnol*, 22:538-545 (2004).

(56) References Cited

OTHER PUBLICATIONS

Stallard et al., "New Approach Could Boost Immunotherapy for Breast Cancer," *Memorial Cloan Kettering Cancer Center*, Press Release, pp. 1-5 (2016).
Stavenhagen et al., "Fc optimization of therapeutic antibodies enhances their ability to kill tumor cells in vitro and controls tumor expansion in vivo via low-affinity activating Fcgamma receptors," *Cancer Res.*, 67:8882-8890 (2007).
Stewart-Jones et al., "Rational development of high-affinity T-cell receptor-like antibodies," *Proc Natl Acad Sci USA*, 106(14):5784-5788 (2009).
Takeuchi et al., "Roles of regulatory T cells in cancer immunity," *Int. Immunol.*, 28(8):401-409 (2016).
Tanaka et al., "Regulatory T cells in cancer immunotherapy," *Cell Res.*, 27:109-118 (2017).
Teli et al., "Pharmacophore generation and atom-based 3D-QSAR of novel quinoline-3-carbonitrile derivatives as Tp12 kinase inhibitors," *J. Enzyme Inhib. Med. Chem.*, 27(4):558-570 (2012).
Tong et al., "Metformin inhibits castration-induced EMT in prostate cancer by repressing COX2/PGE2/STAT3 axis," *Cancer Lett.*, 389:23-32 (2017).
Van Dijk et al., "Human antibodies as next generation therapeutics," *Curr. Opin. Pharmacol.*, 5:368-374 (2001).
Vaughan et al., "Human antibodies with sub-nanomolar affinities isolated from a large non-immunized phage display library," *Nat. Biotechnol.*, 14:309-314 (1996).
Vollmers et al., "Death by stress: natural IgM-induced apoptosis," *Methods Find. Exp. Clin. Pharmacol.*, 27(3): 185-191 (2005).
Vollmers et al., "The "early birds": natural IgM antibodies and immune surveillance," *Histol. Histopathol.*, 20(3):927-937 (2005).
Willner et al., "(6-Maleimidocaproyl)hydrazone of doxorubicin—a new derivative for the preparation of immunoconjugates of doxorubicin," *Bioconjugate Chem.*, 4:521-527 (1993).
Winter et al., "Making antibodies by phage display technology," *Ann. Rev. Immunol.*, 12:433-455 (1994).
Wong, *Chemistry of protein conjugation and cross-linking*, CRC Press, Inc., Boca Raton, Fla.,pp. 20-22 (1991).
Wu et al., "Selective inhibitors of tumor progression loci-2 (Tp12) kinase with potent inhibition of TNF-alpha production in human whole blood," *Bioorg. Med. Chem. Lett.*, 19(13):3485-3488 (2009).
Xu et al., "Immune checkpoint therapy in liver cancer," *J. Exp. Clin. Cancer Res.*, 37:110 (2018).
Yamane-Ohnuki et al., "Establishment of FUT8 knockout Chinese hamster ovary cells: an ideal host cell line for producing completely defucosylated antibodies with enhanced antibody-dependent cellular cytotoxicity," *Biotech. Bioeng.*, 87:614-622 (2004).
Yang et al., "Targeting EGFRvIII for glioblastoma multiforme," *Cancer Lett.*, 403:224-230 (2017).
Yoshida, "Declaration Under 37 C.F.R. 1.132", submitted in U.S. Appl. No. 16/183,216, pp. 1-34, Oct. 30, 2019 and Jun. 5, 2019.
Zhou et al., "Palbociclib, a selective CDK4/6 inhibitor, enhances the effect of selumetinib in RAS-driven non-small cell lung cancer," *Cancer Lett.*, 408:130-137 (2017).
Labome, "CCR8 antibody". Retrieved from the Internet on Jan. 26, 2023: "www.labome.com/review/gene/human/CCR8-antibody.html".

\* cited by examiner

SEQUENCE LISTING

<160> NUMBER OF SEQ ID NOS: 129

<210> SEQ ID NO 1
<211> LENGTH: 339
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

Met Gln Ile Ile Thr Thr Ala Leu Val Cys Leu Leu Leu Ala Gly Met
1               5                   10                  15

Trp Pro Glu Asp Val Asp Ser Lys Ser Met Gln Val Pro Phe Ser Arg
            20                  25                  30

Cys Cys Phe Ser Phe Ala Glu Gln Glu Ile Pro Leu Arg Ala Ile Leu
            35                  40                  45

Cys Tyr Arg Asn Thr Ser Ser Ile Cys Ser Asn Glu Gly Leu Ile Phe
50                  55                  60

Lys Leu Lys Arg Gly Lys Glu Ala Cys Ala Leu Asp Thr Val Gly Trp
65                  70                  75                  80

Val Gln Arg His Arg Lys Met Leu Arg His Cys Pro Ser Lys Arg Lys
                85                  90                  95

Ser Gly Ser Gly Gly Gly Ser Gly Asp Lys Thr His Thr Cys Pro
            100                 105                 110

Pro Cys Pro Ala Pro Glu Leu Leu Gly Gly Pro Ser Val Phe Leu Phe
            115                 120                 125

Pro Pro Lys Pro Lys Asp Thr Leu Met Ile Ser Arg Thr Pro Glu Val
            130                 135                 140

Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
            180                 185                 190

Val Leu His Gln Asp Trp Leu Asn Gly Lys Glu Tyr Lys Cys Lys Val
            195                 200                 205

Ser Asn Lys Ala Leu Pro Ala Pro Ile Glu Lys Thr Ile Ser Lys Ala
210                 215                 220

Lys Gly Gln Pro Arg Glu Pro Gln Val Tyr Thr Leu Pro Pro Ser Arg
225                 230                 235                 240

Glu Glu Met Thr Lys Asn Gln Val Ser Leu Thr Cys Leu Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Lys Thr Thr Pro Pro Val Leu Asp Ser Asp Gly Ser
            275                 280                 285

Phe Phe Leu Tyr Ser Lys Leu Thr Val Asp Lys Ser Arg Trp Gln Gln
            290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly Lys Gly Ser Gly Glu
                325                 330                 335

Pro Glu Ala

<210> SEQ ID NO 2
<211> LENGTH: 96
<212> TYPE: PRT
<213> ORGANISM: Homo sapiens

<400> SEQUENCE: 2

Met Gln Ile Ile Thr Thr Ala Leu Val Cys Leu Leu Leu Ala Gly Met
1               5                   10                  15

Trp Pro Glu Asp Val Asp Ser Lys Ser Met Gln Val Pro Phe Ser Arg
            20                  25                  30

```
Cys Cys Phe Ser Phe Ala Glu Gln Glu Ile Pro Leu Arg Ala Ile Leu
         35                  40                  45

Cys Tyr Arg Asn Thr Ser Ser Ile Cys Ser Asn Glu Gly Leu Ile Phe
 50                  55                  60

Lys Leu Lys Arg Gly Lys Glu Ala Cys Ala Leu Asp Thr Val Gly Trp
 65                  70                  75                  80

Val Gln Arg His Arg Lys Met Leu Arg His Cys Pro Ser Lys Arg Lys
             85                  90                  95

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Gly Gly Ser Gly Gly Gly Ser Gly
 1               5

<210> SEQ ID NO 4
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Lys Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
             20                  25                  30

Ile Ser Arg Thr Pro Glu Val Thr Cys Val Val Val Asp Val Ser His
         35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
             85                  90                  95

Lys Glu Tyr Lys Cys Lys Val Ser Asn Lys Ala Leu Pro Ala Pro Ile
        100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
        210                 215                 220
```

Pro Gly Lys Gly Ser Gly Glu Pro Glu Ala
225                 230

<210> SEQ ID NO 5
<211> LENGTH: 322
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Leu Ala Arg Arg Lys Cys Cys Leu Asn Pro Thr Asn Arg Pro Ile Pro
1               5                   10                  15

Asn Pro Leu Leu Gln Asp Leu Ser Arg Val Asp Tyr Gln Ala Ile Gly
            20                  25                  30

His Asp Cys Gly Arg Glu Ala Phe Arg Val Thr Leu Gln Asp Gly Arg
        35                  40                  45

Gln Gly Cys Val Ser Val Gly Asn Lys Ser Leu Leu Asp Trp Leu Arg
    50                  55                  60

Gly His Lys Asp Leu Cys Pro Gln Ile Trp Ser Gly Cys Glu Ser Leu
65                  70                  75                  80

Gly Gly Ser Gly Gly Ser Asp Lys Thr His Thr Cys Pro Pro
                85                  90                  95

Cys Pro Ala Pro Glu Leu Leu Gly Gly Pro Ser Val Phe Leu Phe Pro
            100                 105                 110

Pro Lys Pro Lys Asp Thr Leu Met Ile Ser Arg Thr Pro Glu Val Thr
        115                 120                 125

Cys Val Val Val Asp Val Ser His Glu Asp Pro Glu Val Lys Phe Asn
    130                 135                 140

Trp Tyr Val Asp Gly Val Glu Val His Asn Ala Lys Thr Lys Pro Arg
145                 150                 155                 160

Glu Glu Gln Tyr Asn Ser Thr Tyr Arg Val Val Ser Val Leu Thr Val
                165                 170                 175

Leu His Gln Asp Trp Leu Asn Gly Lys Glu Tyr Lys Cys Lys Val Ser
            180                 185                 190

Asn Lys Ala Leu Pro Ala Pro Ile Glu Lys Thr Ile Ser Lys Ala Lys
        195                 200                 205

Gly Gln Pro Arg Glu Pro Gln Val Tyr Thr Leu Pro Pro Ser Arg Glu
    210                 215                 220

Glu Met Thr Lys Asn Gln Val Ser Leu Thr Cys Leu Val Lys Gly Phe
225                 230                 235                 240

Tyr Pro Ser Asp Ile Ala Val Glu Trp Glu Ser Asn Gly Gln Pro Glu
                245                 250                 255

Asn Asn Tyr Lys Thr Thr Pro Pro Val Leu Asp Ser Asp Gly Ser Phe
            260                 265                 270

Phe Leu Tyr Ser Lys Leu Thr Val Asp Lys Ser Arg Trp Gln Gln Gly
        275                 280                 285

Asn Val Phe Ser Cys Ser Val Met His Glu Ala Leu His Asn His Tyr
    290                 295                 300

Thr Gln Lys Ser Leu Ser Leu Ser Pro Gly Lys Gly Ser Gly Glu Pro
305                 310                 315                 320

Glu Ala

<210> SEQ ID NO 6
<211> LENGTH: 80

<212> TYPE: PRT
<213> ORGANISM: Molluscum contagiosum virus

<400> SEQUENCE: 6

```
Leu Ala Arg Arg Lys Cys Cys Leu Asn Pro Thr Asn Arg Pro Ile Pro
1               5                   10                  15

Asn Pro Leu Leu Gln Asp Leu Ser Arg Val Asp Tyr Gln Ala Ile Gly
            20                  25                  30

His Asp Cys Gly Arg Glu Ala Phe Arg Val Thr Leu Gln Asp Gly Arg
        35                  40                  45

Gln Gly Cys Val Ser Val Gly Asn Lys Ser Leu Leu Asp Trp Leu Arg
    50                  55                  60

Gly His Lys Asp Leu Cys Pro Gln Ile Trp Ser Gly Cys Glu Ser Leu
65                  70                  75                  80
```

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

```
Gly Gly Gly Ser Gly Gly Gly Ser
1               5
```

<210> SEQ ID NO 8
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Glu Val Gln Leu Val Glu Thr Gly Gly Gly Leu Val Gln Pro Lys Gly
1               5                   10                  15

Ser Leu Lys Leu Ser Cys Ala Ala Ser Gly Phe Thr Phe Asn Ile Asn
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gly Gly Tyr Gly Ser Ser Pro Tyr Asp Met Asp Tyr
            100                 105                 110

Trp Gly Gln Gly Thr Ser Val Thr Val Ser Ser
        115                 120
```

<210> SEQ ID NO 9
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
                20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Met Ser Asn Leu Ala Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ala Gly Thr Lys Leu Glu Leu Lys
            100                 105                 110
```

<210> SEQ ID NO 10
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Glu Val Gln Leu Val Glu Thr Gly Gly Gly Leu Val Gln Pro Lys Gly
1               5                   10                  15

Ser Leu Lys Leu Ser Cys Ala Ala Ser Gly Phe Thr Phe Asn Ile Asn
                20                  25                  30

Ala Met Asn Trp Val Arg Gln Ala Pro Gly Lys Gly Leu Glu Trp Val
            35                  40                  45

Ala Arg Ile Arg Ser Lys Ser Asn Asn Tyr Ala Thr Tyr Tyr Ala Asp
        50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gly Gly Tyr Gly Ser Ser Pro Tyr Asp Met Asp Tyr
            100                 105                 110

Trp Gly Gln Gly Thr Ser Val Thr Val Ser Ser Ala Lys Thr Thr Pro
        115                 120                 125

Pro Ser Val Tyr Pro Leu Ala Pro Gly Ser Ala Ala Gln Thr Asn Ser
        130                 135                 140

Met Val Thr Leu Gly Cys Leu Val Lys Gly Tyr Phe Pro Glu Pro Val
145                 150                 155                 160

Thr Val Thr Trp Asn Ser Gly Ser Leu Ser Ser Gly Val His Thr Phe
                165                 170                 175

Pro Ala Val Leu Glu Ser Asp Leu Tyr Thr Leu Ser Ser Ser Val Thr
            180                 185                 190

Val Pro Ser Ser Pro Arg Pro Ser Glu Thr Val Thr Cys Asn Val Ala
        195                 200                 205

His Pro Ala Ser Ser Thr Lys Val Asp Lys Lys Ile Val Pro Arg Asp
        210                 215                 220

Cys Gly Cys Lys Pro Cys Ile Cys Thr Val Pro Glu Val Ser Ser Val
225                 230                 235                 240

Phe Ile Phe Pro Pro Lys Pro Lys Asp Val Leu Thr Ile Thr Leu Thr
```

```
                     245                 250                 255
Pro Lys Val Thr Cys Val Val Asp Ile Ser Lys Asp Asp Pro Glu
            260                 265                 270

Val Gln Phe Ser Trp Phe Val Asp Asp Val Glu Val His Thr Ala Gln
            275                 280                 285

Thr Gln Pro Arg Glu Glu Gln Phe Asn Ser Thr Phe Arg Ser Val Ser
            290                 295                 300

Glu Leu Pro Ile Met His Gln Asp Trp Leu Asn Gly Lys Glu Phe Lys
305                 310                 315                 320

Cys Arg Val Asn Ser Ala Ala Phe Pro Ala Pro Ile Glu Lys Thr Ile
                325                 330                 335

Ser Lys Thr Lys Gly Arg Pro Lys Ala Pro Gln Val Tyr Thr Ile Pro
                340                 345                 350

Pro Pro Lys Glu Gln Met Ala Lys Asp Lys Val Ser Leu Thr Cys Met
                355                 360                 365

Ile Thr Asp Phe Phe Pro Glu Asp Ile Thr Val Glu Trp Gln Trp Asn
            370                 375                 380

Gly Gln Pro Ala Glu Asn Tyr Lys Asn Thr Gln Pro Ile Met Asn Thr
385                 390                 395                 400

Asn Gly Ser Tyr Phe Val Tyr Ser Lys Leu Asn Val Gln Lys Ser Asn
                405                 410                 415

Trp Glu Ala Gly Asn Thr Phe Thr Cys Ser Val Leu His Glu Gly Leu
                420                 425                 430

His Asn His His Thr Glu Lys Ser Leu Ser His Ser Pro Gly
                435                 440                 445

<210> SEQ ID NO 11
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ala Gly Thr Lys Leu Glu Leu Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160
```

Gln Asn Gly Val Leu Asn Ser Trp Thr Asp Gln Asp Ser Lys Asp Ser
            165                 170                 175

Thr Tyr Ser Met Ser Ser Thr Leu Thr Leu Thr Lys Asp Glu Tyr Glu
        180                 185                 190

Arg His Asn Ser Tyr Thr Cys Glu Ala Thr His Lys Thr Ser Thr Ser
    195                 200                 205

Pro Ile Val Lys Ser Phe Asn Arg Asn Glu Cys
    210                 215

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Phe Thr Phe Asn Ile Asn Ala Met Asn
1               5                   10

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Ile Arg Ser Lys Ser Asn Asn Tyr Ala Thr Tyr Tyr Ala Asp Ser
1               5                   10                  15
Val

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Val Arg Gly Gly Tyr Gly Ser Ser Pro Tyr Asp Met Asp Tyr
1               5                   10

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Ser Ser Lys Ser Leu Leu His Ser Asn Gly Asn Thr Tyr Leu Tyr
1               5                   10                  15

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 16

Arg Met Ser Asn Leu Ala Ser
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Met Gln His Leu Glu Tyr Pro Phe Thr
1               5

<210> SEQ ID NO 18
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Val Gln Leu Val Glu Thr Gly Gly Gly Leu Val Gln Pro Lys Gly
1               5                   10                  15

Ser Leu Lys Leu Ser Cys Ala Ala Ser Gly Phe Thr Phe Asn Ile Asn
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gly Gly Tyr Gly Ser Ser Pro Tyr Asp Met Asp Tyr
            100                 105                 110

Trp Gly Gln Gly Thr Ser Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
```

```
                    260                 265                 270
Ser His Glu Asp Pro Glu Val Lys Phe Asn Trp Tyr Val Asp Gly Val
            275                 280                 285
Glu Val His Asn Ala Lys Thr Lys Pro Arg Glu Glu Gln Tyr Asn Ser
        290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
            325                 330                 335
Pro Ile Glu Lys Thr Ile Ser Lys Ala Lys Gly Gln Pro Arg Glu Pro
        340                 345                 350
Gln Val Tyr Thr Leu Pro Pro Ser Arg Glu Glu Met Thr Lys Asn Gln
        355                 360                 365
Val Ser Leu Thr Cys Leu Val Lys Gly Phe Tyr Pro Ser Asp Ile Ala
        370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
            405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
            435                 440                 445
Leu Ser Pro Gly
        450

<210> SEQ ID NO 19
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Val Met Thr Gln Ala Ala Pro Ser Val Pro Val Thr Pro Gly
1               5                   10                  15
Glu Ser Val Ser Ile Ser Cys Arg Ser Ser Lys Ser Leu Leu His Ser
            20                  25                  30
Asn Gly Asn Thr Tyr Leu Tyr Trp Phe Leu Gln Arg Pro Gly Gln Ser
        35                  40                  45
Pro Gln Leu Leu Ile Tyr Arg Met Ser Asn Leu Ala Ser Gly Val Pro
    50                  55                  60
Asp Arg Phe Ser Gly Ser Gly Ser Gly Thr Ala Phe Thr Leu Arg Ile
65                  70                  75                  80
Ser Arg Val Glu Ala Glu Asp Val Gly Val Tyr Tyr Cys Met Gln His
                85                  90                  95
Leu Glu Tyr Pro Phe Thr Phe Gly Ala Gly Thr Lys Leu Glu Leu Lys
            100                 105                 110
Arg Thr Val Ala Ala Pro Ser Val Phe Ile Phe Pro Pro Ser Asp Glu
        115                 120                 125
Gln Leu Lys Ser Gly Thr Ala Ser Val Val Cys Leu Leu Asn Asn Phe
    130                 135                 140
Tyr Pro Arg Glu Ala Lys Val Gln Trp Lys Val Asp Asn Ala Leu Gln
145                 150                 155                 160
```

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 20
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ala Arg Tyr
            20                  25                  30

Asp Ile Ser Trp Ile Arg Gln Pro Pro Gly Lys Gly Leu Glu Trp Leu
        35                  40                  45

Gly Val Ile Trp Thr Gly Gly Gly Thr Asn Tyr Asn Ser Ala Phe Met
    50                  55                  60

Ser Arg Leu Ser Ile Ser Lys Asp Asn Ser Lys Ser Gln Val Phe Leu
65                  70                  75                  80

Lys Met Asn Gly Leu Gln Thr Asp Asp Thr Ala Ile Tyr Tyr Cys Val
                85                  90                  95

Ser Ile Arg Tyr Asp Glu Thr Tyr Trp Gly Gln Gly Thr Leu Val Thr
            100                 105                 110

Val Ser Ala
        115

<210> SEQ ID NO 21
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ile Tyr Met
            20                  25                  30

His Trp Phe Gln Gln Lys Pro Gly Thr Ser Pro Lys Leu Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Leu Thr
                85                  90                  95

Phe Gly Ala Gly Thr Lys Leu Glu Leu Lys
            100                 105

<210> SEQ ID NO 22
<211> LENGTH: 444
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ala Arg Tyr
            20                  25                  30

Asp Ile Ser Trp Ile Arg Gln Pro Pro Gly Lys Gly Leu Glu Trp Leu
        35                  40                  45

Gly Val Ile Trp Thr Gly Gly Thr Asn Tyr Asn Ser Ala Phe Met
    50                  55                  60

Ser Arg Leu Ser Ile Ser Lys Asp Asn Ser Lys Ser Gln Val Phe Leu
65                  70                  75                  80

Lys Met Asn Gly Leu Gln Thr Asp Asp Thr Ala Ile Tyr Tyr Cys Val
                85                  90                  95

Ser Ile Arg Tyr Asp Glu Thr Tyr Trp Gly Gln Gly Thr Leu Val Thr
            100                 105                 110

Val Ser Ala Ala Lys Thr Thr Ala Pro Ser Val Tyr Pro Leu Ala Pro
        115                 120                 125

Val Cys Gly Asp Thr Thr Gly Ser Ser Val Thr Leu Gly Cys Leu Val
    130                 135                 140

Lys Gly Tyr Phe Pro Glu Pro Val Thr Leu Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Thr Ser Ser Thr Trp Pro Ser
            180                 185                 190

Gln Ser Ile Thr Cys Asn Val Ala His Pro Ala Ser Ser Thr Lys Val
        195                 200                 205

Asp Lys Lys Ile Glu Pro Arg Gly Pro Thr Ile Lys Pro Cys Pro Pro
    210                 215                 220

Cys Lys Cys Pro Ala Pro Asn Leu Leu Gly Gly Pro Ser Val Phe Ile
225                 230                 235                 240

Phe Pro Pro Lys Ile Lys Asp Val Leu Met Ile Ser Leu Ser Pro Ile
                245                 250                 255

Val Thr Cys Val Val Asp Val Ser Glu Asp Asp Pro Asp Val Gln
            260                 265                 270

Ile Ser Trp Phe Val Asn Asn Val Glu Val His Thr Ala Gln Thr Gln
        275                 280                 285

Thr His Arg Glu Asp Tyr Asn Ser Thr Leu Arg Val Val Ser Ala Leu
    290                 295                 300

Pro Ile Gln His Gln Asp Trp Met Ser Gly Lys Glu Phe Lys Cys Lys
305                 310                 315                 320

Val Asn Asn Lys Asp Leu Pro Ala Pro Ile Glu Arg Thr Ile Ser Lys
                325                 330                 335

Pro Lys Gly Ser Val Arg Ala Pro Gln Val Tyr Val Leu Pro Pro Pro
            340                 345                 350

Glu Glu Glu Met Thr Lys Lys Gln Val Thr Leu Thr Cys Met Val Thr
        355                 360                 365

Asp Phe Met Pro Glu Asp Ile Tyr Val Glu Trp Thr Asn Asn Gly Lys
370                 375                 380

Thr Glu Leu Asn Tyr Lys Asn Thr Glu Pro Val Leu Asp Ser Asp Gly
385                 390                 395                 400

Ser Tyr Phe Met Tyr Ser Lys Leu Arg Val Glu Lys Lys Asn Trp Val
            405                 410                 415

Glu Arg Asn Ser Tyr Ser Cys Ser Val Val His Glu Gly Leu His Asn
            420                 425                 430

His His Thr Thr Lys Ser Phe Ser Arg Thr Pro Gly
            435                 440

<210> SEQ ID NO 23
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ile Tyr Met
                20                  25                  30

His Trp Phe Gln Gln Lys Pro Gly Thr Ser Pro Lys Leu Trp Ile Tyr
            35                  40                  45

Ala Thr Ser Asn Leu Ala Ser Gly Val Pro Ala Arg Phe Ser Gly Ser
50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Leu Thr
                85                  90                  95

Phe Gly Ala Gly Thr Lys Leu Glu Leu Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
            165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
            195                 200                 205

Asn Arg Asn Glu Cys
            210

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

```
Gly Phe Ser Leu Ala Arg Tyr Asp Ile Ser
1               5                   10

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Gly Thr Asn Tyr Asn Ser Ala Phe Met Ser Arg Leu Ser Ile Ser
1               5                   10                  15

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Val Ser Ile Arg Tyr Asp Glu Thr Tyr
1               5

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Ala Ser Ser Ser Val Ile Tyr Met His
1               5                   10

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Thr Ser Asn Leu Ala Ser Gly
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Gln Arg Ser Ser Tyr Pro Leu Thr
1               5

<210> SEQ ID NO 30
<211> LENGTH: 444
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 30

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ala Arg Tyr
            20                  25                  30

Asp Ile Ser Trp Ile Arg Gln Pro Pro Gly Lys Gly Leu Glu Trp Leu
        35                  40                  45

Gly Val Ile Trp Thr Gly Gly Thr Asn Tyr Asn Ser Ala Phe Met
    50                  55                  60

Ser Arg Leu Ser Ile Ser Lys Asp Asn Ser Lys Ser Gln Val Phe Leu
65              70                  75                  80

Lys Met Asn Gly Leu Gln Thr Asp Asp Thr Ala Ile Tyr Tyr Cys Val
                85                  90                  95

Ser Ile Arg Tyr Asp Glu Thr Tyr Trp Gly Gln Gly Thr Leu Val Thr
            100                 105                 110

Val Ser Ala Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
```

```
385                 390                 395                 400
Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
            435                 440
```

<210> SEQ ID NO 31
<211> LENGTH: 213
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

```
Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ile Tyr Met
            20                  25                  30

His Trp Phe Gln Gln Lys Pro Gly Thr Ser Pro Lys Leu Trp Ile Tyr
        35                  40                  45

Ala Thr Ser Asn Leu Ala Ser Gly Val Pro Ala Arg Phe Ser Gly Ser
50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Leu Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 32
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

```
Glu Val Gln Leu Val Glu Thr Gly Gly Gly Leu Val Gln Pro Lys Gly
1               5                   10                  15

Ser Leu Lys Leu Ser Cys Ala Ala Ser Gly Phe Thr Phe Ser Thr Asn
```

```
                    20                  25                  30

Ala Met Asn Trp Val Arg Gln Ala Pro Gly Lys Gly Leu Glu Trp Ile
            35                  40                  45

Ala Arg Ile Arg Ser Lys Ser Asn Asn Tyr Ala Thr His Tyr Ala Asp
        50                  55                  60

Ser Val Lys Asp Arg Phe Thr Ile Ser Arg Asp Asp Ser Gln Ser Ile
65                  70                  75                  80

Leu His Leu Gln Met Asn Asn Leu Lys Asn Glu Asp Thr Ala Met Tyr
                85                  90                  95

Tyr Cys Val Arg Asp Ser His Tyr Tyr Val Ser Thr Tyr Val Gly Leu
            100                 105                 110

Ala Trp Phe Ala Tyr Trp Gly Gln Gly Thr Leu Val Thr Val Ser Ala
        115                 120                 125

<210> SEQ ID NO 33
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Phe Leu Thr Ile Ser Arg Met Glu Ala Glu
65                  70                  75                  80

Asp Ala Ala Thr Tyr Tyr Cys Gln Gln Arg Ser Ser Tyr Pro Tyr Thr
                85                  90                  95

Phe Gly Gly Gly Thr Lys Leu Glu Arg Lys
            100                 105

<210> SEQ ID NO 34
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Val Gln Leu Val Glu Thr Gly Gly Gly Leu Val Gln Pro Lys Gly
1               5                   10                  15

Ser Leu Lys Leu Ser Cys Ala Ala Ser Gly Phe Thr Phe Ser Thr Asn
            20                  25                  30

Ala Met Asn Trp Val Arg Gln Ala Pro Gly Lys Gly Leu Glu Trp Ile
        35                  40                  45

Ala Arg Ile Arg Ser Lys Ser Asn Asn Tyr Ala Thr His Tyr Ala Asp
    50                  55                  60

Ser Val Lys Asp Arg Phe Thr Ile Ser Arg Asp Asp Ser Gln Ser Ile
65                  70                  75                  80

Leu His Leu Gln Met Asn Asn Leu Lys Asn Glu Asp Thr Ala Met Tyr
```

85                  90                  95
Tyr Cys Val Arg Asp Ser His Tyr Tyr Val Ser Thr Tyr Val Gly Leu
            100                 105                 110

Ala Trp Phe Ala Tyr Trp Gly Gln Gly Thr Leu Val Thr Val Ser Ala
            115                 120                 125

Ala Lys Thr Thr Ala Pro Ser Val Tyr Pro Leu Ala Pro Val Cys Gly
        130                 135                 140

Asp Thr Thr Gly Ser Ser Val Thr Leu Gly Cys Leu Val Lys Gly Tyr
145                 150                 155                 160

Phe Pro Glu Pro Val Thr Leu Thr Trp Asn Ser Gly Ser Leu Ser Ser
                165                 170                 175

Gly Val His Thr Phe Pro Ala Val Leu Gln Ser Asp Leu Tyr Thr Leu
            180                 185                 190

Ser Ser Ser Val Thr Val Thr Ser Ser Thr Trp Pro Ser Gln Ser Ile
            195                 200                 205

Thr Cys Asn Val Ala His Pro Ala Ser Ser Thr Lys Val Asp Lys Lys
        210                 215                 220

Ile Glu Pro Arg Gly Pro Thr Ile Lys Pro Cys Pro Pro Cys Lys Cys
225                 230                 235                 240

Pro Ala Pro Asn Leu Leu Gly Gly Pro Ser Val Phe Ile Phe Pro Pro
                245                 250                 255

Lys Ile Lys Asp Val Leu Met Ile Ser Leu Ser Pro Ile Val Thr Cys
            260                 265                 270

Val Val Val Asp Val Ser Glu Asp Asp Pro Asp Val Gln Ile Ser Trp
            275                 280                 285

Phe Val Asn Asn Val Glu Val His Thr Ala Gln Thr Gln Thr His Arg
        290                 295                 300

Glu Asp Tyr Asn Ser Thr Leu Arg Val Val Ser Ala Leu Pro Ile Gln
305                 310                 315                 320

His Gln Asp Trp Met Ser Gly Lys Glu Phe Lys Cys Lys Val Asn Asn
                325                 330                 335

Lys Asp Leu Pro Ala Pro Ile Glu Arg Thr Ile Ser Lys Pro Lys Gly
            340                 345                 350

Ser Val Arg Ala Pro Gln Val Tyr Val Leu Pro Pro Glu Glu Glu
            355                 360                 365

Met Thr Lys Lys Gln Val Thr Leu Thr Cys Met Val Thr Asp Phe Met
        370                 375                 380

Pro Glu Asp Ile Tyr Val Glu Trp Thr Asn Asn Gly Lys Thr Glu Leu
385                 390                 395                 400

Asn Tyr Lys Asn Thr Glu Pro Val Leu Asp Ser Asp Gly Ser Tyr Phe
                405                 410                 415

Met Tyr Ser Lys Leu Arg Val Glu Lys Lys Asn Trp Val Glu Arg Asn
            420                 425                 430

Ser Tyr Ser Cys Ser Val Val His Glu Gly Leu His Asn His His Thr
            435                 440                 445

Thr Lys Ser Phe Ser Arg Thr Pro Gly
450                 455

<210> SEQ ID NO 35
<211> LENGTH: 213
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 35

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Phe Leu Thr Ile Ser Arg Met Glu Ala Glu
65                  70                  75                  80

Asp Ala Ala Thr Tyr Tyr Cys Gln Gln Arg Ser Ser Tyr Pro Tyr Thr
                85                  90                  95

Phe Gly Gly Gly Thr Lys Leu Glu Arg Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
        210

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Phe Thr Phe Ser Thr Asn Ala Met Asn
1               5                   10

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Ile Arg Ser Lys Ser Asn Asn Tyr Ala Thr His Tyr Ala Asp Ser
1               5                   10                  15

Val

<210> SEQ ID NO 38
<211> LENGTH: 15
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 38

Val Arg Asp Ser His Tyr Tyr Val Ser Thr Tyr Val Gly Leu Ala
1               5                   10                  15

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ser Ala Ser Ser Ser Val Ser Tyr Met His
1               5                   10

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Thr Ser Asn Leu Ala Ser
1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gln Gln Arg Ser Ser Tyr Pro Tyr Thr
1               5

<210> SEQ ID NO 42
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Val Gln Leu Val Glu Thr Gly Gly Gly Leu Val Gln Pro Lys Gly
1               5                   10                  15

Ser Leu Lys Leu Ser Cys Ala Ala Ser Gly Phe Thr Phe Ser Thr Asn
            20                  25                  30

Ala Met Asn Trp Val Arg Gln Ala Pro Gly Lys Gly Leu Glu Trp Ile
        35                  40                  45

Ala Arg Ile Arg Ser Lys Ser Asn Asn Tyr Ala Thr His Tyr Ala Asp
    50                  55                  60

Ser Val Lys Asp Arg Phe Thr Ile Ser Arg Asp Asp Ser Gln Ser Ile
65                  70                  75                  80

Leu His Leu Gln Met Asn Asn Leu Lys Asn Glu Asp Thr Ala Met Tyr
```

```
            85                  90                  95
Tyr Cys Val Arg Asp Ser His Tyr Tyr Val Ser Thr Tyr Val Gly Leu
                100                 105                 110

Ala Trp Phe Ala Tyr Trp Gly Gln Gly Thr Leu Val Thr Val Ser Ala
            115                 120                 125

Ala Ser Thr Lys Gly Pro Ser Val Phe Pro Leu Ala Pro Ser Ser Lys
        130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Leu Gly Thr Gln Thr
        195                 200                 205

Tyr Ile Cys Asn Val Asn His Lys Pro Ser Asn Thr Lys Val Asp Lys
        210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
        290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Glu Glu
        355                 360                 365

Met Thr Lys Asn Gln Val Ser Leu Thr Cys Leu Val Lys Gly Phe Tyr
        370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly
        450                 455

<210> SEQ ID NO 43
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 43

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Phe Leu Thr Ile Ser Arg Met Glu Ala Glu
65                  70                  75                  80

Asp Ala Ala Thr Tyr Tyr Cys Gln Gln Arg Ser Ser Tyr Pro Tyr Thr
                85                  90                  95

Phe Gly Gly Gly Thr Lys Leu Glu Arg Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 44
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Val Gln Leu Gln Gln Ser Val Ala Glu Leu Val Arg Pro Gly Ala
1               5                   10                  15

Ser Val Lys Leu Ser Cys Thr Ala Ser Gly Phe Asn Ile Lys Asn Thr
            20                  25                  30

Gln Met His Trp Val Lys Gln Arg Pro Glu Gln Gly Leu Glu Trp Ile
        35                  40                  45

Gly Arg Ile Asp Pro Ala Asn Gly Asn Thr Lys Tyr Ala Pro Lys Phe
    50                  55                  60

Gln Gly Lys Ala Thr Ile Thr Gly Asp Thr Ser Ser Asn Thr Ala Tyr
65                  70                  75                  80

Leu Gln Leu Ser Ser Leu Thr Ser Glu Asp Thr Ala Ile Tyr Tyr Cys
                85                  90                  95

Ala Arg Phe Asp Tyr Tyr Gly Ser Gly Asp Tyr Ala Met Asp Tyr
            100                 105                 110

Trp Gly Gln Gly Thr Ser Val Thr Val Ser Ser
        115                 120

```
<210> SEQ ID NO 45
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Thr Arg Phe Pro Trp Thr Phe Gly Gly Gly Thr Asn Leu Glu Ile Lys
            100                 105                 110

<210> SEQ ID NO 46
<211> LENGTH: 521
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Val Gln Leu Gln Gln Ser Val Ala Glu Leu Val Arg Pro Gly Ala
1               5                   10                  15

Ser Val Lys Leu Ser Cys Thr Ala Ser Gly Phe Asn Ile Lys Asn Thr
            20                  25                  30

Gln Met His Trp Val Lys Gln Arg Pro Glu Gln Gly Leu Glu Trp Ile
        35                  40                  45

Gly Arg Ile Asp Pro Ala Asn Gly Asn Thr Lys Tyr Ala Pro Lys Phe
    50                  55                  60

Gln Gly Lys Ala Thr Ile Thr Gly Asp Thr Ser Ser Asn Thr Ala Tyr
65                  70                  75                  80

Leu Gln Leu Ser Ser Leu Thr Ser Glu Asp Thr Ala Ile Tyr Tyr Cys
                85                  90                  95

Ala Arg Phe Asp Tyr Tyr Gly Ser Gly Asp Tyr Ala Met Asp Tyr
            100                 105                 110

Trp Gly Gln Gly Thr Ser Val Thr Val Ser Ser Thr Thr Thr Ala Pro
            115                 120                 125

Ser Val Tyr Pro Leu Val Pro Gly Cys Ser Asp Thr Ser Gly Ser Ser
        130                 135                 140

Val Thr Leu Gly Cys Leu Val Lys Gly Tyr Phe Pro Glu Pro Val Thr
145                 150                 155                 160

Val Lys Trp Asn Tyr Gly Ala Leu Ser Ser Gly Val Arg Thr Val Ser
                165                 170                 175

Ser Val Leu Gln Ser Gly Phe Tyr Ser Leu Ser Ser Leu Val Thr Val
            180                 185                 190
```

```
Pro Ser Ser Thr Trp Pro Ser Gln Thr Val Ile Cys Asn Val Ala His
        195                 200                 205

Pro Ala Ser Lys Thr Glu Leu Ile Lys Arg Ile Glu Pro Arg Ile Pro
        210                 215                 220

Lys Pro Ser Thr Pro Pro Gly Ser Ser Cys Pro Pro Gly Asn Ile Leu
225                 230                 235                 240

Gly Gly Pro Ser Val Phe Ile Phe Pro Pro Lys Pro Lys Asp Ala Leu
                245                 250                 255

Met Ile Ser Leu Thr Pro Lys Val Thr Cys Val Val Val Asp Val Ser
            260                 265                 270

Glu Asp Asp Pro Asp Val His Val Ser Trp Phe Val Asp Asn Lys Glu
        275                 280                 285

Val His Thr Ala Trp Thr Gln Pro Arg Glu Ala Gln Tyr Asn Ser Thr
    290                 295                 300

Phe Arg Val Val Ser Ala Leu Pro Ile Gln His Gln Asp Trp Met Arg
305                 310                 315                 320

Gly Lys Glu Phe Lys Cys Lys Val Asn Asn Lys Ala Leu Pro Ala Pro
                325                 330                 335

Ile Glu Arg Thr Ile Ser Lys Pro Lys Gly Arg Ala Gln Thr Pro Gln
            340                 345                 350

Val Tyr Thr Ile Pro Pro Pro Arg Glu Gln Met Ser Lys Lys Lys Val
        355                 360                 365

Ser Leu Thr Cys Leu Val Thr Asn Phe Phe Ser Glu Ala Ile Ser Val
    370                 375                 380

Glu Trp Glu Arg Asn Gly Glu Leu Glu Gln Asp Tyr Lys Asn Thr Pro
385                 390                 395                 400

Pro Ile Leu Asp Ser Asp Gly Thr Tyr Phe Leu Tyr Ser Lys Leu Thr
                405                 410                 415

Val Asp Thr Asp Ser Trp Leu Gln Gly Glu Ile Phe Thr Cys Ser Val
            420                 425                 430

Val His Glu Ala Leu His Asn His His Thr Gln Lys Asn Leu Ser Arg
        435                 440                 445

Ser Pro Glu Leu Glu Leu Asn Glu Thr Cys Ala Glu Ala Gln Asp Gly
    450                 455                 460

Glu Leu Asp Gly Leu Trp Thr Thr Ile Thr Ile Phe Ile Ser Leu Phe
465                 470                 475                 480

Leu Leu Ser Val Cys Tyr Ser Ala Ser Val Thr Leu Phe Lys Val Lys
                485                 490                 495

Trp Ile Phe Ser Ser Val Val Gln Val Lys Gln Thr Ala Ile Pro Asp
            500                 505                 510

Tyr Arg Asn Met Ile Gly Gln Gly Ala
        515                 520

<210> SEQ ID NO 47
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
```

```
                    20                  25                  30
Asn Gly Lys Thr Tyr Leu Asn Trp Leu Leu Gln Arg Pro Gly Gln Ser
            35                  40                  45
Pro Lys Arg Leu Ile Tyr Leu Val Ser Lys Leu Asp Ser Gly Val Pro
        50                  55                  60
Asp Arg Phe Thr Gly Ser Gly Ser Gly Thr Asp Phe Thr Leu Lys Ile
65                  70                  75                  80
Ser Arg Val Glu Ala Glu Asp Leu Gly Val Tyr Tyr Cys Val Gln Gly
                85                  90                  95
Thr Arg Phe Pro Trp Thr Phe Gly Gly Gly Thr Asn Leu Glu Ile Lys
            100                 105                 110
Arg Ala Asp Ala Ala Pro Thr Val Ser Ile Phe Pro Pro Ser Ser Glu
        115                 120                 125
Gln Leu Thr Ser Gly Gly Ala Ser Val Val Cys Phe Leu Asn Asn Phe
    130                 135                 140
Tyr Pro Lys Asp Ile Asn Val Lys Trp Lys Ile Asp Gly Ser Glu Arg
145                 150                 155                 160
Gln Asn Gly Val Leu Asn Ser Trp Thr Asp Gln Asp Ser Lys Asp Ser
                165                 170                 175
Thr Tyr Ser Met Ser Ser Thr Leu Thr Leu Thr Lys Asp Glu Tyr Glu
            180                 185                 190
Arg His Asn Ser Tyr Thr Cys Glu Ala Thr His Lys Thr Ser Thr Ser
        195                 200                 205
Pro Ile Val Lys Ser Phe Asn Arg Asn Glu Cys
    210                 215

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Phe Asn Ile Lys Asn Thr Gln Met His
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Arg Ile Asp Pro Ala Asn Gly Asn Thr Lys Tyr Ala Pro
1               5                   10

<210> SEQ ID NO 50
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ala Arg Phe Asp Tyr Tyr Tyr Gly Ser Gly Asp Tyr Ala Met Asp Tyr
1               5                   10                  15
```

```
<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Lys Ser Ser Gln Ser Leu Leu Tyr Ser Asn Gly Lys Thr Tyr Leu Asn
1               5                   10                  15

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Leu Val Ser Lys Leu Asp Ser
1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Val Gln Gly Thr Arg Phe Pro Trp Thr
1               5

<210> SEQ ID NO 54
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Glu Val Gln Leu Gln Gln Ser Val Ala Glu Leu Val Arg Pro Gly Ala
1               5                   10                  15

Ser Val Lys Leu Ser Cys Thr Ala Ser Gly Phe Asn Ile Lys Asn Thr
            20                  25                  30

Gln Met His Trp Val Lys Gln Arg Pro Glu Gln Gly Leu Glu Trp Ile
        35                  40                  45

Gly Arg Ile Asp Pro Ala Asn Gly Asn Thr Lys Tyr Ala Pro Lys Phe
    50                  55                  60

Gln Gly Lys Ala Thr Ile Thr Gly Asp Thr Ser Ser Asn Thr Ala Tyr
65                  70                  75                  80

Leu Gln Leu Ser Ser Leu Thr Ser Glu Asp Thr Ala Ile Tyr Tyr Cys
                85                  90                  95

Ala Arg Phe Asp Tyr Tyr Gly Ser Gly Asp Tyr Ala Met Asp Tyr
            100                 105                 110

Trp Gly Gln Gly Thr Ser Val Thr Val Ser Ser Ala Ser Thr Lys Gly
        115                 120                 125

Pro Ser Val Phe Pro Leu Ala Pro Ser Ser Lys Ser Thr Ser Gly Gly
```

```
                    130                 135                 140
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450

<210> SEQ ID NO 55
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30
```

```
Asn Gly Lys Thr Tyr Leu Asn Trp Leu Leu Gln Arg Pro Gly Gln Ser
            35                  40                  45

Pro Lys Arg Leu Ile Tyr Leu Val Ser Lys Leu Asp Ser Gly Val Pro
 50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Val Gln Gly
                 85                  90                  95

Thr Arg Phe Pro Trp Thr Phe Gly Gly Gly Thr Asn Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 56
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Ala Ile Tyr Pro Gly Asn Gly Asp Thr Ser Tyr Asn Gln Lys Phe
 50                  55                  60

Lys Gly Lys Ala Thr Leu Thr Ala Asp Lys Ser Ser Ser Thr Ala Tyr
 65                  70                  75                  80

Met His Leu Ser Ser Leu Thr Ser Glu Asp Ser Ala Val Tyr Tyr Cys
                 85                  90                  95

Ala Arg Lys Gly Gly Thr Pro Phe Ala Tyr Trp Gly Gln Gly Thr Leu
            100                 105                 110

Leu Thr Val Ser Ala
        115

<210> SEQ ID NO 57
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 57

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Tyr Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

<210> SEQ ID NO 58
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65              70                  75                  80

Met His Leu Ser Ser Leu Thr Ser Glu Asp Ser Ala Val Tyr Tyr Cys
                85                  90                  95

Ala Arg Lys Gly Gly Thr Pro Phe Ala Tyr Trp Gly Gln Gly Thr Leu
            100                 105                 110

Leu Thr Val Ser Ala Ala Lys Thr Thr Pro Pro Ser Val Tyr Pro Leu
            115                 120                 125

Ala Pro Gly Ser Ala Ala Gln Thr Asn Ser Met Val Thr Leu Gly Cys
    130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Glu Ser
                165                 170                 175

Asp Leu Tyr Thr Leu Ser Ser Ser Val Thr Val Pro Ser Ser Pro Arg
            180                 185                 190

Pro Ser Glu Thr Val Thr Cys Asn Val Ala His Pro Ala Ser Ser Thr
        195                 200                 205

Lys Val Asp Lys Lys Ile Val Pro Arg Asp Cys Gly Cys Lys Pro Cys
    210                 215                 220

Ile Cys Thr Val Pro Glu Val Ser Ser Val Phe Ile Phe Pro Pro Lys
225                 230                 235                 240

```
Pro Lys Asp Val Leu Thr Ile Thr Leu Thr Pro Lys Val Thr Cys Val
                245                 250                 255

Val Val Asp Ile Ser Lys Asp Pro Glu Val Gln Phe Ser Trp Phe
            260                 265                 270

Val Asp Asp Val Glu Val His Thr Ala Gln Thr Gln Pro Arg Glu Glu
            275                 280                 285

Gln Phe Asn Ser Thr Phe Arg Ser Val Ser Glu Leu Pro Ile Met His
    290                 295                 300

Gln Asp Trp Leu Asn Gly Lys Glu Phe Lys Cys Arg Val Asn Ser Ala
305                 310                 315                 320

Ala Phe Pro Ala Pro Ile Glu Lys Thr Ile Ser Lys Thr Lys Gly Arg
                325                 330                 335

Pro Lys Ala Pro Gln Val Tyr Thr Ile Pro Pro Lys Glu Gln Met
            340                 345                 350

Ala Lys Asp Lys Val Ser Leu Thr Cys Met Ile Thr Asp Phe Phe Pro
        355                 360                 365

Glu Asp Ile Thr Val Glu Trp Gln Trp Asn Gly Gln Pro Ala Glu Asn
    370                 375                 380

Tyr Lys Asn Thr Gln Pro Ile Met Asn Thr Asn Gly Ser Tyr Phe Val
385                 390                 395                 400

Tyr Ser Lys Leu Asn Val Gln Lys Ser Asn Trp Glu Ala Gly Asn Thr
                405                 410                 415

Phe Thr Cys Ser Val Leu His Glu Gly Leu His Asn His His Thr Glu
            420                 425                 430

Lys Ser Leu Ser His Ser Pro Gly
            435                 440

<210> SEQ ID NO 59
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Tyr Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
```

```
                145                 150                 155                 160
Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Tyr Thr Phe Thr Ser Tyr Asn Met His
1               5                   10

<210> SEQ ID NO 61
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ala Ile Tyr Pro Gly Asn Gly Asp Thr Ser Tyr Asn Gln
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ala Arg Lys Gly Gly Thr Pro Phe Ala Tyr
1               5                   10

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Ser Ser Gln Ser Leu Val His Ser Asn Gly Asn Thr Tyr Leu Tyr
1               5                   10                  15

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 64

Lys Val Ser Asn Arg Phe Ser
1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ser Gln Ser Thr His Val Pro Tyr Thr
1               5

<210> SEQ ID NO 66
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Asn Met His Trp Val Lys Gln Thr Pro Gly Gln Gly Leu Glu Trp Ile
            35                  40                  45

Gly Ala Ile Tyr Pro Gly Asn Gly Asp Thr Ser Tyr Asn Gln Lys Phe
        50                  55                  60

Lys Gly Lys Ala Thr Leu Thr Ala Asp Lys Ser Ser Ser Thr Ala Tyr
65                  70                  75                  80

Met His Leu Ser Ser Leu Thr Ser Glu Asp Ser Ala Val Tyr Tyr Cys
                85                  90                  95

Ala Arg Lys Gly Gly Thr Pro Phe Ala Tyr Trp Gly Gln Gly Thr Leu
                100                 105                 110

Leu Thr Val Ser Ala Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
```

```
                  260                 265                 270
Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 67
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Tyr Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175
```

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 68
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Arg Leu Glu Trp Ile
        35                  40                  45

Gly Ala Ile Tyr Pro Gly Gln Gly Asp Thr Ser Tyr Asn Gln Lys Phe
    50                  55                  60

Lys Gly Arg Ala Thr Leu Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Lys Gly Gly Thr Pro Phe Ala Tyr Trp Gly Gln Gly Thr Leu
            100                 105                 110

Val Thr Val Ser Ser
        115

<210> SEQ ID NO 69
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Ala Gln Thr Tyr Leu Tyr Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Tyr Thr Phe Gly Gln Gly Thr Lys Leu Glu Ile Lys
            100                 105                 110

<210> SEQ ID NO 70
<211> LENGTH: 446

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asn Met His Trp Val Arg Gln Ala Pro Gly Gln Arg Leu Glu Trp Ile
            35                  40                  45

Gly Ala Ile Tyr Pro Gly Gln Gly Asp Thr Ser Tyr Asn Gln Lys Phe
        50                  55                  60

Lys Gly Arg Ala Thr Leu Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Lys Gly Gly Thr Pro Phe Ala Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly
        435                 440                 445

<210> SEQ ID NO 71
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Ala Gln Thr Tyr Leu Tyr Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 72
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ala Ile Tyr Pro Gly Gln Gly Asp Thr Ser Tyr Asn Gln
1               5                   10

<210> SEQ ID NO 73
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Arg Ser Ser Gln Ser Leu Val His Ser Asn Ala Gln Thr Tyr Leu Tyr
1               5                   10                  15

<210> SEQ ID NO 74
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asn Met His Trp Val Arg Gln Ala Pro Gly Gln Gly Leu Glu Trp Ile
            35                  40                  45

Gly Ala Ile Tyr Pro Gly Ala Gly Asp Thr Ser Tyr Asn Gln Lys Phe
        50                  55                  60

Lys Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Lys Gly Gly Thr Pro Phe Ala Tyr Trp Gly Gln Gly Thr Leu
            100                 105                 110

Val Thr Val Ser Ser
        115

<210> SEQ ID NO 75
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
                20                  25                  30

Asn Ala Ala Thr Tyr Leu Tyr Trp Tyr Gln Gln Arg Pro Gly Gln Ser
            35                  40                  45

Pro Arg Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

```
Thr His Val Pro Tyr Thr Phe Gly Gln Gly Thr Lys Leu Glu Ile Lys
            100                 105                 110
```

<210> SEQ ID NO 76
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Ile
        35                  40                  45

Gly Ala Ile Tyr Pro Gly Ala Gly Asp Thr Ser Tyr Asn Gln Lys Phe
    50                  55                  60

Lys Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Lys Gly Gly Thr Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350
```

```
Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly
                435                 440                 445

<210> SEQ ID NO 77
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Ala Ala Thr Tyr Leu Tyr Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 78
<211> LENGTH: 13
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 78

Ala Ile Tyr Pro Gly Ala Gly Asp Thr Ser Tyr Asn Gln
1               5                   10

<210> SEQ ID NO 79
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Arg Ser Ser Gln Ser Leu Val His Ser Asn Ala Ala Thr Tyr Leu Tyr
1               5                   10                  15

<210> SEQ ID NO 80
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Ser Asn Asn Tyr Ala Thr Tyr Tyr Ala Asp
        50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gly Leu Leu Arg Tyr Arg Phe Phe Asp Val Trp Gly
            100                 105                 110

Ala Gly Thr Thr Val Thr Val Ser Ser
        115                 120

<210> SEQ ID NO 81
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Asp Ile Val Met Thr Gln Ala Glu Pro Ser Val Pro Val Thr Pro Gly
1               5                   10                  15

Glu Ser Ile Ser Ile Ser Cys Arg Ser Ser Lys Ser Leu Leu His Ser
                20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Met Ser Asn Leu Ala Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
            85                  90                  95

Leu Glu Tyr Pro Phe Thr Phe Gly Gly Gly Thr Lys Leu Glu Ile Lys
        100                 105                 110

<210> SEQ ID NO 82
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
            85                  90                  95

Tyr Cys Val Arg Gly Leu Leu Arg Tyr Arg Phe Phe Asp Val Trp Gly
        100                 105                 110

Ala Gly Thr Thr Val Thr Val Ser Ser Ala Lys Thr Thr Pro Pro Ser
    115                 120                 125

Val Tyr Pro Leu Ala Pro Gly Ser Ala Ala Gln Thr Asn Ser Met Val
130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
            165                 170                 175

Val Leu Glu Ser Asp Leu Tyr Thr Leu Ser Ser Ser Val Thr Val Pro
        180                 185                 190

Ser Ser Pro Arg Pro Ser Glu Thr Val Thr Cys Asn Val Ala His Pro
    195                 200                 205

Ala Ser Ser Thr Lys Val Asp Lys Lys Ile Val Pro Arg Asp Cys Gly
210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
            245                 250                 255

Val Thr Cys Val Val Asp Ile Ser Lys Asp Asp Pro Glu Val Gln
        260                 265                 270

Phe Ser Trp Phe Val Asp Asp Val Glu Val His Thr Ala Gln Thr Gln
    275                 280                 285

Pro Arg Glu Glu Gln Phe Asn Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

```
Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asp Phe Phe Pro Glu Asp Ile Thr Val Glu Trp Gln Trp Asn Gly Gln
    370                 375                 380

Pro Ala Glu Asn Tyr Lys Asn Thr Gln Pro Ile Met Asn Thr Asn Gly
385                 390                 395                 400

Ser Tyr Phe Val Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
                420                 425                 430

His His Thr Glu Lys Ser Leu Ser His Ser Pro Gly
            435                 440

<210> SEQ ID NO 83
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Asp Ile Val Met Thr Gln Ala Glu Pro Ser Val Pro Val Thr Pro Gly
1               5                   10                  15

Glu Ser Ile Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Leu Glu Ile Lys
                100                 105                 110

Arg Ala Asp Ala Ala Pro Thr Val Ser Ile Phe Pro Pro Ser Ser Glu
            115                 120                 125

Gln Leu Thr Ser Gly Gly Ala Ser Val Val Cys Phe Leu Asn Asn Phe
        130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215
```

```
<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Phe Thr Phe Asn Thr Tyr Ala Met Asn
1               5                   10

<210> SEQ ID NO 85
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Arg Ile Arg Ser Lys Ser Asn Asn Tyr Ala Thr Tyr Tyr Ala Asp Ser
1               5                   10                  15

Val Lys Asp

<210> SEQ ID NO 86
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Val Arg Gly Leu Leu Arg Tyr Arg Phe Phe Asp Val
1               5                   10

<210> SEQ ID NO 87
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Arg Ser Ser Lys Ser Leu Leu His Ser Asn Gly Asn Thr Tyr Leu Tyr
1               5                   10                  15

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Arg Met Ser Asn Leu Ala Ser
1               5

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 89

Met Gln His Leu Glu Tyr Pro Phe Thr
1               5

<210> SEQ ID NO 90
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gly Leu Leu Arg Tyr Arg Phe Phe Asp Val Trp Gly
            100                 105                 110

Ala Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

```
Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly
    450

<210> SEQ ID NO 91
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Asp Ile Val Met Thr Gln Ala Glu Pro Ser Val Pro Val Thr Pro Gly
1               5                   10                  15

Glu Ser Ile Ser Ile Ser Cys Arg Ser Ser Lys Ser Leu Leu His Ser
                20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

```
<210> SEQ ID NO 92
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Gly Leu Glu Trp Val
        35                  40                  45

Gly Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Val Arg Gly Leu Leu Arg Tyr Arg Phe Phe Asp Val Trp Gly
            100                 105                 110

Gln Gly Thr Thr Val Thr Val Ser Ser
        115                 120

<210> SEQ ID NO 93
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Asn Thr Tyr Leu Tyr Trp Phe Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Val Glu Ile Lys
            100                 105                 110

<210> SEQ ID NO 94
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Glu Val Gln Leu Val Glu Ser Gly Gly Gly Leu Val Gln Pro Gly Gly
1               5                   10                  15
```

```
Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Gly Leu Glu Trp Val
        35                  40                  45

Gly Arg Ile Arg Ser Lys Ser Asn Asn Tyr Ala Thr Tyr Tyr Ala Asp
50                  55                  60

Ser Val Lys Asp Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Val Arg Gly Leu Leu Arg Tyr Arg Phe Phe Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430
```

His Glu Ala Leu His Asn His Tyr Thr Gln Lys Ser Leu Ser Leu Ser
            435                 440                 445

Pro Gly
    450

<210> SEQ ID NO 95
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Asn Thr Tyr Leu Tyr Trp Phe Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 96
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Ala Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Ser Ile
 65                  70                  75                  80

Leu Tyr Leu Gln Met Asn Ser Leu Lys Thr Glu Asp Thr Ala Val Tyr
                 85                  90                  95

Tyr Cys Val Arg Gly Leu Leu Arg Tyr Arg Phe Phe Asp Val Trp Gly
             100                 105                 110

Gln Gly Thr Thr Val Thr Val Ser Ser
            115                 120

<210> SEQ ID NO 97
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Asp Ile Val Met Thr Gln Ser Pro Leu Ser Leu Pro Val Thr Pro Gly
 1               5                  10                  15

Glu Pro Ala Ser Ile Ser Cys Arg Ser Ser Lys Ser Leu Leu His Ser
                 20                  25                  30

Asn Gly Asn Thr Tyr Leu Tyr Trp Phe Leu Gln Lys Pro Gly Gln Ser
             35                  40                  45

Pro Gln Leu Leu Ile Tyr Arg Met Ser Asn Leu Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln His
                 85                  90                  95

Leu Glu Tyr Pro Phe Thr Phe Gly Gly Gly Thr Lys Val Glu Ile Lys
             100                 105                 110

<210> SEQ ID NO 98
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Glu Val Gln Leu Val Glu Ser Gly Gly Gly Leu Val Gln Pro Gly Arg
 1               5                  10                  15

Ser Leu Arg Leu Ser Cys Thr Ala Ser Gly Phe Thr Phe Ala Thr Tyr
                 20                  25                  30

Ala Met Asn Trp Val Arg Gln Ala Pro Gly Lys Gly Leu Glu Trp Val
             35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Ser Ile
 65                  70                  75                  80

Leu Tyr Leu Gln Met Asn Ser Leu Lys Thr Glu Asp Thr Ala Val Tyr
                 85                  90                  95

Tyr Cys Val Arg Gly Leu Leu Arg Tyr Arg Phe Phe Asp Val Trp Gly
             100                 105                 110

Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 99
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Asp Ile Val Met Thr Gln Ser Pro Leu Ser Leu Pro Val Thr Pro Gly
1               5                   10                  15

```
Glu Pro Ala Ser Ile Ser Cys Arg Ser Ser Lys Ser Leu Leu His Ser
             20                  25                  30

Asn Gly Asn Thr Tyr Leu Tyr Trp Phe Leu Gln Lys Pro Gly Gln Ser
         35                  40                  45

Pro Gln Leu Leu Ile Tyr Arg Met Ser Asn Leu Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln His
                 85                  90                  95

Leu Glu Tyr Pro Phe Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gly Phe Thr Phe Ala Thr Tyr Ala Met Asn
1               5                   10

<210> SEQ ID NO 101
<211> LENGTH: 355
<212> TYPE: PRT
<213> ORGANISM: Homo sapiens

<400> SEQUENCE: 101

Met Asp Tyr Thr Leu Asp Leu Ser Val Thr Thr Val Thr Asp Tyr Tyr
1               5                   10                  15

Tyr Pro Asp Ile Phe Ser Ser Pro Cys Asp Ala Glu Leu Ile Gln Thr
            20                  25                  30

Asn Gly Lys Leu Leu Leu Ala Val Phe Tyr Cys Leu Leu Phe Val Phe
        35                  40                  45

Ser Leu Leu Gly Asn Ser Leu Val Ile Leu Val Leu Val Val Cys Lys
    50                  55                  60

Lys Leu Arg Ser Ile Thr Asp Val Tyr Leu Leu Asn Leu Ala Leu Ser
65                  70                  75                  80

Asp Leu Leu Phe Val Phe Ser Phe Pro Phe Gln Thr Tyr Tyr Leu Leu
                85                  90                  95
```

-continued

Asp Gln Trp Val Phe Gly Thr Val Met Cys Lys Val Val Ser Gly Phe
                100                 105                 110

Tyr Tyr Ile Gly Phe Tyr Ser Ser Met Phe Phe Ile Thr Leu Met Ser
            115                 120                 125

Val Asp Arg Tyr Leu Ala Val Val His Ala Val Tyr Ala Leu Lys Val
130                 135                 140

Arg Thr Ile Arg Met Gly Thr Thr Leu Cys Leu Ala Val Trp Leu Thr
145                 150                 155                 160

Ala Ile Met Ala Thr Ile Pro Leu Leu Val Phe Tyr Gln Val Ala Ser
                165                 170                 175

Glu Asp Gly Val Leu Gln Cys Tyr Ser Phe Tyr Asn Gln Gln Thr Leu
            180                 185                 190

Lys Trp Lys Ile Phe Thr Asn Phe Lys Met Asn Ile Leu Gly Leu Leu
195                 200                 205

Ile Pro Phe Thr Ile Phe Met Phe Cys Tyr Ile Lys Ile Leu His Gln
            210                 215                 220

Leu Lys Arg Cys Gln Asn His Asn Lys Thr Lys Ala Ile Arg Leu Val
225                 230                 235                 240

Leu Ile Val Val Ile Ala Ser Leu Leu Phe Trp Val Pro Phe Asn Val
                245                 250                 255

Val Leu Phe Leu Thr Ser Leu His Ser Met His Ile Leu Asp Gly Cys
            260                 265                 270

Ser Ile Ser Gln Gln Leu Thr Tyr Ala Thr His Val Thr Glu Ile Ile
        275                 280                 285

Ser Phe Thr His Cys Cys Val Asn Pro Val Ile Tyr Ala Phe Val Gly
        290                 295                 300

Glu Lys Phe Lys Lys His Leu Ser Glu Ile Phe Gln Lys Ser Cys Ser
305                 310                 315                 320

Gln Ile Phe Asn Tyr Leu Gly Arg Gln Met Pro Arg Glu Ser Cys Glu
                325                 330                 335

Lys Ser Ser Ser Cys Gln Gln His Ser Ser Arg Ser Ser Ser Val Asp
            340                 345                 350

Tyr Ile Leu
        355

<210> SEQ ID NO 102
<211> LENGTH: 353
<212> TYPE: PRT
<213> ORGANISM: Mus musculus

<400> SEQUENCE: 102

Met Asp Tyr Thr Met Glu Pro Asn Val Thr Met Thr Asp Tyr Tyr Pro
1               5                   10                  15

Asp Phe Phe Thr Ala Pro Cys Asp Ala Glu Phe Leu Leu Arg Gly Ser
                20                  25                  30

Met Leu Tyr Leu Ala Ile Leu Tyr Cys Val Leu Phe Val Leu Gly Leu
            35                  40                  45

Leu Gly Asn Ser Leu Val Ile Leu Val Leu Val Gly Cys Lys Lys Leu
50                  55                  60

Arg Ser Ile Thr Asp Ile Tyr Leu Leu Asn Leu Ala Ala Ser Asp Leu
65                  70                  75                  80

Leu Phe Val Leu Ser Ile Pro Phe Gln Thr His Asn Leu Leu Asp Gln
                85                  90                  95

Trp Val Phe Gly Thr Ala Met Cys Lys Val Val Ser Gly Leu Tyr Tyr

```
                    100                 105                 110
Ile Gly Phe Phe Ser Ser Met Phe Phe Ile Thr Leu Met Ser Val Asp
                115                 120                 125

Arg Tyr Leu Ala Ile Val His Ala Val Tyr Ala Ile Lys Val Arg Thr
            130                 135                 140

Ala Ser Val Gly Thr Ala Leu Ser Leu Thr Val Trp Leu Ala Ala Val
145                 150                 155                 160

Thr Ala Thr Ile Pro Leu Met Val Phe Tyr Gln Val Ala Ser Glu Asp
                165                 170                 175

Gly Met Leu Gln Cys Phe Gln Phe Tyr Glu Glu Gln Ser Leu Arg Trp
            180                 185                 190

Lys Leu Phe Thr His Phe Glu Ile Asn Ala Leu Gly Leu Leu Leu Pro
        195                 200                 205

Phe Ala Ile Leu Leu Phe Cys Tyr Val Arg Ile Leu Gln Gln Leu Arg
    210                 215                 220

Gly Cys Leu Asn His Asn Arg Thr Arg Ala Ile Lys Leu Val Leu Thr
225                 230                 235                 240

Val Val Ile Val Ser Leu Leu Phe Trp Val Pro Phe Asn Val Ala Leu
                245                 250                 255

Phe Leu Thr Ser Leu His Asp Leu His Ile Leu Asp Gly Cys Ala Thr
            260                 265                 270

Arg Gln Arg Leu Ala Leu Ala Ile His Val Thr Glu Val Ile Ser Phe
        275                 280                 285

Thr His Cys Cys Val Asn Pro Val Ile Tyr Ala Phe Ile Gly Glu Lys
    290                 295                 300

Phe Lys Lys His Leu Met Asp Val Phe Gln Lys Ser Cys Ser His Ile
305                 310                 315                 320

Phe Leu Tyr Leu Gly Arg Gln Met Pro Val Gly Ala Leu Glu Arg Gln
                325                 330                 335

Leu Ser Ser Asn Gln Arg Ser Ser His Ser Thr Leu Asp Asp Ile
            340                 345                 350

Leu

<210> SEQ ID NO 103
<211> LENGTH: 355
<212> TYPE: PRT
<213> ORGANISM: Macaca fascicularis

<400> SEQUENCE: 103

Met Asp Tyr Thr Leu Asp Pro Ser Met Thr Thr Met Thr Asp Tyr Tyr
1               5                   10                  15

Tyr Pro Asp Ser Leu Ser Ser Pro Cys Asp Gly Glu Leu Ile Gln Arg
            20                  25                  30

Asn Asp Lys Leu Leu Leu Ala Val Phe Tyr Cys Leu Leu Phe Val Phe
        35                  40                  45

Ser Leu Leu Gly Asn Ser Leu Val Ile Leu Val Leu Val Val Cys Lys
    50                  55                  60

Lys Leu Arg Asn Ile Thr Asp Ile Tyr Leu Leu Asn Leu Ala Leu Ser
65                  70                  75                  80

Asp Leu Leu Phe Val Phe Ser Phe Pro Phe Gln Thr Tyr Tyr Gln Leu
                85                  90                  95

Asp Gln Trp Val Phe Gly Thr Val Met Cys Lys Val Val Ser Gly Phe
            100                 105                 110

Tyr Tyr Ile Gly Phe Tyr Ser Ser Met Phe Phe Ile Thr Leu Met Ser
```

```
                    115                 120                 125
Val Asp Arg Tyr Leu Ala Val His Ala Val Tyr Ala Ile Lys Val
130                 135                 140

Arg Thr Ile Arg Met Gly Thr Thr Leu Ser Leu Val Val Trp Leu Thr
145                 150                 155                 160

Ala Ile Met Ala Thr Ile Pro Leu Leu Val Phe Tyr Gln Val Ala Ser
                165                 170                 175

Glu Asp Gly Val Leu Gln Cys Tyr Ser Phe Tyr Asn Gln Gln Thr Leu
            180                 185                 190

Lys Trp Lys Ile Phe Thr Asn Phe Glu Met Asn Ile Leu Gly Leu Leu
        195                 200                 205

Ile Pro Phe Thr Ile Phe Met Phe Cys Tyr Ile Lys Ile Leu His Gln
    210                 215                 220

Leu Lys Arg Cys Gln Asn His Asn Lys Thr Lys Ala Ile Arg Leu Val
225                 230                 235                 240

Leu Ile Val Val Ile Ala Ser Leu Leu Phe Trp Val Pro Phe Asn Val
                245                 250                 255

Val Leu Phe Leu Thr Ser Leu His Ser Met His Ile Leu Asp Gly Cys
            260                 265                 270

Ser Ile Ser Gln Gln Leu Asn Tyr Ala Thr His Val Thr Glu Ile Ile
        275                 280                 285

Ser Phe Thr His Cys Cys Val Asn Pro Val Ile Tyr Ala Phe Val Gly
    290                 295                 300

Glu Lys Phe Lys Lys His Leu Ser Glu Ile Phe Gln Lys Ser Cys Ser
305                 310                 315                 320

His Ile Phe Ile Tyr Leu Gly Arg Gln Met Pro Arg Glu Ser Cys Glu
                325                 330                 335

Lys Ser Ser Ser Cys Gln Gln His Ser Phe Arg Ser Ser Ile Asp
            340                 345                 350

Tyr Ile Leu
        355

<210> SEQ ID NO 104
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ala Arg Gly Leu Leu Arg Tyr Arg Phe Phe Asp Val
1               5                   10

<210> SEQ ID NO 105
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Val Ala Gly Leu Leu Arg Tyr Arg Phe Phe Asp Val
1               5                   10

<210> SEQ ID NO 106
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 106

Val Arg Ala Leu Leu Arg Tyr Arg Phe Phe Asp Val
1               5                   10

<210> SEQ ID NO 107
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Val Arg Gly Ala Leu Arg Tyr Arg Phe Phe Asp Val
1               5                   10

<210> SEQ ID NO 108
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Val Arg Gly Leu Ala Arg Tyr Arg Phe Phe Asp Val
1               5                   10

<210> SEQ ID NO 109
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Val Arg Gly Leu Leu Ala Tyr Arg Phe Phe Asp Val
1               5                   10

<210> SEQ ID NO 110
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Val Arg Gly Leu Leu Arg Ala Arg Phe Phe Asp Val
1               5                   10

<210> SEQ ID NO 111
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Val Arg Gly Leu Leu Arg Tyr Ala Phe Phe Asp Val
1               5                   10
```

<210> SEQ ID NO 112
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Val Arg Gly Leu Leu Arg Tyr Arg Ala Phe Asp Val
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Val Arg Gly Leu Leu Arg Tyr Arg Phe Ala Asp Val
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Val Arg Gly Leu Leu Arg Tyr Arg Phe Phe Ala Val
1               5                   10

<210> SEQ ID NO 115
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Val Arg Gly Leu Leu Arg Tyr Arg Phe Phe Asp Ala
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ala Arg Gly Leu Leu Arg Ala Arg Phe Phe Asp Val
1               5                   10

<210> SEQ ID NO 117
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Ala Arg Gly Leu Leu Arg Tyr Arg Phe Phe Asp Ala
1               5                   10

<210> SEQ ID NO 118
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Val Arg Gly Leu Leu Arg Ala Arg Phe Phe Asp Ala
1               5                   10

<210> SEQ ID NO 119
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ala Arg Gly Leu Leu Arg Ala Arg Phe Phe Asp Ala
1               5                   10

<210> SEQ ID NO 120
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Arg Ser Ser Gln Ser Leu Leu His Ser Asn Gly Tyr Asn Tyr Leu Asp
1               5                   10                  15

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Leu Gly Ser Asn Arg Ala Ser
1               5

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Met Gln Ala Leu Gln Thr Pro Phe Val
1               5

<210> SEQ ID NO 123
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gly Phe Thr Phe Ser Gly Ser Ala Met His
1               5                   10

<210> SEQ ID NO 124
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Arg Ile Arg Ser Lys Ala Asn Ser Tyr Ala Thr Ala Tyr Ala Ala Ser
1               5                   10                  15

Val Lys Asp

<210> SEQ ID NO 125
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Thr Arg Tyr Tyr Tyr Tyr Tyr Gly Met Asp Val
1               5                   10

<210> SEQ ID NO 126
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Arg Arg Cys Pro Leu Tyr Ile Ser Tyr Asp Pro Val Cys Arg Arg
1               5                   10                  15

<210> SEQ ID NO 127
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Arg Arg Arg Arg Cys Pro Leu Tyr Ile Ser Tyr Asp Pro Val Cys Arg
1               5                   10                  15

Arg Arg Arg

<210> SEQ ID NO 128
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 128

Glu Glu Gly Lys Leu Val Ile Trp Ile Asn Gly Asp Lys Gly Tyr Asn
1               5                   10                  15

Gly Leu Ala Glu Val Gly Lys Lys Phe Glu Lys Asp Thr Gly Ile Lys
            20                  25                  30

Val Thr Val Glu His Pro Asp Lys Leu Glu Glu Lys Phe Pro Gln Val
        35                  40                  45

Ala Ala Thr Gly Asp Gly Pro Asp Ile Ile Phe Trp Ala His Asp Arg
    50                  55                  60

Phe Gly Gly Tyr Ala Gln Ser Gly Leu Leu Ala Glu Ile Thr Pro Asp
65                  70                  75                  80

Lys Ala Phe Gln Asp Lys Leu Tyr Pro Phe Thr Trp Asp Ala Val Arg
                85                  90                  95

Tyr Asn Gly Lys Leu Ile Ala Tyr Pro Ile Ala Val Glu Ala Leu Ser
            100                 105                 110

Leu Ile Tyr Asn Lys Asp Leu Leu Pro Asn Pro Pro Lys Thr Trp Glu
        115                 120                 125

Glu Ile Pro Ala Leu Asp Lys Glu Leu Lys Ala Lys Gly Lys Ser Ala
    130                 135                 140

Leu Met Phe Asn Leu Gln Glu Pro Tyr Phe Thr Trp Pro Leu Ile Ala
145                 150                 155                 160

Ala Asp Gly Gly Tyr Ala Phe Lys Tyr Glu Asn Gly Lys Tyr Asp Ile
                165                 170                 175

Lys Asp Val Gly Val Asp Asn Ala Gly Ala Lys Ala Gly Leu Thr Phe
            180                 185                 190

Leu Ile Asp Leu Ile Lys Asn Lys His Met Asn Ala Asp Thr Asp Tyr
        195                 200                 205

Ser Ile Ala Glu Ala Ala Phe Asn Lys Gly Glu Thr Ala Met Thr Ile
    210                 215                 220

Asn Gly Pro Trp Ala Trp Ser Asn Ile Asp Thr Ser Lys Val Asn Tyr
225                 230                 235                 240

Gly Val Thr Val Leu Pro Thr Phe Lys Gly Gln Pro Ser Lys Pro Phe
                245                 250                 255

Val Gly Val Leu Ser Ala Gly Ile Asn Ala Ala Ser Pro Asn Lys Glu
            260                 265                 270

Leu Ala Lys Glu Phe Leu Glu Asn Tyr Leu Leu Thr Asp Glu Gly Leu
        275                 280                 285

Glu Ala Val Asn Lys Asp Lys Pro Leu Gly Ala Val Ala Leu Lys Ser
    290                 295                 300

Tyr Glu Glu Glu Leu Ala Lys Asp Pro Arg Ile Ala Ala Thr Met Glu
305                 310                 315                 320

Asn Ala Gln Lys Gly Glu Ile Met Pro Asn Ile Pro Gln Met Ser Ala
                325                 330                 335

Phe Trp Tyr Ala Val Arg Thr Ala Val Ile Asn Ala Ala Ser Gly Arg
            340                 345                 350

Gln Thr Val Asp Glu Ala Leu Lys Asp Ala Gln Thr Ser Gly Gly Gly
        355                 360                 365

Ser Gly Gly Gly Ser Gly Gly Gly Ser Gly Gly Gly Ser His His His
    370                 375                 380

His His His Gly Gly Gly Ser Gly Gly Gly Gly Ser Gly Gly Glu Asn
385                 390                 395                 400

Leu Tyr Phe Gln Gly Met Asp Tyr Thr Leu Asp Leu Ser Val Thr Thr

-continued

```
                405                 410                 415
Val Thr Asp Tyr Tyr Tyr Pro Asp Ile Phe Ser Ser Pro Cys Asp Ala
            420                 425                 430

Glu Leu Ile Gln Thr Asn Gly Lys
        435                 440

<210> SEQ ID NO 129
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ala Leu Ala Leu
1
```

ANTIBODIES THAT BIND CHEMOKINE (C-C MOTIF) RECEPTOR 8 (CCR8)

CROSS REFERENCE STATEMENT

This application claims priority under 35 U.S.C. § 119(e) to U.S. Provisional Application 62/976,869 filed Feb. 14, 2020, and to U.S. Provisional Application 63/130,157 filed Dec. 23, 2020. The entire contents of both provisional applications are incorporated herein by reference.

SEQUENCE LISTING

The instant application contains a Sequence Listing, which has been submitted electronically in ASCII format and is hereby incorporated by reference in its entirety. Said ASCII copy, created on Feb. 8, 2021, is named 119835-0179_SL.txt and is 155 KB in size.

FIELD OF THE INVENTION

Antibodies and fusion proteins that bind to CCR8 are provided. Methods of treatment comprising administering such antibodies and/or fusion proteins are also provided.

BACKGROUND

Chemokine (C-C motif) receptor 8 (CCR8) belongs to the G protein-coupled receptor (GPCR) family. CCR8 is primarily expressed on tumor regulatory T (Treg) cells, a type of immune-suppressive cell found in the tumor microenvironment.

There remains a need for antibodies and fusion proteins that bind CCR8 for treatment of cancer and other diseases and disorders.

SUMMARY

This disclosure describes an isolated antibody that binds human CCR8, wherein the antibody comprises:
a) an HCDR1 comprising the amino acid sequence of SEQ ID NO: 12, an HCDR2 comprising the amino acid sequence of SEQ ID NO: 13, an HCDR3 comprising the amino acid sequence of SEQ ID NO: 14, an LCDR1 comprising the amino acid sequence of SEQ ID NO: 15, an LCDR2 comprising the amino acid sequence of SEQ ID NO: 16, and an LCDR3 comprising the amino acid sequence of SEQ ID NO: 17;
b) an HCDR1 comprising the amino acid sequence of SEQ ID NO: 24, an HCDR2 comprising the amino acid sequence of SEQ ID NO: 25, an HCDR3 comprising the amino acid sequence of SEQ ID NO: 26, an LCDR1 comprising the amino acid sequence of SEQ ID NO: 27, an LCDR2 comprising the amino acid sequence of SEQ ID NO: 28, and an LCDR3 comprising the amino acid sequence of SEQ ID NO: 29;
c) an HCDR1 comprising the amino acid sequence of SEQ ID NO: 36, an HCDR2 comprising the amino acid sequence of SEQ ID NO: 37, an HCDR3 comprising the amino acid sequence of SEQ ID NO: 38, an LCDR1 comprising the amino acid sequence of SEQ ID NO: 39, an LCDR2 comprising the amino acid sequence of SEQ ID NO: 40, and an LCDR3 comprising the amino acid sequence of SEQ ID NO: 41;
d) an HCDR1 comprising the amino acid sequence of SEQ ID NO: 48, an HCDR2 comprising the amino acid sequence of SEQ ID NO: 49, an HCDR3 comprising the amino acid sequence of SEQ ID NO: 50, an LCDR1 comprising the amino acid sequence of SEQ ID NO: 51, an LCDR2 comprising the amino acid sequence of SEQ ID NO: 52, and an LCDR3 comprising the amino acid sequence of SEQ ID NO: 53; or
e) an HCDR1 comprising the amino acid sequence of SEQ ID NO: 60, an HCDR2 comprising the amino acid sequence of SEQ ID NO: 61, 72, or 78, an HCDR3 comprising the amino acid sequence of SEQ ID NO: 62, 73, or 79, an LCDR1 comprising the amino acid sequence of SEQ ID NO: 63, an LCDR2 comprising the amino acid sequence of SEQ ID NO: 64, and an LCDR3 comprising the amino acid sequence of SEQ ID NO: 65; or
f) an HCDR1 comprising the amino acid sequence of SEQ ID NO: 84 or 100, an HCDR2 comprising the amino acid sequence of SEQ ID NO: 85, an HCDR3 comprising the amino acid sequence of SEQ ID NO: 86, an LCDR1 comprising the amino acid sequence of SEQ ID NO: 87, an LCDR2 comprising the amino acid sequence of SEQ ID NO: 88, and an LCDR3 comprising the amino acid sequence of SEQ ID NO: 89.

This application also describes an isolated antibody, wherein the antibody comprises:
a) an HCDR1 comprising the amino acid sequence of SEQ ID NO: 60, an HCDR2 comprising the amino acid sequence of SEQ ID NO: 61, 72, or 78, an HCDR3 comprising the amino acid sequence of SEQ ID NO: 62, 73, or 79, an LCDR1 comprising the amino acid sequence of SEQ ID NO: 63, an LCDR2 comprising the amino acid sequence of SEQ ID NO: 64, and an LCDR3 comprising the amino acid sequence of SEQ ID NO: 65; or
b) an HCDR1 comprising the amino acid sequence of SEQ ID NO: 84 or 100, an HCDR2 comprising the amino acid sequence of SEQ ID NO: 85, an HCDR3 comprising the amino acid sequence of SEQ ID NO: 86, an LCDR1 comprising the amino acid sequence of SEQ ID NO: 87, an LCDR2 comprising the amino acid sequence of SEQ ID NO: 88, and an LCDR3 comprising the amino acid sequence of SEQ ID NO: 89.

In some embodiments, the antibody comprises:
a) a heavy chain variable region (VH) comprising an amino acid sequence that is at least 90%, 91%, 92%, 93%, 94%, 95%, 96%, 97%, 98%, or 99% identical to the amino acid sequence of SEQ ID NO: 68 or 74, and a light chain variable region (VL) comprising an amino acid sequence that is at least 90%, 91%, 92%, 93%, 94%, 95%, 96%, 97%, 98%, or 99% identical to the amino acid sequence of SEQ ID NO: 69 or 75; or
b) a heavy chain variable region (VH) comprising an amino acid sequence that is at least 90%, 91%, 92%, 93%, 94%, 95%, 96%, 97%, 98%, or 99% identical to the amino acid sequence of SEQ ID NO: 92 or 96, and a light chain variable region (VL) comprising an amino acid sequence that is at least 90%, 91%, 92%, 93%, 94%, 95%, 96%, 97%, 98%, or 99% identical to the amino acid sequence of SEQ ID NO: 93 or 97.

In some embodiments, the antibody comprises:
a) a heavy chain variable region (VH) comprising the amino acid sequence of SEQ ID NO: 68 or 74, and a light chain variable region (VL) comprising the amino acid sequence of SEQ ID NO: 69 or 75; or
b) a heavy chain variable region (VH) comprising the amino acid sequence of SEQ ID NO: 92 or 96, and a light chain variable region (VL) comprising the amino acid sequence of SEQ ID NO: 93 or 97.

In some embodiments, the antibody is a monoclonal antibody. In some embodiments, the antibody is a humanized antibody. In some embodiments, the antibody is a full-length antibody. In some embodiments, the antibody is an IgG1 or IgG3 antibody.

In some embodiments, the antibody comprises:
a) a heavy chain (HC) comprising an amino acid sequence that is at least 90%, 91%, 92%, 93%, 94%, 95%, 96%, 97%, 98%, or 99% identical to the amino acid sequence of SEQ ID NO: 70 or 76, and a light chain (LC) comprising an amino acid sequence that is at least 90%, 91%, 92%, 93%, 94%, 95%, 96%, 97%, 98%, or 99% identical to the amino acid sequence of SEQ ID NO: 71 or 77; or
b) a heavy chain (HC) comprising an amino acid sequence that is at least 90%, 91%, 92%, 93%, 94%, 95%, 96%, 97%, 98%, or 99% identical to the amino acid sequence of SEQ ID NO: 94 or 98, and a light chain (LC) comprising an amino acid sequence that is at least 90%, 91%, 92%, 93%, 94%, 95%, 96%, 97%, 98%, or 99% identical to the amino acid sequence of SEQ ID NO: 95 or 99.

In some embodiments, the antibody comprises a heavy chain (HC) comprising the amino acid sequence of SEQ ID NO: 70 or 76, and a light chain (LC) comprising the amino acid sequence of SEQ ID NO: 71 or 77; or a heavy chain (HC) comprising the amino acid sequence of SEQ ID NO: 94 or 98, and a light chain (LC) comprising the amino acid sequence of SEQ ID NO: 95 or 99.

In some embodiments, the antibody comprises at least one modification that enhances cell killing. In some embodiments, the enhanced cell killing is enhanced antibody-dependent cellular cytotoxicity (ADCC) and/or complement-dependent cytotoxicity (CDC). In some embodiments, the at least one modification is afucosylation. In some embodiments, the at least one modification is one or more heavy chain constant regions mutations at one or more positions selected from L234, L235, G236, S239, F243, H268, D270, R292, S298, Y300, V305, K326, A330, I332, E333, K334, and P396. In some embodiments, the one or more heavy chain constant region mutations are one or more mutation selected from S239D, S239M, F243L, H268D, D270E, R292P, S298A, Y300L, V305I, K326D, A330L, A330M, I332E, E333A, K334A, K334E, and P396L. In some embodiments, the one or more heavy chain constant region mutations are selected from: F243L/R292P/Y300L/V305I/P396L, S239D/I332E, S239D/I332E/A330L, S298A/E333A/K334A, L234Y/L235Q/G236W/S239M/H268D/D270E/S298A, and D270E/K326D/A330M/K334E. In some embodiments, the at least one modification is galactosylation.

In some embodiments, the antibody binds human CCR8 with an affinity ($K_D$) (as determined by Kinetic Exclusion Assay (i.e., KinExA), for example) of less than 10 nM, or less than 5 nM, or less than 1 nM, or less than 500 pM, or less than 250 pM, or less than 100 pM, or less than 75 pM, or less than 50 pM, or less than 25 pM. In some embodiments, the antibody binds human CCR8 with an on-cell affinity ($K_D$) of less than 10 nM, or less than 5 nM, or less than 1 nM, or less than 500 pM, or less than 250 pM, or less than 100 pM, or less than 75, or less than 50 pM, or less than 25 pM, as determined by, for example, Kinetic Exclusion Assay (i.e., KinExA).

This disclosure also describes an isolated nucleic acid that encodes an antibody. In some embodiments, vector comprises an isolated nucleic acid. In some embodiments, a host cell comprises a nucleic acid or a vector. In some embodiments, a host cell expresses an antibody. In some embodiments, the host cell is engineered to produce afucosylated antibodies.

In some embodiments, a method of producing an antibody that binds CCR8 comprises culturing a host cell under conditions suitable for expressing the antibody. In some embodiments, the method further comprises isolating the antibody.

In some embodiments, a fusion protein comprises (a) CCL1 or an active fragment thereof or MC148 or an active fragment thereof, and (b) an Fc region. In some embodiments, the Fc region is an IgG1 or IgG3 Fc region. In some embodiments, the Fc region comprises the amino acid sequence of SEQ ID NO: 4.

In some embodiments, the Fc region comprises at least one modification that enhances cell killing. In some embodiments, the enhanced cell killing is enhanced antibody-dependent cellular cytotoxicity (ADCC) and/or complement-dependent cytotoxicity (CDC). In some embodiments, the at least one modification is afucosylation. In some embodiments, the at least one modification is one or more Fc region mutations at one or more positions selected from L234, L235, G236, S239, F243, H268, D270, R292, S298, Y300, V305, K326, A330, I332, E333, K334, and P396. In some embodiments, the one or more Fc region mutations are one or more mutation selected from S239D, S239M, F243L, H268D, D270E, R292P, S298A, Y300L, V305I, K326D, A330L, A330M, I332E, E333A, K334A, K334E, and P396L. In some embodiments, the one or more Fc region mutations are selected from: F243L/R292P/Y300L/V305I/P396L, S239D/I332E, S239D/I332E/A330L, S298A/E333A/K334A, L234Y/L235Q/G236W/S239M/H268D/D270E/S298A, and D270E/K326D/A330M/K334E. In some embodiments, the at least one modification is galactosylation. In some embodiments, the fusion protein comprises CCL1 or an active fragment thereof. In some embodiments, the CCL1 or active fragment thereof comprises the amino acid sequence of SEQ ID NO: 2 or amino acids 24-96 of SEQ ID NO: 2. In some embodiments, the fusion protein comprises the amino acid sequence of SEQ ID NO: 1 or amino acids 24-316 of SEQ ID NO: 1. In some embodiments, the fusion protein comprises MC148 or an active fragment thereof. In some embodiments, the MC148 or active fragment thereof comprises the amino acid sequence of SEQ ID NO: 6. In some embodiments, the fusion protein comprises the amino acid sequence of SEQ ID NO: 5.

In some embodiments, an isolated nucleic acid encodes a fusion protein. In some embodiments, a vector comprises an isolated nucleic acid. In some embodiments, a host cell comprises a nucleic acid of or a vector. In some embodiments, a host cell expresses a fusion protein. In some embodiments, the host cell is engineered to produce afucosylated antibodies.

In some embodiments, a method of producing a fusion protein comprises culturing the host cell under conditions suitable for expressing the fusion protein. In some embodiments, the method further comprises isolating the fusion protein.

In some embodiments, a method of treating cancer comprises administering to a subject with cancer an effective amount of an antibody provided herein (e.g., 7-B16, 1-K17, etc.). In some embodiments, a method of treating cancer comprises administering to a subject with cancer an effective amount of a fusion protein provided herein, which binds to CCR8.

In some embodiments, the cancer comprises tumor-infiltrating Treg cells. In some embodiments, the cancer comprises cells that express CCR8 (as determined, for example, by immunohistochemistry, fluorescence-activated cell sorting (FACS), gene expression analysis (such as Q-PCR or RT-PCR), Western blot, ELISA, etc.). In some embodiments, the cells that express CCR8 are Treg cells. In some embodiments, the Treg cells are a subpopulation of T cells that are immunosuppressive and generally suppress or downregulate induction and proliferation of effector T cells. In some embodiments, the Treg cells express CD4, FOXP3, and CD25 (IL-2 receptor α-chain). In some embodiments, CCR8 is expressed on the surface of the Treg cells at fewer than 10,000 copies per cell, which can be determined by, for example, fluorescence-activated cell sorting (FACS) and flow cytometry. In some embodiments, 5%, 10%, 15%, 20%, 25%, 30%, 35%, 40%, 45%, 50%, 55%, 60%, 65%, 70%, 75%, 80%, 85%, 90%, 95%, 99%, or 100% of the tumor-infiltrating Tregs express on the surface of the cell fewer than 10,000 copies of CCR8 per cell. In some embodiments, 5%, 10%, 15%, 20%, 25%, 30%, 35%, 40%, 45%, 50%, 55%, 60%, 65%, 70%, 75%, 80%, 85%, 90%, 95%, 99%, or 100% of the tumor-infiltrating Tregs in a sample obtained from a tumor express fewer than 10,000 copies of CCR8 per cell. In some embodiments the cancer is selected from breast cancer, colorectal cancer, head and neck cancer, lung cancer, ovarian cancer, gastric cancer, stomach adenocarcinoma, and thymoma. In some embodiments the cancer is breast cancer (e.g., triple negative breast cancer).

In some embodiments, the cancer comprises cells that express CCR8 (as determined, for example, by immunohistochemistry, fluorescence-activated cell sorting (FACS), gene expression analysis (such as Q-PCR or RT-PCR), Western blot, ELISA, etc.). In some embodiments, the CCR8 expressing cells are Treg cells. In some embodiments, the Treg cells are a subpopulation of T cells that are immunosuppressive and generally suppress or downregulate induction and proliferation of effector T cells. In some embodiments, the Treg cells express CD4, FOXP3, and CD25 (IL-2 receptor α-chain). In some embodiments, the cancer is a solid cancer. In some embodiments, the cancer is selected from breast cancer, colorectal cancer, head and neck cancer, lung cancer, ovarian cancer, gastric cancer, stomach adenocarcinoma, and thymoma. In some embodiments the cancer is breast cancer (e.g., triple negative breast cancer). In some embodiments, a method of treating solid cancer comprises administering to a subject with solid cancer an effective amount of an antibody that binds human CCR8 (e.g., 7-B16, 1-K17, etc.). In some embodiments, the antibody inhibits binding of CCL1 to CCR8. In some embodiments, the cancer is a blood cancer. In some embodiments, a method of treating blood cancer comprises administering to a subject with blood cancer an effective amount of an antibody that binds human CCR8. In some embodiments, the antibody inhibits binding of CCL1 to CCR8. In some embodiments, the blood cancer expresses CCR8. In some embodiments, the subject has previously received treatment with a checkpoint inhibitor (CPI), and, optionally, wherein the cancer was resistant to the CPI. In some embodiments, the cancer is a refractory cancer or resistant to checkpoint inhibitor (CPI) therapy. In some embodiments, the CPI therapy comprises an anti-PDL1 antibody, an anti-CTLA4 antibody, or an anti-TIGIT antibody. In some embodiments, the anti-PDL1 antibody is selected from pembrolizumab, nivolumab, atezolizumab, avelumab, durvalumab, cemiplimab-rwlc, and zimberelimab; the anti-CLTA4 antibody is ipilimumab or tremelimumab; or the anti-TIGIT antibody is selected from tiragolumab, vibostolimab, domvanalimab, AB308, BMS-986207, and durvalumab.

In some embodiments, a method of selecting a subject with a solid cancer for treatment with an antibody that binds human CCR8 comprises detecting CCR8 expression in a sample from the subject. In some embodiments, a method further comprises administering an effective amount of an antibody that binds human CCR8.

In some embodiments, a method of selecting a subject with blood cancer for treatment with an antibody that binds human CCR8 comprises detecting CCR8 expression in a sample from the subject. In some embodiments, a method further comprises administering an effective amount of an antibody that binds human CCR8.

In some embodiments, a method of treating blood cancer comprises administering to a subject with blood cancer an effective amount of the fusion protein provided herein that binds to CCR8. In some embodiments, a method of selecting a subject with blood cancer for treatment with a fusion protein comprising (a) CCL1 or an active fragment thereof or MC148 or an active fragment thereof, and (b) an Fc region, comprises detecting CCR8 expression in a sample from the subject. In some embodiments, a method further comprises administering an effective amount of a fusion protein comprising (a) CCL1 or an active fragment thereof or MC148 or an active fragment thereof, and (b) an Fc region. In some embodiments, the blood cancer is T-cell adult acute lymphocytic leukemia, T-cell childhood acute lymphocytic leukemia, lymphoblastic lymphoma, acute lymphocytic leukemia, cutaneous T cell lymphoma, T-cell acute lymphocytic leukemia, adult T cell leukemia/lymphoma, T cell lymphoblastic leukemia/lymphoma, or anaplastic large cell lymphoma.

In one aspect, the present disclosure provides an isolated antibody that binds human CCR8, wherein the antibody comprises a HCDR3 comprising SEQ ID NO: 86 or a variant of SEQ ID NO: 86 comprising 1, 2, or 3 mutations, and wherein the antibody binds to human CCR8 and possesses ADCC activity. In some embodiments, the mutation is a substitution (e.g., a conservative and/or a non-conservative substitution), a deletion, or an insertion. In some embodiments, the 1, 2, or 3 mutations are located in at least one of amino acid positions 1-4, 6, 7, or 12 of SEQ ID NO: 86. In some embodiments, the substitution is a conservative substitution. In some embodiments, the conservative substitution is at amino acid position 1, 4, or 12 of SEQ ID NO: 86. In some embodiments, the substitution is a non-conservative substitution. In some embodiments, the non-conservative substitution is at amino acid position 7 of SEQ ID NO: 86. In some embodiments, the antibody comprises at least 2 substitutions in HCDR3. In some embodiments, the at least 2 substitutions are located in at least one of amino acid positions 1-4, 6, 7, or 12 of SEQ ID NO: 86. In some embodiments, the at least 2 substitutions are conservative substitutions. In some embodiments, at least one of the conservative substitutions are at amino acid position 1, 4, or 12 of SEQ ID NO: 86. In some embodiments, the at least 2 substitutions are non-conservative substitutions. In some embodiments, at least one of the non-conservative substitutions is at amino acid position 7 of SEQ ID NO: 86. In some embodiments, the mutations comprise a conservative substitution and a non-conservative substitution when more than one substitution mutation is present. In another aspect, the present disclosure provides an isolated antibody that binds human CCR8, wherein the antibody comprises a HCDR3 that is at least 80%, 85%, 90%, 91%, 92%, 93%, 94%, 95%, 96%, 97%, 98%, or 99% identical to SEQ ID NO: 86, and wherein the antibody binds to human CCR8 and possesses ADCC activity. In some embodiments, the HCDR3 comprises an amino acid sequence selected from SEQ ID NO: 86 and any one of SEQ ID NOs: 104-119. In some embodiments, the antibody comprises a HCDR1 comprising SEQ ID NO: 84 or SEQ ID NO: 123. In some embodiments, the antibody comprises a HCDR2 comprising SEQ ID NO: 85 or SEQ ID NO: 124. In some embodiments, the antibody comprises a LCDR1 comprising SEQ ID NO: 87 or SEQ ID NO: 120. In some embodiments, the antibody comprises a LCDR2 comprising SEQ ID NO: 88 or SEQ ID NO: 121. In some embodiments, the antibody comprises a LCDR3 comprising SEQ ID NO: 89 or SEQ ID NO: 122. In some embodiments, the ADCC activity comprises an EC50 value of less than 200, 175, 150, 125, 100, 75, 50, 25, 20, 15, 10, 9, 8, 7, 6, 5, 4, 3, 2, or 1 ng/ml as measured by an ADCC reporter mechanism of action (MOA)-based bioassay. In some embodiments, the ADCC activity is more potent than a 7-B16 antibody. In some embodiments, the ADCC activity is at least as potent as a 7-B16 antibody. In some embodiments, the antibody possesses a $K_D$ for human CCR8 that is equal to or lower than a 7-B16 antibody (as determined by Kinetic Exclusion Assay (i.e., KinExA), for example). In some embodiments, the antibody possesses an on-cell $K_D$ for human CCR8 that is equal to or lower than a 7-B16 antibody (as determined by Kinetic Exclusion Assay (i.e., KinExA), for example). In some embodiments, the antibody comprises at least one modification that enhances cell killing. In some embodiments, the enhanced cell killing is enhanced antibody-dependent cellular cytotoxicity (ADCC) and/or complement-dependent cytotoxicity (CDC). In some embodiments, the at least one modification is afucosylation. In some embodiments, the at least one modification is one or more heavy chain constant regions mutations at one or more positions selected from L234, L235, G236, S239, F243, H268, D270, R292, S298, Y300, V305, K326, A330, I332, E333, K334, and P396. In some embodiments, the one or more heavy chain constant region mutations are one or more mutation selected from S239D, S239M, F243L, H268D, D270E, R292P, S298A, Y300L, V305I, K326D, A330L, A330M, I332E, E333A, K334A, K334E, and P396L. In some embodiments, the one or more heavy chain constant region mutations are selected from: F243L/R292P/Y300L/V305I/P396L, S239D/I332E, S239D/I332E/A330L, S298A/E333A/K334A, L234Y/L235Q/G236W/S239M/H268D/D270E/S298A, and D270E/K326D/A330M/K334E. In some embodiments, the at least one modification is galactosylation. In some embodiments, the antibody binds human CCR8 with an affinity ($K_D$) (as determined by Kinetic Exclusion Assay (i.e., KinExA), for example) of less than 10 nM, or less than 5 nM, or less than 1 nM, or less than 500 pM, or less then 250 pM, or less than 100 pM, or less than 75 pM, or less than 50 pM, or less than 25 pM. In some embodiments, the antibody binds human CCR8 with an on-cell affinity ($K_D$) of less than 10 nM, or less than 5 nM, or less than 1 nM, or less than 500 pM, or less than 250 pM, or less than 100 pM, or less than 75, or less than 50 pM, or less than 25 pM, as determined by, for example, Kinetic Exclusion Assay (i.e., KinExA). In some embodiments, the antibody is a monoclonal antibody. In some embodiments, the antibody is a human or humanized antibody. In some embodiments, the antibody is a full-length antibody. In some embodiments, the antibody is an IgG1 or IgG3 antibody.

The disclosure also provides isolated antibodies or fusion proteins of any one of the aspects or embodiments described herein for treating cancer. In some embodiments, the cancer is a blood cancer or a solid cancer/solid tumor. In some embodiments, the cancer expresses CCR8. In some embodiments, the blood cancer is T-cell adult acute lymphocytic leukemia, T-cell childhood acute lymphocytic leukemia, lymphoblastic lymphoma, acute lymphocytic leukemia, cutaneous T cell lymphoma, T-cell acute lymphocytic leukemia, adult T cell leukemia/lymphoma, T cell lymphoblastic leukemia/lymphoma, or anaplastic large cell lymphoma. In some embodiments, the cancer is selected from breast cancer, colorectal cancer, head and neck cancer, lung cancer, ovarian cancer, gastric cancer, stomach adenocarcinoma, and thymoma. In some embodiments the cancer is breast cancer (e.g., triple negative breast cancer). In some embodiments, the method of treatments may further comprise administering to the subject one or more additional therapeutic agents (e.g., other anti-cancer agents). In some embodiments, the one or more additional therapeutic agents are selected from an anti-Trop-2 antibody (e.g., sacituzumab govitecan, SKB-264, JS-108 (DAC-002), datopotamab deruxtecan, BAT-8003), an anti-CD47 antibody or a CD47-blocking agent (e.g., magrolimab, DSP-107, AO-176, ALX-148, IBI-188, lemzoparlimab, TTI-621, TTI-622), an anti-SIRPα antibody (e.g., GS-0189), a FLT3L-Fc fusion protein (e.g., GS-3583), an anti-PD-1 antibody (pembrolizumab, nivolumab, zimberelimab), a small molecule PD-L1 inhibitor (e.g., GS-4224), an anti-PD-L1 antibody (e.g., atezolizumab), a small molecule MCL1 inhibitor (e.g., GS-9716), a small molecule HPK1 inhibitor (e.g., GS-6451), an HPK1 degrader (PROTAC; e.g., ARV-766), a small molecule DGKa inhibitor, a small molecule CD73 inhibitor (e.g., AB680), an anti-CD73 antibody (e.g., oleclumab), a dual $A_{2a}/A_{2b}$ adenosine receptor antagonist (e.g., etrumadenant (AB928)), an anti-TIGIT antibody (e.g., tiragolumab, vibostolimab, domvanalimab, AB308), an anti-TREM1 antibody (e.g., PY159), an anti-TREM2 antibody (e.g., PY314), a TGFβ-trap (e.g., bintrafusp alpha, AGEN-1423), an anti-TGFβ1 antibody (e.g., SRK-181), and a CAR-T cell therapy (e.g., axicabtagene ciloleucel, brexucabtagene autoleucel, tisagenlecleucel). In some embodiments, the one or more additional therapeutic agents are selected from sacituzumab govitecan-hziy, magrolimab, GS-0189, GS-3583, zimberelimab, GS-4224, GS-9716, GS-6451, AB680, etrumadenant (AB928), domvanalimab, AB308, PY159, PY314, SRK-181, axicabtagene ciloleucel, and brexucabtagene autoleucel. In some embodiments, administration of the one or more additional therapeutic agents is concurrent with the administration of the antibody, while in some embodiments, administration of the one or more additional therapeutic agents is before or after the administration of the antibody. In some embodiments, the cancer is a refractory cancer or resistant to checkpoint inhibitor (CPI) therapy. In some embodiments, the CPI therapy comprises an anti-PDL1 antibody, an anti-CTLA4 antibody, or an anti-TIGIT antibody. In some embodiments, the anti-PDL1 antibody is selected from pembrolizumab, nivolumab, atezolizumab, avelumab, durvalumab, cemiplimab-rwlc, and zimberelimab; the anti-CLTA4 antibody is ipilimumab or tremelimumab; or the anti-TIGIT antibody is selected from tiragolumab, vibostolimab, domvanalimab, AB308, BMS-986207, and durvalumab.

The disclosure also provides, a nucleic acid encoding an antibody of any one of aspects or embodiments described herein.

The disclosure also provides a method of treating cancer, comprising administering to a subject with cancer an antibody according to any one of the aspects or embodiments described herein. In some embodiments, the cancer is a blood cancer or a solid cancer/solid tumor. In some embodiments, the cancer expresses CCR8. In some embodiments, the blood cancer is T-cell adult acute lymphocytic leukemia, T-cell childhood acute lymphocytic leukemia, lymphoblastic lymphoma, acute lymphocytic leukemia, cutaneous T cell lymphoma, T-cell acute lymphocytic leukemia, adult T cell leukemia/lymphoma, T cell lymphoblastic leukemia/lymphoma, or anaplastic large cell lymphoma. In some embodiments, the cancer is selected from breast cancer, colorectal cancer, head and neck cancer, lung cancer, ovarian cancer, gastric cancer, stomach adenocarcinoma, and thymoma. In some embodiments the cancer is breast cancer (e.g., triple negative breast cancer). In some embodiments, the method of treatments may further comprise administering to the subject one or more additional therapeutic agents (e.g., other anti-cancer agents). In some embodiments, administration of the one or more additional therapeutic agents is concurrent with the administration of the antibody, while in some embodiments, administration of the one or more additional therapeutic agents is before or after the administration of the antibody. In some embodiments, the one or more additional therapeutic agents are selected from an anti-Trop-2 antibody (e.g., sacituzumab govitecan, SKB-264, JS-108 (DAC-002), datopotamab deruxtecan, BAT-8003), an anti-CD47 antibody or a CD47-blocking agent (e.g., magrolimab, DSP-107, AO-176, ALX-148, IBI-188, lemzoparlimab, TTI-621, TTI-622), an anti-SIRPα antibody (e.g., GS-0189), a FLT3L-Fc fusion protein (e.g., GS-3583), an anti-PD-1 antibody (pembrolizumab, nivolumab, zimberelimab), a small molecule PD-L1 inhibitor (e.g., GS-4224), an anti-PD-L1 antibody (e.g., atezolizumab), a small molecule MCL1 inhibitor (e.g., GS-9716), a small molecule HPK1 inhibitor (e.g., GS-6451), a HPK1 degrader (PROTAC; e.g., ARV-766), a small molecule DGKa inhibitor, a small molecule CD73 inhibitor (e.g., AB680), an anti-CD73 antibody (e.g., oleclumab), a dual $A_{2a}/A_{2b}$ adenosine receptor antagonist (e.g., etrumadenant (AB928)), an anti-TIGIT antibody (e.g., tiragolumab, vibostolimab, domvanalimab, AB308), an anti-TREM1 antibody (e.g., PY159), an anti-TREM2 antibody (e.g., PY314), a TGFβ-trap (e.g., bintrafusp alpha, AGEN-1423), an anti-TGFβ1 antibody (e.g., SRK-181), and a CAR-T cell therapy (e.g., axicabtagene ciloleucel, brexucabtagene autoleucel, tisagenlecleucel). In some embodiments, the one or more additional therapeutic agents are selected from sacituzumab govitecan-hziy, magrolimab, GS-0189, GS-3583, zimberelimab, GS-4224, GS-9716, GS-6451, AB680, etrumadenant (AB928), domvanalimab, AB308, PY159, PY314, SRK-181, axicabtagene ciloleucel, and brexucabtagene autoleucel.

The disclosure also provides a use of treating cancer, comprising administering to a subject with cancer an antibody according to any one of the aspects or embodiments described herein. In some embodiments, the cancer is a blood cancer or a solid cancer/solid tumor. In some embodiments, the cancer expresses CCR8. In some embodiments, the blood cancer is T-cell adult acute lymphocytic leukemia, T-cell childhood acute lymphocytic leukemia, lymphoblastic lymphoma, acute lymphocytic leukemia, cutaneous T cell lymphoma, T-cell acute lymphocytic leukemia, adult T cell leukemia/lymphoma, T cell lymphoblastic leukemia/lymphoma, or anaplastic large cell lymphoma. In some embodiments, the cancer is selected from breast cancer, colorectal cancer, head and neck cancer, lung cancer, ovarian cancer, gastric cancer, stomach adenocarcinoma, and thymoma. In some embodiments the cancer is breast cancer (e.g., triple negative breast cancer). In some embodiments, the method of treatments may further comprise administering to the subject one or more additional therapeutic agents (e.g., other anti-cancer agents). In some embodiments, administration of the one or more additional therapeutic agents is concurrent with the administration of the antibody, while in some embodiments, administration of the one or more additional therapeutic agents is before or after the administration of the antibody. In some embodiments, the cancer is a refractory cancer or resistant to checkpoint inhibitor (CPI) therapy. In some embodiments, the CPI therapy comprises an anti-PDL1 antibody, an anti-CTLA4 antibody, or an anti-TIGIT antibody. In some embodiments, the anti-PDL1 antibody is selected from pembrolizumab, nivolumab, atezolizumab, avelumab, durvalumab, cemiplimab-rwlc, and zimberelimab; the anti-CLTA4 antibody is ipilimumab or tremelimumab; or the anti-TIGIT antibody is selected from tiragolumab, vibostolimab, domvanalimab, AB308, BMS-986207, and durvalumab.

The disclosure also provides a method of treating a refractory or checkpoint inhibitor (CPI)-resistant cancer, comprising administering to a subject with cancer the isolated antibody according to any one of the foregoing aspects or embodiments or the fusion protein according to any one of the foregoing aspects or embodiments, wherein the subject has previously been treated with chemotherapy or CPI therapy without responding to the chemotherapy or CPI therapy. In some embodiments, the CPI therapy comprises an anti-PDL1 antibody, an anti-CTLA4 antibody, or an anti-TIGIT antibody. In some embodiments, the anti-PDL1 antibody is selected from pembrolizumab, nivolumab, atezolizumab, avelumab, durvalumab, cemiplimab-rwlc, and zimberelimab; the anti-CLTA4 antibody is ipilimumab or tremelimumab; or the anti-TIGIT antibody is selected from tiragolumab, vibostolimab, domvanalimab, AB308, BMS-986207, and durvalumab. In some embodiments, the cancer is a blood cancer or a solid cancer. In some embodiments, the cancer expresses CCR8. In some embodiments, the cancer is T-cell adult acute lymphocytic leukemia, T-cell childhood acute lymphocytic leukemia, lymphoblastic lymphoma, acute lymphocytic leukemia, cutaneous T cell lymphoma, T-cell acute lymphocytic leukemia, adult T cell leukemia/lymphoma, T cell lymphoblastic leukemia/lymphoma, or anaplastic large cell lymphoma. In some embodiments, the cancer is selected from breast cancer, colorectal cancer, head and neck cancer, lung cancer, ovarian cancer, gastric cancer, stomach adenocarcinoma, and thymoma. In some embodiments the cancer is breast cancer (e.g., triple negative breast cancer). In some embodiments, the methods may further comprise administering to the subject one or more additional therapeutic agents. In some embodiments, the one or more additional therapeutic agents are selected from an anti-Trop-2 antibody (e.g., sacituzumab govitecan, SKB-264, JS-108 (DAC-002), datopotamab deruxtecan, BAT-8003), an anti-CD47 antibody or a CD47-blocking agent (e.g., magrolimab, DSP-107, AO-176, ALX-148, IBI-188, lemzoparlimab, TTI-621, TTI-622), an anti-SIRPα antibody (e.g., GS-0189), a FLT3L-Fc fusion protein (e.g., GS-3583), an anti-PD-1 antibody (pembrolizumab, nivolumab, zimberelimab), a small molecule PD-L1 inhibitor (e.g., GS-4224), an anti-PD-L1 antibody (e.g., atezolizumab), a small molecule MCL1 inhibitor (e.g., GS-9716), a small molecule HPK1 inhibitor (e.g., GS-6451), a HPK1 degrader (PROTAC; e.g., ARV-766), a small molecule DGKa inhibitor, a small molecule CD73 inhibitor (e.g., AB680), an anti-CD73 antibody (e.g., oleclumab), a dual $A_{2a}/A_{2b}$ adenosine receptor antagonist (e.g., etrumadenant (AB928)), an anti-TIGIT antibody (e.g., tiragolumab, vibostolimab, domvanalimab, AB308), an anti-TREM1 antibody (e.g., PY159), an anti-TREM2 antibody (e.g., PY314), a TGFβ-trap (e.g., bintrafusp alpha, AGEN-1423), an anti-TGFβ1 antibody (e.g., SRK-181), and a CAR-T cell therapy (e.g., axicabtagene ciloleucel, brexucabtagene autoleucel, tisagenlecleucel). In some embodiments, the one or more additional therapeutic agents are selected from sacituzumab govitecan-hziy, magrolimab, GS-0189, GS-3583, zimberelimab, GS-4224, GS-9716, GS-6451, AB680, etrumadenant (AB928), domvanalimab, AB308, PY159, PY314, SRK-181, axicabtagene ciloleucel, and brexucabtagene autoleucel. In some embodiments, administration of the one or more additional therapeutic agents is concurrent with the administration of the antibody. In some embodiments, administration of the one or more additional therapeutic agents is before or after the administration of the antibody.

DETAILED DESCRIPTION

Figure 1:
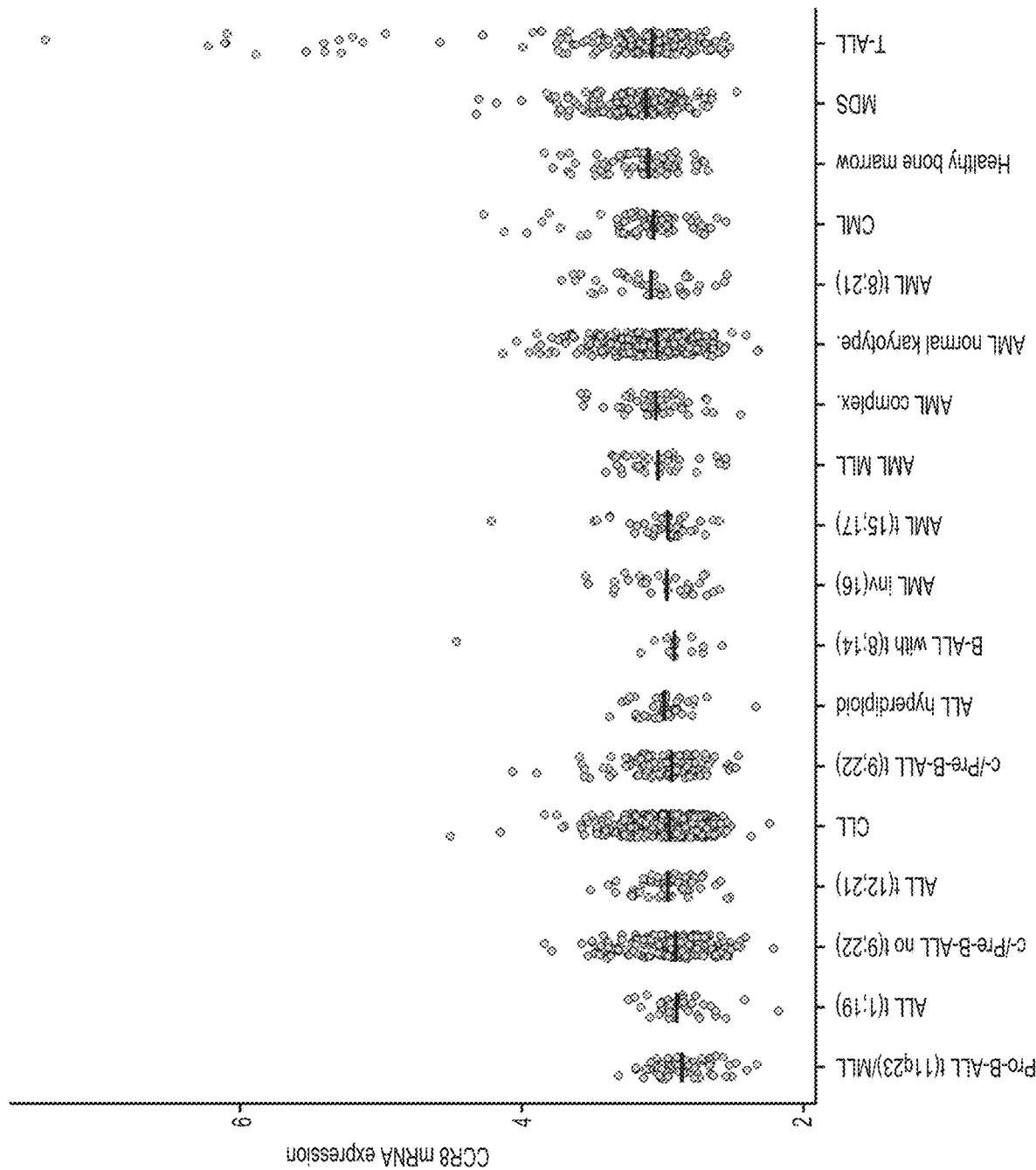
FIG. 1 shows a scatter plot of CCR8 mRNA expression levels determined by microarray. On the y-axis is CCR8 gene expression as measured by fluorescence intensity (AU). The x-axis represents leukemia subtypes or healthy bone marrow. For each group on the x-axis, a straight line represents the median CCR8 expression level for that leukemia subtype. Leukemia subtypes shown include acute lymphocytic leukemia (ALL), T-cell acute lymphocytic leukemia (TALL), B-cell acute lymphocytic leukemia (BALL), acute myeloid leukemia (AML), chronic lymphocytic leukemia (CLL), chronic myeloid leukemia (CML), myelodysplastic syndromes (MDS).

Antibodies that bind CCR8 are provided. Antibody heavy chains and light chains that are capable of forming antibodies that bind CCR8 are also provided. In addition, antibodies, heavy chains, and light chains comprising one or more particular complementarity determining regions (CDRs) are provided. Polynucleotides encoding antibodies to CCR8 are provided. Polynucleotides encoding antibody heavy chains or lights chains are also provided. Methods of producing and/or purifying antibodies to CCR8 are provided. Fusion proteins comprising CCL1 or MC148 and an Fc region are also provided. Polynucleotides encoding such fusion proteins are also provided. Methods of producing and/or purifying the fusion proteins are provided. Methods of treatment using the antibodies and/or fusion proteins are provided. Such methods include, but are not limited to, methods of treating cancer. Methods of detecting CCR8 are provided. Such methods include methods to identify an individual who may benefit from treatment with an antibody or fusion protein provided herein, to monitor treatment of an individual with an antibody or fusion protein provided herein, and to improve therapeutic efficacy of an antibody or fusion protein provided herein in an individual.

The section headings used herein are for organizational purposes only and are not to be construed as limiting the subject matter described.

All references cited herein, including patent applications, patent publications, and Genbank Accession numbers are herein incorporated by reference, as if each individual reference were specifically and individually indicated to be incorporated by reference in its entirety.

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3rd. edition (2001) Cold Spring Harbor Laboratory Press, Cold Spring Harbor, N.Y. CURRENT PROTOCOLS IN MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)); Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney), ed., 1987); Introduction to Cell and Tissue Culture (J. P. Mather and P. E. Roberts, 1998) Plenum Press; Cell and Tissue Culture Laboratory Procedures (A. Doyle, J. B. Griffiths, and D. G. Newell, eds., 1993-8) J. Wiley and Sons; Handbook of Experimental Immunology (D. M. Weir and C. C. Blackwell, eds.); Gene Transfer Vectors for Mammalian Cells (J. M. Miller and M. P. Calos, eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: A Practical Approach (D. Catty, ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J. B. Lippincott Company, 1993); and updated versions thereof.

I. Definitions

Unless otherwise defined, scientific and technical terms used in connection with the present disclosure shall have the meanings that are commonly understood by those of ordinary skill in the art. Further, unless otherwise required by context or expressly indicated, singular terms shall include pluralities and plural terms shall include the singular. For any conflict in definitions between various sources or references, the definition provided herein will control.

It is understood that embodiments of the invention described herein include "consisting" and/or "consisting essentially of" embodiments. As used herein, the singular form "a", "an", and "the" includes plural references unless indicated otherwise. Use of the term "or" herein is not meant to imply that alternatives are mutually exclusive.

In this application, the use of "or" means "and/or" unless expressly stated or understood by one skilled in the art. In the context of a multiple dependent claim, the use of "or" refers back to more than one preceding independent or dependent claim.

As is understood by one skilled in the art, reference to "about" a value or parameter herein includes (and describes) embodiments that are directed to that value or parameter per se. For example, description referring to "about X" includes description of "X".

The terms "nucleic acid molecule", "nucleic acid" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present disclosure, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts, which produce the proteins or errors due to PCR amplification.

"CCR8" and "C-C chemokine receptor type 8" and "chemokine receptor 8," as used herein refer to any native CCR8 that results from expression and processing of CCR8 in a cell. The term includes CCR8 from any vertebrate source, including mammals such as primates (e.g., humans and cynomolgus monkeys) and rodents (e.g., mice and rats), unless otherwise indicated. The term also includes naturally occurring variants of CCR8, e.g., splice variants or allelic variants. The amino acid sequence of an exemplary human CCR8 protein is shown in SEQ ID NO: 101 (UniProt Identifier P51685). The amino acid sequence of an exemplary mouse CCR8 protein is shown in SEQ ID NO: 102 (UniProt Identifier P56484). The amino acid sequence of an exemplary cynomolgus monkey CCR8 protein is shown in SEQ ID NO: 103 (UniProt Identifier G7NYJ2).

"CCL1" and "C-C motif chemokine 1," as used herein refer to any native CCR1 that results from expression and processing of CCR1 in a cell. The term includes CCR1 from any vertebrate source, including mammals such as primates (e.g., humans and cynomolgus monkeys) and rodents (e.g., mice and rats), unless otherwise indicated. The term also includes naturally occurring variants of CCR1, e.g., splice variants or allelic variants. The amino acid sequence of an exemplary human CCR1 protein is shown in SEQ ID NO: 2 (UniProt Identifier P22362.1). An exemplary mature CCR1 protein comprises amino acids 24-96 of SEQ ID NO: 2.

"MC148" as used herein refer to any native MC148 that results from expression and processing of MC148 in a cell. The term includes MC148 from any viral source, including molluscum contagiosum virus (subtype 1 or subtype 2), unless otherwise indicated. The term also includes naturally occurring variants of MC148, e.g., truncated variants or allelic variants. The amino acid sequence of an exemplary MC148 protein is shown in SEQ ID NO: 6 (amino acids 25-104 of UniProt Identifier Q98314.1).

As used herein, a "7-B16 antibody" should be understood as any antibody that binds to CCR8 and comprises (i) a heavy chain comprising SEQ ID NO:82 and a light chain comprising SEQ ID NO: 83, (ii) a variable heavy chain region comprising SEQ ID NO: 80 and a variable light chain region comprising SEQ ID NO: 81, or (iii) an HCDR1, an HCDR2, and an HCDR 3 comprising SEQ ID NOs: 84, 85, and 86, respectively, and an LCDR1, an LCDR2, and an LCDR 3 comprising SEQ ID NOs: 87, 88, and 89, respectively; as well as chimeric, human, or humanized versions of any of the foregoing (i), (ii), or (iii). In some embodiments, a "7-B16 antibody" may be used to specifically refer to an antibody comprising a heavy chain of SEQ ID NO: 82 and a light chain of SEQ ID NO: 83.

The term "specifically binds" to an antigen or epitope is a term that is well understood in the art, and methods to determine such specific binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a CCR8 epitope is an antibody that binds this epitope with greater affinity, avidity, more readily, and/or with greater duration than it binds to other CCR8 epitopes or non-CCR8 epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding. "Specificity" refers to the ability of a binding protein to selectively bind an antigen.

As used herein, "substantially pure" refers to material which is at least 50% pure (that is, free from contaminants), more preferably, at least 90% pure, more preferably, at least 95% pure, yet more preferably, at least 98% pure, and most preferably, at least 99% pure.

As used herein, the term "epitope" refers to a site on a target molecule (for example, an antigen, such as a protein, nucleic acid, carbohydrate or lipid) to which an antigen-binding molecule (for example, an antibody, antibody fragment, or scaffold protein containing antibody binding regions) binds. Epitopes often include a chemically active surface grouping of molecules such as amino acids, polypeptides or sugar side chains and have specific three-dimensional structural characteristics as well as specific charge characteristics. Epitopes can be formed both from contiguous and/or juxtaposed noncontiguous residues (for example, amino acids, nucleotides, sugars, lipid moiety) of the target molecule. Epitopes formed from contiguous residues (for example, amino acids, nucleotides, sugars, lipid moiety) typically are retained on exposure to denaturing solvents whereas epitopes formed by tertiary folding typically are lost on treatment with denaturing solvents. An epitope may include but is not limited to at least 3, at least 5 or 8-10 residues (for example, amino acids or nucleotides). In some examples an epitope is less than 20 residues (for example, amino acids or nucleotides) in length, less than 15 residues or less than 12 residues. Two antibodies may bind the same epitope within an antigen if they exhibit competitive binding for the antigen. In some embodiments, an epitope can be identified by a certain minimal distance to a CDR residue on the antigen-binding molecule. In some embodiments, an epitope can be identified by the above distance, and further limited to those residues involved in a bond (for example, a hydrogen bond) between an antibody residue and an antigen residue. An epitope can be identified by various scans as well, for example, an alanine or arginine scan can indicate one or more residues that the antigen-binding molecule can interact with. Unless explicitly denoted, a set of residues as an epitope does not exclude other residues from being part of the epitope for a particular antibody. Rather, the presence of such a set designates a minimal series (or set of species) of epitopes. Thus, in some embodiments, a set of residues identified as an epitope designates a minimal epitope of relevance for the antigen, rather than an exclusive list of residues for an epitope on an antigen.

A "nonlinear epitope" or "conformational epitope" comprises noncontiguous polypeptides, amino acids and/or sugars within the antigenic protein to which an antibody specific to the epitope binds. In some embodiments, at least one of the residues will be noncontiguous with the other noted residues of the epitope; however, one or more of the residues can also be contiguous with the other residues.

A "linear epitope" comprises contiguous polypeptides, amino acids and/or sugars within the antigenic protein to which an antibody specific to the epitope binds. It is noted that, in some embodiments, not every one of the residues within the linear epitope need be directly bound (or involved in a bond) with the antibody. In some embodiments, linear epitopes can be from immunizations with a peptide that effectively consisted of the sequence of the linear epitope, or from structural sections of a protein that are relatively isolated from the remainder of the protein (such that the antibody can interact, at least primarily, just with that sequence section.

The term "antibody" herein is used in the broadest sense and encompasses various antibody structures, including but not limited to monoclonal antibodies, polyclonal antibodies, multispecific antibodies (for example, bispecific (such as Bi-specific T-cell engagers) and trispecific antibodies), and antibody fragments so long as they exhibit the desired antigen-binding activity.

The term antibody includes, but is not limited to, fragments that are capable of binding to an antigen, such as Fv, single-chain Fv (scFv), Fab, Fab', di-scFv, sdAb (single domain antibody) and (Fab')$_2$ (including a chemically linked F(ab')$_2$). Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen. The term antibody also includes, but is not limited to, chimeric antibodies, humanized antibodies, and antibodies of various species such as mouse, human, cynomolgus monkey, etc. Furthermore, for all antibody constructs provided herein, variants having the sequences from other organisms are also contemplated. Thus, if a human version of an antibody is disclosed, one of skill in the art will appreciate how to transform the human sequence based antibody into a mouse, rat, cat, dog, horse, etc. sequence. Antibody fragments also include either orientation of single chain scFvs, tandem di-scFv, diabodies, tandem tri-sdcFv, minibodies, etc. Antibody fragments also include nanobodies (sdAb, an antibody having a single, monomeric domain, such as a pair of variable domains of heavy chains, without a light chain). An antibody fragment can be referred to as being a specific species in some embodiments (for example, human scFv or a mouse scFv). This denotes the sequences of at least part of the non-CDR regions, rather than the source of the construct.

The term "monoclonal antibody" refers to an antibody of a substantially homogeneous population of antibodies, that is, the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. Thus, a sample of monoclonal antibodies can bind to the same epitope on the antigen. The modifier "monoclonal" indicates the character of the antibody as being obtained from a substantially homogeneous population of antibodies, and is not to be construed as requiring production of the antibody by any particular method. For example, the monoclonal antibodies may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example.

The term "CDR" denotes a complementarity determining region as defined by at least one manner of identification to one of skill in the art. In some embodiments, CDRs can be defined in accordance with any of the Chothia numbering schemes, the Kabat numbering scheme, a combination of Kabat and Chothia, the AbM definition, the contact definition, and/or a combination of the Kabat, Chothia, AbM, and/or contact definitions. Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., Sequences of Proteins of Immunological Interest, 5th Ed. Public Health Service, National Institutes of Health, Bethesda, Md. (1991)). The AbM definition can include, for example, CDRs (CDR-L1, CDR-L2, CDR-L3, CDR-H1, CDR-H2, and CDR-H3) at amino acid residues 24-34 of L1, 50-56 of L2, 89-97 of L3, H26-H35B of H1, 50-58 of H2, and 95-102 of H3. The Contact definition can include, for example, CDRs (CDR-L1, CDR-L2, CDR-L3, CDR-H1, CDR-H2, and CDR-H3) at amino acid residues 30-36 of L1, 46-55 of L2, 89-96 of L3, 30-35 of H1, 47-58 of H2, and 93-101 of H3. The Chothia definition can include, for example, CDRs (CDR-L1, CDR-L2, CDR-L3, CDR-H1, CDR-H2, and CDR-H3) at amino acid residues 24-34 of L1, 50-56 of L2, 89-97 of L3, 26-32 . . . 34 of H1, 52-56 of H2, and 95-102 of H3. CDRs can also be provided as shown in any one or more of the accompanying figures. With the exception of CDR1 in $V_H$, CDRs generally comprise the amino acid residues that form the hypervariable loops. The various CDRs within an antibody can be designated by their appropriate number and chain type, including, without limitation as: a) CDR-L1, CDR-L2, CDR-L3, CDR-H1, CDR-H2, and CDR-H3; b) CDRL1, CDRL2, CDRL3, CDRH1, CDRH2, and CDRH3; c) LCDR-1, LCDR-2, LCDR-3, HCDR-1, HCDR-2, and HCDR-3; or d) LCDR1, LCDR2, LCDR3, HCDR1, HCDR2, and HCDR3; etc. The term "CDR" is used herein to also encompass HVR or a "hyper variable region", including hypervariable loops. Exemplary hypervariable loops occur at amino acid residues 26-32 (L1), 50-52 (L2), 91-96 (L3), 26-32 (H1), 53-55 (H2), and 96-101 (H3). (Chothia and Lesk, J. Mol. Biol. 196:901-917 (1987).)

The term "heavy chain variable region" as used herein refers to a region comprising at least three heavy chain CDRs. In some embodiments, the heavy chain variable region includes the three CDRs and at least FR2 and FR3. In some embodiments, the heavy chain variable region includes at least heavy chain HCDR1, framework (FR) 2, HCDR2, FR3, and HCDR3. In some embodiments, a heavy chain variable region also comprises at least a portion of an FR1 and/or at least a portion of an FR4.

The term "heavy chain constant region" as used herein refers to a region comprising at least three heavy chain constant domains, CH1, CH2, and CH3. Of course, non-function-altering deletions and alterations within the domains are encompassed within the scope of the term "heavy chain constant region," unless designated otherwise. Nonlimiting exemplary heavy chain constant regions include γ, δ, and α. Nonlimiting exemplary heavy chain constant regions also include ε and μ. Each heavy constant region corresponds to an antibody isotype. For example, an antibody comprising a γ constant region is an IgG antibody, an antibody comprising a δ constant region is an IgD antibody, and an antibody comprising an α constant region is an IgA antibody. Further, an antibody comprising a constant region is an IgM antibody, and an antibody comprising an F constant region is an IgE antibody. Certain isotypes can be further subdivided into subclasses. For example, IgG antibodies include, but are not limited to, IgG1 (comprising a $\gamma_1$ constant region), IgG2 (comprising a $\gamma_2$ constant region), IgG3 (comprising a $\gamma_3$ constant region), and IgG4 (comprising a 74 constant region) antibodies; IgA antibodies include, but are not limited to, IgA1 (comprising an $\alpha_1$ constant region) and IgA2 (comprising an $\alpha_2$ constant region) antibodies; and IgM antibodies include, but are not limited to, IgM1 and IgM2.

The term "heavy chain" as used herein refers to a polypeptide comprising at least a heavy chain variable region, with or without a leader sequence. In some embodiments, a heavy chain comprises at least a portion of a heavy chain constant region. The term "full-length heavy chain" as used herein refers to a polypeptide comprising a heavy chain variable region and a heavy chain constant region, with or without a leader sequence.

The term "light chain variable region" as used herein refers to a region comprising at least three light chain CDRs. In some embodiments, the light chain variable region includes the three CDRs and at least FR2 and FR3. In some embodiments, the light chain variable region includes at least light chain LCDR1, framework (FR) 2, LCDR2, FR3, and LCDR3. For example, a light chain variable region may comprise light chain CDR1, framework (FR) 2, CDR2, FR3, and CDR3. In some embodiments, a light chain variable region also comprises at least a portion of an FR1 and/or at least a portion of an FR4.

The term "light chain constant region" as used herein refers to a region comprising a light chain constant domain, $C_L$. Nonlimiting exemplary light chain constant regions include λ and κ. Of course, non-function-altering deletions and alterations within the domains are encompassed within the scope of the term "light chain constant region," unless designated otherwise.

The term "light chain" as used herein refers to a polypeptide comprising at least a light chain variable region, with or without a leader sequence. In some embodiments, a light chain comprises at least a portion of a light chain constant region. The term "full-length light chain" as used herein refers to a polypeptide comprising a light chain variable region and a light chain constant region, with or without a leader sequence.

An "acceptor human framework" for the purposes herein is a framework comprising the amino acid sequence of a light chain variable domain ($V_L$) framework or a heavy chain variable domain ($V_H$) framework derived from a human immunoglobulin framework or a human consensus framework, as defined below. An acceptor human framework derived from a human immunoglobulin framework or a human consensus framework can comprise the same amino acid sequence thereof, or it can contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the $V_L$ acceptor human framework is identical in sequence to the $V_L$ human immunoglobulin framework sequence or human consensus framework sequence.

"Affinity" refers to the strength of the sum total of noncovalent interactions between a single binding site of a molecule (for example, an antibody) and its binding partner (for example, an antigen). The affinity of a molecule X for its partner Y can generally be represented by the dissociation constant ($K_D$). Affinity can be measured by common methods known in the art (such as, for example, ELISA $K_D$, KinExA, bio-layer interferometry (BLI), and/or surface plasmon resonance devices (such as a BIAcore® device), including those described herein).

The term "$K_D$", as used herein, refers to the equilibrium dissociation constant of an antibody-antigen interaction.

In some embodiments, the "$K_D$," "$K_d$," "Kd" or "Kd value" of the antibody is measured by using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µL/minute to achieve approximately 10 response units (RU) of coupled protein. Following the injection of antigen, 1 M ethanolamine is injected to block unreacted groups. For kinetics measurements, serial dilutions of polypeptide, for example, full length antibody, are injected in PBS with 0.05% TWEEN-20™ surfactant (PBST) at 25° C. at a flow rate of approximately 25 µL/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant ($K_d$) is calculated as the ratio $k_{off}/k_{on}$. See, for example, Chen et al., J. Mol. Biol. 293:865-881 (1999). If the on-rate exceeds $10^6$ $M^{-1}s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

In some embodiments, the difference between said two values (for example, $K_d$ values) is substantially the same, for example, less than about 50%, less than about 40%, less than about 30%, less than about 20%, and/or less than about 10% as a function of the reference/comparator value.

In some embodiments, the difference between said two values (for example, $K_d$ values) is substantially different, for example, greater than about 10%, greater than about 20%, greater than about 30%, greater than about 40%, and/or greater than about 50% as a function of the value for the reference/comparator molecule.

"Surface plasmon resonance" denotes an optical phenomenon that allows for the analysis of real-time biospecific interactions by detection of alterations in protein concentrations within a biosensor matrix, for example using the BIAcore™ system (BIAcore International AB, a GE Healthcare company, Uppsala, Sweden and Piscataway, N.J.). For further descriptions, see Jonsson et al. (1993) Ann. Biol. Clin. 51:19-26.

"Biolayer interferometry" refers to an optical analytical technique that analyzes the interference pattern of light reflected from a layer of immobilized protein on a biosensor tip and an internal reference layer. Changes in the number of molecules bound to the biosensor tip cause shifts in the interference pattern that can be measured in real-time. A nonlimiting exemplary device for biolayer interferometry is ForteBio Octet® RED96 system (Pall Corporation). See, e.g., Abdiche et al., 2008, Anal. Biochem. 377: 209-277.

The term "$k_{on}$", as used herein, refers to the rate constant for association of an antibody to an antigen. Specifically, the rate constants ($k_{on}$ and $k_{off}$) and equilibrium dissociation constants are measured using IgGs (bivalent) with monovalent CCR8 antigen. "$K_{on}$", "$k_{on}$", "association rate constant", or "ka", are used interchangeably herein. The value indicates the binding rate of a binding protein to its target antigen or the rate of complex formation between an antibody and antigen, shown by the equation: Antibody("Ab")+Antigen("Ag")→Ab-Ag.

The term "$k_{off}$", as used herein, refers to the rate constant for dissociation of an antibody from the antibody/antigen complex. $k_{off}$ is also denoted as "$K_{off}$" or the "dissociation rate constant". This value indicates the dissociation rate of an antibody from its target antigen or separation of Ab-Ag complex over time into free antibody and antigen as shown by the equation:

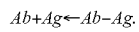

$$Ab+Ag \leftarrow Ab-Ag.$$

The term "biological activity" refers to any one or more biological properties of a molecule (whether present naturally as found in vivo, or provided or enabled by recombinant means). Biological properties include, but are not limited to, binding a cytokine, inducing cell proliferation, inhibiting cell growth, inducing other cytokines, inducing apoptosis, and enzymatic activity. In some embodiments, biological activities of CCR8 include antiapoptotic activities, cell chemotaxis, immune suppressive functions, and capacity to polarize cells toward various cell differentiation paths.

An "affinity matured" antibody refers to an antibody with one or more alterations in one or more CDRs compared to a parent antibody which does not possess such alterations, such alterations resulting in an improvement in the affinity of the antibody for antigen.

A "chimeric antibody" as used herein refers to an antibody in which a portion of the heavy and/or light chain is derived from a particular source or species, while at least a part of the remainder of the heavy and/or light chain is derived from a different source or species. In some embodiments, a chimeric antibody refers to an antibody comprising at least one variable region from a first species (such as mouse, rat, cynomolgus monkey, etc.) and at least one constant region from a second species (such as human, cynomolgus monkey, etc.). In some embodiments, a chimeric antibody comprises at least one mouse variable region and at least one human constant region. In some embodiments, a chimeric antibody comprises at least one cynomolgus variable region and at least one human constant region. In some embodiments, all of the variable regions of a chimeric antibody are from a first species and all of the constant regions of the chimeric antibody are from a second species. The chimeric construct can also be a functional fragment, as noted above.

A "humanized antibody" as used herein refers to an antibody in which at least one amino acid in a framework region of a non-human variable region has been replaced with the corresponding amino acid from a human variable region. In some embodiments, a humanized antibody comprises at least one human constant region or fragment thereof. In some embodiments, a humanized antibody is an antibody fragment, such as Fab, an scFv, a (Fab')$_2$, etc. The term humanized also denotes forms of non-human (for example, murine) antibodies that are chimeric immunoglobulins, immunoglobulin chains, or fragments thereof (such as Fv, Fab, Fab', F(ab')$_2$ or other antigen-binding subsequences of antibodies) that contain minimal sequence of non-human immunoglobulin. Humanized antibodies can include human immunoglobulins (recipient antibody) in which residues from a complementary determining region (CDR) of the recipient are substituted by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody can comprise residues that are found neither in the recipient antibody nor in the imported CDR or framework sequences, but are included to further refine and optimize antibody performance. In general, the humanized antibody can comprise substantially all of at least one, and typically two, variable domains, in which all or substantially all of the CDR regions correspond to those of a non-human immunoglobulin and all or substantially all of the FR regions are those of a human immunoglobulin consensus sequence. In some embodiments, the humanized antibody can also comprise at least a portion of an immunoglobulin constant region or domain (Fc), typically that of a human immunoglobulin. Other forms of humanized antibodies have one or more CDRs (CDR L1, CDR L2, CDR L3, CDR H1, CDR H2, and/or CDR H3) which are altered with respect to the original antibody, which are also termed one or more CDRs "derived from" one or more CDRs from the original antibody. As will be appreciated, a humanized sequence can be identified by its primary sequence and does not necessarily denote the process by which the antibody was created.

An "CDR-grafted antibody" as used herein refers to a humanized antibody in which one or more complementarity determining regions (CDRs) of a first (non-human) species have been grafted onto the framework regions (FRs) of a second (human) species.

A "human antibody" as used herein encompasses antibodies produced in humans, antibodies produced in non-human animals that comprise human immunoglobulin genes, such as XenoMouse® mice, and antibodies selected using in vitro methods, such as phage display (Vaughan et al., 1996, Nature Biotechnology, 14:309-314; Sheets et al., 1998, Proc. Natl. Acad. Sci. (USA) 95:6157-6162; Hoogenboom and Winter, 1991, J. Mol. Biol., 227:381; Marks et al., 1991, J. Mol. Biol., 222:581), wherein the antibody repertoire is based on a human immunoglobulin sequence. The term "human antibody" denotes the genus of sequences that are human sequences. Thus, the term is not designating the process by which the antibody was created, but the genus of sequences that are relevant.

A "functional Fc region" possesses an "effector function" of a native sequence Fc region. Exemplary "effector functions" include Fc receptor binding; Clq binding; CDC; ADCC; phagocytosis; down regulation of cell surface receptors (for example B cell receptor; BCR), etc. Such effector functions generally require the Fc region to be combined with a binding domain (for example, an antibody variable domain) and can be assessed using various assays.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification. In some embodiments, a "variant Fc region" comprises an amino acid sequence which differs from that of a native sequence Fc region by virtue of at least one amino acid modification, yet retains at least one effector function of the native sequence Fc region. In some embodiments, the variant Fc region has at least one amino acid substitution compared to a native sequence Fc region or to the Fc region of a parent polypeptide, for example, from about one to about ten amino acid substitutions, and preferably, from about one to about five amino acid substitutions in a native sequence Fc region or in the Fc region of the parent polypeptide. In some embodiments, the variant Fc region herein will possess at least about 80% sequence identity with a native sequence Fc region and/or with an Fc region of a parent polypeptide, at least about 90% sequence identity therewith, at least about 95%, at least about 96%, at least about 97%, at least about 98%, or at least about 99% sequence identity therewith.

"Fc receptor" or "FcR" describes a receptor that binds to the Fc region of an antibody. In some embodiments, an FcTR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (see, for example, Daeron, *Annu. Rev. Immunol.* 15:203-234 (1997)). FcRs are reviewed, for example, in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known (see, for example, Ghetie and Ward, *Immunol. Today* 18(12):592-598 (1997);

Ghetie et al., *Nature Biotechnology,* 15(7):637-640 (1997); Hinton et al., *J. Biol. Chem.* 279(8):6213-6216 (2004); WO 2004/92219 (Hinton et al.).

"Effector functions" refer to biological activities attributable to the Fc region of an antibody, which vary with the antibody isotype. Examples of antibody effector functions include: Clq binding and complement dependent cytotoxicity (CDC); Fc receptor binding; antibody-dependent cell-mediated cytotoxicity (ADCC); phagocytosis; down regulation of cell surface receptors (for example B cell receptor); and B cell activation.

"Human effector cells" are leukocytes which express one or more FcRs and perform effector functions. In some embodiments, the cells express at least FcγRIII and perform ADCC effector function(s). Examples of human leukocytes which mediate ADCC include peripheral blood mononuclear cells (PBMC), natural killer (NK) cells, monocytes, cytotoxic T cells, and neutrophils. The effector cells may be isolated from a native source, for example, from blood.

"Antibody-dependent cell-mediated cytotoxicity" or "ADCC" refers to a form of cytotoxicity in which secreted Ig bound onto Fc receptors (FcRs) present on certain cytotoxic cells (for example NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. Nos. 5,500,362 or 5,821,337 or U.S. Pat. No. 6,737,056 (Presta), may be performed. Useful effector cells for such assays include PBMC and NK cells. Alternatively, or additionally, ADCC activity of the molecule of interest may be assessed in vivo, for example, in an animal model such as that disclosed in Clynes et al. *Proc. Natl. Acad. Sci. (USA)* 95:652-656 (1998). Additional polypeptide variants with altered Fc region amino acid sequences (polypeptides with a variant Fc region) and increased or decreased ADCC activity are described, for example, in U.S. Pat. Nos. 7,923, 538, and 7,994,290.

"Complement dependent cytotoxicity" or "CDC" refers to the lysis of a target cell in the presence of complement. Activation of the classical complement pathway is initiated by the binding of the first component of the complement system (Clq) to antibodies (of the appropriate subclass), which are bound to their cognate antigen. To assess complement activation, a CDC assay, for example, as described in Gazzano-Santoro et al., *J. Immunol. Methods* 202:163 (1996), may be performed. Polypeptide variants with altered Fc region amino acid sequences (polypeptides with a variant Fc region) and increased or decreased Clq binding capability are described, for example, in U.S. Pat. No. 6,194,551 B1, U.S. Pat. Nos. 7,923,538, 7,994,290 and WO 1999/51642. See also, for example, Idusogie et al., *J. Immunol.* 164: 4178-4184 (2000).

A polypeptide variant with "altered" FcR binding affinity or ADCC activity is one which has either enhanced or diminished FcR binding activity and/or ADCC activity compared to a parent polypeptide or to a polypeptide comprising a native sequence Fc region. The polypeptide variant which "displays increased binding" to an FcR binds at least one FcR with better affinity than the parent polypeptide. The polypeptide variant which "displays decreased binding" to an FcR, binds at least one FcR with lower affinity than a parent polypeptide. Such variants which display decreased binding to an FcR may possess little or no appreciable binding to an FcR, for example, 0-20% binding to the FcR compared to a native sequence IgG Fc region.

The polypeptide variant which "mediates antibody-dependent cell-mediated cytotoxicity (ADCC) in the presence of human effector cells more effectively" than a parent antibody is one which in vitro or in vivo is more effective at mediating ADCC, when the amounts of polypeptide variant and parent antibody used in the assay are essentially the same. Generally, such variants will be identified using the in vitro ADCC assay as herein disclosed, but other assays or methods for determining ADCC activity, for example in an animal model etc., are contemplated.

The term "substantially similar" or "substantially the same," as used herein, denotes a sufficiently high degree of similarity between two or more numeric values such that one of skill in the art would consider the difference between the two or more values to be of little or no biological and/or statistical significance within the context of the biological characteristic measured by said value. In some embodiments the two or more substantially similar values differ by no more than about any one of 5%, 10%, 15%, 20%, 25%, or 50%.

The phrase "substantially different," as used herein, denotes a sufficiently high degree of difference between two numeric values such that one of skill in the art would consider the difference between the two values to be of statistical significance within the context of the biological characteristic measured by said values. In some embodiments, the two substantially different numeric values differ by greater than about any one of 10%, 20%, 25%, 30%, 35%, 40%, 45%, 50%, 60%, 70%, 80%, 90%, or 100%.

The phrase "substantially reduced," as used herein, denotes a sufficiently high degree of reduction between a numeric value and a reference numeric value such that one of skill in the art would consider the difference between the two values to be of statistical significance within the context of the biological characteristic measured by said values. In some embodiments, the substantially reduced numeric values is reduced by greater than about any one of 10%, 20%, 25%, 30%, 35%, 40%, 45%, 50%, 60%, 70%, 80%, 90%, or 100% compared to the reference value.

The term "leader sequence" refers to a sequence of amino acid residues located at the N-terminus of a polypeptide that facilitates secretion of a polypeptide from a mammalian cell. A leader sequence can be cleaved upon export of the polypeptide from the mammalian cell, forming a mature protein. Leader sequences can be natural or synthetic, and they can be heterologous or homologous to the protein to which they are attached.

A "native sequence" polypeptide comprises a polypeptide having the same amino acid sequence as a polypeptide found in nature. Thus, a native sequence polypeptide can have the amino acid sequence of naturally occurring polypeptide from any mammal. Such native sequence polypeptide can be isolated from nature or can be produced by recombinant or synthetic means. The term "native sequence" polypeptide specifically encompasses naturally occurring truncated or secreted forms of the polypeptide (for example, an extracellular domain sequence), naturally occurring variant forms (for example, alternatively spliced forms) and naturally occurring allelic variants of the polypeptide.

A polypeptide "variant" means a biologically active polypeptide having at least about 80% amino acid sequence identity with the native sequence polypeptide after aligning the sequences and introducing gaps, if necessary, to achieve the maximum percent sequence identity, and not considering any conservative substitutions as part of the sequence identity. Such variants include, for instance, polypeptides wherein one or more amino acid residues are added, or deleted, at the N- or C-terminus of the polypeptide. In some embodiments, a variant will have at least about 80% amino acid sequence identity. In some embodiments, a variant will have at least about 90% amino acid sequence identity. In some embodiments, a variant will have at least about 95% amino acid sequence identity with the native sequence polypeptide.

As used herein, "Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

An amino acid substitution may include but are not limited to the replacement of one amino acid in a polypeptide with another amino acid. Exemplary conservative substitutions are shown in Table 1. Amino acid substitutions may be introduced into an antibody of interest and the products screened for a desired activity, for example, retained/improved antigen binding, decreased immunogenicity, or improved ADCC or CDC.

TABLE 1

| Original Residue | Exemplary Substitutions |
| --- | --- |
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

The term "vector" is used to describe a polynucleotide that can be engineered to contain a cloned polynucleotide or polynucleotides that can be propagated in a host cell. A vector can include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that can be used in colorimetric assays, for example, β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NSO cells, PER.C6® cells (Crucell), and 293 and CHO cells, and their derivatives, such as 293-6E and DG44 cells, respectively. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) a provided herein.

The term "isolated" as used herein refers to a molecule that has been separated from at least some of the components with which it is typically found in nature or produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, for example, in the case of an RNA polynucleotide. Thus, a DNA polynucleotide that is contained in a vector inside a host cell may be referred to as "isolated".

The terms "individual" or "subject" are used interchangeably herein to refer to an animal; for example, a mammal. In some embodiments, methods of treating mammals, including, but not limited to, humans, rodents, simians, felines, canines, equines, bovines, porcines, ovines, caprines, mammalian laboratory animals, mammalian farm animals, mammalian sport animals, and mammalian pets, are provided. In some examples, an "individual" or "subject" refers to an individual or subject in need of treatment for a disease or disorder. In some embodiments, the subject to receive the treatment can be a patient, designating the fact that the subject has been identified as having a disorder of relevance to the treatment, or being at adequate risk of contracting the disorder.

A "disease" or "disorder" as used herein refers to a condition where treatment is needed and/or desired.

"Cancer" and "tumor," as used herein, are interchangeable terms that refer to any abnormal cell or tissue growth or proliferation in an animal. As used herein, the terms "cancer" and "tumor" encompass solid and hematological/lymphatic cancers and also encompass malignant, pre-malignant, and benign growth, such as dysplasia. Examples of cancer include but are not limited to, carcinoma, lymphoma, blastoma, sarcoma, and leukemia. More particular nonlimiting examples of such cancers include squamous cell cancer, small-cell lung cancer, pituitary cancer, esophageal cancer, astrocytoma, soft tissue sarcoma, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, renal cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, mesothelioma, and various types of head and neck cancer. In some embodiments, hematological/lymphatic cancers are referred to as "blood cancers." Nonlimiting exemplary blood cancers include B- and T-cell mixed leukemia, B-cell lymphoma, chronic myeloid leukemia (CML), chronic myelomonocytic leukemia, diffuse large B-cell lymphoma (DLBC), lymphoma, mantle cell lymphoma (MCL), multiple myeloma, myelodysplastic syndromes (MDS), myeloproliferative disorders, peripheral T-cell lymphoma, T-cell leukemia, acute myeloid leukemia (AML), chronic lymphocytic leukemia (CLL), small lymphocytic lymphoma (SLL), CLL/SLL, mature T-cell and NK-cell lymphoma, follicular lymphoma, acute lymphocytic leukemia (ALL), T-cell acute lymphocytic leukemia (TALL), T-cell adult acute lymphocytic leukemia, T-cell childhood acute lymphocytic leukemia, lymphoblastic lymphoma, cutaneous T cell lymphoma (CTCL), adult T cell leukemia/lymphoma (ATLL), T cell lymphoblastic leukemia/lymphoma (TLLL), angioimmunoblastic T cell lymphoma (ATCL), hepatosplenic T cell lymphoma (HTCL), peripheral T cell lymphoma not otherwise specified (PTCL NOS), Burkitt lymphoma (BL), chronic myelomonocytic leukemia (CMML), extranodal NK/T cell lymphoma (NKTCL), primary effusion lymphoma (PEL), acute lymphocytic leukemia/acute myeloid leukemia (ALL, AML), histiocytic lymphoma (HL), marginal zone lymphoma (MZL), B-cell acute lymphocytic leukemia, and anaplastic large cell lymphoma (ALCL).

As used herein, "treatment" is an approach for obtaining beneficial or desired clinical results. "Treatment" as used herein, covers any administration or application of a therapeutic for disease in a mammal, including a human. For purposes of this disclosure, beneficial or desired clinical results include, but are not limited to, any one or more of: alleviation of one or more symptoms, diminishment of extent of disease, preventing or delaying spread (for example, metastasis, for example metastasis to the lung or to the lymph node) of disease, preventing or delaying recurrence of disease, delay or slowing of disease progression, amelioration of the disease state, inhibiting the disease or progression of the disease, inhibiting or slowing the disease or its progression, arresting its development, and remission (whether partial or total). Also encompassed by "treatment" is a reduction of pathological consequence of a proliferative disease. The methods provided herein contemplate any one or more of these aspects of treatment. In-line with the above, the term treatment does not require one-hundred percent removal of all aspects of the disorder.

"Ameliorating" means a lessening or improvement of one or more symptoms as compared to not administering an anti-CCR8 antibody. "Ameliorating" also includes shortening or reduction in duration of a symptom.

In the context of cancer, the term "treating" includes any or all of: inhibiting growth of cancer cells, inhibiting replication of cancer cells, lessening of overall tumor burden and ameliorating one or more symptoms associated with the disease.

As used herein, the term "Regulatory T cells" (also known as "Tregs" or "Treg cells" or "suppressor T cells") are a subpopulation of T cells that are immunosuppressive and generally suppress or downregulate induction and proliferation of effector T cells. Tregs express CD4, FOXP3, and CD25 (IL-2 receptor α-chain). Human Foxp3+CD4+ T cells have been divided into three subfractions based upon the expression level of Foxp3 and the cell surface molecules CD25 and CD45RA. The Foxp3hiCD45RA-CD25hi and Foxp3loCD45RA+CD25lo phenotypes correspond to suppressive Treg cells, whereas the Foxp3loCD45RA-CD25lo fraction marks activated T effector (Teff) cells without suppressive activity. In addition, Treg cells from cancer patients, as compared to those in healthy subjects, are usually characterized by a distinct expression profile of chemokine receptors, such as CCR4, CXCR4, and CCR5, which facilitates their migration into tumors in response to the corresponding chemokine ligands derived from tumor microenvironment. See, e.g., Liu, et al., FEBS J. (2016) 283(14):2731-48 and Miyara, et al., Immunity (2009) 30, 899-911.

"Conventional T cells" or "Tconv" are a population of T cells that are generally CD4 positive (i.e., CD4+), but which are distinguishable from Tregs in that Tconv are generally FoxP3 negative (i.e., FoxP3−).

The term "biological sample" means a quantity of a substance from a living thing or formerly living thing. Such substances include, but are not limited to, blood, (for example, whole blood), plasma, serum, urine, amniotic fluid, synovial fluid, endothelial cells, leukocytes, monocytes, other cells, organs, tissues, bone marrow, lymph nodes and spleen.

The term "control" refers to a composition known to not contain an analyte ("negative control") or to contain analyte ("positive control"). A positive control can comprise a known concentration of analyte. "Control," "positive control," and "calibrator" may be used interchangeably herein to refer to a composition comprising a known concentration of analyte. A "positive control" can be used to establish assay performance characteristics and is a useful indicator of the integrity of reagents (for example, analytes).

"Predetermined cutoff" and "predetermined level" refer generally to an assay cutoff value that is used to assess diagnostic/prognostic/therapeutic efficacy results by comparing the assay results against the predetermined cutoff/level, where the predetermined cutoff/level already has been linked or associated with various clinical parameters (for example, severity of disease, progression/nonprogression/improvement, etc.). While the present disclosure may provide exemplary predetermined levels, it is well-known that cutoff values may vary depending on the nature of the immunoassay (for example, antibodies employed, etc.). It further is well within the skill of one of ordinary skill in the art to adapt the disclosure herein for other immunoassays to obtain immunoassay-specific cutoff values for those other immunoassays based on this disclosure. Whereas the precise value of the predetermined cutoff/level may vary between assays, correlations as described herein (if any) may be generally applicable.

The terms "inhibition" or "inhibit" refer to a decrease or cessation of any phenotypic characteristic or to the decrease or cessation in the incidence, degree, or likelihood of that characteristic. To "reduce" or "inhibit" is to decrease, reduce or arrest an activity, function, and/or amount as compared to a reference. In some embodiments, by "reduce" or "inhibit" is meant the ability to cause an overall decrease of 20% or greater. In some embodiments, by "reduce" or "inhibit" is meant the ability to cause an overall decrease of 50% or greater. In some embodiments, by "reduce" or "inhibit" is meant the ability to cause an overall decrease of 75%, 85%, 90%, 95%, or greater. In some embodiments, the amount noted above is inhibited or decreased over a period of time, relative to a control dose (such as a placebo) over the same period of time. A "reference" as used herein, refers to any sample, standard, or level that is used for comparison purposes. A reference may be obtained from a healthy and/or non-diseased sample. In some examples, a reference may be obtained from an untreated sample. In some examples, a reference is obtained from a non-diseased on non-treated sample of a subject individual. In some examples, a reference is obtained from one or more healthy individuals who are not the subject or patient.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. Unless otherwise specified, the terms "reduce", "inhibit", or "prevent" do not denote or require complete prevention over all time.

As used herein, to "suppress" a function or activity is to reduce the function or activity when compared to otherwise same conditions except for a condition or parameter of interest, or alternatively, as compared to another condition. For example, an antibody which suppresses tumor growth reduces the rate of growth of the tumor compared to the rate of growth of the tumor in the absence of the antibody.

A "therapeutically effective amount" of a substance/molecule, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A therapeutically effective amount may be delivered in one or more administrations. A therapeutically effective amount refers to an amount effective, at dosages and for periods of time necessary, to achieve the desired therapeutic and/or prophylactic result.

A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount will be less than the therapeutically effective amount.

The terms "pharmaceutical formulation" and "pharmaceutical composition" refer to a preparation which is in such form as to permit the biological activity of the active ingredient(s) to be effective, and which contains no additional components which are unacceptably toxic to a subject to which the formulation would be administered. Such formulations may be sterile.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed.

A "sterile" formulation is aseptic or essentially free from living microorganisms and their spores.

The term "IDO inhibitor" refers to an agent capable of inhibiting the activity of indoleamine 2,3-dioxygenase (IDO) and thereby reversing IDO-mediated immunosuppression. The IDO inhibitor may inhibit IDO1 and/or IDO2 (INDOL1). An IDO inhibitor may be a reversible or irreversible IDO inhibitor. A "reversible IDO inhibitor" is a compound that reversibly inhibits IDO enzyme activity either at the catalytic site or at a non-catalytic site and an "irreversible IDO inhibitor" is a compound that irreversibly inhibits IDO enzyme activity by forming a covalent bond with the enzyme. Nonlimiting exemplary IDO inhibitors include Indoximod (New Link Genetics), INCB024360 (Incyte Corp.), 1-methyl-D-tryptophan (New Link Genetics), and GDC-0919 (Genentech, Inc.).

A "chimeric antigen receptor T cell therapy" or "CAR-T therapy" refers to a therapeutic agent comprising a T cell genetically modified to express a receptor that recognizes an antigen expressed by tumor cell. The antigen may be an antigen specifically expressed by the tumor or an antigen expressed by both cancerous cells and healthy tissue. In some embodiments CAR-T therapy is adoptive CAR-T therapy, in which a patients T cells are removed and modified to express the chimeric antigen receptor, and then returned to the patient. See, e.g., Dai et al., 2016, *J Natl Cancer Inst*, 108 (7): djv439, doi: 10.1093/jnci/djv439; Gill et al., 2015, *Blood Rev*, pii: S0268-960X(15)00080-6, doi: 10.1016/j.blre.2015.10.003; Gill et al., 2015, *Immunol Rev*, 263(1):68-89. doi: 10.1111/imr.12243.

Administration "in combination with" one or more further therapeutic agents includes simultaneous (concurrent) and consecutive or sequential administration in any order.

The term "concurrently" is used herein to refer to administration of two or more therapeutic agents, where at least part of the administration overlaps in time or where the administration of one therapeutic agent falls within a short period of time relative to administration of the other therapeutic agent. For example, the two or more therapeutic agents are administered with a time separation of no more than about a specified number of minutes.

The term "sequentially" is used herein to refer to administration of two or more therapeutic agents where the administration of one or more agent(s) continues after discontinuing the administration of one or more other agent(s), or wherein administration of one or more agent(s) begins before the administration of one or more other agent(s). For example, administration of the two or more therapeutic agents are administered with a time separation of more than about a specified number of minutes.

As used herein, "in conjunction with" refers to administration of one treatment modality in addition to another treatment modality. As such, "in conjunction with" refers to administration of one treatment modality before, during or after administration of the other treatment modality to the individual.

The term "package insert" is used to refer to instructions customarily included in commercial packages of therapeutic products, that contain information about the indications, usage, dosage, administration, combination therapy, contraindications and/or warnings concerning the use of such therapeutic products.

An "article of manufacture" is any manufacture (for example, a package or container) or kit comprising at least one reagent, for example, a medicament for treatment of a disease or disorder (for example, cancer), or a probe for specifically detecting a biomarker described herein. In some embodiments, the manufacture or kit is promoted, distributed, or sold as a unit for performing the methods described herein.

The terms "label" and "detectable label" mean a moiety attached to an antibody or its analyte to render a reaction (for example, binding) between the members of the specific binding pair, detectable. The labeled member of the specific binding pair is referred to as "detectably labeled." Thus, the term "labeled binding protein" refers to a protein with a label incorporated that provides for the identification of the binding protein. In some embodiments, the label is a detectable marker that can produce a signal that is detectable by visual or instrumental means, for example, incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Examples of labels for polypeptides include, but are not limited to, the following: radioisotopes or radionuclides (for example, $^3$H, $^{14}$C, $^{35}$S, $^{90}$Y $^{99}$Tc, $^{111}$In, $^{125}$I, $^{131}$I, $^{177}$Lu, $^{166}$Ho, or $^{153}$Sm); chromogens, fluorescent labels (for example, FITC, rhodamine, lanthanide phosphors), enzymatic labels (for example, horseradish peroxidase, luciferase, alkaline phosphatase); chemiluminescent markers; biotinyl groups; predetermined polypeptide epitopes recognized by a secondary reporter (for example, leucine zipper pair sequences, binding sites for secondary antibodies, metal binding domains, epitope tags); and magnetic agents, such as gadolinium chelates. Representative examples of labels commonly employed for immunoassays include moieties that produce light, for example, acridinium compounds, and moieties that produce fluorescence, for example, fluorescein. In this regard, the moiety itself may not be detectably labeled but may become detectable upon reaction with yet another moiety.

The term "conjugate" refers to an antibody that is chemically linked to a second chemical moiety, such as a therapeutic or cytotoxic agent. The term "agent" includes a chemical compound, a mixture of chemical compounds, a biological macromolecule, or an extract made from biological materials. In some embodiments, the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. When employed in the context of an immunoassay, the conjugate antibody may be a detectably labeled antibody used as the detection antibody.

II. Anti-CCR8 Antibodies

Novel antibodies directed against CCR8 are provided. Anti-CCR8 antibodies include, but are not limited to, humanized antibodies, chimeric antibodies, mouse antibodies, human antibodies, and antibodies comprising the heavy chain and/or light chain CDRs discussed herein. In some embodiments, an isolated antibody that binds to CCR8 is provided. In some embodiments, a monoclonal antibody that binds to CCR8 is provided. In some embodiments, an anti-CCR8 antibody is an antagonist anti-CCR8 antibody. In some embodiments, an anti-CCR8 antibody provided herein inhibits binding of CCR8 to CCL1. In some embodiments, administration of the anti-CCR8 antibodies described herein reduces infiltrating Treg cells in a cancer in a subject. In some embodiments, administration of the anti-CCR8 antibodies herein treats blood cancer that expresses CCR8.

In some embodiments, an anti-CCR8 antibody comprises at least one, two, three, four, five, or six CDRs selected from (a) HCDR1 comprising the amino acid sequence of SEQ ID NO: 12; (b) HCDR2 comprising the amino acid sequence of SEQ ID NO: 13; (c) HCDR3 comprising the amino acid sequence of SEQ ID NO: 14; (d) LCDR1 comprising the amino acid sequence of SEQ ID NO: 15; (e) LCDR2 comprising the amino acid sequence of SEQ ID NO: 16; and (f) LCDR3 comprising the amino acid sequence of SEQ ID NO: 17.

In some embodiments, an anti-CCR8 antibody comprises at least one, two, three, four, five, or six CDRs selected from (a) HCDR1 comprising the amino acid sequence of SEQ ID NO: 24; (b) HCDR2 comprising the amino acid sequence of SEQ ID NO: 25; (c) HCDR3 comprising the amino acid sequence of SEQ ID NO: 26; (d) LCDR1 comprising the amino acid sequence of SEQ ID NO: 27; (e) LCDR2 comprising the amino acid sequence of SEQ ID NO: 28; and (f) LCDR3 comprising the amino acid sequence of SEQ ID NO: 29.

In some embodiments, an anti-CCR8 antibody comprises at least one, two, three, four, five, or six CDRs selected from (a) HCDR1 comprising the amino acid sequence of SEQ ID NO: 36; (b) HCDR2 comprising the amino acid sequence of SEQ ID NO: 37; (c) HCDR3 comprising the amino acid sequence of SEQ ID NO: 38; (d) LCDR1 comprising the amino acid sequence of SEQ ID NO: 39; (e) LCDR2 comprising the amino acid sequence of SEQ ID NO: 40; and (f) LCDR3 comprising the amino acid sequence of SEQ ID NO: 41.

In some embodiments, an anti-CCR8 antibody comprises at least one, two, three, four, five, or six CDRs selected from (a) HCDR1 comprising the amino acid sequence of SEQ ID NO: 48; (b) HCDR2 comprising the amino acid sequence of SEQ ID NO: 49; (c) HCDR3 comprising the amino acid sequence of SEQ ID NO: 50; (d) LCDR1 comprising the amino acid sequence of SEQ ID NO: 51; (e) LCDR2 comprising the amino acid sequence of SEQ ID NO: 52; and (f) LCDR3 comprising the amino acid sequence of SEQ ID NO: 53.

In some embodiments, an anti-CCR8 antibody comprises at least one, two, three, four, five, or six CDRs selected from (a) HCDR1 comprising the amino acid sequence of SEQ ID NO: 60; (b) HCDR2 comprising the amino acid sequence of SEQ ID NO: 61, 72, or 78; (c) HCDR3 comprising the amino acid sequence of SEQ ID NO: 62, 73, or 79; (d) LCDR1 comprising the amino acid sequence of SEQ ID NO: 63; (e) LCDR2 comprising the amino acid sequence of SEQ ID NO: 64; and (f) LCDR3 comprising the amino acid sequence of SEQ ID NO: 65.

In some embodiments, an anti-CCR8 antibody comprises at least one, two, three, four, five, or six CDRs selected from (a) HCDR1 comprising the amino acid sequence of SEQ ID NO: 84 or 100; (b) HCDR2 comprising the amino acid sequence of SEQ ID NO: 85; (c) HCDR3 comprising the amino acid sequence of SEQ ID NO: 86; (d) LCDR1 comprising the amino acid sequence selected of SEQ ID NO: 87; (e) LCDR2 comprising the amino acid sequence of SEQ ID NO: 88; and (f) LCDR3 comprising the amino acid sequence of SEQ ID NO: 89.

In some embodiments, an anti-CCR8 antibody comprises a heavy chain variable region and a light chain variable region. In some embodiments, an anti-CCR8 antibody comprises at least one heavy chain comprising a heavy chain variable region and at least a portion of a heavy chain constant region, and at least one light chain comprising a light chain variable region and at least a portion of a light chain constant region. In some embodiments, an anti-CCR8 antibody comprises two heavy chains, wherein each heavy chain comprises a heavy chain variable region and at least a portion of a heavy chain constant region, and two light chains, wherein each light chain comprises a light chain variable region and at least a portion of a light chain constant region. As used herein, a single-chain Fv (scFv), or any other antibody that comprises, for example, a single polypeptide chain comprising all six CDRs (three heavy chain CDRs and three light chain CDRs) is considered to have a heavy chain and a light chain. In some embodiments, the heavy chain is the region of the anti-CCR8 antibody that comprises the three heavy chain CDRs. In some embodiments, the light chain is the region of the anti-CCR8 antibody that comprises the three light chain CDRs.

In some embodiments, the anti-CCR8 antibody comprises six CDRs including (a) HCDR1 comprising the amino acid sequence of SEQ ID NO: 12; (b) HCDR2 comprising the amino acid sequence of SEQ ID NO: 13; (c) HCDR3 comprising the amino acid sequence of SEQ ID NO: 14; (d) LCDR1 comprising the amino acid sequence of SEQ ID NO: 15; (e) LCDR2 comprising the amino acid sequence of SEQ ID NO: 16; and (f) LCDR3 comprising the amino acid sequence of SEQ ID NO: 17.

In some embodiments, the anti-CCR8 antibody comprises six CDRs including (a) HCDR1 comprising the amino acid sequence of SEQ ID NO: 24; (b) HCDR2 comprising the amino acid sequence of SEQ ID NO: 25; (c) HCDR3 comprising the amino acid sequence of SEQ ID NO: 26; (d) LCDR1 comprising the amino acid sequence of SEQ ID NO: 27; (e) LCDR2 comprising the amino acid sequence of SEQ ID NO: 28; and (f) LCDR3 comprising the amino acid sequence of SEQ ID NO: 29.

In some embodiments, the anti-CCR8 antibody comprises six CDRs including (a) HCDR1 comprising the amino acid sequence of SEQ ID NO: 36; (b) HCDR2 comprising the amino acid sequence of SEQ ID NO: 37; (c) HCDR3 comprising the amino acid sequence of SEQ ID NO: 38; (d) LCDR1 comprising the amino acid sequence of SEQ ID NO: 39; (e) LCDR2 comprising the amino acid sequence of SEQ ID NO: 40; and (f) LCDR3 comprising the amino acid sequence of SEQ ID NO: 41.

In some embodiments, the anti-CCR8 antibody comprises six CDRs including (a) HCDR1 comprising the amino acid sequence of SEQ ID NO: 48; (b) HCDR2 comprising the amino acid sequence of SEQ ID NO: 49; (c) HCDR3 comprising the amino acid sequence of SEQ ID NO: 50; (d) LCDR1 comprising the amino acid sequence of SEQ ID NO: 51; (e) LCDR2 comprising the amino acid sequence of SEQ ID NO: 52; and (f) LCDR3 comprising the amino acid sequence of SEQ ID NO: 53.

In some embodiments, the anti-CCR8 antibody comprises six CDRs including (a) HCDR1 comprising the amino acid sequence of SEQ ID NO: 60; (b) HCDR2 comprising the amino acid sequence of SEQ ID NO: 61, 72, or 78; (c) HCDR3 comprising the amino acid sequence of SEQ ID NO: 62, 73, or 79; (d) LCDR1 comprising the amino acid sequence of SEQ ID NO: 63; (e) LCDR2 comprising the amino acid sequence of SEQ ID NO: 64; and (f) LCDR3 comprising the amino acid sequence of SEQ ID NO: 65.

In some embodiments, the anti-CCR8 antibody comprises six CDRs including (a) HCDR1 comprising the amino acid sequence of SEQ ID NO: 84 or 100; (b) HCDR2 comprising the amino acid sequence of SEQ ID NO: 85; (c) HCDR3 comprising the amino acid sequence of SEQ ID NO: 86; (d) LCDR1 comprising the amino acid sequence of SEQ ID NO: 87; (e) LCDR2 comprising the amino acid sequence of SEQ ID NO: 88; and (f) LCDR3 comprising the amino acid sequence of SEQ ID NO: 89.

In some embodiments, the anti-CCR8 antibody comprises the six CDRs as described above and binds to CCR8. In some embodiments, the anti-CCR8 antibody comprises the six CDRs as described above, binds to CCR8 and inhibits binding of CCR8 to CCL1. In some embodiments, the anti-CCR8 antibody comprises the six CDRs as described above, binds to CCR8 and enhances an immune response in a subject, and/or increases activation of T cells in a subject following administration of the antibody to the subject.

In some embodiments, an anti-CCR8 antibody is provided that competes with an anti-CCR8 antibody described herein for binding to CCR8. In some embodiments, an antibody that competes for binding with any of the antibodies provided herein can be made and/or used.

In some embodiments, the anti-CCR8 antibody comprises at least one, at least two, or all three VH CDR sequences selected from (a) HCDR1 comprising the amino acid sequence of SEQ ID NO: 12; (b) HCDR2 comprising the amino acid sequence of SEQ ID NO: 13; (c) HCDR3 comprising the amino acid sequence of SEQ ID NO: 14.

In some embodiments, the anti-CCR8 antibody comprises at least one, at least two, or all three VH CDR sequences selected from (a) HCDR1 comprising the amino acid sequence of SEQ ID NO: 24; (b) HCDR2 comprising the amino acid sequence of SEQ ID NO: 25; (c) HCDR3 comprising the amino acid sequence of SEQ ID NO: 26.

In some embodiments, the anti-CCR8 antibody comprises at least one, at least two, or all three VH CDR sequences selected from (a) HCDR1 comprising the amino acid sequence of SEQ ID NO: 36; (b) HCDR2 comprising the amino acid sequence of SEQ ID NO: 37; (c) HCDR3 comprising the amino acid sequence of SEQ ID NO: 38.

In some embodiments, the anti-CCR8 antibody comprises at least one, at least two, or all three VH CDR sequences selected from (a) HCDR1 comprising the amino acid sequence of SEQ ID NO: 48; (b) HCDR2 comprising the amino acid sequence of SEQ ID NO: 49; (c) HCDR3 comprising the amino acid sequence of SEQ ID NO: 50.

In some embodiments, the anti-CCR8 antibody comprises at least one, at least two, or all three VH CDR sequences selected from (a) HCDR1 comprising the amino acid sequence of SEQ ID NO: 60; (b) HCDR2 comprising the amino acid sequence of SEQ ID NO: 61, 72, or 78; (c) HCDR3 comprising the amino acid sequence of SEQ ID NO: 62, 73, or 79.

In some embodiments, the anti-CCR8 antibody comprises at least one, at least two, or all three VH CDR sequences selected from (a) HCDR1 comprising the amino acid sequence of SEQ ID NO: 84 or 100; (b) HCDR2 comprising the amino acid sequence of SEQ ID NO: 85; and (c) HCDR3 comprising the amino acid sequence of SEQ ID NO: 86.

In some embodiments, the anti-CCR8 antibody comprises at least one, at least two, or all three VL CDR sequences selected from (a) LCDR1 comprising the amino acid sequence of SEQ ID NO: 15; (b) LCDR2 comprising the amino acid sequence of SEQ ID NO: 16; and (c) LCDR3 comprising the amino acid sequence of SEQ ID NO: 17.

In some embodiments, the anti-CCR8 antibody comprises at least one, at least two, or all three VL CDR sequences selected from (a) LCDR1 comprising the amino acid sequence of SEQ ID NO: 27; (b) LCDR2 comprising the amino acid sequence of SEQ ID NO: 28; and (c) LCDR3 comprising the amino acid sequence of SEQ ID NO: 29.

In some embodiments, the anti-CCR8 antibody comprises at least one, at least two, or all three VL CDR sequences selected from (a) LCDR1 comprising the amino acid sequence of SEQ ID NO: 39; (b) LCDR2 comprising the amino acid sequence of SEQ ID NO: 40; and (c) LCDR3 comprising the amino acid sequence of SEQ ID NO: 41.

In some embodiments, the anti-CCR8 antibody comprises at least one, at least two, or all three VL CDR sequences selected from (a) LCDR1 comprising the amino acid sequence of SEQ ID NO: 51; (b) LCDR2 comprising the amino acid sequence of SEQ ID NO: 52; and (c) LCDR3 comprising the amino acid sequence of SEQ ID NO: 53.

In some embodiments, the anti-CCR8 antibody comprises at least one, at least two, or all three VL CDR sequences selected from (a) LCDR1 comprising the amino acid sequence of SEQ ID NO: 63; (b) LCDR2 comprising the amino acid sequence of SEQ ID NO: 64; and (c) LCDR3 comprising the amino acid sequence of SEQ ID NO: 65.

In some embodiments, the anti-CCR8 antibody comprises at least one, at least two, or all three VL CDR sequences selected from (a) LCDR1 comprising the amino acid sequence of SEQ ID NO: 87; (b) LCDR2 comprising the amino acid sequence of SEQ ID NO: 88; and (c) LCDR3 comprising the amino acid sequence of SEQ ID NO: 89.

In some embodiments, any of the six CDRs provided herein can be combined as subparts with any of the other CDRs provided herein, for a total of six CDRs in a construct. Thus, in some embodiments, two CDRs from a first antibody (for example, HCDR1 and HCDR2) can be combined with four CDRs from a second antibody (HCDR3, LCDR1, LCDR2, and LCDR3). In some embodiments, two or fewer residues in one or more of the CDRs can be replaced to obtain a variant thereof. In some embodiments, two or fewer residues can be replaced in 1, 2, 3, 4, 5, or 6 of the CDRs.

In some embodiments, the anti-CCR8 antibody comprises (I) a VH domain comprising at least one, at least two, or all three VH CDR sequences selected from (a) HCDR1 comprising the amino acid sequence of SEQ ID NO: 12; (b) HCDR2 comprising the amino acid sequence of SEQ ID NO: 13; (c) HCDR3 comprising the amino acid sequence of SEQ ID NO: 14; and (II) a VL domain comprising at least one, at least two, or all three VL CDR sequences selected from (d) LCDR1 comprising the amino acid sequence of SEQ ID NO: 15; (e) LCDR2 comprising the amino acid sequence of SEQ ID NO: 16; and (f) LCDR3 comprising the amino acid sequence of SEQ ID NO: 17.

In some embodiments, the anti-CCR8 antibody comprises (I) a VH domain comprising at least one, at least two, or all three VH CDR sequences selected from (a) HCDR1 comprising the amino acid sequence of SEQ ID NO: 24; (b) HCDR2 comprising the amino acid sequence of SEQ ID NO: 25; (c) HCDR3 comprising the amino acid sequence of SEQ ID NO: 26; and (II) a VL domain comprising at least one, at least two, or all three VL CDR sequences selected from (d) LCDR1 comprising the amino acid sequence of SEQ ID NO: 27; (e) LCDR2 comprising the amino acid sequence of SEQ ID NO: 28; and (f) LCDR3 comprising the amino acid sequence of SEQ ID NO: 29.

In some embodiments, the anti-CCR8 antibody comprises (I) a VH domain comprising at least one, at least two, or all three VH CDR sequences selected from (a) HCDR1 comprising the amino acid sequence of SEQ ID NO: 36; (b) HCDR2 comprising the amino acid sequence of SEQ ID NO: 37; (c) HCDR3 comprising the amino acid sequence of SEQ ID NO: 38; and (II) a VL domain comprising at least one, at least two, or all three VL CDR sequences selected from (d) LCDR1 comprising the amino acid sequence of SEQ ID NO: 39; (e) LCDR2 comprising the amino acid sequence of SEQ ID NO: 40; and (f) LCDR3 comprising the amino acid sequence of SEQ ID NO: 41.

In some embodiments, the anti-CCR8 antibody comprises (I) a VH domain comprising at least one, at least two, or all three VH CDR sequences selected from (a) HCDR1 comprising the amino acid sequence of SEQ ID NO: 48; (b) HCDR2 comprising the amino acid sequence of SEQ ID NO: 49; (c) HCDR3 comprising the amino acid sequence of SEQ ID NO: 50; and (II) a VL domain comprising at least one, at least two, or all three VL CDR sequences selected from (d) LCDR1 comprising the amino acid sequence of SEQ ID NO: 51; (e) LCDR2 comprising the amino acid sequence of SEQ ID NO: 52; and (f) LCDR3 comprising the amino acid sequence of SEQ ID NO: 53.

In some embodiments, the anti-CCR8 antibody comprises (I) a VH domain comprising at least one, at least two, or all three VH CDR sequences selected from (a) HCDR1 comprising the amino acid sequence of SEQ ID NO: 60; (b) HCDR2 comprising the amino acid sequence of SEQ ID NO: 61, 72, or 78; (c) HCDR3 comprising the amino acid sequence of SEQ ID NO: 62, 73, or 79; and (II) a VL domain comprising at least one, at least two, or all three VL CDR sequences selected from (d) LCDR1 comprising the amino acid sequence of SEQ ID NO: 63; (e) LCDR2 comprising the amino acid sequence of SEQ ID NO: 64; and (f) LCDR3 comprising the amino acid sequence of SEQ ID NO: 65.

In some embodiments, the anti-CCR8 antibody comprises (I) a VH domain comprising at least one, at least two, or all three VH CDR sequences selected from (a) HCDR1 comprising the amino acid sequence of SEQ ID NO: 84 or 100; (b) HCDR2 comprising the amino acid sequence of SEQ ID NO: 85; (c) HCDR3 comprising the amino acid sequence of SEQ ID NO: 86; and (II) a VL domain comprising at least one, at least two, or all three VL CDR sequences selected from (d) LCDR1 comprising the amino acid sequence of SEQ ID NO: 87; (e) LCDR2 comprising the amino acid sequence of SEQ ID NO: 88; and (f) LCDR3 comprising the amino acid sequence of SEQ ID NO: 89.

In some embodiments, an anti-CCR8 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 68 or 74. In some embodiments, a VH sequence having at least 90%, 91%, 92%, 93%, 94%, 95%, 96%, 97%, 98%, or 99% identity contains substitutions (for example, conservative substitutions), insertions, or deletions relative to the reference sequence, but an anti-CCR8 antibody comprising that sequence retains the ability to bind to CCR8. In some embodiments, a total of 1 to 10 amino acids (e.g., 1, 2, 3, 4, 5, 6, 7, 8, 9, or 10 amino acids) have been substituted, inserted and/or deleted in SEQ ID NO: 68 or 74. In some embodiments, substitutions, insertions, or deletions occur in regions outside the CDRs (that is, in the FRs). Optionally, the anti-CCR8 antibody comprises the VH sequence in SEQ ID NO: 68 or 74, including post-translational modifications of that sequence.

In some embodiments, the VH comprises: (a) HCDR1 comprising the amino acid sequence of SEQ ID NO: 60; (b) HCDR2 comprising the amino acid sequence of SEQ ID NO: 61, 72, or 78; (c) HCDR3 comprising the amino acid sequence of SEQ ID NO: 62, 73, or 79.

In some embodiments, an anti-CCR8 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 92 or 96. In some embodiments, a VH sequence having at least 90%, 91%, 92%, 93%, 94%, 95%, 96%, 97%, 98%, or 99% identity contains substitutions (for example, conservative substitutions), insertions, or deletions relative to the reference sequence, but an anti-CCR8 antibody comprising that sequence retains the ability to bind to CCR8. In some embodiments, a total of 1 to 10 amino acids (e.g., 1, 2, 3, 4, 5, 6, 7, 8, 9, or 10 amino acids) have been substituted, inserted and/or deleted in SEQ ID NO: 92 or 96. In some embodiments, substitutions, insertions, or deletions occur in regions outside the CDRs (that is, in the FRs). Optionally, the anti-CCR8 antibody comprises the VH sequence in SEQ ID NO: 92 or 96, including post-translational modifications of that sequence.

In some embodiments, the VH comprises: (a) HCDR1 comprising the amino acid sequence of SEQ ID NO: 84 or 100; (b) HCDR2 comprising the amino acid sequence of SEQ ID NO: 85; (c) HCDR3 comprising the amino acid sequence of SEQ ID NO: 86.

In some embodiments, an anti-CCR8 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 69 or 75. In some embodiments, a VL sequence having at least 90%, 91%, 92%, 93%, 94%, 95%, 96%, 97%, 98%, or 99% identity contains substitutions (for example, conservative substitutions), insertions, or deletions relative to the reference sequence, but an anti-CCR8 antibody comprising that sequence retains the ability to bind to CCR8. In some embodiments, a total of 1 to 10 amino acids (e.g., 1, 2, 3, 4, 5, 6, 7, 8, 9, or 10 amino acids) have been substituted, inserted and/or deleted in SEQ ID NO: 69 or 75. In some embodiments, the substitutions, insertions, or deletions occur in regions outside the CDRs (that is, in the FRs). Optionally, the anti-CCR8 antibody comprises the VL sequence in SEQ ID NO: 69 or 75, including post-translational modifications of that sequence.

In some embodiments, the VL comprises: (a) LCDR1 comprising the amino acid sequence of SEQ ID NO: 63; (b) LCDR2 comprising the amino acid sequence of SEQ ID NO: 64; and (c) LCDR3 comprising the amino acid sequence of SEQ ID NO: 65.

In some embodiments, an anti-CCR8 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 93 or 97. In some embodiments, a VL sequence having at least 90%, 91%, 92%, 93%, 94%, 95%, 96%, 97%, 98%, or 99% identity contains substitutions (for example, conservative substitutions), insertions, or deletions relative to the reference sequence, but an anti-CCR8 antibody comprising that sequence retains the ability to bind to CCR8. In some embodiments, a total of 1 to 10 amino acids (e.g., 1, 2, 3, 4, 5, 6, 7, 8, 9, or 10 amino acids) have been substituted, inserted and/or deleted in SEQ ID NO: 93 or 97. In some embodiments, the substitutions, insertions, or deletions occur in regions outside the CDRs (that is, in the FRs). Optionally, the anti-CCR8 antibody comprises the VL sequence in SEQ ID NO: 93 or 97, including post-translational modifications of that sequence.

In some embodiments, the VL comprises: (a) LCDR1 comprising the amino acid sequence of SEQ ID NO: 87; (b) LCDR2 comprising the amino acid sequence of SEQ ID NO: 88; and (c) LCDR3 comprising the amino acid sequence of SEQ ID NO: 89.

In some embodiments, an anti-CCR8 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 68 or 74 and a light chain variable domain (VL) having at least 90%, 91%, 92%, 93%, 94%, 95%, 96%, 97%, 98%, 99%, or 100% sequence identity to the amino acid sequence of SEQ ID NO: 69 or 75. In some embodiments, a VH sequence having at least 90%, 91%, 92%, 93%, 94%, 95%, 96%, 97%, 98%, or 99% identity contains substitutions (for example, conservative substitutions), insertions, or deletions relative to the reference sequence, and a VL sequence having at least 90%, 91%, 92%, 93%, 94%, 95%, 96%, 97%, 98%, or 99% identity contains substitutions (for example, conservative substitutions), insertions, or deletions relative to the reference sequence, but an anti-CCR8 antibody comprising that sequence retains the ability to bind to CCR8. In some embodiments, a total of 1 to 10 amino acids (e.g., 1, 2, 3, 4, 5, 6, 7, 8, 9, or 10 amino acids) have been substituted, inserted and/or deleted in SEQ ID NO: 68 or 74. In some embodiments, a total of 1 to 10 amino acids (e.g., 1, 2, 3, 4, 5, 6, 7, 8, 9, or 10 amino acids) have been substituted, inserted and/or deleted in SEQ ID NO: 69 or 75. In some embodiments, substitutions, insertions, or deletions occur in regions outside the CDRs (that is, in the FRs). In some embodiments, the anti-CCR8 antibody comprises (a) HCDR1 comprising the amino acid sequence of SEQ ID NO: 60; (b) HCDR2 comprising the amino acid sequence of SEQ ID NO: 61, 72, or 78; (c) HCDR3 comprising the amino acid sequence of SEQ ID NO: 62, 73, or 79; (d) LCDR1 comprising the amino acid sequence of SEQ ID NO: 63; (e) LCDR2 comprising the amino acid sequence of SEQ ID NO: 64; and (f) LCDR3 comprising the amino acid sequence of SEQ ID NO: 65.

In some embodiments, the anti-CCR8 antibody comprises the VH sequence in SEQ ID NO: 68 or 74, including post-translational modifications of one or both sequences, and comprises the VL sequence in SEQ ID NO: 69 or 75, including post-translational modifications of one or both sequences.

In some embodiments, an anti-CCR8 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 92 or 96 and a light chain variable domain (VL) having at least 90%, 91%, 92%, 93%, 94%, 95%, 96%, 97%, 98%, 99%, or 100% sequence identity to the amino acid sequence of SEQ ID NO: 93 or 97. In some embodiments, a VH sequence having at least 90%, 91%, 92%, 93%, 94%, 95%, 96%, 97%, 98%, or 99% identity contains substitutions (for example, conservative substitutions), insertions, or deletions relative to the reference sequence, and a VL sequence having at least 90%, 91%, 92%, 93%, 94%, 95%, 96%, 97%, 98%, or 99% identity contains substitutions (for example, conservative substitutions), insertions, or deletions relative to the reference sequence, but an anti-CCR8 antibody comprising that sequence retains the ability to bind to CCR8. In some embodiments, a total of 1 to 10 amino acids (e.g., 1, 2, 3, 4, 5, 6, 7, 8, 9, or 10 amino acids) have been substituted, inserted and/or deleted in SEQ ID NO: 92 or 96. In some embodiments, a total of 1 to 10 amino acids (e.g., 1, 2, 3, 4, 5, 6, 7, 8, 9, or 10 amino acids) have been substituted, inserted and/or deleted in SEQ ID NO: 93 or 97. In some embodiments, substitutions, insertions, or deletions occur in regions outside the CDRs (that is, in the FRs). In some embodiments, the anti-CCR8 antibody comprises (a) HCDR1 comprising the amino acid sequence of SEQ ID NO: 84 or 100; (b) HCDR2 comprising the amino acid sequence of SEQ ID NO: 85; (c) HCDR3 comprising the amino acid sequence of SEQ ID NO: 86; (d) LCDR1 comprising the amino acid sequence of SEQ ID NO: 87; (e) LCDR2 comprising the amino acid sequence of SEQ ID NO: 88; and (f) LCDR3 comprising the amino acid sequence of SEQ ID NO: 89.

In some embodiments, the anti-CCR8 antibody comprises the VH sequence in SEQ ID NO: 92 or 96, including post-translational modifications of one or both sequences, and comprises the VL sequence in SEQ ID NO: 93 or 97, including post-translational modifications of one or both sequences.

In some embodiments, an anti-CCR8 antibody comprises a VH as in any of the embodiments provided herein, and a VL as in any of the embodiments provided herein. In some embodiments, the antibody comprises the VH and VL sequences in SEQ ID NO: 68 or 74 and SEQ ID NO: 69 or 75, respectively, including post-translational modifications of those sequences. In some embodiments, the antibody comprises the VH and VL sequences in SEQ ID NO: 92 or 96 and SEQ ID NO: 93 or 97, respectively, including post-translational modifications of those sequences.

In some embodiments, an anti-CCR8 antibody is provided, wherein the antibody comprises a heavy chain (HC) having at least 90%, 91%, 92%, 93%, 94%, 95%, 96%, 97%, 98%, 99%, or 100% sequence identity to the amino acid sequence of SEQ ID NO: 70 or 76. Optionally, the anti-CCR8 antibody comprises the HC sequence in SEQ ID NO: 70 or 76, including post-translational modifications.

In some embodiments, an anti-CCR8 antibody is provided, wherein the antibody comprises a HC having at least 90%, 91%, 92%, 93%, 94%, 95%, 96%, 97%, 98%, 99%, or 100% sequence identity to the amino acid sequence of SEQ ID NO: 94 or 98. Optionally, the anti-CCR8 antibody comprises the HC sequence in SEQ ID NO: 94 or 98, including post-translational modifications.

In some embodiments, an anti-CCR8 antibody is provided, wherein the antibody comprises a light chain (LC) having at least 90%, 91%, 92%, 93%, 94%, 95%, 96%, 97%, 98%, 99%, or 100% sequence identity to the amino acid sequence of SEQ ID NO: 71 or 77. Optionally, the anti-CCR8 antibody comprises the LC sequence in SEQ ID NO: 71 or 77, including post-translational modifications.

In some embodiments, an anti-CCR8 antibody is provided, wherein the antibody comprises a LC having at least 90%, 91%, 92%, 93%, 94%, 95%, 96%, 97%, 98%, 99%, or 100% sequence identity to the amino acid sequence of SEQ ID NO: 95 or 99. Optionally, the anti-CCR8 antibody comprises the LC sequence in SEQ ID NO: 95 or 99, including post-translational modifications.

In some embodiments, an anti-CCR8 antibody comprises a HC as in any of the embodiments provided herein, and a LC as in any of the embodiments provided herein. In some embodiments, the antibody comprises the HC and LC sequences in SEQ ID NO: 70 or 76 and SEQ ID NO: 71 or 77, respectively, including post-translational modifications of those sequences. In some embodiments, the antibody comprises the HC and LC sequences in SEQ ID NO: 94 or 98 and SEQ ID NO: 95 or 99, respectively, including post-translational modifications of those sequences.

In some embodiments, antibodies that compete with the anti-CCR8 antibodies provided herein for binding to CCR8 are provided. In some embodiments, antibodies compete with the anti-CCR8 antibodies provided herein for binding to an epitope on CCR8.

In some embodiments, competition assays may be used to identify a monoclonal antibody that competes with an anti-CCR8 antibody described herein (such as 1-K16, 1-K17, 6-B09, 7-B16, 13-E16, and/or 19-O07) for binding to CCR8. Competition assays can be used to determine whether two antibodies bind the same epitope by recognizing identical or sterically overlapping epitopes or one antibody competitively inhibits binding of another antibody to the antigen. In some embodiments, such a competing antibody binds to the same epitope that is bound by an antibody described herein. Exemplary competition assays include, but are not limited to, routine assays such as those provided in Harlow and Lane (1988) Antibodies: A Laboratory Manual ch. 14 (Cold Spring Harbor Laboratory, Cold Spring Harbor, N.Y.). Detailed exemplary methods for mapping an epitope to which an antibody binds are provided in Morris (1996) "Epitope Mapping Protocols," in Methods in Molecular Biology vol. 66 (Humana Press, Totowa, N.J.). In some embodiments, two antibodies are said to bind to the same epitope if each blocks binding of the other by 50% or more. In some embodiments, the antibody that competes with an anti-CCR8 antibody described herein is a chimeric, humanized or human antibody. In some embodiments, an antibody that competes with a chimeric, humanized, or human anti-CCR8 antibody as described herein is provided.

Additionally, the present disclosure also provides variants of the foregoing disclosed antibodies, such as variants of a 7-B16 antibody. For example, in some embodiments, the disclosure provides an isolated antibody that binds human CCR8, wherein the antibody comprises a HCDR3 comprising SEQ ID NO: 86 or a variant of SEQ ID NO: 86 comprising 1, 2, or 3 mutations, and wherein the antibody binds to human CCR8 and possesses ADCC activity. In some embodiments, the mutation is a substitution (e.g., a conservative or a non-conservative substitution), a deletion, or an insertion. In some embodiments, the 1, 2, or 3 mutations are located in at least one of amino acid positions 1-4, 6, 7, or 12 of SEQ ID NO: 86. In some embodiments, the substitution is a conservative substitution. In some embodiments, the conservative substitution is at amino acid position 1, 4, or 12 of SEQ ID NO: 86. In some embodiments, the substitution is a non-conservative substitution. In some embodiments, the non-conservative substitution is at amino acid position 7 of SEQ ID NO: 86. In some embodiments, the antibody comprises at least 2 substitutions in HCDR3. In some embodiments, the at least 2 substitutions are located in at least one of amino acid positions 1-4, 6, 7, or 12 of SEQ ID NO: 86. In some embodiments, the at least 2 substitutions are conservative substitutions. In some embodiments, at least one of the conservative substitutions are at amino acid position 1, 4, or 12 of SEQ ID NO: 86. In some embodiments, the at least 2 substitutions are non-conservative substitutions. In some embodiments, at least one of the non-conservative substitutions is at amino acid position 7 of SEQ ID NO: 86. In some embodiments, the mutations comprise a conservative substitution and a non-conservative substitution when more than one substitution mutation is present. In some embodiments, the disclosure provides an isolated antibody that binds human CCR8, wherein the antibody comprises a HCDR3 that is at least 90%, 91%, 92%, 93%, 94%, 95%, 96%, 97%, 98%, or 99% identical to SEQ ID NO: 86, and wherein the antibody binds to human CCR8 and possesses ADCC activity. In some embodiments, the HCDR3 comprises an amino acid sequence selected from SEQ ID NO: 86 and any one of SEQ ID NOs: 104-119. In some embodiments, the antibody comprises a HCDR1 comprising SEQ ID NO: 84 or SEQ ID NO: 123. In some embodiments, the antibody comprises a HCDR2 comprising SEQ ID NO: 85 or SEQ ID NO: 124. In some embodiments, the antibody comprises a LCDR1 comprising SEQ ID NO: 87 or SEQ ID NO: 120. In some embodiments, the antibody comprises a LCDR2 comprising SEQ ID NO: 88 or SEQ ID NO: 121. In some embodiments, the antibody comprises a LCDR3 comprising SEQ ID NO: 89 or SEQ ID NO: 122. In some embodiments, the ADCC activity comprises an EC50 value of less than 200, 175, 150, 125, 100, 75, 50, 25, 20, 15, 10, 9, 8, 7, 6, 5, 4, 3, 2, or 1 ng/ml as measured by an ADCC reporter mechanism of action (MOA)-based bioassay, such as the Promega reporter assay disclosed in Example 7 below. In some embodiments, the ADCC activity is more potent than a 7-B16 antibody. In some embodiments, the ADCC activity is at least as potent as a 7-B16 antibody. In some embodiments, the antibody possesses a $K_D$ for human CCR8 that is equal to or lower than a 7-B16 antibody (as determined by Kinetic Exclusion Assay (i.e., KinExA), for example). In some embodiments, the antibody possesses an on-cell $K_D$ for human CCR8 that is equal to or lower than a 7-B16 antibody (as determined by Kinetic Exclusion Assay (i.e., KinExA), for example). In some embodiments, the antibody comprises at least one modification that enhances cell killing. In some embodiments, the enhanced cell killing is enhanced antibody-dependent cellular cytotoxicity (ADCC) and/or complement-dependent cytotoxicity (CDC). In some embodiments, the at least one modification is afucosylation. In some embodiments, the at least one modification is one or more heavy chain constant regions mutations at one or more positions selected from L234, L235, G236, S239, F243, H268, D270, R292, S298, Y300, V305, K326, A330, I332, E333, K334, and P396. In some embodiments, the one or more heavy chain constant region mutations are one or more mutation selected from S239D, S239M, F243L, H268D, D270E, R292P, S298A, Y300L, V305I, K326D, A330L, A330M, I332E, E333A, K334A, K334E, and P396L. In some embodiments, the one or more heavy chain constant region mutations are selected from: F243L/R292P/Y300L/V305I/P396L, S239D/I332E, S239D/I332E/A330L, S298A/E333A/K334A, L234Y/L235Q/G236W/S239M/H268D/D270E/S298A, and D270E/K326D/A330M/K334E. In some embodiments, the at least one modification is galactosylation. In some embodiments, the antibody binds human CCR8 with an affinity ($K_D$) (as determined by Kinetic Exclusion Assay (i.e., KinExA), for example) of less than 10 nM, or less than 5 nM, or less than 1 nM, or less than 500 pM, or less than 250 pM, or less than 100 pM, or less than 75 pM, or less than 50 pM, or less than 25 pM. In some embodiments, the antibody binds human CCR8 with an on-cell affinity ($K_D$) of less than 10 nM, or less than 5 nM, or less than 1 nM, or less than 500 pM, or less than 250 pM, or less than 100 pM, or less than 75 pM, or less than 50 pM, or less than 25 pM, as determined by, for example, Kinetic Exclusion Assay (i.e., KinExA). In some embodiments, the antibody is a monoclonal antibody. In some embodiments, the antibody is a human or humanized antibody. In some embodiments, the antibody is a full-length antibody. In some embodiments, the antibody is an IgG1 or IgG3 antibody. Such variants can be utilized in methods of treating cancer, including both blood cancers and solid tumors.

In some embodiments, antibodies that bind to any one or more of the epitopes that the antibodies provided herein are provided. In some embodiments, antibodies that bind and overlap an epitope to which the present antibodies bind to are provided. In some embodiments, an antibody is provided that competes with at least one of the antibodies provided herein. In some embodiments, an antibody is provided that competes with at least two of the antibodies provided herein. In some embodiments, an antibody is provided that competes with at least three of the antibodies provided herein. In some embodiments, the antibody binds to an overlapping epitope as an antibody described in the examples herein. In some embodiments, the entire epitope is bound and/or obstructed by the competing antibody. In some embodiments, a part of the epitope is bound and/or obstructed by the competing antibody. In some embodiments, the competing antibody's paratope binds to at least a part of the epitope of an antibody provided herein. In some embodiments, the competing antibody's paratope binds the target, and a different section of the competing antibody's structure obstruct at least a part of the epitope of an antibody provided herein.

Exemplary Chimeric Antibodies

In some embodiments, an antibody provided herein is a chimeric antibody. Certain chimeric antibodies are described, for example, in U.S. Pat. No. 4,816,567; and Morrison et al., (1984) Proc. Natl. Acad. Sci. USA, 81:6851-6855 (1984)). In one example, a chimeric antibody comprises a non-human variable region (for example, a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

Nonlimiting exemplary chimeric antibodies include chimeric antibodies comprising the heavy and/or light chain variable regions of an antibody selected from, e.g., antibody 1-K16, 1-K17, 6-B09, 7-B16, 13-E16 and 19-O07, as disclosed herein. Additional nonlimiting exemplary chimeric antibodies include chimeric antibodies comprising heavy chain CDR1, CDR2, and CDR3, and/or light chain CDR1, CDR2, and CDR3 of an antibody selected from antibody 1-K16, 1-K17, 6-B09, 7-B16, 13-E16 and 19-O07, as disclosed herein. In some embodiments, the chimeric anti-CCR8 antibody comprises the variable regions described above and binds to CCR8. In some embodiments, the chimeric anti-CCR8 antibody comprises the variable regions described above, binds to CCR8 and inhibits binding of CCR8 to CCL1. In some embodiments, the anti-CCR8 antibody comprises the variable regions described above, binds to CCR8 and enhances an immune response in a subject, and/or increases activation of T cells in a subject following administration of the antibody to the subject. In some embodiments, administration of the anti-CCR8 antibodies described herein stimulates the activity of an immune cell, reduces the downmodulation of an immune cell, or increases a T cell response in a subject.

In some embodiments, a chimeric antibody described herein comprises one or more human constant regions. In some embodiments, the human heavy chain constant region is of an isotype selected from IgA, IgG, IgD, and IgE. In some embodiments, the human light chain constant region is of an isotype selected from κ and λ. In some embodiments, a chimeric antibody described herein comprises a human IgG constant region. In some embodiments, a chimeric antibody described herein comprises a human IgG4 heavy chain constant region. In some embodiments, a chimeric antibody described herein comprises a human IgG4 constant region and a human κ light chain.

As noted above, whether or not effector function is desirable may depend on the particular method of treatment intended for an antibody. Thus, in some embodiments, when effector function is desirable, a chimeric anti-CCR8 antibody comprising a human IgG1 heavy chain constant region or a human IgG3 heavy chain constant region is selected. In some embodiments, when effector function is not desirable, a chimeric anti-CCR8 antibody comprising a human IgG4 or IgG2 heavy chain constant region is selected. In some embodiments, enhanced effector function is desirable.

Exemplary Humanized Antibodies

In some embodiments, humanized antibodies that bind CCR8 are provided. Humanized antibodies are useful as therapeutic molecules because humanized antibodies reduce or eliminate the human immune response as compared to non-human antibodies, which can result in an immune response to an antibody therapeutic (such as the human anti-mouse antibody (HAMA) response), and decreased effectiveness of the therapeutic.

In some embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (for example, the antibody from which the CDR residues are derived), for example, to restore or improve antibody specificity or affinity.

Humanized antibodies and methods of making them are reviewed, for example, in Almagro and Fransson, (2008) Front. Biosci. 13: 1619-1633, and are further described, for example, in Riechmann et al., (1988) *Nature* 332:323-329; Queen et al., (1989) *Proc. Natl Acad. Sci. USA* 86: 10029-10033; U.S. Pat. Nos. 5,821,337, 7,527,791, 6,982,321, and 7,087,409; Kashmiri et al., (2005) *Methods* 36:25-34; Padlan, (1991) *Mol. Immunol.* 28:489-498 (describing "resurfacing"); Dall'Acqua et al., (2005) *Methods* 36:43-60 (describing "FR shuffling"); and Osbourn et al., (2005) *Methods* 36:61-68 and Klimka et al., (2000) *Br. J. Cancer,* 83:252-260 (describing the "guided selection" approach to FR shuffling).

Human framework regions that can be used for humanization include but are not limited to: framework regions selected using the "best-fit" method (see, for example, Sims et al. (1993) *J. Immunol.* 151:2296); framework regions derived from the consensus sequence of human antibodies of a particular subgroup of light or heavy chain variable regions (see, for example, Carter et al. (1992) *Proc. Natl. Acad. Sci. USA,* 89:4285; and Presta et al. (1993) *J. Immunol,* 151:2623); human mature (somatically mutated) framework regions or human germline framework regions (see, for example, Almagro and Fransson, (2008) *Front. Biosci.* 13:1619-1633); and framework regions derived from screening FR libraries (see, for example, Baca et al., (1997) *J. Biol. Chem.* 272: 10678-10684 and Rosok et al., (1996) *J. Biol. Chem.* 271 :22611-22618).

In some embodiments, a humanized anti-CCR8 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 68 or 74 and a light chain variable domain (VL) having at least 90%, 91%, 92%, 93%, 94%, 95%, 96%, 97%, 98%, 99%, or 100% sequence identity to the amino acid sequence of SEQ ID NO: 69 or 75. In some embodiments, a VH sequence having at least 90%, 91%, 92%, 93%, 94%, 95%, 96%, 97%, 98%, or 99% identity contains substitutions (for example, conservative substitutions), insertions, or deletions relative to the reference sequence, and a VL sequence having at least 90%, 91%, 92%, 93%, 94%, 95%, 96%, 97%, 98%, or 99% identity contains substitutions (for example, conservative substitutions), insertions, or deletions relative to the reference sequence, but an anti-CCR8 antibody comprising that sequence retains the ability to bind to CCR8. In some embodiments, a total of 1 to 10 amino acids (e.g., 1, 2, 3, 4, 5, 6, 7, 8, 9, or 10 amino acids) have been substituted, inserted and/or deleted in SEQ ID NO: 68 or 74. In some embodiments, a total of 1 to 10 amino acids (e.g., 1, 2, 3, 4, 5, 6, 7, 8, 9, or 10 amino acids) have been substituted, inserted and/or deleted in SEQ ID NO: 69 or 75. In some embodiments, substitutions, insertions, or deletions occur in regions outside the CDRs (that is, in the FRs). In some embodiments, the anti-CCR8 antibody comprises (a) HCDR1 comprising the amino acid sequence of SEQ ID NO: 60; (b) HCDR2 comprising the amino acid sequence of SEQ ID NO: 61, 72, or 78; (c) HCDR3 comprising the amino acid sequence of SEQ ID NO: 62, 73, or 79; (d) LCDR1 comprising the amino acid sequence of SEQ ID NO: 63; (e) LCDR2 comprising the amino acid sequence of SEQ ID NO: 64; and (f) LCDR3 comprising the amino acid sequence of SEQ ID NO: 65. In some embodiments, the antibody possesses ADCC activity. In some embodiments, the ADCC activity comprises an EC50 value of less than 200, 175, 150, 125, 100, 75, 50, 25, 20, 15, 10, 9, 8, 7, 6, 5, 4, 3, 2, or 1 ng/ml as measured by an ADCC reporter mechanism of action (MOA)-based bioassay. In some embodiments, the ADCC activity is more potent than a 7-B16 antibody. In some embodiments, the ADCC activity is at least as potent as a 7-B16 antibody. In some embodiments, the antibody possesses a $K_D$ for human CCR8 that is equal to or lower than a 7-B16 antibody (as determined by Kinetic Exclusion Assay (i.e., KinExA), for example). In some embodiments, the antibody possesses an on-cell $K_D$ for human CCR8 that is equal to or lower than a 7-B16 antibody (as determined by Kinetic Exclusion Assay (i.e., KinExA), for example).

In some embodiments, the humanized anti-CCR8 antibody comprises the VH sequence in SEQ ID NO: 68 or 74, including post-translational modifications of one or both sequences, and comprises the VL sequence in SEQ ID NO: 69 or 75, including post-translational modifications of one or both sequences.

In some embodiments, a humanized anti-CCR8 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 92 or 96 and a light chain variable domain (VL) having at least 90%, 91%, 92%, 93%, 94%, 95%, 96%, 97%, 98%, 99%, or 100% sequence identity to the amino acid sequence of SEQ ID NO: 93 or 97. In some embodiments, a VH sequence having at least 90%, 91%, 92%, 93%, 94%, 95%, 96%, 97%, 98%, or 99% identity contains substitutions (for example, conservative substitutions), insertions, or deletions relative to the reference sequence, and a VL sequence having at least 90%, 91%, 92%, 93%, 94%, 95%, 96%, 97%, 98%, or 99% identity contains substitutions (for example, conservative substitutions), insertions, or deletions relative to the reference sequence, but an anti-CCR8 antibody comprising that sequence retains the ability to bind to CCR8. In some embodiments, a total of 1 to 10 amino acids (e.g., 1, 2, 3, 4, 5, 6, 7, 8, 9, or 10 amino acids) have been substituted, inserted and/or deleted in SEQ ID NO: 92 or 96. In some embodiments, a total of 1 to 10 amino acids (e.g., 1, 2, 3, 4, 5, 6, 7, 8, 9, or 10 amino acids) have been substituted, inserted and/or deleted in SEQ ID NO: 93 or 97. In some embodiments, substitutions, insertions, or deletions occur in regions outside the CDRs (that is, in the FRs). In some embodiments, the anti-CCR8 antibody comprises (a) HCDR1 comprising the amino acid sequence of SEQ ID NO: 84 or 100; (b) HCDR2 comprising the amino acid sequence of SEQ ID NO: 85; (c) HCDR3 comprising the amino acid sequence of SEQ ID NO: 86; (d) LCDR1 comprising the amino acid sequence of SEQ ID NO: 87; (e) LCDR2 comprising the amino acid sequence of SEQ ID NO: 88; and (f) LCDR3 comprising the amino acid sequence of SEQ ID NO: 89.

In some embodiments, the humanized anti-CCR8 antibody comprises the VH sequence in SEQ ID NO: 92 or 96, including post-translational modifications of one or both sequences, and comprises the VL sequence in SEQ ID NO: 93 or 97, including post-translational modifications of one or both sequences.

Exemplary humanized anti-CCR8 antibodies include antibodies that compete for binding to CCR8 with an antibody or fragment thereof described herein. Thus, in some embodiments, a humanized anti-CCR8 antibody is provided that competes for binding to CCR8 with an antibody or fragment thereof selected from antibody 1-K16, 1-K17, 6-B09, 7-B16, 13-E16 and 19-O07. In some embodiments, the humanized anti-CCR8 antibody competes for binding to CCR8 with an antibody described herein and inhibits binding of CCR8 to CCL1. In some embodiments, the humanized anti-CCR8 antibody competes for binding to CCR8 with an antibody described herein.

Exemplary Human Antibodies

In some embodiments, an anti-CCR8 antibody provided herein is a human antibody. Human antibodies can be produced using various techniques known in the art. Human antibodies are described generally in van Dijk and van de Winkel, (2001) *Curr. Opin. Pharmacol.* 5:368-374 and Lonberg, (2008) *Curr. Opin. Immunol.* 20:450-459. In some embodiments, the human antibody is not a naturally occurring antibody. In some embodiments, the human antibody is a monoclonal antibody; thus, in some embodiments, each of the human antibodies in a set can bind to the same epitope on the antigen.

Human antibodies can be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, (2005) *Nat. Biotech.* 23: 1117-1125. See also, for example, U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, for example, by combining with a different human constant region.

Human antibodies can also be made by hybridoma-based methods. Human myeloma and mouse-human heteromyeloma cell lines for the production of human monoclonal antibodies have been described. (See, for example, Kozbor (1984) *J. Immunol*, 133: 3001; Brodeur et al., *Monoclonal Antibody Production Techniques and Applications*, pp. 51-63 (Marcel Dekker, Inc., New York, 1987); and Boerner et al, (1991) *J. Immunol.*, 147:86). Human antibodies generated via human B-cell hybridoma technology are also described in Li et al., (2006) *Proc. Natl. Acad. Sci. USA*, 103:3557-3562. Additional methods include those described, for example, in U.S. Pat. No. 7,189,826 (describing production of monoclonal human IgM antibodies from hybridoma cell lines) and Ni, (2006) *Xiandai Mianyixue*, 26(4):265-268 (describing human-human hybridomas). Human hybridoma technology (Trioma technology) is also described in Vollmers and Brandlein, (2005) *Histology and Histopathology*, 20(3):927-937 (2005) and Vollmers and Brandlein, (2005) *Methods and Findings in Experimental and Clinical Pharmacology*, 27(3): 185-191.

Human antibodies can also be generated by isolating Fv clone variable domain sequences selected from human-derived phage display libraries. Such variable domain sequences may then be combined with a desired human constant domain. Techniques for selecting human antibodies from antibody libraries are described below.

Antibodies may be isolated by screening combinatorial libraries for antibodies with the desired activity or activities. For example, a variety of methods are known in the art for generating phage display libraries and screening such libraries for antibodies possessing the desired binding characteristics. Such methods are reviewed, for example, in Hoogenboom et al. in Methods in Molecular Biology 178: 1-37 (O'Brien et al., ed., Human Press, Totowa, N.J., 2001) and further described, for example, in the McCafferty et al, (1990) *Nature* 348:552-554; Clackson et al, (1991) *Nature* 352: 624-628; Marks et al, (1992) *J. Mol. Biol* 222: 581-597; Marks and Bradbury, in *Methods in Molecular Biology* 248: 161-175 (Lo, ed., Human Press, Totowa, N.J., 2003); Sidhu et al, (2004) *J. Mol. Biol.* 338(2): 299-310; Lee et al., (2004) *J. Mol. Biol.* 340(5): 1073-1093; Fellouse, (2004) *Proc.*

*Natl. Acad. Sci. USA* 101(34): 12467-12472; and Lee et al, (2004) *J. Immunol. Methods* 284(1-2): 119-132 and PCT publication WO 99/10494.

In certain phage display methods, repertoires of $V_H$ and $V_L$ genes are separately cloned by polymerase chain reaction (PCR) and recombined randomly in phage libraries, which can then be screened for antigen-binding phage as described in Winter et al., (1994) *Ann. Rev. Immunol.*, 12:433-455. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (for example, from human) to provide a single source of antibodies to a wide range of non-self and also self-antigens without any immunization as described by Griffiths et al., (1993) *EMBO J* 12:725-734. Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter (1992), *J. Mol. Biol,* 227:381-388. Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

In some embodiments, the human anti-CCR8 antibody binds to CCR8 and inhibits binding of CCR8 to CCL1.

Exemplary human anti-CCR8 antibodies also include antibodies that compete for binding to CCR8 with a human antibody or fragment thereof described herein. Thus, in some embodiments, a human anti-CCR8 antibody is provided that competes for binding to CCR8 with an antibody or fragment thereof selected from antibody 1-K16, 1-K17, 6-B09, 7-B16, 13-E16 and 19-O07. In some embodiments, the human anti-CCR8 antibody competes for binding to CCR8 with an antibody described herein and inhibits binding of CCR8 to CCL1.

In some embodiments, a chimeric human anti-CCR8 antibody is provided, where the antibody comprises the variable region from a human antibody that binds CCR8 and the constant region from a different human antibody. In some embodiments, a chimeric human anti-CCR8 antibody, where the antibody comprises the CDRs from a human antibody that binds CCR8 and a framework from a different human antibody is provided. In some embodiments, the antibody is not a naturally occurring human antibody.

In some embodiments, a human anti-CCR8 antibody comprises one or more human constant regions. In some embodiments, the human heavy chain constant region is of an isotype selected from IgA, IgG, IgD, and IgE. In some embodiments, the human light chain constant region is of an isotype selected from κ and λ. In some embodiments, a human antibody described herein comprises a human IgG constant region. In some embodiments, a human antibody described herein comprises a human IgG4 heavy chain constant region. In some embodiments, a human antibody described herein comprises a human IgG4 constant region and a human κ light chain.

In some embodiments, when effector function is desirable, a human anti-CCR8 antibody comprising a human IgG1 heavy chain constant region or a human IgG3 heavy chain constant region is selected. In some embodiments, when effector function is not desirable, a human anti-CCR8 antibody comprising a human IgG4 or IgG2 heavy chain constant region is selected.

As noted herein, the term "human antibody" denotes the genus of possible sequences for the antibody construct, rather than a source of the antibody.

II. Fusion Proteins

In some embodiments, a fusion protein described herein comprises CCL1 or an active fragment of CCL1. An "active fragment" of CCL1, as used herein, refers to a fragment of CCL1 that binds CCR8. One of ordinary skill in the art can identify an active fragment of CCL1 that binds CCR8. In some embodiments, an active fragment of CCL1 binds CCR8 with an affinity that is at least 50%, at least 60%, at least 70%, at least 80%, at least 90%, or at least 95% as strong as the affinity of native CCL1 for CCR8. For the avoidance of doubt, an affinity that is at least 50% as strong as an affinity of 1 nM is 2 nM or less. One of ordinary skill in the art can determine the affinity of an active fragment of CCL1 for CCR8, and compare it to the affinity of native CCL1 for CCR8. In some embodiments, a fusion protein described herein comprises SEQ ID NO: 2 or amino acids 24-96 of SEQ ID NO: 2.

In some embodiments, a fusion protein comprising CCL1 or an active fragment thereof comprises an Fc region, such as an Fc region provided herein. In some embodiments, the Fc region comprises at least one modification that enhances cell killing. In some such embodiments, the enhanced cell killing is enhanced antibody-dependent cellular cytotoxicity (ADCC) and/or complement-dependent cytotoxicity (CDC). Nonlimiting exemplary modifications that enhance cell killing are provided herein, and include, for example, afucosylation.

In some embodiments, a fusion protein described herein comprises MC148 or an active fragment of MC148. An "active fragment" of MC148, as used herein, refers to a fragment of MC148 that binds CCR8. One of ordinary skill in the art can identify an active fragment of MC148 that binds CCR8. In some embodiments, an active fragment of MC148 binds CCR8 with an affinity that is at least 50%, at least 60%, at least 70%, at least 80%, at least 90%, or at least 95% as strong as the affinity of native MC148 for CCR8. For the avoidance of doubt, an affinity that is at least 50% as strong as an affinity of 1 nM is 2 nM or less. One of ordinary skill in the art can determine the affinity of an active fragment of MC148 for CCR8, and compare it to the affinity of native MC148 for CCR8. In some embodiments, a fusion protein described herein comprises SEQ ID NO: 2 or amino acids 24-96 of SEQ ID NO: 2.

In some embodiments, a fusion protein comprising MC148 or an active fragment thereof comprises an Fc region, such as an Fc region provided herein. In some embodiments, the Fc region comprises at least one modification that enhances cell killing. In some such embodiments, the enhanced cell killing is enhanced antibody-dependent cellular cytotoxicity (ADCC) and/or complement-dependent cytotoxicity (CDC). Nonlimiting exemplary modifications that enhance cell killing are provided herein, and include, for example, afucosylation.

III. Exemplary Antibody Constant Regions and Fc Regions

In some embodiments, an antibody described herein comprises one or more human constant regions. In some embodiments, the human heavy chain constant region is of an isotype selected from IgA, IgG, IgD, and IgE. In some embodiments, an antibody described herein comprises a human IgG constant region. In some embodiments, when effector function is desirable, an anti-CCR8 antibody comprising a human IgG1 heavy chain constant region or a human IgG3 heavy chain constant region is selected. In some embodiments, when effector function is not desirable, an anti-CCR8 antibody comprising a human IgG4 or IgG2 heavy chain constant region is selected. In some embodiments, the human light chain constant region is of an isotype selected from κ and λ. In some embodiments, an antibody described herein comprises a human IgG1 heavy chain constant region. In some embodiments, an antibody described herein comprises a human IgG1 constant region and a human κ light chain.

In some embodiments, a fusion protein described herein comprises one or more human Fc regions. In some embodiments, the Fc region is of an isotype selected from IgA, IgG, IgD, and IgE. In some embodiments, a fusion protein described herein comprises a human Fc region. In some embodiments, when effector function is desirable, a fusion protein comprising a human IgG1 Fc region or a human IgG3 Fc region is selected. In some embodiments, when effector function is not desirable, a fusion protein comprising a human IgG4 or IgG2 Fc region is selected.

Throughout the present specification and claims unless explicitly stated or known to one skilled in the art, the numbering of the residues in an immunoglobulin heavy chain is that of the EU index as in Kabat et al., *Sequences of Proteins of Immunological Interest,* 5th Ed. Public Health Service, National Institutes of Health, Bethesda, Md. (1991), expressly incorporated herein by reference. The "EU index as in Kabat" refers to the residue numbering of the human IgG1 EU antibody.

As noted above, whether or not effector function is desirable may depend on the particular method of treatment intended for an antibody. Thus, in some embodiments, when effector function is desirable, an anti-CCR8 antibody comprising a human IgG1 heavy chain constant region or a human IgG3 heavy chain constant region is selected. In some embodiments, when effector function is desirable, a fusion protein comprising a human IgG1 Fc region or a human IgG3 Fc region is selected.

In some embodiments, an antibody or fusion protein comprises a variant Fc region having at least one amino acid substitution compared to the Fc region of a wild-type IgG Fc region. In some embodiments, the variant Fc region has two or more amino acid substitutions compared to the wild-type Fc region. In some embodiments, the variant Fc region has three or more amino acid substitutions compared to a wild-type Fc region. In some embodiments, the variant Fc region has at least one, two or three or more Fc region amino acid substitutions described herein. In some embodiments, the variant Fc region herein will possess at least about 80% homology with a native sequence Fc region and/or with an Fc region of a parent polypeptide. In some embodiments, the variant Fc region herein will possess at least about 90% homology with a native sequence Fc region and/or with an Fc region of a parent polypeptide. In some embodiments, the variant Fc region herein will possess at least about 95% homology with a native sequence Fc region and/or with an Fc region of a parent polypeptide. In some embodiments, a heavy chain constant region or Fc region lacks the C-terminal lysine (K) residue. In some such embodiments, the heavy chain constant region or Fc region may be referred to as "desK." In some embodiments, the heavy chain constant region or Fc region lacking the C-terminal lysine is an IgG, such as an IgG1, IgG2, IgG3, or IgG4.

In some embodiments, an antibody or fusion protein provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

The carbohydrate attached to an Fc region may be altered. Native antibodies produced by mammalian cells typically comprise a branched, biantennary oligosaccharide that is generally attached by an N-linkage to Asn297 of the CH2 domain of the Fc region. See, for example, Wright et al. *TIBTECH* 15:26-32 (1997). The oligosaccharide may include various carbohydrates, for example, mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody or fusion protein may be made in order to create antibody variants with certain improved properties.

In some embodiments, antibody or fusion protein variants are provided having a carbohydrate structure that lacks fucose attached (directly or indirectly) to an Fc region (i.e., afucosylated). For example, the amount of fucose in such variants may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn297 (for example, complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, that is, between positions 294 and 300, due to minor sequence variations in antibodies. Such fucosylation variants may have improved ADCC function. See, for example, US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Patent Application No. US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, for example, Yamane-Ohnuki et al. *Biotech. Bioeng.* 87: 614 (2004); Kanda, Y. et al., *Biotechnol. Bioeng.,* 94(4):680-688 (2006); and WO2003/085107).

Antibody and fusion protein variants are further provided with bisected oligosaccharides, for example, in which a biantennary oligosaccharide attached to the Fc region of the antibody is bisected by GlcNAc. Such antibody or fusion protein variants may have reduced fucosylation and/or improved ADCC function. Examples of such variants are described, for example, in WO 2003/011878 (Jean-Mairet et al.); U.S. Pat. No. 6,602,684 (Umana et al.); and US 2005/0123546 (Umana et al.). Variants with at least one galactose residue in the oligosaccharide attached to the Fc region are also provided. Such variants may have improved CDC function. Such variants are described, for example, in WO 1997/30087 (Patel et al.); WO 1998/58964 (Raju, S.); and WO 1999/22764 (Raju, S.).

Antibody or Fc region variants are provided with Fc mutations that increase ADCC activity. In some embodiments, an antibody or Fc region variant comprises one or more mutations that enhance FcγRIIIa binding and/or decreased FcγRIIIb binding. Nonlimiting exemplary such mutations may be made at one or more amino acid positions selected from L234, L235, G236, S239, F243, H268, D270, R292, S298, Y300, V305, K326, A330, I332, E333, K334, and P396. Nonlimiting exemplary mutations include L234Y, L235Q, G236W, S239D, S239M, F243L, H268D, D270E, R292P, S298A, Y300L, V305I, K326D, A330L, A330M, I332E, E333A, K334A, K334E, and P396L. In some embodiments, an antibody or Fc region variant comprises mutations F243L/R292P/Y300L/V305I/P396L. See, e.g., Stavenhagen et al., 2007, *Cancer Res.* 67:8882-8890. In some embodiments, an antibody or Fc region variant comprises mutations S239D/I332E or S239D/I332E/A330L. See, e.g., Lazar et al., 2006, *PNAS USA*, 103: 4005-4010. In some embodiments, an antibody or Fc region variant comprises mutations S298A/E333A/K334A. See, e.g., Shields et al., 2001, *J. Biol. Chem.*, 276: 6591-6604. In some embodiments, an antibody or Fc region variant comprises mutations L234Y/L235Q/G236W/S239M/H268D/D270E/S298A or mutations D270E/K326D/A330M/K334E, or one heavy chain constant region or Fc comprises mutations L234Y/L235Q/G236W/S239M/H268D/D270E/S298A and the other heavy chain constant region or Fc comprises mutations D270E/K326D/A330M/K334E. See, e.g., Mimoto et al., 2013, *MAbs*, 5:229-236.

Antibody and Fc region variants are also provided with amino-terminal leader extensions. For example, one or more amino acid residues of the amino-terminal leader sequence are present at the amino-terminus of any one or more heavy or light chains of an antibody. An exemplary amino-terminal leader extension comprises or consists of three amino acid residues, VHS, present on one or both light chains of an antibody variant.

The in vivo or serum half-life of human FcRn high affinity binding polypeptides can be assayed, for example, in transgenic mice, in humans, or in non-human primates to which the polypeptides with a variant Fc region are administered. See also, for example, Petkova et al. *International Immunology* 18(12):1759-1769 (2006).

In some embodiments, the antibody or Fc region variant mediates ADCC in the presence of human effector cells more effectively than a parent antibody. In some embodiments, the antibody or Fc region variant is substantially more effective at mediating ADCC in vitro, when the amounts of polypeptide variant and parent antibody or Fc region used in the assay are essentially the same. In some embodiments, the antibody or Fc region variant is substantially more effective at mediating ADCC in vivo, when the amounts of polypeptide variant and parent antibody or Fc region used in the assay are essentially the same. Generally, such variants will be identified using the in vitro ADCC assay as herein disclosed, but other assays or methods for determining ADCC activity, for example in an animal model etc., are contemplated.

IV. Exemplary Conjugates

In some embodiments, an antibody or fusion protein provided herein is conjugated to another molecule. In some embodiments, the additional molecule can be a detectable marker, such as a label. In some embodiments, the additional molecule can be a therapeutic molecule, such as a cytotoxic agent. In some embodiments, a label and/or a cytotoxic agent can be conjugated to the antibody or fusion protein provided herein. As used herein, a label is a moiety that facilitates detection of the antibody or fusion protein and/or facilitates detection of a molecule to which the antibody or fusion protein binds. Nonlimiting exemplary labels include, but are not limited to, radioisotopes, fluorescent groups, enzymatic groups, chemiluminescent groups, biotin, epitope tags, metal-binding tags, etc. One skilled in the art can select a suitable label according to the specific application.

As used herein, a cytotoxic agent is a moiety that reduces the proliferative capacity of one or more cells. A cell has reduced proliferative capacity when the cell becomes less able to proliferate, for example, because the cell undergoes apoptosis or otherwise dies, the cell fails to proceed through the cell cycle and/or fails to divide, the cell differentiates, etc. Nonlimiting exemplary cytotoxic agents include, but are not limited to, radioisotopes, toxins, and chemotherapeutic agents. One skilled in the art can select a suitable cytotoxic according to the intended application. In some embodiments, the cytotoxic agent is at least one of an anti-metabolite, an alkylating agent, an antibiotic, a growth factor, a cytokine, an anti-angiogenic agent, an anti-mitotic agent, an anthracycline, toxin, or an apoptotic agent In some embodiments, a label and/or a cytotoxic agent is conjugated to an antibody or fusion protein provided herein using chemical methods in vitro. Nonlimiting exemplary chemical methods of conjugation are known in the art, and include services, methods and/or reagents commercially available from, for example, Thermo Scientific Life Science Research Produces (formerly Pierce; Rockford, Ill.), Prozyme (Hayward, Calif.), SACRI Antibody Services (Calgary, Canada), AbD Serotec (Raleigh, N.C.), etc. In some embodiments, when a label and/or cytotoxic agent is a polypeptide, the label and/or cytotoxic agent can be expressed from the same expression vector with at least one antibody chain or fusion protein to produce a polypeptide comprising the label and/or cytotoxic agent fused to the antibody or fusion protein. One skilled in the art can select a suitable method for conjugating a label and/or cytotoxic agent to an antibody or fusion protein according to the intended application.

In some embodiments, conjugation can be covalent. In some embodiments, conjugation can be non-covalent. In some embodiments, conjugation can be via a specific binding interaction, for example, through the binding of a secondary antibody.

An exemplary embodiment of a conjugate comprising a drug (or drug derivative) and an antibody of fusion protein as disclosed herein may have the general formula 1:

Mab-[Linker]-Drug                                    (formula 1)

wherein the linker is a cleavable or non-cleavable linker, Mab is an antibody or fusion protein disclosed herein, and Drug is any drug or cytotoxic agent.

In some embodiments, the conjugate may comprise the general formula 2:

MAb-[L2]-[L1]-[AA]$_m$-[A']-Drug                    (formula 2)

where MAb is an antibody or fusion protein disclosed herein; L2 is a component of the cross-linker comprising an antibody-coupling moiety and one or more of acetylene (or azide) groups; L1 comprises a defined PEG with azide (or acetylene) at one end, complementary to the acetylene (or azide) moiety in L2, and a reactive group such as carboxylic acid or hydroxyl group at the other end; AA is an L-amino acid; m is an integer with values of 0, 1, 2, 3, or 4; and A' is an additional spacer, selected from the group of ethanolamine, 4-hydroxybenzyl alcohol, 4-aminobenzyl alcohol, or substituted or unsubstituted ethylenediamine. The L amino acids of 'AA' are selected from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. If the A' group contains hydroxyl, it is linked to the hydroxyl group or amino group of the drug in the form of a carbonate or carbamate, respectively.

In some embodiments of formula 2, A' is a substituted ethanolamine derived from an L-amino acid, wherein the carboxylic acid group of the amino acid is replaced by a hydroxymethyl moiety. A' may be derived from any one of the following L-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.

In an example of the conjugate of such an embodiment of formula 2, m is 0, A' is L-valinol, and the drug is exemplified by SN-38. The resultant structure is shown in formula 3.

coupled to an L2 component carrying the targeting vector-binding moiety as well as the complementary acetylene (or azide) group involved in the click cycloaddition chemistry. Finally, removal of protecting groups at both lysine side chain and SN-38 gives the product of this example, shown in formula 3.

While not wishing to be bound by theory, the small MW SN-38 product, namely valinol-SN-38 carbonate, generated after intracellular proteolysis, has the additional pathway of liberation of intact SN-38 through intramolecular cyclization involving the amino group of valinol and the carbonyl of the carbonate.

In another embodiment, A' of the general formula 2 is A-OH, whereby A-OH is a collapsible moiety such as 4-aminobenzyl alcohol or a substituted 4-aminobenzyl alcohol substituted with a $C_1$-$C_{10}$ alkyl group at the benzylic position, and the latter, via its amino group, is attached to an L-amino acid or a polypeptide comprising up to four L-amino acid moieties; wherein the N-terminus is attached to a cross-linker terminating in the targeting moiety-binding group.

(3)

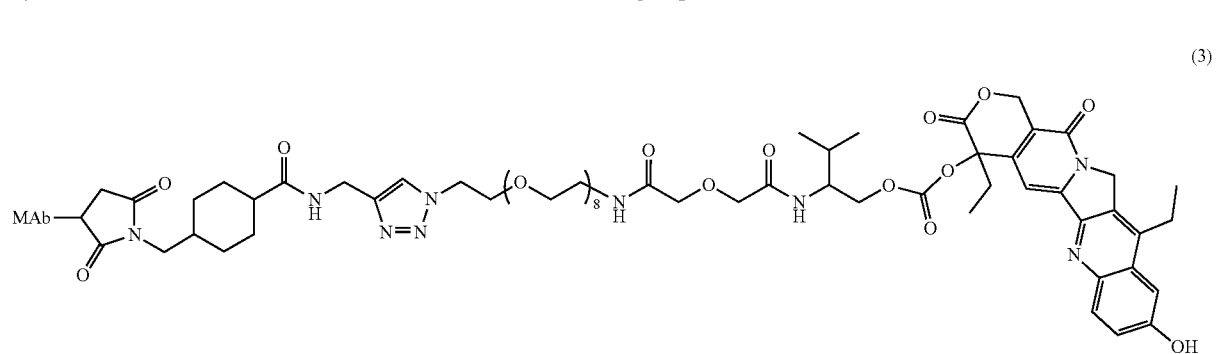

In another example of the conjugate of this embodiment of formula 2, m is 1 and represented by a derivatized L-lysine, A' is L-valinol, and the drug is exemplified by SN-38. The structure is shown in formula 4.

An example of such embodiment is given below, wherein the A-OH embodiment of A' of general formula (2) is derived from substituted 4-aminobenzyl alcohol, and 'AA' is comprised of a single L-amino acid with m=1 in the general (4)

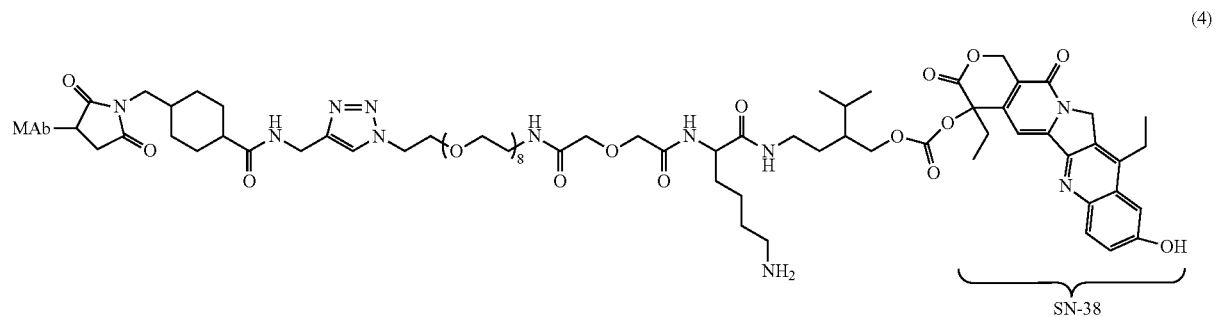

In this embodiment, an amide bond is first formed between the carboxylic acid of an amino acid such as lysine and the amino group of valinol, using orthogonal protecting groups for the lysine amino groups. The protecting group on the N-terminus of lysine is removed, keeping the protecting group on the side chain of lysine intact, and the N-terminus is coupled to the carboxyl group on the defined PEG with azide (or acetylene) at the other end. The hydroxyl group of valinol is then attached to the 20-chloroformate derivative of 10-hydroxy-protected SN-38, and this intermediate is formula (2), and the drug is exemplified with SN-38. The structure is represented below (formula 5, referred to as MAb-CLX-SN-38). Single amino acid of AA is selected from any one of the following L-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. The substituent R on 4-aminobenzyl alcohol moiety (A-OH embodiment of A') is hydrogen or an alkyl group selected from C1-C10 alkyl groups.

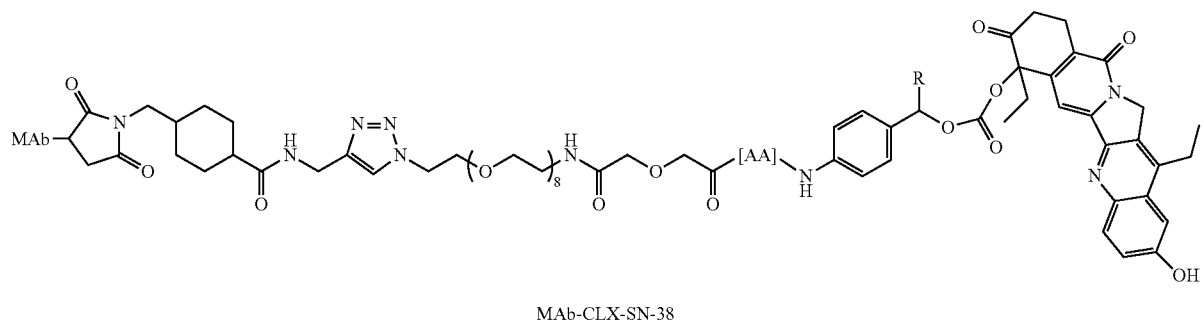

MAb-CLX-SN-38 (5)

An embodiment of MAb-CLX-SN-38 of formula 5, wherein the single amino acid AA is L-lysine and R=H, and the drug is exemplified by SN-38 (formula 6; referred to as MAb-CL2A-SN-38).

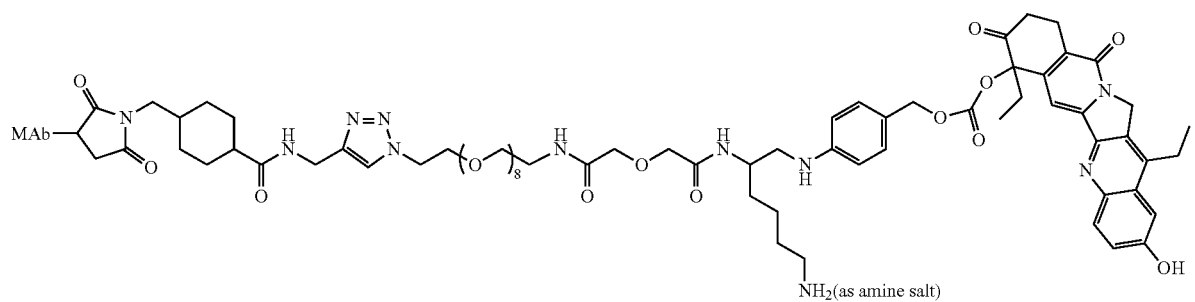

MAb-CL2A-SN-38 (6)

(7)

Other embodiments are possible within the context 10-hydroxy-containing camptothecins, such as SN-38. In the example of SN-38 as the drug, the more reactive 10-hydroxy group of the drug is derivatized leaving the 20-hydroxyl group unaffected. Within the general formula 2, A' is a substituted ethylenediamine. An example of this embodiment is represented by the formula '7' below, wherein the phenolic hydroxyl group of SN-38 is derivatized as a carbamate with a substituted ethylenediamine, with the other amine of the diamine derivatized as a carbamate with a 4-aminobenzyl alcohol, and the latter's amino group is attached to Phe-Lys dipeptide. In this structure (formula 7), R and R' are independently hydrogen or methyl. It is referred to as MAb-CL17-SN-38 or MAb-CL2E-SN-38, when R=R'=methyl.

(7)

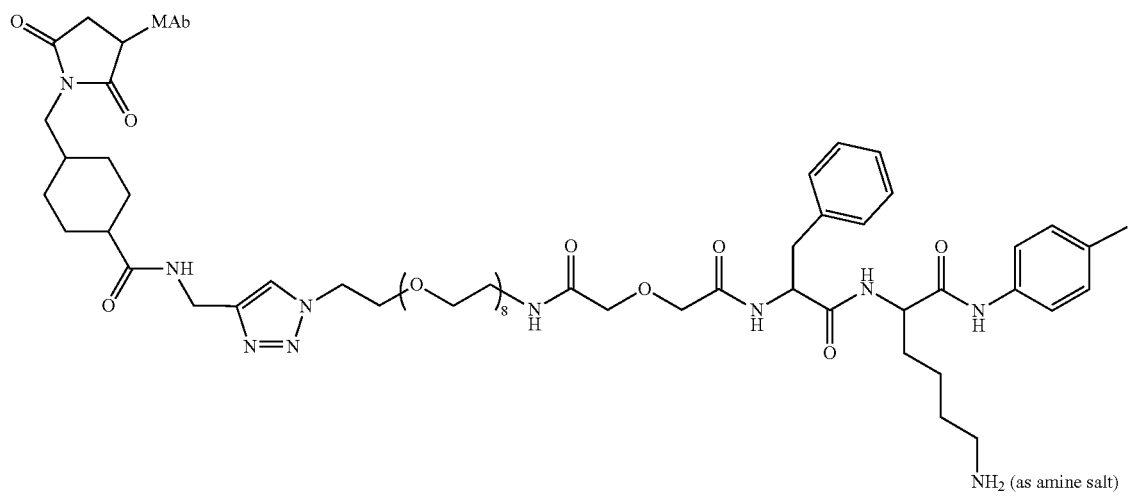

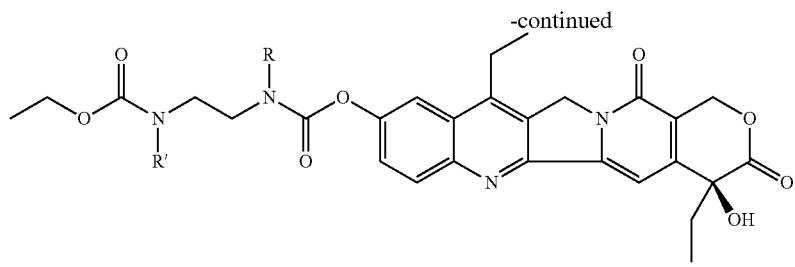

In some embodiments, AA comprises a polypeptide moiety, such as a di, tri or tetrapeptide, that is cleavable by intracellular peptidase. Examples are: Ala-Leu, Leu-Ala-Leu, and Ala-Leu-Ala-Leu (SEQ ID NO: 129; Trouet et al., 1982).

In some embodiments, the L1 component of the conjugate contains a defined polyethyleneglycol (PEG) spacer with 1-30 repeating monomeric units. In a further embodiment, PEG is a defined PEG with 1-12 repeating monomeric units. The introduction of PEG may involve using heterobifunctionalized PEG derivatives which are available commercially. The heterobifunctional PEG may contain an azide or acetylene group. An example of a heterobifunctional defined PEG containing 8 repeating monomeric units, with 'NHS' being succinimidyl, is given below in formula 8:

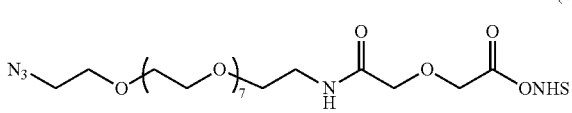

(8)

In some embodiments, L2 has a plurality of acetylene (or azide) groups, ranging from 2-40, but preferably 2-20, and more preferably 2-5, and a single targeting vector-binding moiety.

A representative SN-38 conjugate of an antibody containing multiple drug molecules and a single targeting vector-binding moiety is shown below. The 'L2' component of this structure is appended to 2 acetylenic groups, resulting in the attachment of two azide-appended SN-38 molecules. The bonding to MAb is represented as a succinimide.

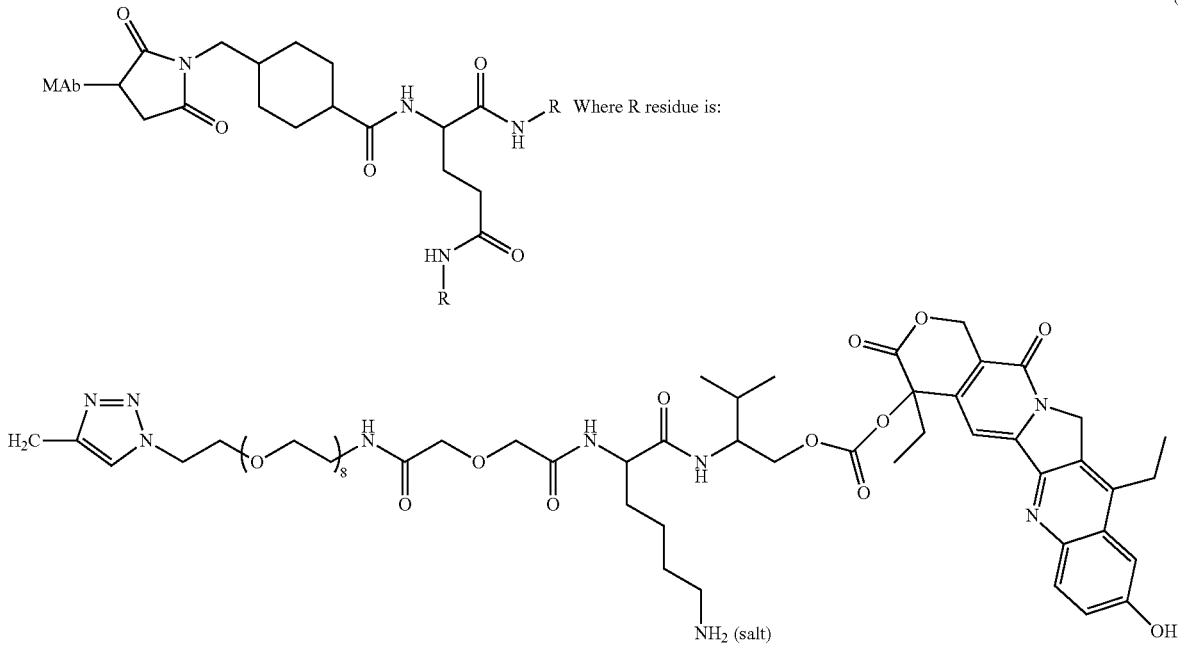

(9)

In some embodiments, when a bifunctional drug contains a thiol-reactive moiety as the antibody-binding group, the thiols on the antibody are generated on the lysine groups of the antibody using a thiolating reagent. Methods for introducing thiol groups onto antibodies by modifications of MAb's lysine groups are well known in the art (Wong in *Chemistry of protein conjugation and cross-linking*, CRC Press, Inc., Boca Raton, Fla. (1991), pp 20-22). Alternatively, mild reduction of interchain disulfide bonds on the antibody (Willner et al., *Bioconjugate Chem.* 4:521-527 (1993)) using reducing agents such as dithiothreitol (DTT) can generate 7-to-10 thiols on the antibody; which has the advantage of incorporating multiple drug moieties in the interchain region of the MAb away from the antigen-binding region.

In some embodiments, the chemotherapeutic moiety is selected from the group consisting of doxorubicin (DOX), epirubicin, morpholinodoxorubicin (morpholino-DOX), cyanomorpholino-doxorubicin (cyanomorpholino-DOX), 2-pyrrolino-doxorubicin (2-PDOX), CPT, 10-hydroxy camptothecin, SN-38, topotecan, lurtotecan, 9-aminocamptothecin, 9-nitrocamptothecin, taxanes, geldanamycin, ansamycins, and epothilones. In another embodiment, the chemotherapeutic moiety is SN-38. Preferably, in the conjugates of some embodiments, the targeting moiety links to at least one chemotherapeutic moiety; preferably 1 to about 12 chemotherapeutic moieties; most preferably about 6 to about 12 chemotherapeutic moieties.

Furthermore, in some embodiments, the linker component 'L2' comprises a thiol group that reacts with a thiol-reactive residue introduced at one or more lysine side chain amino groups of said targeting moiety. In such cases, the antibody may be pre-derivatized with a thiol-reactive group such as a maleimide, vinylsulfone, bromoacetamide, or iodoacetamide by procedures well described in the art.

Exemplary Leader Sequences

In order for some secreted proteins to express and secrete in large quantities, a leader sequence from a heterologous protein may be desirable. In some embodiments, employing heterologous leader sequences can be advantageous in that a resulting mature polypeptide can remain unaltered as the leader sequence is removed in the ER during the secretion process. The addition of a heterologous leader sequence can be useful to express and secrete some proteins.

Certain exemplary leader sequence sequences are described, for example, in the online Leader sequence Database maintained by the Department of Biochemistry, National University of Singapore. See Choo et al., *BMC Bioinformatics*, 6: 249 (2005); and PCT Publication No. WO 2006/081430.

V. Polypeptide Expression and Production

Nucleic Acid Molecules Encoding Antibodies or Fusion Proteins

Nucleic acid molecules comprising polynucleotides that encode one or more chains of an anti-CCR8 antibody are provided herein. In some embodiments, a nucleic acid molecule comprises a polynucleotide that encodes a heavy chain or a light chain of an anti-CCR8 antibody. In some embodiments, a nucleic acid molecule comprises both a polynucleotide that encodes a heavy chain and a polynucleotide that encodes a light chain, of an anti-CCR8 antibody. In some embodiments, a first nucleic acid molecule comprises a first polynucleotide that encodes a heavy chain and a second nucleic acid molecule comprises a second polynucleotide that encodes a light chain.

In some embodiments, the heavy chain and the light chain are expressed from one nucleic acid molecule, or from two separate nucleic acid molecules, as two separate polypeptides. In some embodiments, such as when an antibody is an scFv, a single polynucleotide encodes a single polypeptide comprising both a heavy chain and a light chain linked together.

In some embodiments, a polynucleotide encoding a heavy chain or light chain of an anti-CCR8 antibody comprises a nucleotide sequence that encodes at least one of the CDRs provided herein. In some embodiments, a polynucleotide encoding a heavy chain or light chain of an anti-CCR8 antibody comprises a nucleotide sequence that encodes at least 3 of the CDRs provided herein. In some embodiments, a polynucleotide encoding a heavy chain or light chain of an anti-CCR8 antibody comprises a nucleotide sequence that encodes at least 6 of the CDRs provided herein. In some embodiments, a polynucleotide encoding a heavy chain or light chain of an anti-CCR8 antibody comprises a nucleotide sequence that encodes a leader sequence, which, when translated, is located at the N terminus of the heavy chain or light chain. As discussed above, the leader sequence may be the native heavy or light chain leader sequence, or may be another heterologous leader sequence.

Nucleic acid molecules comprising polynucleotides that encode a fusion protein are provided herein. In some embodiments, a polynucleotide encoding a fusion protein comprises a nucleotide sequence that encodes a leader sequence, which, when translated, is located at the N terminus of the fusion protein. The leader sequence may be the native leader sequence, or may be another heterologous leader sequence.

In some embodiments, the nucleic acid is one that encodes for any of the amino acid sequences for the antibodies and fusion proteins in the Sequence Table herein. In some embodiments, the nucleic acid is one that is at least 80% identical to a nucleic acid encoding any of the amino acid sequences for the antibodies and fusion proteins in the Sequence Table herein, for example, at least 80, 85, 90, 91, 92, 93, 94, 95, 96, 97, 98, or 99% identical. In some embodiments, the nucleic acid is one that hybridizes to any one or more of the nucleic acid sequences provided herein. In some of the embodiments, the hybridization is under moderate conditions. In some embodiments, the hybridization is under highly stringent conditions, such as: at least about 6×SSC and 1% SDS at 65° C., with a first wash for 10 minutes at about 42° C. with about 20% (v/v) formamide in 0.1×SSC, and with a subsequent wash with 0.2×SSC and 0.1% SDS at 65° C.

Nucleic acid molecules can be constructed using recombinant DNA techniques conventional in the art. In some embodiments, a nucleic acid molecule is an expression vector that is suitable for expression in a selected host cell.

Vectors comprising polynucleotides that encode anti-CCR8 heavy chains and/or anti-CCR8 light chains are provided. Vectors comprising polynucleotides that encode anti-CCR8 heavy chains and/or anti-CCR8 light chains are also provided. Such vectors include, but are not limited to, DNA vectors, phage vectors, viral vectors, retroviral vectors, etc. In some embodiments, a vector comprises a first polynucleotide sequence encoding a heavy chain and a second polynucleotide sequence encoding a light chain. In some embodiments, the heavy chain and light chain are expressed from the vector as two separate polypeptides. In some embodiments, the heavy chain and light chain are expressed as part of a single polypeptide, such as, for example, when the antibody is an scFv.

In some embodiments, a first vector comprises a polynucleotide that encodes a heavy chain and a second vector comprises a polynucleotide that encodes a light chain. In some embodiments, the first vector and second vector are transfected into host cells in similar amounts (such as similar molar amounts or similar mass amounts). In some embodiments, a mole- or mass-ratio of between 5:1 and 1:5 of the first vector and the second vector is transfected into host cells. In some embodiments, a mass ratio of between 1:1 and 1:5 for the vector encoding the heavy chain and the vector encoding the light chain is used. In some embodiments, a mass ratio of 1:2 for the vector encoding the heavy chain and the vector encoding the light chain is used.

Vectors comprising polynucleotides that encode fusion proteins are provided. Such vectors include, but are not limited to, DNA vectors, phage vectors, viral vectors, retroviral vectors, etc.

In some embodiments, a vector is selected that is optimized for expression of polypeptides in CHO or CHO-derived cells, or in NSO cells. Exemplary such vectors are described, for example, in Running Deer et al., *Biotechnol. Prog.* 20:880-889 (2004).

Host Cells

In some embodiments, an antibody or fusion protein provided herein may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S, DG44. Lec13 CHO cells, and FUT8 CHO cells; PER.C6® cells (Crucell); and NSO cells. In some embodiments, an antibody or fusion protein provided herein may be expressed in yeast. See, for example, U.S. Publication No. US 2006/0270045 A1. In some embodiments, a particular eukaryotic host cell is selected based on its ability to make desired post-translational modifications to the antibody or fusion protein provided herein. For example, in some embodiments, CHO cells produce polypeptides that have a higher level of sialylation than the same polypeptide produced in 293 cells.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc. Nonlimiting exemplary methods are described, for example, in Sambrook et al., Molecular Cloning, A Laboratory Manual, 3$^{rd}$ ed. Cold Spring Harbor Laboratory Press (2001). Nucleic acids may be transiently or stably transfected in the desired host cells, according to any suitable method.

Host cells comprising any of the polynucleotides or vectors described herein are also provided. In some embodiments, a host cell comprising an antibody or fusion protein is provided. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe*; or *K. lactis*).

Purification of Polypeptides

Antibodies and fusion proteins provided herein can be purified by any suitable method. Such methods include, but are not limited to, the use of affinity matrices or hydrophobic interaction chromatography. Suitable affinity ligands include the ROR1 ECD and ligands that bind antibody constant regions. For example, a Protein A, Protein G, Protein A/G, or an antibody affinity column may be used to bind the constant region or Fc region and to purify an antibody or fusion protein. Hydrophobic interactive chromatography, for example, a butyl or phenyl column, may also suitable for purifying some polypeptides. Ion exchange chromatography (for example anion exchange chromatography and/or cation exchange chromatography) may also suitable for purifying some polypeptides. Mixed-mode chromatography (for example reversed phase/anion exchange, reversed phase/cation exchange, hydrophilic interaction/anion exchange, hydrophilic interaction/cation exchange, etc.) may also suitable for purifying some polypeptides. Many methods of purifying polypeptides are known in the art.

Cell-Free Production of Polypeptides

In some embodiments, an antibody or fusion protein is produced in a cell-free system. Nonlimiting exemplary cell-free systems are described, for example, in Sitaraman et al., *Methods Mol. Biol.* 498: 229-44 (2009); Spirin, *Trends Biotechnol.* 22: 538-45 (2004); Endo et al., *Biotechnol. Adv.* 21: 695-713 (2003).

Compositions

In some embodiments, antibodies or fusion proteins prepared by the methods described above are provided. In some embodiments, the antibody or fusion protein is prepared in a host cell. In some embodiments, the antibody or fusion protein is prepared in a cell-free system. In some embodiments, the antibody or fusion protein is purified. In some embodiments, a cell culture media comprising an antibody or fusion protein is provided. In some embodiments, a host cell culture fluid comprising an antibody or fusion protein is provided.

In some embodiments, compositions comprising antibodies or fusion proteins prepared by the methods described above are provided. In some embodiments, the composition comprises an antibody or fusion protein prepared in a host cell. In some embodiments, the composition comprises an antibody or fusion protein prepared in a cell-free system. In some embodiments, the composition comprises a purified antibody or fusion protein.

In some embodiments, a composition comprising an antibody or fusion protein at a concentration of more than about any one of 10 mg/mL, 20 mg/mL, 30 mg/mL, 40 mg/mL, 50 mg/mL, 60 mg/mL, 70 mg/mL, 80 mg/mL, 90 mg/mL, 100 mg/mL, 125 mg/mL, 150 mg/mL, 175 mg/mL, 200 mg/mL, 225 mg/mL, or 250 mg/mL is provided.

VI. Therapeutic Compositions and Methods

Methods of Treating Diseases Using Antibodies or Fusion Proteins

Antibodies (e.g., 7-B16, 1-K17, etc.) and fusion proteins and compositions comprising antibodies and fusion proteins are provided for use in methods of treatment for humans or animals. Also provided herein are pharmaceutical and therapeutic uses of the disclosed antibodies and fusion proteins. Methods of treating disease and pharmaceutical/therapeutic uses comprising administering the antibodies and fusion proteins provided herein are also provided. Nonlimiting exemplary diseases that can be treated with the antibodies and fusion proteins provided herein include, but are not limited to, cancer.

In some embodiments, a method of treating cancer (or therapeutic/pharmaceutical use of the disclosed antibodies or fusion proteins) comprises administering to a subject with cancer an effective amount of an antibody (e.g., 7-B16, 1-K17, etc.) or a fusion protein provided herein. In some embodiments, the cancer is a solid cancer. In some embodiments, the cancer is a blood (i.e., liquid) cancer. In some embodiments, the cancer comprises tumor-infiltrating Treg cells. In some embodiments, the subject has received prior checkpoint inhibitor therapy (CPI) or has CPI-resistant or refractory cancer, as many subjects with CPI-resistant or refractory cancer will present with elevated levels of intratumoral Tregs. In some embodiments, the CPI therapy comprises an anti-PDL1 antibody, an anti-CTLA4 antibody, or an anti-TIGIT antibody. In some embodiments, the anti-PDL1 antibody is selected from pembrolizumab, nivolumab, atezolizumab, avelumab, durvalumab, cemiplimab-rwlc, and zimberelimab; the anti-CLTA4 antibody is ipilimumab or tremelimumab; or the anti-TIGIT antibody is selected from tiragolumab, vibostolimab, domvanalimab, AB308, BMS-986207, and durvalumab. In some embodiments, the cancer comprises cells that express CCR8 (e.g., CCR8-expressing Tregs). Expression of CCR8 may be determined with, for example, by immunohistochemistry, fluorescence-activated cell sorting (FACS), gene expression analysis (such as Q-PCR or RT-PCR), Western blot, ELISA, or other known methods of assessing expression at a genetic- or protein-level. In some embodiments, the cells that express CCR8 are Treg cells (e.g., intratumoral Tregs), and in some embodiments the level of CCR8 expression of such intratumoral Tregs is elevated relevative to peripheral Tregs. In some embodiments, CCR8 is expressed on the surface of the Treg cells at fewer than 10,000 copies per cell, which can be determined by, for example, fluorescence-activated cell sorting (FACS) and flow cytometry. In some embodiments, the cancer comprises tumor cells that express CCR8. In some embodiments, 5%, 10%, 15%, 20%, 25%, 30%, 35%, 40%, 45%, 50%, 55%, 60%, 65%, 70%, 75%, 80%, 85%, 90%, 95%, 99%, or 100% of the tumor-infiltrating Tregs express the surface of the cell fewer than 10,000 copies of CCR8 per cell.

In some embodiments, the cancer is selected from breast cancer, colorectal cancer, head and neck cancer, lung cancer, ovarian cancer, gastric cancer, stomach adenocarcinoma, and thymoma. In some embodiments, the cancer may be metastatic. In some embodiments when the cancer is breast cancer, the breast cancer is triple negative breast cancer (i.e., TNBC). In some embodiments when the cancer is breast cancer, the breast cancer is metastatic TNBC.

In some embodiments, a method of treating a solid cancer with tumor infiltrating Tregs that express CCR8 comprises administering to a subject with cancer an effective amount of an antibody (e.g., 7-B16, 1-K17, etc.) or a fusion protein provided herein. In some embodiments, the tumor infiltrating Tregs express CCR8 at levels that are elevated relative to the CCR8 expression levels of peripheral Tregs. Expression of CCR8 may be determined with, for example, by immunohistochemistry, fluorescence-activated cell sorting (FACS), gene expression analysis (such as Q-PCR or RT-PCR), Western blot, ELISA, or other known methods of assessing expression at a genetic- or protein-level. In some embodiments, the solid cancer may be selected from breast cancer, colorectal cancer, head and neck cancer, lung cancer, ovarian cancer, gastric cancer, stomach adenocarcinoma, and thymoma.

In some embodiments, a method of treating blood cancer (or therapeutic/pharmaceutical use) comprises administering to a subject with blood cancer an effective amount of an antibody (e.g., 7-B16, 1-K17, etc.) that binds human CCR8. In some embodiments, the antibody inhibits binding of CCL1 to CCR8. In some embodiments, the blood cancer expresses CCR8. In some embodiments, the subject has received prior checkpoint inhibitor therapy (CPI) or has CPI-resistant or refractory cancer, as many subjects with CPI-resistant or refractory cancer will present with elevated levels of CCR8-expressing Tregs. In some embodiments, the CPI therapy comprises an anti-PDL1 antibody, an anti-CTLA4 antibody, or an anti-TIGIT antibody. In some embodiments, the anti-PDL1 antibody is selected from pembrolizumab, nivolumab, atezolizumab, avelumab, durvalumab, cemiplimab-rwlc, and zimberelimab; the anti-CLTA4 antibody is ipilimumab or tremelimumab; or the anti-TIGIT antibody is selected from tiragolumab, vibostolimab, domvanalimab, AB308, BMS-986207, and durvalumab. In some embodiments, the blood cancer comprises cells that express CCR8 (e.g., CCR8-expressing Tregs). In some embodiments, the cells that express CCR8 are Treg cells. In some embodiments, the blood cancer may be metastatic.

In some embodiments, a method or use of selecting a subject with blood cancer for treatment with an antibody that binds human CCR8 comprises detecting CCR8 expression in a sample from the subject. In some embodiments, a method or use further comprising administering an effective amount of an antibody that binds human CCR8.

In some embodiments, a method of treating blood cancer (or therapeutic/pharmaceutical use) comprises administering to a subject with blood cancer an effective amount of a fusion protein. In some embodiments, a method of selecting a subject with blood cancer for treatment with a fusion protein comprising (a) CCL1 or an active fragment thereof or MC148 or an active fragment thereof, and (b) an Fc region, comprises detecting CCR8 expression in a sample from the subject. In some embodiments, a method further comprises administering an effective amount of a fusion protein comprising (a) CCL1 or an active fragment thereof or MC148 or an active fragment thereof, and (b) an Fc region. In some embodiments, the blood cancer expresses CCR8. In some embodiments, the subject has received prior checkpoint inhibitor therapy (CPI) or has CPI-resistant or refractory cancer, as many subjects with CPI-resistant or refractory cancer will present with elevated levels of CCR8-expressing Tregs. In some embodiments, the CPI therapy comprises an anti-PDL1 antibody, an anti-CTLA4 antibody, or an anti-TIGIT antibody. In some embodiments, the anti-PDL1 antibody is selected from pembrolizumab, nivolumab, atezolizumab, avelumab, durvalumab, cemiplimab-rwlc, and zimberelimab; the anti-CLTA4 antibody is ipilimumab or tremelimumab; or the anti-TIGIT antibody is selected from tiragolumab, vibostolimab, domvanalimab, AB308, BMS-986207, and durvalumab. In some embodiments, the blood cancer comprises cells that express CCR8 (e.g., CCR8-expressing Tregs). In some embodiments, the cells that express CCR8 are Treg cells. In some embodiments, the Tregs express CCR8 at fewer that 10,000 copies per cell, which can be determined by, for example, fluorescence-activated cell sorting (FACS) and flow cytometry. In some embodiments, 5%, 10%, 15%, 20%, 25%, 30%, 35%, 40%, 45%, 50%, 55%, 60%, 65%, 70%, 75%, 80%, 85%, 90%, 95%, 99%, or 100% of the tumor-infiltrating Tregs express the surface of the cell fewer than 10,000 copies of CCR8 per cell. In some embodiments, 5%, 10%, 15%, 20%, 25%, 30%, 35%, 40%, 45%, 50%, 55%, 60%, 65%, 70%, 75%, 80%, 85%, 90%, 95%, 99%, or 100% of the tumor-infiltrating Tregs in a sample obtained from a tumor express fewer than 10,000 copies of CCR8 per cell. In some embodiments, the blood cancer may be metastatic.

In some embodiments, the blood cancer is B- and T-cell mixed leukemia, B-cell lymphoma, chronic myeloid leukemia (CML), chronic myelomonocytic leukemia, diffuse large B-cell lymphoma (DLBC), lymphoma, mantle cell lymphoma (MCL), multiple myeloma, myelodysplastic syndromes (MDS), myeloproliferative disorders, peripheral T-cell lymphoma, T-cell leukemia, acute myeloid leukemia (AML), chronic lymphocytic leukemia (CLL), small lymphocytic lymphoma (SLL), CLL/SLL, mature T-cell and NK-cell lymphoma, follicular lymphoma, acute lymphocytic leukemia (ALL), T-cell acute lymphocytic leukemia (TALL), T-cell adult acute lymphocytic leukemia, T-cell childhood acute lymphocytic leukemia, lymphoblastic lymphoma, cutaneous T cell lymphoma (CTCL), adult T cell leukemia/lymphoma (ATLL), T cell lymphoblastic leukemia/lymphoma (TLLL), angioimmunoblastic T cell lymphoma (ATCL), hepatosplenic T cell lymphoma (HTCL), peripheral T cell lymphoma not otherwise specified (PTCL NOS), Burkitt lymphoma (BL), chronic myelomonocytic leukemia (CMML), extranodal NK/T cell lymphoma (NKTCL), primary effusion lymphoma (PEL), acute lymphocytic leukemia/acute myeloid leukemia (ALL, AML), histiocytic lymphoma (HL), marginal zone lymphoma (MZL), B-cell acute lymphocytic leukemia, or anaplastic large cell lymphoma (ALCL).

In some embodiments, the blood cancer is T-cell adult acute lymphocytic leukemia, T-cell childhood acute lymphocytic leukemia, lymphoblastic lymphoma, acute lymphocytic leukemia, cutaneous T cell lymphoma, T-cell acute lymphocytic leukemia, adult T cell leukemia/lymphoma, T cell lymphoblastic leukemia/lymphoma, or anaplastic large cell lymphoma.

In some embodiments, a method of treating a solid cancer (or therapeutic/pharmaceutical use) comprises administering to a subject with a solid cancer an effective amount of an antibody (e.g., 7-B16, 1-K17, etc.) that binds human CCR8. In some embodiments, the antibody inhibits binding of CCL1 to CCR8. In some embodiments, the solid cancer (or tumor infiltrating Tregs) expresses CCR8. In some embodiments the solid cancer comprises intratumoral Tregs. In some embodiments the intratumoral Tregs have elevated levels of CCR8 expression relative to peripheral Tregs. In some embodiments CCR8 is expressed on the surface of the intratumoral Treg cells at fewer than 10,000 copies per cell (e.g., if the entire Treg population has low Treg expression), which can be determined by, for example, fluorescence-activated cell sorting (FACS) and flow cytometry. In some embodiments the intratumoral Tregs comprise Tregs expressing CCR8 at fewer than 10,000 copies per cell (referring to a subpopulation of Tregs with low CCR8 expression). In some embodiments, 5%, 10%, 15%, 20%, 25%, 30%, 35%, 40%, 45%, 50%, 55%, 60%, 65%, 70%, 75%, 80%, 85%, 90%, 95%, 99%, or 100% of the tumor-infiltrating Tregs express the surface of the cell fewer than 10,000 copies of CCR8 per cell. In some embodiments, 5%, 10%, 15%, 20%, 25%, 30%, 35%, 40%, 45%, 50%, 55%, 60%, 6%5%, 70%, 75%, 80%, 85%, 90%, 95%, 99%, or 100% of the tumor-infiltrating Tregs in a sample obtained from a tumor express fewer than 10,000 copies of CCR8 per cell. In some embodiments, the subject has received prior checkpoint inhibitor therapy (CPI) or has CPI-resistant or refractory cancer, as many subjects with CPI-resistant or refractory cancer will present with elevated levels of intratumoral Tregs. In some embodiments, the CPI therapy comprises an anti-PDL1 antibody, an anti-CTLA4 antibody, or an anti-TIGIT antibody. In some embodiments, the anti-PDL1 antibody is selected from pembrolizumab, nivolumab, atezolizumab, avelumab, durvalumab, cemiplimab-rwlc, and zimberelimab; the anti-CLTA4 antibody is ipilimumab or tremelimumab; or the anti-TIGIT antibody is selected from tiragolumab, vibostolimab, domvanalimab, AB308, BMS-986207, and durvalumab. In some embodiments, the intratumoral Tregs are depleted. The depletion of the Tregs may be as a result of the ADCC and/or CDC activity possessed by the disclosed antibodies.

In some embodiments, a method or use of selecting a subject with a solid cancer for treatment with an antibody that binds human CCR8 comprises detecting CCR8 expression in a sample from the subject. In some embodiments, CCR8 expression is detected in a population of tumor infiltrating Tregs in the sample. In some embodiments, the tumor infiltrating Tregs express CCR8 at fewer that 10,000 copies per cell, which can be determined by, for example, fluorescence-activated cell sorting (FACS) and flow cytometry. In some embodiments, 5%, 10%, 15%, 20%, 25%, 30%, 35%, 40%, 45%, 50%, 55%, 60%, 65%, 70%, 75%, 80%, 85%, 90%, 95%, 99%, or 100% of the tumor-infiltrating Tregs express the surface of the cell fewer than 10,000 copies of CCR8 per cell. In some embodiments, a method or use further comprising administering an effective amount of an antibody that binds human CCR8.

In some embodiments, a method of treating a solid cancer (or therapeutic/pharmaceutical use) comprises administering to a subject with a solid cancer an effective amount of a fusion protein. In some embodiments, a method of selecting a subject with a solid cancer for treatment with a fusion protein comprising (a) CCL1 or an active fragment thereof or MC148 or an active fragment thereof, and (b) an Fc region, comprises detecting CCR8 expression in a sample from the subject. In some embodiments, a method further comprises administering an effective amount of a fusion protein comprising (a) CCL1 or an active fragment thereof or MC148 or an active fragment thereof, and (b) an Fc region. In some embodiments, the solid cancer expresses CCR8. In some embodiments, the subject has received prior checkpoint inhibitor therapy (CPI) or has CPI-resistant or refractory cancer, as many subjects with CPI-resistant or refractory cancer will present with elevated levels of CCR8-expressing Tregs. In some embodiments, the CPI therapy comprises an anti-PDL1 antibody, an anti-CTLA4 antibody, or an anti-TIGIT antibody. In some embodiments, the anti-PDL1 antibody is selected from pembrolizumab, nivolumab, atezolizumab, avelumab, durvalumab, cemiplimab-rwlc, and zimberelimab; the anti-CLTA4 antibody is ipilimumab or tremelimumab; or the anti-TIGIT antibody is selected from tiragolumab, vibostolimab, domvanalimab, AB308, BMS-986207, and durvalumab. In some embodiments, the solid cancer comprises cells that express CCR8 (e.g., CCR8-expressing Tregs). In some embodiments, the cells that express CCR8 are Treg cells. In some embodiments, the Tregs express CCR8 at fewer that 10,000 copies per cell (as determined by, for example, FACS and flow cytometry), and may be tumor infiltrating Tregs. In some embodiments, 5%, 10%, 15%, 20%, 25%, 30%, 35%, 40%, 45%, 50%, 55%, 60%, 65%, 70%, 75%, 80%, 85%, 90%, 95%, 99%, or 100% of the tumor-infiltrating Tregs express the surface of the cell fewer than 10,000 copies of CCR8 per cell. In some embodiments, the blood cancer may be metastatic.

In some embodiments, the solid cancer may be selected from breast cancer, colorectal cancer, head and neck cancer, lung cancer, ovarian cancer, gastric cancer, stomach adenocarcinoma, and thymoma. In some embodiments, the solid cancer may be metastatic. In some embodiments when the solid cancer is breast cancer, the breast cancer is triple negative breast cancer (i.e., TNBC). In some embodiments when the solid cancer is breast cancer, the breast cancer is metastatic TNBC.

In some embodiments of any of the foregoing method or uses, the administered antibody (e.g., 7-B16, 1-K17, etc.) or fusion protein may deplete Tregs in the subject as a result of the ADCC and/or CDC properties of the disclosed antibodies and fusion proteins.

An antibody or fusion protein can be administered as needed to subjects. Determination of the frequency of administration can be made by persons skilled in the art, such as an attending physician based on considerations of the condition being treated, age of the subject being treated, severity of the condition being treated, general state of health of the subject being treated and the like. In some embodiments, an effective dose of an antibody or fusion protein is administered to a subject one or more times. In some embodiments, an effective dose of an antibody or fusion protein is administered to the subject once a month, less than once a month, such as, for example, every two months or every three months. In some embodiments, an effective dose of an antibody or fusion protein is administered less than once a month, such as, for example, once every three weeks, once every two weeks, or once every week. An effective dose of an antibody or fusion protein is administered to the subject at least once. In some embodiments, the effective dose of an antibody or fusion protein may be administered multiple times, including for periods of at least a month, at least six months, or at least a year.

In some embodiments, pharmaceutical compositions are administered in an amount effective for treatment of (including prophylaxis of) cancer. The therapeutically effective amount is typically dependent on the weight of the subject being treated, his or her physical or health condition, the extensiveness of the condition to be treated, or the age of the subject being treated. In general, antibodies and fusion proteins may be administered in an amount in the range of about 10 µg/kg body weight to about 100 mg/kg body weight per dose. In some embodiments, antibodies and fusion proteins may be administered in an amount in the range of about 50 µg/kg body weight to about 5 mg/kg body weight per dose. In some embodiments, antibodies and fusion proteins may be administered in an amount in the range of about 100 g/kg body weight to about 10 mg/kg body weight per dose. In some embodiments, antibodies and fusion proteins may be administered in an amount in the range of about 100 µg/kg body weight to about 20 mg/kg body weight per dose. In some embodiments, antibodies and fusion proteins may be administered in an amount in the range of about 0.5 mg/kg body weight to about 20 mg/kg body weight per dose.

Pharmaceutical Compositions

In some embodiments, compositions comprising antibodies and fusion proteins provided herein are provided in formulations with a wide variety of pharmaceutically acceptable carriers (see, for example, Gennaro, Remington: The Science and Practice of Pharmacy with Facts and Comparisons: Drugfacts Plus, 20th ed. (2003); Ansel et al., Pharmaceutical Dosage Forms and Drug Delivery Systems, 7$^{th}$ ed., Lippencott Williams and Wilkins (2004); Kibbe et al., Handbook of Pharmaceutical Excipients, 3$^{rd}$ ed., Pharmaceutical Press (2000)). Various pharmaceutically acceptable carriers, which include vehicles, adjuvants, and diluents, are available. Moreover, various pharmaceutically acceptable auxiliary substances, such as pH adjusting and buffering agents, tonicity adjusting agents, stabilizers, wetting agents and the like, are also available. Non-limiting exemplary carriers include saline, buffered saline, dextrose, water, glycerol, ethanol, and combinations thereof.

In some embodiments, a pharmaceutical composition comprising an antibody or fusion protein is provided. In some embodiments, the pharmaceutical composition comprises a humanized antibody. In some embodiments, the pharmaceutical composition comprises an antibody or fusion protein prepared in a host cell or cell-free system as described herein. In some embodiments, the pharmaceutical composition comprises pharmaceutically acceptable carrier.

In some embodiments, pharmaceutical compositions are administered in an amount effective for treatment of (including prophylaxis of) cancer. The therapeutically effective amount is typically dependent on the weight of the subject being treated, his or her physical or health condition, the extensiveness of the condition to be treated, or the age of the subject being treated.

Routes of Administration

In some embodiments, the antibodies and/or fusion proteins provided herein can be administered in vivo by various routes, including, but not limited to, intravenous, intra-arterial, parenteral, intratumoral, intraperitoneal or subcutaneous. The appropriate formulation and route of administration may be selected according to the intended application.

Combination Therapy

Antibodies and/or fusion proteins provided herein (e.g., 7-B16, 1-K17, etc.) can be administered alone or with other modes of treatment. They can be provided before, substantially contemporaneous with, and/or after other modes of treatment, for example, surgery, chemotherapy, radiation therapy, or the administration of a biologic, such as another therapeutic antibody. In some embodiments, an antibody and/or fusion protein provided herein (e.g., 7-B16, 1-K17, etc.) is administered in conjunction with another anti-cancer agent. In some embodiments, an antibody and/or fusion protein provided herein is administered in conjunction with radiation therapy, such as ablative or non-ablative radiation therapy.

In some embodiments, the antibody and/or fusion protein (e.g., 7-B16, 1-K17, etc.) is given concurrently with a second therapeutic agent. For example, the two or more therapeutic agents are administered with a time separation of no more than about 60 minutes, such as no more than about any of 30, 15, 10, 5, or 1 minutes. In some embodiments, the antibody and/or or fusion protein is administered sequentially with a second therapeutic agent. For example, administration of the two or more therapeutic agents are administered with a time separation of more than about 15 minutes, such as about any of 20, 30, 40, 50, or 60 minutes, 1 day, 2 days, 3 days, 1 week, 2 weeks, or 1 month, or longer.

In some embodiments, the antibody and/or fusion protein (e.g., 7-B16, 1-K17, etc.) is administered with a second therapeutic method for treatment. Thus, the administration of an antibody provided herein can be in combination with another system of treatment.

In some embodiments, an antibody and/or fusion protein provided herein (e.g., 7-B16, 1-K17, etc.) is administered with an anti-PD-1 or anti-PD-L1 therapy. In some embodiments, an antibody and/or fusion protein provided herein is administered with an anti-PD-1 antibody or anti-PD-L1 antibody (e.g., atezolizumab).

In some embodiments, an antibody and/or fusion protein provided herein (e.g., 7-B16, 1-K17, etc.) is administered with an anti-ICOS therapy. In some embodiments, an antibody and/or fusion protein provided herein is administered with an antibody that binds Inducible T-Cell Costimulator (ICOS). In some embodiments, the antibody and/or fusion protein provided herein is administered with an isolated antibody that binds ICOS, wherein the anti-ICOS antibody is an agonist of CD4+ T cells (such as CD4+T effector (Teff) cells). In some embodiments, the antibody that binds ICOS is an agonist of CD4+ T cells (such as CD4+ Teff cells) and depletes T regulatory (Treg) cells.

In some embodiments, the antibody and/or fusion protein provided herein (e.g., 7-B16, 1-K17, etc.) is administered with an agonist anti-OX40 antibody (such as Medi6469, MedImmune; MOXR0916/RG7888, Roche). In some embodiments, the antibody and/or fusion protein provided herein is administered with an anti-CTLA4 antibody (such as ipilimumab, YERVOY®, BMS).

In some embodiments, an additional therapeutic agent is a chemotherapeutic agent. Exemplary chemotherapeutic agents that may be combined with the antibody and/or fusion protein provided herein include, but are not limited to, capectiabine, cyclophosphamide, dacarbazine, temozolomide, cyclophosphamide, docetaxel, doxorubicin, daunorubicin, cisplatin, carboplatin, epirubicin, eribulin, 5-FU, gemcitabine, irinotecan, ixabepilone, methotrexate, mitoxantrone, oxaliplatin, paclitaxel, nab-paclitaxel, ABRAXANE® (protein-bound paclitaxel), pemetrexed, vinorelbine, and vincristine. In some embodiments, an antibody and/or fusion protein provided herein is administered with at least one kinase inhibitor. Nonlimiting exemplary kinase inhibitors include erlotinib, afatinib, gefitinib, crizotinib, dabrafenib, trametinib, vemurafenib, and cobimetanib.

In some embodiments, the additional therapeutic agent is an IDO inhibitor. Nonlimiting exemplary IDO inhibitors are described, e.g., in US 2016/0060237; and US 2015/0352206. Nonlimiting exemplary IDO inhibitors include Indoximod (New Link Genetics), INCB024360 (Incyte Corp), 1-methyl-D-tryptophan (New Link Genetics), and GDC-0919 (Genentech).

In some embodiments, an antibody and/or fusion protein provided herein is administered in combination with an immune-modifying drug (IMiD). Nonlimiting exemplary IMiDs include thalidomide, lenalidomide, and pomalidomide.

In some embodiments, an additional therapeutic agent is a cancer vaccine. Cancer vaccines have been investigated as a potential approach for antigen transfer and activation of dendritic cells. In particular, vaccination in combination with immunologic checkpoints or agonists for co-stimulatory pathways have shown evidence of overcoming tolerance and generating increased anti-tumor response. A range of cancer vaccines have been tested that employ different approaches to promoting an immune response against the tumor (see, e.g., Emens L A, Expert Opin Emerg Drugs 13(2): 295-308 (2008)). Approaches have been designed to enhance the response of B cells, T cells, or professional antigen-presenting cells against tumors. Exemplary types of cancer vaccines include, but are not limited to, peptide-based vaccines that employ targeting distinct tumor antigens, which may be delivered as peptides/proteins or as genetically-engineered DNA vectors, viruses, bacteria, or the like; and cell biology approaches, for example, for cancer vaccine development against less well-defined targets, including, but not limited to, vaccines developed from patient-derived dendritic cells, autologous tumor cells or tumor cell lysates, allogeneic tumor cells, and the like.

Thus, in certain embodiments, the antibody and/or fusion protein provided herein (e.g., 7-B16, 1-K17, etc.) may be used in combination with a cancer vaccine. Exemplary cancer vaccines include, but are not limited to, dendritic cell vaccines, oncolytic viruses, tumor cell vaccines, etc. In some embodiments, such vaccines augment the anti-tumor response. Examples of cancer vaccines that can be used in combination with an antibody and/or fusion protein provided herein include, but are not limited to, MAGE3 vaccine (e.g., for melanoma and bladder cancer), MUC1 vaccine (e.g., for breast cancer), EGFRv3 (such as Rindopepimut, e.g., for brain cancer, including glioblastoma multiforme), or ALVAC-CEA (e.g., for CEA+ cancers).

Nonlimiting exemplary cancer vaccines also include Sipuleucel-T, which is derived from autologous peripheral-blood mononuclear cells (PBMCs) that include antigen-presenting cells (see, e.g., Kantoff P W et al., N Engl J Med 363:411-22 (2010)). In Sipuleucel-T generation, the patient's PBMCs are activated ex vivo with PA2024, a recombinant fusion protein of prostatic acid phosphatase (a prostate antigen) and granulocyte-macrophage colony-stimulating factor (an immune-cell activator). Another approach to a candidate cancer vaccine is to generate an immune response against specific peptides mutated in tumor tissue, such as melanoma (see, e.g., Carreno B M et al., Science 348:6236 (2015)). Such mutated peptides may, in some embodiments, be referred to as neoantigens. As a nonlimiting example of the use of neoantigens in tumor vaccines, neoantigens in the tumor predicted to bind the major histocompatibility complex protein HLA-A*02:01 are identified for individual patients with a cancer, such as melanoma. Dendritic cells from the patient are matured ex vivo, then incubated with neoantigens. The activated dendritic cells are then administered to the patient. In some embodiments, following administration of the cancer vaccine, robust T-cell immunity against the neoantigen is detectable.

In some such embodiments, the cancer vaccine is developed using a neoantigen. In some embodiments, the cancer vaccine is a DNA vaccine. In some embodiments, the cancer vaccine is an engineered virus comprising a cancer antigen, such as PROSTVAC (rilimogene galvacirepvec/rilimogene glafolivec). In some embodiments, the cancer vaccine comprises engineered tumor cells, such as GVAX, which is a granulocyte-macrophage colony-stimulating factor (GM-CSF) gene-transfected tumor cell vaccine (see, e.g., Nemunaitis, 2005, Expert Rev Vaccines, 4: 259-74).

In some embodiments, an antibody and/or fusion protein described herein is administered before, concurrently, and/or after a cancer vaccine. In some embodiments, cancer vaccines developed using neoantigens are used in combination with the antibody and/or fusion protein described herein. In some such embodiments, the combination is used to treat a cancer with a high mutational burden, such as melanoma, lung, bladder, or colorectal cancer.

In some embodiments, an antibody and/or fusion protein provided herein is administered in combination with a chimeric antigen receptor T cell therapy (CAR-T therapy).

In some embodiments an antibody and/or fusion protein provided herein (e.g., 7-B16, 1-K17, etc.), is administered with one or more (e.g., one, two, three, or four) additional therapeutic agents. In some embodiments the additional therapeutic agent includes, e.g., an inhibitory immune checkpoint blocker or inhibitor, a stimulatory immune checkpoint stimulator, agonist or activator, a chemotherapeutic agent, an anti-cancer agent, a radiotherapeutic agent, an anti-neoplastic agent, an anti-proliferation agent, an anti-angiogenic agent, an anti-inflammatory agent, an immunotherapeutic agent, a therapeutic antigen-binding molecule (e.g., a mono- and multi-specific antibody, or fragment thereof, in any format, such as DART®, Duobody®, BiTE®, BiKE, TriKE, XmAb®, TandAb®, scFv, Fab, Fab derivative), a bi-specific antibody, a non-immunoglobulin antibody mimetic (e.g., including adnectin, affibody, affilin, affimer, affitin, alphabody, anticalin, peptide aptamer, armadillo repeat protein (ARM), atrimer, avimer, designed ankyrin repeat protein (DARPin®), fynomer, knottin, Kunitz domain peptide, monobody, and nanoCLAMPs), an antibody-drug conjugate (ADC), antibody-peptide conjugate), an oncolytic virus, a gene modifier or editor, a cell comprising a chimeric antigen receptor (CAR), e.g., including a T-cell immunotherapeutic agent, an NK-cell immunotherapeutic agent, or a macrophage immunotherapeutic agent, a cell comprising an engineered T-cell receptor (TCR-T), or any combination thereof.

Illustrative Targets

In some embodiments, the one or more additional therapeutic agents include, e.g., an inhibitor, agonist, antagonist, ligand, modulator, stimulator, blocker, activator or suppressor of a target (e.g., polypeptide or polynucleotide), such as: 2'-5'-oligoadenylate synthetase (OAS1; NCBI Gene ID: 4938); 5'-3' exoribonuclease 1 (XRN1; NCBI Gene ID: 54464); 5'-nucleotidase ecto (NT5E, CD73; NCBI Gene ID: 4907); ABL proto-oncogene 1, non-receptor tyrosine kinase (ABL1, BCR-ABL, c-ABL, v-ABL; NCBI Gene ID: 25); absent in melanoma 2 (AIM2; NCBI Gene ID: 9447); acetyl-CoA acyltransferase 2 (ACAA2; NCBI Gene ID: 10499); acid phosphatase 3 (ACP3; NCBI Gene ID: 55); adenosine deaminase (ADA, ADA1; NCBI Gene ID: 100); adenosine receptors (e.g., ADORA1 (A1), ADORA2A (A2a, A2AR), ADORA2B (A2b, A2BR), ADORA3 (A3); NCBI Gene IDs: 134, 135, 136, 137); AKT serine/threonine kinase 1 (AKT1, AKT, PKB; NCBI Gene ID: 207); alanyl aminopeptidase, membrane (ANPEP, CD13; NCBI Gene ID: 290); ALK receptor tyrosine kinase (ALK, CD242; NCBI Gene ID: 238); alpha fetoprotein (AFP; NCBI Gene ID: 174); amine oxidase copper containing (e.g., AOC1 (DAO1), AOC2, AOC3 (VAP1); NCBI Gene IDs: 26, 314, 8639); androgen receptor (AR; NCBI Gene ID: 367); angiopoietins (ANGPT1, ANGPT2; NCBI Gene IDs: 284, 285); angiotensin II receptor type 1 (AGTR1; NCBI Gene ID: 185); angiotensinogen (AGT; NCBI Gene ID: 183); apolipoprotein A1 (APOA1; NCBI Gene ID: 335); apoptosis inducing factor mitochondria associated 1 (AIFM1, AIF; NCBI Gene ID: 9131); arachidonate 5-lipoxygenase (ALOX5; NCBI Gene ID: 240); asparaginase (ASPG; NCBI Gene ID: 374569); asteroid homolog 1 (ASTE1; NCBI Gene ID: 28990); ATM serine/threonine kinase (ATM; NCBI Gene ID: 472); ATP binding cassette subfamily B member 1 (ABCB1, CD243, GP170; NCBI Gene ID: 5243); ATP-dependent Clp-protease (CLPP; NCBI Gene ID: 8192); ATR serine/threonine kinase (ATR; NCBI Gene ID: 545); AXL receptor tyrosine kinase (AXL; NCBI Gene ID: 558); B and T lymphocyte associated (BTLA, CD272; NCBI Gene ID: 151888); baculoviral IAP repeat containing proteins (BIRC2 (cIAP1), BIRC3 (cIAP2), XIAP (BIRC4, IAP3), BIRC5 (survivin); NCBI Gene IDs: 329, 330, 331, 332); basigin (Ok blood group) (BSG, CD147; NCBI Gene ID: 682); B-cell lymphoma 2 (BCL2; NCBI Gene ID: 596); BCL2 binding component 3 (BBC3, PUMA; NCBI Gene ID: 27113); BCL2 like (e.g., BCL2L1 (Bcl-x), BCL2L2 (BIM); Bcl-x; NCBI Gene IDs: 598, 10018); beta 3-adrenergic receptor (ADRB3; NCBI Gene ID: 155); bone gamma-carboxyglutamate protein (BGLAP; NCBI Gene ID: 632); bone morphogenetic protein-10 ligand (BMP10; NCBI Gene ID: 27302); bradykinin receptors (e.g., BDKRB1, BDKRB2; NCBI Gene IDs: 623, 624); B-RAF (BRAF; NCBI Gene ID: 273); breakpoint cluster region (BCR; NCBI Gene ID: 613); bromodomain and external domain (BET) bromodomain containing proteins (e.g., BRD2, BRD3, BRD4, BRDT; NCBI Gene IDs: 6046, 8019, 23476, 676); Bruton's tyrosine kinase (BTK; NCBI Gene ID: 695); cadherins (e.g., CDH3 (p-cadherin), CDH6 (k-cadherin); NCBI Gene IDs: 1001, 1004); cancer/testis antigens (e.g., CTAG1A, CTAG1B, CTAG2; NCBI Gene IDs: 1485, 30848, 246100); cannabinoid receptors (e.g., CNR1 (CB1), CNR2 (CB2); NCBI Gene IDs: 1268, 1269); carbohydrate sulfotransferase 15 (CHST15; NCBI Gene ID: 51363); carbonic anhydrases (e.g., CA1, CA2, CA3, CA4, CA5A, CA5B, CA6, CA7, CA8, CA9, CA10, CA11, CA12, CA13, CA14; NCBI Gene IDs: 759, 760, 761, 762, 763, 765, 766, 767, 768, 770, 771, 11238, 23632, 56934, 377677); carcinoembryonic antigen related cell adhesion molecules (e.g., CEACAM3 (CD66d), CEACAM5 (CD66e), CEACAM6 (CD66c); NCBI Gene IDs: 1048, 1084, 4680); casein kinases (e.g., CSNK1A1 (CK1), CSNK2A1 (CK2); NCBI Gene IDs: 1452, 1457); caspases (e.g., CASP3, CASP7, CASP8; NCBI Gene IDs: 836, 840, 841, 864); catenin beta 1 (CTNNB1; NCBI Gene ID: 1499); cathepsin G (CTSG; NCBI Gene ID: 1511); Cbl proto-oncogene B (CBLB, Cbl-b; NCBI Gene ID: 868); C-C motif chemokine ligand 21 (CCL21; NCBI Gene ID: 6366); C-C motif chemokine receptor 2 (CCR2; NCBI Gene ID: 729230); C-C motif chemokine receptors (e.g., CCR3 (CD193), CCR4 (CD194), CCR5 (CD195), CCR8 (CDw198); NCBI Gene IDs: 1232, 1233, 1234, 1237); CCAAT enhancer binding protein alpha (CEBPA, CEBP; NCBI Gene ID: 1050); cell adhesion molecule 1 (CADM1; NCBI Gene ID: 23705); cell division cycle 7 (CDC7; NCBI Gene ID: 8317); cellular communication network factor 2 (CCN2; NCBI Gene ID: 1490); cereblon (CRBN; NCBI Gene ID: 51185); checkpoint kinases (e.g., CHEK1 (CHK1), CHEK2 (CHK2); NCBI Gene IDs: 1111, 11200); cholecystokinin B receptor (CCKBR; NCBI Gene ID: 887); chorionic somatomammotropin hormone 1 (CSH1; NCBI Gene ID: 1442); claudins (e.g., CLDN6, CLDN18; NCBI Gene IDs: 9074, 51208); cluster of differentiation markers (e.g., CD1A, CD1C, CD1D, CD1E, CD2, CD3 alpha (TRA), CD beta (TRB), CD gamma (TRG), CD delta (TRD), CD4, CD8A, CD8B, CD19, CD20 (MS4A1), CD22, CD24, CD25 (IL2RA, TCGFR), CD28, CD33 (SIGLEC3), CD37, CD38, CD39 (ENTPD1), CD40 (TNFRSF5), CD44 (MIC4, PGP1), CD47 (IAP), CD48 (BLAST1), CD52, CD55 (DAF), CD58 (LFA3), CD74, CD79a, CD79b, CD80 (B7-1), CD84, CD86 (B7-2), CD96 (TACTILE), CD99 (MIC2), CD115 (CSF1R), CD116 (GMCSFR, CSF2RA), CD122 (IL2RB), CD123 (IL3RA), CD128 (IL8R1), CD132 (IL2RG), CD135 (FLT3), CD137 (TNFRSF9, 4-1BB), CD142 (TF, TFA), CD152 (CTLA4), CD160, CD182 (IL8R2), CD193 (CCR3), CD194 (CCR4), CD195 (CCR5), CD207, CD221 (IGF1R), CD222 (IGF2R), CD223 (LAG3), CD226 (DNAM1), CD244, CD247, CD248, CD276 (B7-H3), CD331 (FGFR1), CD332 (FGFR2), CD333 (FGFR3), CD334 (FGFR4); NCBI Gene IDs: 909, 911, 912, 913, 914, 919, 920, 923, 925, 926, 930, 931, 933, 940, 941, 942, 945, 951, 952, 953, 958,960, 961, 962, 965, 972, 973, 974, 1043, 1232, 1233, 1234, 1237, 1436, 1438, 1493, 1604, 2152, 2260, 2261, 2263, 2322, 3480, 3482, 3559, 3560, 3561, 3563, 3577, 3579, 3604, 3902, 4267, 6955, 6957, 6964, 6965, 8832, 10666, 11126, 50489, 51744, 80381, 100133941); clusterin (CLU; NCBI Gene ID: 1191); coagulation factors (e.g., F7, FXA; NCBI Gene IDs: 2155, 2159); collagen type IV alpha chains (e.g., COL4A1, COL4A2, COL4A3, COL4A4, COL4A5; NCBI Gene IDs: 1282, 1284, 1285, 1286, 1287); collectin subfamily member 10 (COLEC10; NCBI Gene ID: 10584); colony stimulating factors (e.g., CSF1 (MCSF), CSF2 (GMCSF), CSF3 (GCSF); NCBI Gene IDs: 1435, 1437, 1440); complement factors (e.g., C3, C5; NCBI Gene IDs: 718, 727); COP9 signalosome subunit 5 (COPS5; NCBI Gene ID: 10987); C-type lectin domain family member (e.g., CLEC4C (CD303), CLEC9A (CD370), CLEC12A (CD371); CD371; NCBI Gene ID: 160364, 170482, 283420); C-X-C motif chemokine ligand 12 (CXCL12; NCBI Gene ID: 6387); C-X-C motif chemokine receptors (CXCR1 (IL8R1, CD128), CXCR2 (IL8R2, CD182), CXCR3 (CD182, CD183, IP-10R), CXCR4 (CD184); NCBI Gene ID: 2833, 3577, 3579, 7852); cyclin D1 (CCND1, BCL1; NCBI Gene ID: 595); cyclin dependent kinases (e.g., CDK1, CDK2, CDK3, CDK4, CDK5, CDK6, CDK7, CDK8, CDK9, CDK10, CDK12; NCBI Gene ID: 983, 1017, 1018, 1019, 1020, 1021, 1022, 1024, 1025, 8558, 51755); cyclin G1 (CCNG1; NCBI Gene ID: 900); cytochrome P450 family members (e.g., CYP2D6, CYP3A4, CYP11A1, CYP11B2, CYP17A1, CYP19A1, CYP51A1; NCBI Gene IDs: 1565, 1576, 1583, 1585, 1586, 1588, 1595); cytochrome p450 oxidoreductase (POR; NCBI Gene ID: 5447); cytokine inducible SH2 containing protein (CISH; NCBI Gene ID: 1154); cytotoxic T-lymphocyte associated protein 4 (CTLA4, CD152; NCBI Gene ID: 1493); DEAD-box helicases (e.g., DDX5, DDX6, DDX58; NCBI Gene IDs: 1655, 1656, 23586); delta like canonical Notch ligands (e.g., DLL3, DLL4; NCBI Gene IDs: 10683, 54567); diablo IAP-binding mitochondrial protein (DIABLO, SMAC; NCBI Gene ID: 56616); diacylglycerol kinases (e.g., DGKA, DGKZ; NCBI Gene IDs: 1606, 8525); dickkopf WNT signaling pathway inhibitors (e.g., DKK1, DKK3; NCBI Gene ID: 22943, 27122); dihydrofolate reductase (DHFR; NCBI Gene ID: 1719); dihydropyrimidine dehydrogenase (DPYD; NCBI Gene ID: 1806); dipeptidyl peptidase 4 (DPP4; NCBI Gene ID: 1803); discoidin domain receptor tyrosine kinases (e.g., DDR1 (CD167), DDR2; CD167; NCBI Gene ID: 780, 4921); DNA dependent protein kinase (PRKDC; NCBI Gene ID: 5591); DNA topoisomerases (e.g., TOP1, TOP2A, TOP2B, TOP3A, TOP3B; NCBI Gene ID: 7150, 7153, 7155, 7156, 8940); dopachrome tautomerase (DCT; NCBI Gene ID: 1638); dopamine receptor D2 (DRD2; NCBI Gene ID: 1318); DOT1 like histone lysine methyltransferase (DOT1L; NCBI Gene ID: 84444); ectonucleotide pyrophosphatase/phosphodiesterase 3 (ENPP3, CD203c; NCBI Gene ID: 5169); EMAP like 4 (EML4; NCBI Gene ID: 27436); endoglin (ENG; NCBI Gene ID: 2022); endoplasmic reticulum aminopeptidases (e.g., ERAP1, ERAP2; NCBI Gene ID: 51752, 64167); enhancer of zeste 2 polycomb repressive complex 2 subunit (EZH2; NCBI Gene ID: 2146); ephrin receptors (e.g., EPHA1, EPHA2EPHA3, EPHA4, EPHA5, EPHA7, EPHB4; NCBIGene ID:1969, 2041, 2042, 2043, 2044, 2045, 2050); ephrins (e.g., EFNA1, EFNA4, EFNB2; NCBI Gene ID: 1942, 1945, 1948); epidermal growth factor receptors (e.g., ERBB1 (HER1, EGFR), ERBB1 variant III (EGFRvIII), ERBB2 (HER2, NEU, CD340), ERBB3 (HER3), ERBB4 (HER4); NCBI Gene ID: 1956, 2064, 2065, 2066); epithelial cell adhesion molecule (EPCAM; NCBI Gene ID: 4072); epithelial mitogen (EPGN; NCBI Gene ID: 255324); eukaryotic translation elongation factors (e.g., EEF1A2, EEF2; NCBI Gene ID: 1917, 1938); eukaryotic translation initiation factors (e.g., EIF4A1, EIF5A; NCBI Gene ID: 1973, 1984); exportin-1 (XPO1; NCBI Gene ID: 7514); farnesoid X receptor (NR1H4, FXR; NCBI Gene ID: 9971); Fas ligand (FASLG, FASL, CD95L, CD178, TNFSF6; NCBI Gene ID: 356); fatty acid amide hydrolase (FAAH; NCBI Gene ID: 2166); fatty acid synthase (FASN; FAS; NCBI Gene ID: 2194); Fc fragment of Ig receptors (e.g., FCER1A, FCGRT, FCGR3A (CD16); NCBI Gene IDs: 2205, 2214, 2217); Fc receptor like 5 (FCRL5, CD307; NCBI Gene ID: 83416); fibroblast activation protein alpha (FAP; NCBI Gene ID: 2191); fibroblast growth factor receptors (e.g., FGFR1 (CD331), FGFR2 (CD332), FGFR3 (CD333), FGFR4 (CD334); NCBI Gene IDs: 2260, 2261, 2263, 2264); fibroblast growth factors (e.g., FGF1 (FGF alpha), FGF2 (FGF beta), FGF4, FGF5; NCBI Gene IDs: 2246, 2247, 2249, 2250); fibronectin 1 (FN1, MSF; NCBI Gene ID: 2335); fms related receptor tyrosine kinases (e.g., FLT1 (VEGFR1), FLT3 (STK1, CD135), FLT4 (VEGFR2); NCBI Gene IDs: 2321, 2322, 2324); fms related receptor tyrosine kinase 3 ligand (FLT3LG; NCBI Gene ID: 2323); focal adhesion kinase 2 (PTK2, FAK1; NCBI Gene ID: 5747); folate hydrolase 1 (FOLH1, PSMA; NCBI Gene ID: 2346); folate receptor 1 (FOLR1; NCBI Gene ID: 2348); forkhead box protein M1 (FOXM1; NCBI Gene ID: 2305); FURIN (FURIN, PACE; NCBI Gene ID: 5045); FYN tyrosine kinase (FYN, SYN; NCBI Gene ID: 2534); galectins (e.g., LGALS3, LGALS8 (PCTA1), LGALS9; NCBI Gene ID: 3958, 3964, 3965); glucocorticoid receptor (NR3C1, GR; NCBI Gene ID: 2908); glucuronidase beta (GUSB; NCBI Gene ID: 2990); glutamate metabotropic receptor 1 (GRM1; NCBI Gene ID: 2911); glutaminase (GLS; NCBI Gene ID: 2744); glutathione S-transferase Pi (GSTP1; NCBI Gene ID: 2950); glycogen synthase kinase 3 beta (GSK3B; NCBI Gene ID: 2932); glypican 3 (GPC3; NCBI Gene ID: 2719); gonadotropin releasing hormone 1 (GNRH1; NCBI Gene ID: 2796); gonadotropin releasing hormone receptor (GNRHR; NCBI Gene ID: 2798); GPNMB glycoprotein nmb (GPNMB, osteoactivin; NCBI Gene ID: 10457); growth differentiation factor 2 (GDF2, BMP9; NCBI Gene ID: 2658); growth factor receptor-bound protein 2 (GRB2, ASH; NCBI Gene ID: 2885); guanylate cyclase 2C (GUCY2C, STAR, MECIL, MUCIL, NCBI Gene ID: 2984); H19 imprinted maternally expressed transcript (H19; NCBI Gene ID: 283120); HCK proto-oncogene, Src family tyrosine kinase (HCK; NCBI Gene ID: 3055); heat shock proteins (e.g., HSPA5 (HSP70, BIP, GRP78), HSPB1 (HSP27), HSP90B1 (GP96); NCBI Gene IDs: 3309, 3315, 7184); heme oxygenases (e.g., HMOX1 (HO1), HMOX2 (HO1); NCBI Gene ID: 3162, 3163); heparanase (HPSE; NCBI Gene ID: 10855); hepatitis A virus cellular receptor 2 (HAVCR2, TIM3, CD366; NCBI Gene ID: 84868); hepatocyte growth factor (HGF; NCBI Gene ID: 3082); HERV-H LTR-associating 2 (HHLA2, B7-H7; NCBI Gene ID: 11148); histamine receptor H2 (HRH2; NCBI Gene ID: 3274); histone deacetylases (e.g., HDAC1, HDAC7, HDAC9; NCBI Gene ID: 3065, 9734, 51564); HRas proto-oncogene, GTPase (HRAS; NCBI Gene ID: 3265); hypoxia-inducible factors (e.g., HIF1A, HIF2A (EPAS1); NCBI Gene IDs: 2034, 3091); I-Kappa-B kinase (IKK beta; NCBI Gene IDs: 3551, 3553); IKAROS family zinc fingers (IKZF1 (LYF1), IKZF3; NCBI Gene ID: 10320, 22806); immunoglobulin superfamily member 11 (IGSF11; NCBI Gene ID: 152404); indoleamine 2,3-dioxygenases (e.g., IDO1, IDO2; NCBI Gene IDs: 3620, 169355); inducible T cell costimulator (ICOS, CD278; NCBI Gene ID: 29851); inducible T cell costimulator ligand (ICOSLG, B7-H2;

NCBI Gene ID: 23308); insulin like growth factor receptors (e.g., IGF1R, IGF2R; NCBI Gene ID: 3480, 3482); insulin like growth factors (e.g., IGF1, IGF2; NCBI Gene IDs: 3479, 3481); insulin receptor (INSR, CD220; NCBI Gene ID: 3643); integrin subunits (e.g., ITGA5 (CD49e), ITGAV (CD51), ITGB1 (CD29), ITGB2 (CD18, LFA1, MAC1), ITGB7; NCBI Gene IDs: 3678, 3685, 3688, 3695, 3698); intercellular adhesion molecule 1 (ICAM1, CD54; NCBI Gene ID: 3383); interleukin 1 receptor associated kinase 4 (IRAK4; NCBI Gene ID: 51135); interleukin receptors (e.g., IL2RA (TCGFR, CD25), IL2RB (CD122), IL2RG (CD132), IL3RA, IL6R, IL13RA2 (CD213A2), IL22RA1; NCBI Gene IDs: 3598, 3559, 3560, 3561, 3563, 3570, 58985); interleukins (e.g., IL1A, IL1B, IL2, IL3, IL6 (HGF), IL7, IL8 (CXCL8), IL10 (TGIF), IL12A, IL12B, IL15, IL17A (CTLA8), IL23A, IL24, IL-29 (IFNL1); NCBI Gene IDs: 3552, 3553, 3558, 3562, 3565, 3569, 3574, 3586, 3592, 3593, 3600, 3605, 11009, 51561, 282618); isocitrate dehydrogenases (NADP(+)1) (e.g., IDH1, IDH2; NCBI Gene IDs: 3417, 3418); Janus kinases (e.g., JAK1, JAK2, JAK3; NCBI Gene IDs: 3716, 3717, 3718); kallikrein related peptidase 3 (KLK3; NCBI Gene ID: 354); killer cell immunoglobulin like receptor, Ig domains and long cytoplasmic tails (e.g., KIR2DL1 (CD158A), KIR2DL2 (CD158B1), KIR2DL3 (CD158B), KIR2DL4 (CD158D), KIR2DL5A (CD158F), KIR2DL5B, KIR3DL1 (CD158E1), KIR3DL2 (CD158K), KIR3DP1 (CD158c), KIR2DS2 (CD158J); NCBI Gene IDs: 3802, 3803, 3804, 3805, 3811, 3812, 57292, 553128, 548594, 100132285); killer cell lectin like receptors (e.g., KLRC1 (CD159A), KLRC2 (CD159c), KLRC3, KLRRC4, KLRD1 (CD94), KLRG1, KLRK1 (NKG2D, CD314); NCBI Gene IDs: 3821, 3822, 3823, 3824, 8302, 10219, 22914); kinase insert domain receptor (KDR, CD309, VEGFR2; NCBI Gene ID: 3791); kinesin family member 11 (KIF11; NCBI Gene ID: 3832); KiSS-1 metastasis suppressor (KISS1; NCBI Gene ID: 3814); KIT proto-oncogene, receptor tyrosine kinase (KIT, C-KIT, CD117; NCBI Gene ID: 3815); KRAS proto-oncogene, GTPase (KRAS; NCBI Gene ID: 3845); lactotransferrin (LTF; NCBI Gene ID: 4057); LCK proto-oncogene, Src family tyrosine kinase (LCK; NCBI Gene ID: 3932); LDL receptor related protein 1 (LRP1, CD91, IGFBP3R; NCBI Gene ID: 4035); leucine rich repeat containing 15 (LRRC15; NCBI Gene ID: 131578); leukocyte immunoglobulin like receptors (e.g., LILRB1 (ILT2, CD85J), LILRB2 (ILT4, CD85D); NCBI Gene ID: 10288, 10859); leukotriene A4 hydrolase (LTA4H; NCBI Gene ID: 4048); linker for activation of T-cells (LAT; NCBI Gene ID: 27040); luteinizing hormone/choriogonadotropin receptor (LHCGR; NCBI Gene ID: 3973); LY6/PLAUR domain containing 3 (LYPD3; NCBI Gene ID: 27076); lymphocyte activating 3 (LAG3; CD223; NCBI Gene ID: 3902); lymphocyte antigens (e.g., LY9 (CD229), LY75 (CD205); NCBI Gene IDs: 4063, 17076); LYN proto-oncogene, Src family tyrosine kinase (LYN; NCBI Gene ID: 4067); lypmphocyte cytosolic protein 2 (LCP2; NCBI Gene ID: 3937); lysine demethylase 1A (KDM1A; NCBI Gene ID: 23028); lysophosphatidic acid receptor 1 (LPAR1, EDG2, LPA1, GPR26; NCBI Gene ID: 1902); lysyl oxidase (LOX; NCBI Gene ID: 4015); lysyl oxidase like 2 (LOXL2; NCBI Gene ID: 4017); macrophage migration inhibitory factor (MIF, GIF; NCBI Gene ID: 4282); macrophage stimulating 1 receptor (MST1R, CD136; NCBI Gene ID: 4486); MAGE family members (e.g., MAGEA1, MAGEA2, MAGEA2B, MAGEA3, MAGEA4, MAGEA5, MAGEA6, MAGEA10, MAGEA11, MAGEC1, MAGEC2, MAGED1, MAGED2; NCBI Gene IDs: 4100, 4101, 4102, 4103, 4104, 4105, 4109, 4110, 9500, 9947, 10916, 51438, 266740); major histocompatibility complexes (e.g., HLA-A, HLA-E, HLA-F, HLA-G; NCBI Gene IDs: 3105, 3133, 3134, 3135); major vault protein (MVP, VAULT1; NCBI Gene ID: 9961); MALT1 paracaspase (MALT1; NCBI Gene ID: 10892); MAPK activated protein kinase 2 (MAPKAPK2; NCBI Gene ID: 9261); MAPK interacting serine/threonine kinases (e.g., MKNK1, MKNK2; NCBI Gene IDs: 2872, 8569); matrix metallopeptidases (e.g., MMP1, MMP2, MMP3, MMP7, MMP8, MMP9, MMP10, MMP11, MMP12, MMP13, MMP14, MMPP15, MMP16, MMP17, MMP19, MMP20, MMP21, MMP24, MMP25, MMP26, MMP27, MMP28; NCBI Gene IDs: 4312, 4313, 4314, 4316, 4317, 4318, 4319, 4320, 4321, 4322, 4323, 4324, 4325, 4326, 4327, 9313, 10893, 56547, 64066, 64386, 79148, 118856); MCL1 apoptosis regulator, BCL2 family member (MCL1; NCBI Gene ID: 4170); MDM2 proto-oncogene (MDM2; NCBI Gene ID: 4193); MDM4 regulator of p53 (MDM4; BMFS6; NCBI Gene ID: 4194); mechanistic target of rapamycin kinase (MTOR, FRAP1; NCBI Gene ID: 2475); melan-A (MLANA; NCBI Gene ID: 2315); melanocortin receptors (MC1R, MC2R; NCBI Gene IDs: 4157, 4148); MER proto-oncogene, tyrosine kinase (MERTK; NCBI Gene ID: 10461); mesothelin (MSLN; NCBI Gene ID: 10232); MET proto-oncogene, receptor tyrosine kinase (MET, c-Met, HGFR; NCBI Gene ID: 4233); methionyl aminopeptidase 2 (METAP2, MAP2; NCBI Gene ID: 10988); MHC class I polypeptide-related sequences (e.g., MICA, MICB; NCBI Gene IDs: 4277, 100507436); mitogen activated protein kinases (e.g., MAPK1 (ERK2), MAPK3 (ERK1), MAPK8 (JNK1), MAPK9 (JNK2), MAPK10 (JNK3), MAPK11 (p38 beta), MAPK12; NCBI Gene IDs: 5594, 5595, 5599, 5600, 5601, 5602, 819251); mitogen-activated protein kinase kinase kinases (e.g., MAP3K5 (ASK1), MAP3K8 (TPL2, AURA2); NCBI Gene IDs: 4217, 1326); mitogen-activated protein kinase kinase kinase kinase 1 (MAP4K1, HPK1; NCBI Gene ID: 11184); mitogen-activated protein kinase kinases (e.g., MAP2K1 (MEK1), MAP2K2 (MEK2), MAP2K7 (MEK7); NCBI Gene IDs: 5604, 5605, 5609); MPL proto-oncogene, thrombopoietin receptor (MPL; NCBI Gene ID: 4352); mucins (e.g., MUC1 (including splice variants thereof (e.g., including MUC1/A, C, D, X, Y, Z and REP)), MUC5AC, MUC16 (CA125); NCBI Gene IDs: 4582, 4586, 94025); MYC proto-oncogene, bHLH transcription factor (MYC; NCBI Gene ID: 4609); myostatin (MSTN, GDF8; NCBI Gene ID: 2660); myristoylated alanine rich protein kinase C substrate (MARCKS; NCBI Gene ID: 4082); natriuretic peptide receptor 3 (NPR3; NCBI Gene ID: 4883); natural killer cell cytotoxicity receptor 3 ligand 1 (NCR3LG1, B7-H6; NCBI Gene ID: 374383); necdin, MAGE family member (NDN; NCBI Gene ID: 4692); nectin cell adhesion molecules (e.g., NECTIN2 (CD112, PVRL2), NECTIN4 (PVRL4); NCBI Gene IDs: 5819, 81607); neural cell adhesion molecule 1 (NCAM1, CD56; NCBI Gene ID: 4684); neuropilins (e.g., NRP1 (CD304, VEGF165R), NRP2 (VEGF165R2); NCBI Gene IDs: 8828, 8829); neurotrophic receptor tyrosine kinases (e.g., NTRK1 (TRKA), NTRK2 (TRKB), NTRK3 (TRKC); NCBI Gene IDs: 4914, 4915, 4916); NFKB activating protein (NKAP; NCBI Gene ID: 79576); NIMA related kinase 9 (NEK9; NCBI Gene ID: 91754); NLR family pyrin domain containing 3 (NLRP3, NALP3; NCBI Gene ID: 114548); notch receptors (e.g., NOTCH1, NOTCH2, NOTCH3, NOTCH4; NCBI Gene IDs: 4851, 4853, 4854, 4855); NRAS proto-oncogene, GTPase (NRAS; NCBI Gene ID: 4893); nuclear factor kappa B (NFKB1, NFKB2; NCBI Gene IDs: 4790, 4791); nuclear factor, erythroid 2 like 2

(NFE2L2; NRF2; NCBI Gene ID: 4780); nuclear receptor subfamily 4 group A member 1 (NR4A1; NCBI Gene ID: 3164); nucleolin (NCL; NCBI Gene ID: 4691); nucleophosmin 1 (NPM1; NCBI Gene ID: 4869); nucleotide binding oligomerization domain containing 2 (NOD2; NCBI Gene ID: 64127); nudix hydrolase 1 (NUDT1; NCBI Gene ID: 4521); O-6-methylguanine-DNA methyltransferase (MGMT; NCBI Gene ID: 4255); opioid receptor delta 1 (OPRD1; NCBI Gene ID: 4985); ornithine decarboxylase 1 (ODC1; NCBI Gene ID: 4953); oxoglutarate dehydrogenase (OGDH; NCBI Gene ID: 4967); parathyroid hormone (PTH; NCBI Gene ID: 5741); PD-L1 (CD274; NCBI Gene ID: 29126); periostin (POSTN; NCBI Gene ID: 10631); peroxisome proliferator activated receptors (e.g., PPARA (PPAR alpha), PPARD (PPAR delta), PPARG (PPAR gamma); NCBI Gene IDs: 5465, 5467, 5468); phosphatase and tensin homolog (PTEN; NCBI Gene ID: 5728); phosphatidylinositol-4,5-bisphosphate 3-kinases (PIK3CA (PI3K alpha), PIK3B (PI3K beta), PIK3D (PI3K delta), PIK3CG (PI3K gamma); NCBI Gene IDs: 5290, 5291, 5293, 5294); phospholipases (e.g., PLA2G1B, PLA2G2A, PLA2G2D, PLA2G3, PLA2G4A, PLA2G5, PLA2G7, PLA2G10, PLA2G12A, PLA2G12B, PLA2G15; NCBI Gene IDs: 5319, 5320, 5321, 5322, 7941, 8399, 50487, 23659, 26279, 81579, 84647); Pim proto-oncogene, serine/threonine kinases (e.g., PIM1, PIM2, PIM3; NCBI Gene IDs: 5292, 11040, 415116); placenta growth factor (PGF; NCBI Gene ID: 5228); plasminogen activator, urokinase (PLAU, u-PA, ATF; NCBI Gene ID: 5328); platelet derived growth factor receptors (e.g., PDGFRA (CD140A, PDGFR2), FDGFRB (CD140B, PDGFR1); NCBI Gene IDs: 5156, 5159); plexin B1 (PLXNB1; NCBI Gene ID: 5364); poliovirus receptor (PVR) cell adhesion molecule (PVR, CD155; NCBI Gene ID: 5817); polo like kinase 1 (PLK1; NCBI Gene ID: 5347); poly(ADP-ribose) polymerases (e.g., PARP1, PARP2, PARP3; NCBI Gene IDs: 142, 10038, 10039); polycomb protein EED (EED; NCBI Gene ID: 8726); porcupine O-acyltransferase (PORCN; NCBI Gene ID: 64840); PRAME nuclear receptor transcriptional regulator (PRAME; NCBI Gene ID: 23532); premelanosome protein (PMEL; NCBI Gene ID: 6490); progesterone receptor (PGR; NCBI Gene ID: 5241); programmed cell death 1 (PDCD1, PD-1, CD279; NCBI Gene ID: 5133); programmed cell death 1 ligand 2 (PDCD1LG2, CD273, PD-L2; NCBI Gene ID: 80380); prominin 1 (PROM1, CD133; NCBI Gene ID: 8842); promyelocytic leukemia (PML; NCBI Gene ID: 5371); prosaposin (PSAP; NCBI Gene ID: 5660); prostaglandin E receptor 4 (PTGER4; NCBI Gene ID: 5734); prostaglandin E synthase (PTGES; NCBI Gene ID: 9536); prostaglandin-endoperoxide synthases (PTGS1 (COX1), PTGS2 (COX2); NCBI Gene ID: 5742, 5743); proteasome 20S subunit beta 9 (PSMB9; NCBI Gene ID: 5698); protein arginine methyltransferases (e.g., PRMT1, PRMT5; NCBI Gene IDs: 3276, 10419); protein kinase N3 (PKN3; NCBI Gene ID: 29941); protein phosphatase 2A (PPP2CA; NCBI Gene ID: 5515); protein tyrosine kinase 7 (inactive) (PTK7; NCBI Gene ID: 5754); protein tyrosine phosphatase receptors (PTPRB (PTPB), PTPRC (CD45R); NCBI Gene IDs: 5787, 5788); prothymosin alpha (PTMA; NCBI Gene ID: 5757); purine nucleoside phosphorylase (PNP; NCBI Gene ID: 4860); purinergic receptor P2X 7 (P2RX7; NCBI Gene ID: 5027); PVR related immunoglobulin domain containing (PVRIG, CD112R; NCBI Gene ID: 79037); Raf-1 proto-oncogene, serine/threonine kinase (RAF1, c-Raf, NCBI Gene ID: 5894); RAR-related orphan receptor gamma (RORC; NCBI Gene ID: 6097); ras homolog family member C (RHOC; NCBI Gene ID: 389); Ras homolog, mTORC1 binding (RHEB; NCBI Gene ID: 6009); RB transcriptional corepressor 1 (RB1; NCBI Gene ID: 5925); receptor-interacting serine/threonine protein kinase 1 (RIPK1; NCBI Gene ID: 8737); ret proto-oncogene (RET; NCBI Gene ID: 5979); retinoic acid early transcripts (e.g., RAET1E, RAET1G, RAET1L; NCBI Gene IDs: 135250, 154064, 353091); retinoic acid receptors alpha (e.g., RARA, RARG; NCBI Gene IDs: 5914, 5916); retinoid X receptors (e.g., RXRA, RXRB, RXRG; NCBI Gene IDs: 6256, 6257, 6258); Rho associated coiled-coil containing protein kinases (e.g., ROCK1, ROCK2; NCBI Gene IDs: 6093, 9475); ribosomal protein S6 kinase B1 (RPS6KB1, S6K-beta 1; NCBI Gene ID: 6198); ring finger protein 128 (RNF128, GRAIL; NCBI Gene ID: 79589); ROS proto-oncogene 1, receptor tyrosine kinase (ROS1; NCBI Gene ID: 6098); roundabout guidance receptor 4 (ROBO4; NCBI Gene ID: 54538); RUNX family transcription factor 3 (RUNX3; NCBI Gene ID: 864); S100 calcium binding protein A9 (S100A9; NCBI Gene ID: 6280); secreted frizzled related protein 2 (SFRP2; NCBI Gene ID: 6423); secreted phosphoprotein 1 (SPP1; NCBI Gene ID: 6696); secretoglobin family 1A member 1 (SCGB1A1; NCBI Gene ID: 7356); selectins (e.g., SELE, SELL (CD62L), SELP (CD62); NCBI Gene IDs: 6401, 6402, 6403); semaphorin 4D (SEMA4D; CD100; NCBI Gene ID: 10507); sialic acid binding Ig like lectins (SIGLEC9 (CD329), SIGLEC10; NCBI Gene ID: 27180, 89790); signal regulatory protein alpha (SIRPA, CD172A; NCBI Gene ID: 140885); signal transducer and activator of transcription (e.g., STAT1, STAT3, STAT5A, STAT5B; NCBI Gene IDs: 6772, 6774, 6776, 6777); sirtuin-3 (SIRT3; NCBI Gene ID: 23410); signaling lymphocytic activation molecule (SLAM) family members (e.g., SLAMF1 (CD150), SLAMF6 (CD352), SLAMF7 (CD319), SLAMF8 (CD353), SLAMF9; NCBI Gene IDs: 56833, 57823, 89886, 114836); SLIT and NTRK like family member 6 (SLITRK6; NCBI Gene ID: 84189); smoothened, frizzled class receptor (SMO; NCBI Gene ID: 6608); soluble epoxide hydrolase 2 (EPHX2; NCBI Gene ID: 2053); solute carrier family members (e.g., SLC3A2 (CD98), SLC5A5, SLC6A2, SLC10A3, SLC34A2, SLC39A6, SLC43A2 (LAT4), SLC44A4; NCBI Gene IDs: 6520, 6528, 6530, 8273, 10568, 25800, 80736, 124935); somatostatin receptors (e.g., SSTR1, SSTR2, SSTR3, SSTR4, SSTR5; NCBI Gene IDs: 6751, 6752, 6753, 6754, 6755); sonic hedgehog signaling molecule (SHH; NCBI Gene ID: 6469); Sp1 transcription factor (SP1; NCBI Gene ID: 6667); sphingosine kinases (e.g., SPHK1, SPHK2; NCBI Gene IDs: 8877, 56848); sphingosine-1-phosphate receptor 1 (S1PR1, CD363; NCBI Gene ID: 1901); spleen associated tyrosine kinase (SYK; NCBI Gene ID: 6850); splicing factor 3B factor 1 (SF3B1; NCBI Gene ID: 23451); SRC proto-oncogene, non-receptor tyrosine kinase (SRC; NCBI Gene ID: 6714); stabilin 1 (STAB1, CLEVER-1; NCBI Gene ID: 23166); STEAP family member 1 (STEAP1; NCBI Gene ID: 26872); steroid sulfatase (STS; NCBI Gene ID: 412); stimulator of interferon response cGAMP interactor 1 (STING1; NCBI Gene ID: 340061); superoxide dismutase 1 (SOD1, ALS1; NCBI Gene ID: 6647); suppressors of cytokine signaling (SOCS1 (CISH1), SOCS3 (CISH3); NCBI Gene ID: 8651, 9021); synapsin 3 (SYN3; NCBI Gene ID: 8224); syndecan 1 (SDC1, CD138, syndecan; NCBI Gene ID: 6382); synuclein alpha (SNCA, PARK1; NCBI Gene ID: 6622); T cell immunoglobulin and mucin domain containing 4 (TIMD4, SMUCKLER; NCBI Gene ID: 91937); T cell immunoreceptor with Ig and ITIM domains (TIGIT; NCBI Gene ID: 201633); tachykinin receptors (e.g., TACR1, TACR3; NCBI Gene ID: 6869, 6870); TANK binding kinase 1 (TBK1; NCBI Gene ID: 29110); tankyrase (TNKS; NCBI Gene ID: 8658); TATA-box binding protein associated factor, RNA polymerase I subunit B (TAF1B; NCBI Gene ID: 9014); T-box transcription factor T (TBXT; NCBI Gene ID: 6862); TCDD inducible poly(ADP-ribose) polymerase (TIPARP, PAPR7; NCBI Gene ID: 25976); tec protein tyrosine kinase (TEC; NCBI Gene ID: 7006); TEK receptor tyrosine kinase (TEK, CD202B, TIE2; NCBI Gene ID: 7010); telomerase reverse transcriptase (TERT; NCBI Gene ID: 7015); tenascin C (TNC; NCBI Gene ID: 3371); three prime repair exonucleases (e.g., TREX1, TREX2; NCBI Gene ID: 11277, 11219); thrombomodulin (THBD, CD141; NCBI Gene ID: 7056); thymidine kinases (e.g., TK1, TK2; NCBI Gene IDs: 7083, 7084); thymidine phosphorylase (TYMP; NCBI Gene ID: 1890); thymidylate synthase (TYMS; NCBI Gene ID: 7298); thyroid hormone receptor (THRA, THRB; NCBI Gene IDs: 7606, 7608); thyroid stimulating hormone receptor (TSHR; NCBI Gene ID: 7253); TNF superfamily members (e.g., TNFSF4 (OX40L, CD252), TNFSF5 (CD40L), TNFSF7 (CD70), TNFSF8 (CD153, CD30L), TNFSF9 (4-1BB-L, CD137L), TNFSF10 (TRAIL, CD253, APO2L), TNFSF11 (CD254, RANKL2, TRANCE), TNFSF13 (APRIL, CD256, TRAIL2), TNFSF13b (BAFF, BLYS, CD257), TNFSF14 (CD258, LIGHT), TNFSF18 (GITRL); NCBI Gene IDs: 944, 959, 970, 7292, 8600, 8740, 8741, 8743, 8744, 8995); toll like receptors (e.g., TLR1 (CD281), TLR2 (CD282), TLR3 (CD283), TLR4 (CD284), TLR5, TLR6 (CD286), TLR7, TLR8 (CD288), TLR9 (CD289), TLR10 (CD290); NCBI Gene IDs: 7096, 7097, 7098, 7099, 10333, 51284, 51311, 54106, 81793); transferrin (TF; NCBI Gene ID: 7018); transferrin receptor (TFRC, CD71; NCBI Gene ID: 7037); transforming growth factors (e.g., TGFA, TGFB1; NCBI Gene ID: 7039, 7040); transforming growth factor receptors (e.g., TGFBR1, TGFBR2, TGFBR3; NCBI Gene ID: 7046, 7048, 7049); transforming protein E7 (E7; NCBI Gene ID: 1489079); transglutaminase 5 (TGM5; NCBI Gene ID: 9333); transient receptor potential cation channel subfamily V member 1 (TRPV1, VR1; NCBI Gene ID: 7442); transmembrane and immunoglobulin domain containing 2 (TMIGD2, CD28H, IGPR1; NCBI Gene ID: 126259); triggering receptors expressed on myeloid cells (e.g., TREM1 (CD354), TREM2; NCBI Gene ID: 54209, 54210); trophinin (TRO, MAGED3; NCBI Gene ID: 7216); trophoblast glycoprotein (TPBG; NCBI Gene ID: 7162); tryptophan 2,3-dioxygenase (TDO2; NCBI Gene ID: 6999); tryptophan hydroxylases (e.g., TPH1, TPH2; NCBI Gene ID: 7166, 121278); tumor associated calcium signal transducer 2 (TACSTD2, TROP2; NCBI Gene ID: 4070); tumor necrosis factor (TNF; NCBI Gene ID: 7124); tumor necrosis factor (TNF) receptor superfamily members (e.g., TNFRSF1A (CD120a), TNFRSF1B (CD120b), TNFRSF4 (OX40), TNFRSF5 (CD40), TNFRSF6 (CD95, FAS receptor), TNFRSF7 (CD27), TNFRSF8 (CD30), TNFRSF9 (CD137, 4-1BB), TNFRSF10A (CD261), TNFRSF10B (TRAIL, DR5, CD262), TNFRSF10C, TNFRSF10D, TNFRSF11A, TNFRSF11B (OPG), TNFRSF12A, TNFRSF13B, TNFR13C (CD268, BAFFR), TNFRSF14 (CD270, LIGHTR), TNFRSF16, TNFRSF17 (CD269, BCMA), TNFRSF18 (GITR, CD357), TNFRSF19, TNFRSF21, TNFRSF25; NCBI Gene IDs: 355, 608, 939, 943, 958, 3604, 4804, 4982, 7132, 7133, 7293, 8718, 8764, 8784, 8792, 8793, 8794, 8795, 8797, 23495, 27242, 51330, 55504); tumor protein p53 (TP53; NCBI Gene ID: 7157); tumor suppressor 2, mitochondrial calcium regulator (TUSC2; NCBI Gene ID: 11334); TYRO3 protein tyrosine kinase (TYRO3; BYK; NCBI Gene ID: 7301); tyrosinase (TYR; NCBI Gene ID: 7299); tyrosine hydroxylase (TH; NCBI Gene ID: 7054); tyrosine kinase with immunoglobulin like and EGF like domains 1 (e.g., TIE1, TIE1; NCBI Gene ID: 7075); tyrosine-protein phosphatase non-receptor type 11 (PTPN11, SHP2; NCBI Gene ID: 5781); ubiquitin conjugating enzyme E2 I (UBE2I, UBC9; NCBI Gene ID: 7329); ubiquitin C-terminal hydrolase L5 (UCHL5; NCBI Gene ID: 51377); ubiquitin specific peptidase 7 (USP7; NCBI Gene ID: 7874); ubiquitin-like modifier activating enzyme 1 (UBA1; NCBI Gene ID: 7317); UL16 binding proteins (e.g., ULBP1, ULBP2, ULBP3; NCBI Gene ID: 79465, 80328, 80328); valosin-containing protein (VCP, CDC48; NCBI Gene ID: 7415); vascular cell adhesion molecule 1 (VCAM1, CD106; NCBI Gene ID: 7412); vascular endothelial growth factors (e.g., VEGFA, VEGFB; NCBI Gene ID: 7422, 7423); vimentin (VIM; NCBI Gene ID: 7431); vitamin D receptor (VDR; NCBI Gene ID: 7421); V-set domain containing T cell activation inhibitor 1 (VTCN1, B7-H4; NCBI Gene ID: 79679); V-set immunoregulatory receptor (VSIR, VISTA, B7-H5; NCBI Gene ID: 64115); WEE1 G2 checkpoint kinase (WEE1; NCBI Gene ID: 7465); WRN RecQ like helicase (WRN; RECQ3; NCBI Gene ID: 7486); WT1 transcription factor (WT1; NCBI Gene ID: 7490); WW domain containing transcription regulator 1 (WWTR1; TAZ; NCBI Gene ID: 25937); X-C motif chemokine ligand 1 (XCL1, ATAC; NCBI Gene ID: 6375); X-C motif chemokine receptor 1 (XCR1, GPR5, CCXCR1; NCBI Gene ID: 2829); Yes1 associated transcriptional regulator (YAP1; NCBI Gene ID: 10413); zeta chain associated protein kinase 70 (ZAP70; NCBI Gene ID: 7535).

In some embodiments, the one or more additional therapeutic agents include, e.g., an inhibitor or antagonist of: protein tyrosine phosphatase, non-receptor type 11 (PTPN11 or SHP2; NCBI Gene ID: 5781); myeloid cell leukemia sequence 1 (MCL1) apoptosis regulator (NCBI Gene ID: 4170); mitogen-activated protein kinase kinase kinase kinase 1 (MAP4K1) (also called Hematopoietic Progenitor Kinase 1 (HPK1), NCBI Gene ID: 11184); phosphatidylinositol-4,5-bisphosphate 3-kinase, including catalytic subunit alpha (PIK3CA; NCBI Gene ID: 5290), catalytic subunit beta (PIK3CB; NCBI Gene ID: 5291), catalytic subunit gamma (PIK3CG; NCBI Gene ID: 5294) and catalytic subunit delta (PIK3CD; NCBI Gene ID: 5293), diacylglycerol kinase alpha (DGKA, DAGK, DAGK1 or DGK-alpha; NCBI Gene ID: 1606); 5'-nucleotidase ecto (NT5E or CD73; NCBI Gene ID: 4907); ectonucleoside triphosphate diphosphohydrolase 1 (ENTPD1 or CD39; NCBI Gene ID: 593); transforming growth factor beta 1 (TGFB1 or TGFβ; NCBI Gene ID: 7040); heme oxygenase 1 (HMOX1, HO-1 or HO1; NCBI Gene ID: 3162); heme oxygenase 2 (HMOX2, HO-2 or H02; NCBI Gene ID: 3163); vascular endothelial growth factor A (VEGFA or VEGF; NCBI Gene ID: 7422); erb-b2 receptor tyrosine kinase 2 (ERBB2, HER2, HER2/neu or CD340; NCBI Gene ID: 2064), epidermal growth factor receptor (EGFR, ERBB, ERBB1 or HER1; NCBI Gene ID: 1956); ALK receptor tyrosine kinase (ALK, CD246; NCBI Gene ID: 238); poly(ADP-ribose) polymerase 1 (PARP1; NCBI Gene ID: 142); poly(ADP-ribose) polymerase 2 (PARP2; NCBI Gene ID: 10038); TCDD inducible poly(ADP-ribose) polymerase (TIPARP, PARP7; NCBI Gene ID: 25976); cyclin dependent kinase 4 (CDK4; NCBI Gene ID: 1019); cyclin dependent kinase 6 (CDK6; NCBI Gene ID: 1021); TNF receptor superfamily member 14 (TNFRSF14, HVEM, CD270; NCBI Gene ID: 8764); T cell immunoreceptor with Ig and ITIM domains (TIGIT; NCBI Gene ID: 201633); X-linked inhibitor of apoptosis (XIAP, BIRC4, IAP-3; NCBI Gene ID: 331);

baculoviral IAP repeat containing 2 (BIRC2, cIAP1; NCBI Gene ID: 329); baculoviral IAP repeat containing 3 (BIRC3, cIAP2; NCBI Gene ID: 330); baculoviral IAP repeat containing 5 (BIRC5, surviving; NCBI Gene ID: 332); C-C motif chemokine receptor 2 (CCR2, CD192; NCBI Gene ID: 729230); C-C motif chemokine receptor 5 (CCR5, CD195; NCBI Gene ID: 1234); C-C motif chemokine receptor 8 (CCR8, CDw198; NCBI Gene ID: 1237); C-X-C motif chemokine receptor 2 (CXCR2, CD182; NCBI Gene ID: 3579); C-X-C motif chemokine receptor 3 (CXCR3, CD182, CD183; NCBI Gene ID: 2833); C-X-C motif chemokine receptor 4 (CXCR4, CD184; NCBI Gene ID: 7852); cytokine inducible SH2 containing protein (CISH; NCBI Gene ID: 1154); arginase (ARG1 (NCBI Gene ID: 383), ARG2 (NCBI Gene ID: 384)), carbonic anhydrase (CA1 (NCBI Gene ID: 759), CA2 (NCBI Gene ID: 760), CA3 (NCBI Gene ID: 761), CA4 (NCBI Gene ID: 762), CA5A (NCBI Gene ID: 763), CA5B (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)), prostaglandin-endoperoxide synthase 1 (PTGS1, COX-1; NCBI Gene ID: 5742), prostaglandin-endoperoxide synthase 2 (PTGS2, COX-2; NCBI Gene ID: 5743), secreted phospholipase A2, prostaglandin E synthase (PTGES, PGES; Gene ID: 9536), arachidonate 5-lipoxygenase (ALOX5, 5-LOX; NCBI Gene ID: 240) and/or soluble epoxide hydrolase 2 (EPHX2, SEH; NCBI Gene ID: 2053); a secreted phospholipase A2 (e.g., PLA2G1B (NCBI Gene ID: 5319); PLA2G7 (NCBI Gene ID: 7941), PLA2G3 (NCBI Gene ID: 50487), PLA2G2A (NCBI Gene ID: 5320); PLA2G4A (NCBI Gene ID: 5321); PLA2G12A (NCBI Gene ID: 81579); PLA2G12B (NCBI Gene ID: 84647); PLA2G10 (NCBI Gene ID: 8399); PLA2G5 (NCBI Gene ID: 5322); PLA2G2D (NCBI Gene ID: 26279); PLA2G15 (NCBI Gene ID: 23659)); indoleamine 2,3-dioxygenase 1 (IDO1; NCBI Gene ID: 3620); indoleamine 2,3-dioxygenase 2 (IDO2; NCBI Gene ID: 169355); hypoxia inducible factor 1 subunit alpha (HIF1A; NCBI Gene ID: 3091); angiopoietin 1 (ANGPT1; NCBI Gene ID: 284); Endothelial TEK tyrosine kinase (TIE-2, TEK, CD202B; NCBI Gene ID: 7010); Janus kinase 1 (JAK1; NCBI Gene ID: 3716); catenin beta 1 (CTNNB1; NCBI Gene ID: 1499); histone deacetylase 9 (HDAC9; NCBI Gene ID: 9734), 5'-3' exoribonuclease 1 (XRN1; NCBI Gene ID: 54464), or WRN RecQ like helicase (WRN; NCBI Gene ID: 7486).

Illustrative Mechanisms of Action

Immune Checkpoint Modulators

In some embodiments an antibody and/or fusion protein provided herein (e.g., 7-B16) is administered with one or more blockers or inhibitors of inhibitory immune checkpoint proteins or receptors and/or with one or more stimulators, activators or agonists of one or more stimulatory immune checkpoint proteins or receptors. Blockade or inhibition of inhibitory immune checkpoints can positively regulate T-cell or NK cell activation and prevent immune escape of cancer cells within the tumor microenvironment. Activation or stimulation of stimulatory immune check points can augment the effect of immune checkpoint inhibitors in cancer therapeutics. In some embodiments, the immune checkpoint proteins or receptors regulate T cell responses (e.g., reviewed in Xu, et al., *J Exp Clin Cancer Res*. (2018) 37:110). In some embodiments, the immune checkpoint proteins or receptors regulate NK cell responses (e.g., reviewed in Davis, et al., *Semin Immunol*. (2017) 31:64-75 and Chiossone, et al., *Nat Rev Immunol*. (2018) 18(11):671-688).

Examples of immune checkpoint proteins or receptors include CD27 (NCBI Gene ID: 939), CD70 (NCBI Gene ID: 970); CD40 (NCBI Gene ID: 958), CD40LG (NCBI Gene ID: 959); CD47 (NCBI Gene ID: 961), SIRPA (NCBI Gene ID: 140885); CD48 (SLAMF2; NCBI Gene ID: 962), transmembrane and immunoglobulin domain containing 2 (TMIGD2, CD28H; NCBI Gene ID: 126259), CD84 (LY9B, SLAMF5; NCBI Gene ID: 8832), CD96 (NCBI Gene ID: 10225), CD160 (NCBI Gene ID: 11126), MS4A1 (CD20; NCBI Gene ID: 931), CD244 (SLAMF4; NCBI Gene ID: 51744); CD276 (B7H3; NCBI Gene ID: 80381); V-set domain containing T cell activation inhibitor 1 (VTCN1, B7H4); V-set immunoregulatory receptor (VSIR, B7H5, VISTA; NCBI Gene ID: 64115); immunoglobulin superfamily member 11 (IGSF11, VSIG3; NCBI Gene ID: 152404); natural killer cell cytotoxicity receptor 3 ligand 1 (NCR3LG1, B7H6; NCBI Gene ID: 374383); HERV-H LTR-associating 2 (HHLA2, B7H7; NCBI Gene ID: 11148); inducible T cell co-stimulator (ICOS, CD278; NCBI Gene ID: 29851); inducible T cell co-stimulator ligand (ICOSLG, B7H2; NCBI Gene ID: 23308); TNF receptor superfamily member 4 (TNFRSF4, OX40; NCBI Gene ID: 7293); TNF superfamily member 4 (TNFSF4, OX40L; NCBI Gene ID: 7292); TNFRSF8 (CD30; NCBI Gene ID: 943), TNFSF8 (CD30L; NCBI Gene ID: 944); TNFRSF10A (CD261, DR4, TRAILR1; NCBI Gene ID: 8797), TNFRSF9 (CD137; NCBI Gene ID: 3604), TNFSF9 (CD137L; NCBI Gene ID: 8744); TNFRSF10B (CD262, DR5, TRAILR2; NCBI Gene ID: 8795), TNFRSF10 (TRAIL; NCBI Gene ID: 8743); TNFRSF14 (HVEM, CD270; NCBI Gene ID: 8764), TNFSF14 (HVEML; NCBI Gene ID: 8740); CD272 (B and T lymphocyte associated (BTLA); NCBI Gene ID: 151888); TNFRSF17 (BCMA, CD269; NCBI Gene ID: 608), TNFSF13B (BAFF; NCBI Gene ID: 10673); TNFRSF18 (GITR; NCBI Gene ID: 8784), TNFSF18 (GITRL; NCBI Gene ID: 8995); MHC class I polypeptide-related sequence A (MICA; NCBI Gene ID: 100507436); MHC class I polypeptide-related sequence B (MICB; NCBI Gene ID: 4277); CD274 (CD274, PDL1, PD-L1; NCBI Gene ID: 29126); programmed cell death 1 (PDCD1, PD1, PD-1; NCBI Gene ID: 5133); cytotoxic T-lymphocyte associated protein 4 (CTLA4, CD152; NCBI Gene ID: 1493); CD80 (B7-1; NCBI Gene ID: 941), CD28 (NCBI Gene ID: 940); nectin cell adhesion molecule 2 (NECTIN2, CD112; NCBI Gene ID: 5819); CD226 (DNAM-1; NCBI Gene ID: 10666); Poliovirus receptor (PVR) cell adhesion molecule (PVR, CD155; NCBI Gene ID: 5817); PVR related immunoglobulin domain containing (PVRIG, CD112R; NCBI Gene ID: 79037); T cell immunoreceptor with Ig and ITIM domains (TIGIT; NCBI Gene ID: 201633); T cell immunoglobulin and mucin domain containing 4 (TIMD4; TIM4; NCBI Gene ID: 91937); hepatitis A virus cellular receptor 2 (HAVCR2, TIMD3, TIM3; NCBI Gene ID: 84868); galectin 9 (LGALS9; NCBI Gene ID: 3965); lymphocyte activating 3 (LAG3, CD223; NCBI Gene ID: 3902); signaling lymphocytic activation molecule family member 1 (SLAMF1, SLAM, CD150; NCBI Gene ID: 6504); lymphocyte antigen 9 (LY9, CD229, SLAMF3; NCBI Gene ID: 4063); SLAM family member 6 (SLAMF6, CD352; NCBI Gene ID: 114836); SLAM family member 7 (SLAMF7, CD319; NCBI Gene ID: 57823); UL16 binding protein 1 (ULBP1; NCBI Gene ID: 80329); UL16 binding protein 2 (ULBP2; NCBI Gene ID: 80328); UL16 binding protein 3 (ULBP3; NCBI Gene ID: 79465); retinoic acid early transcript 1E (RAET1E; ULBP4; NCBI Gene ID: 135250); retinoic acid early transcript 1G (RAET1G; ULBP5; NCBI Gene ID: 353091); retinoic acid early transcript 1L (RAET1L; ULBP6; NCBI Gene ID: 154064); killer cell immunoglobulin like receptor, three Ig domains and long cytoplasmic tail 1 (KIR, CD158E1; NCBI Gene ID: 3811, e.g., lirilumab (IPH-2102, IPH-4102)); killer cell lectin like receptor C1 (KLRC1, NKG2A, CD159A; NCBI Gene ID: 3821); killer cell lectin like receptor K1 (KLRK1, NKG2D, CD314; NCBI Gene ID: 22914); killer cell lectin like receptor C2 (KLRC2, CD159c, NKG2C; NCBI Gene ID: 3822); killer cell lectin like receptor C3 (KLRC3, NKG2E; NCBI Gene ID: 3823); killer cell lectin like receptor C4 (KLRC4, NKG2F; NCBI Gene ID: 8302); killer cell immunoglobulin like receptor, two Ig domains and long cytoplasmic tail 1 (KIR2DL1; NCBI Gene ID: 3802); killer cell immunoglobulin like receptor, two Ig domains and long cytoplasmic tail 2 (KIR2DL2; NCBI Gene ID: 3803); killer cell immunoglobulin like receptor, two Ig domains and long cytoplasmic tail 3 (KIR2DL3; NCBI Gene ID: 3804); killer cell immunoglobulin like receptor, three Ig domains and long cytoplasmic tail 1 (KIR3DL1); killer cell lectin like receptor D1 (KLRD1; NCBI Gene ID: 3824); killer cell lectin like receptor G1 (KLRG1; CLEC15A, MAFA, 2F1; NCBI Gene ID: 10219); sialic acid binding Ig like lectin 7 (SIGLEC7; NCBI Gene ID: 27036); and sialic acid binding Ig like lectin 9 (SIGLEC9; NCBI Gene ID: 27180).

In some embodiments an antibody and/or fusion protein provided herein (e.g., 7-B16) is administered with one or more blockers or inhibitors of one or more T-cell inhibitory immune checkpoint proteins or receptors. Illustrative T-cell inhibitory immune checkpoint proteins or receptors include CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In some embodiments, the antibody and/or fusion protein provided herein is administered with one or more agonist or activators of one or more T-cell stimulatory immune checkpoint proteins or receptors. Illustrative T-cell stimulatory immune checkpoint proteins or receptors include without limitation CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); CD244 (2B4, SLAMF4), Poliovirus receptor (PVR) cell adhesion molecule (PVR, CD155). See, e.g., Xu, et al., *J Exp Clin Cancer Res*. (2018) 37:110.

In some embodiments the antibody and/or fusion protein provided herein (e.g., 7-B16) is administered with one or more blockers or inhibitors of one or more NK-cell inhibitory immune checkpoint proteins or receptors. Illustrative NK-cell inhibitory immune checkpoint proteins or receptors include killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); killer cell lectin like receptor D1 (KLRD1, CD94), killer cell lectin like receptor G1 (KLRG1; CLEC15A, MAFA, 2F1); sialic acid binding Ig like lectin 7 (SIGLEC7); and sialic acid binding Ig like lectin 9 (SIGLEC9). In some embodiments the antibody and/or fusion protein provided herein is administered with one or more agonist or activators of one or more NK-cell stimulatory immune checkpoint proteins or receptors. Illustrative NK-cell stimulatory immune checkpoint proteins or receptors include CD16, CD226 (DNAM-1); CD244 (2B4, SLAMF4); killer cell lectin like receptor K1 (KLRK1, NKG2D, CD314); SLAM family member 7 (SLAMF7). See, e.g., Davis, et al., *Semin Immunol*. (2017) 31:64-75; Fang, et al., *Semin Immunol*. (2017) 31:37-54; and Chiossone, et al., *Nat Rev Immunol*. (2018) 18(11):671-688.

In some embodiments the one or more immune checkpoint inhibitors comprises a proteinaceous (e.g., antibody or fragment thereof, or antibody mimetic) inhibitor of PD-L1 (CD274), PD-1 (PDCD1), CTLA4, or TIGIT. In some embodiments the one or more immune checkpoint inhibitors comprises a small organic molecule inhibitor of PD-L1 (CD274), PD-1 (PDCD1), CTLA4, or TIGIT.

Examples of inhibitors of CTLA4 that can be co-administered include ipilimumab, tremelimumab, BMS-986218, AGEN1181, AGEN1884 (zalifrelimab), BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, BPI-002, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

Examples of inhibitors of PD-L1 (CD274) or PD-1 (PDCD1) that can be co-administered include pembrolizumab, nivolumab, cemiplimab, pidilizumab, AMP-224, MEDI0680 (AMP-514), spartalizumab, atezolizumab, avelumab, durvalumab, BMS-936559, CK-301, PF-06801591, BGB-A317 (tislelizumab), GLS-010 (WBP-3055), AK-103 (HX-008), AK-105, CS-1003, HLX-10, MGA-012, BI-754091, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, (MSB0010718C), CX-072, CBT-502, TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, MDX1105-01, GS-4224, GS-4416, INCB086550, MAX10181, AGEN2034 (balstilimab), zimberelimab, as well as multi-specific inhibitors FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), and INBRX-105 (4-1BB/PDL1).

Examples of inhibitors of TIGIT that can be co-administered include tiragolumab (RG-6058), vibostolimab, domvanalimab, AB308, domvanalimab (AB154), AB308, BMS-986207, AGEN-1307, COM-902, or etigilimab.

TNF Receptor Superfamily (TNFRSF) Member Agonists or Activators

In some embodiments, the antibody and/or fusion protein provided herein (e.g., 7-B16) is administered with an agonist of one or more TNF receptor superfamily (TNFRSF) members, e.g., an agonist of one or more of TNFRSF1A (NCBI Gene ID: 7132), TNFRSF1B (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-1BB, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRAILR4, NCBI Gene ID: 8793), TNFRSF11A (CD265, RANK, NCBI Gene ID: 8792), TNFRSF11B (NCBI Gene ID: 4982), TNFRSF12A (CD266, NCBI Gene ID: 51330), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

Example anti-TNFRSF4 (OX40) antibodies that can be co-administered include MEDI6469, MEDI6383, MEDI0562 (tavolixizumab), MOXR0916, PF-04518600, RG-7888, GSK-3174998, INCAGN1949, BMS-986178, GBR-8383, ABBV-368, and those described in WO2016179517, WO2017096179, WO2017096182, WO2017096281, and WO2018089628.

Example anti-TNFRSF5 (CD40) antibodies that can be co-administered include RG7876, SEA-CD40, APX-005M, and ABBV-428.

In some embodiments, the anti-TNFRSF7 (CD27) antibody varlilumab (CDX-1127) is co-administered.

Example anti-TNFRSF9 (4-1BB, CD137) antibodies that can be co-administered include urelumab, utomilumab (PF-05082566), AGEN2373, and ADG-106.

In some embodiments the anti-TNFRSF17 (BCMA) antibody GSK-2857916 is co-administered.

Example anti-TNFRSF18 (GITR) antibodies that can be co-administered include MEDI1873, FPA-154, INCAGN-1876, TRX-518, BMS-986156, MK-1248, GWN-323, and those described in WO2017096179, WO2017096276, WO2017096189, and WO2018089628. In some embodiments, an antibody, or fragment thereof, co-targeting TNFRSF4 (OX40) and TNFRSF18 (GITR) is co-administered. Such antibodies are described, e.g., in WO2017096179 and WO2018089628.

Bi-specific antibodies targeting TNFRSF family members that can be co-administered include PRS-343 (CD-137/HER2), AFM26 (BCMA/CD16A), AFM-13 (CD16/CD30), REGN-1979 (CD20/CD3), AMG-420 (BCMA/CD3), INHIBRX-105 (4-1BB/PDL1), FAP-4-IBBL (4-1BB/FAP), XmAb-13676 (CD3/CD20), RG-7828 (CD20/CD3), CC-93269 (CD3/BCMA), REGN-5458 (CD3/BCMA), and IMM-0306 (CD47/CD20).

Bi-Specific T-Cell Engagers

In some embodiments antibody and/or fusion protein provided herein (e.g., 7-B16) is administered with a bi-specific T-cell engager (e.g., not having an Fc) or an anti-CD3 bi-specific antibody (e.g., having an Fc). Illustrative anti-CD3 bi-specific antibodies or BiTEs that can be co-administered include JNJ-64052781 (CD19/CD3), AMG-211 (CEA/CD3), RG7802 (CEA/CD3), ERY-974 (CD3/GPC3), PF-06671008 (Cadherins/CD3), APVO436 (CD123/CD3), flotetuzumab (CD123/CD3), REGN-1979 (CD20/CD3), MCLA-117 (CD3/CLEC12A), JNJ-0819, JNJ-7564 (CD3/heme), AMG-757 (DLL3-CD3), AMG-330 (CD33/CD3), AMG-420 (BCMA/CD3), JNJ-63709178 (CD123/CD3), MGD-007 (CD3/gpA33), MGD-009 (CD3/B7H3), IMCgp100 (CD3/gp100), XmAb-14045 (CD123/CD3), XmAb-13676 (CD3/CD20), XmAb-18087 (SSTR2/CD3), catumaxomab (CD3/EpCAM), REGN-4018 (MUC16/CD3), RG-7828 (CD20/CD3), CC-93269 (CD3/BCMA), REGN-5458 (CD3/BCMA), GRB-1302 (CD3/Erbb2), GRB-1342 (CD38/CD3), GEM-333 (CD3/CD33). As appropriate, the anti-CD3 binding bi-specific molecules may or may not have an Fc. Illustrative bi-specific T-cell engagers that can be co-administered target CD3 and a tumor-associated antigen as described herein, including, e.g., CD19 (e.g., blinatumomab); CD33 (e.g., AMG330); CEA (e.g., MEDI-565); receptor tyrosine kinase-like orphan receptor 1 (ROR1) (Gohil, et al., *Oncoimmunology*. (2017) May 17; 6(7):e1326437); PD-L1 (Horn, et al., *Oncotarget*. 2017 Aug. 3; 8(35):57964-57980); and EGFRvIII (Yang, et al., *Cancer Lett*. 2017 Sep. 10; 403:224-230).

Bi- and Tri-Specific Natural Killer (NK)-Cell Engagers

In some embodiments the antibody and/or fusion protein provided herein (e.g., 7-B16) is administered with a bi-specific NK-cell engager (BiKE) or a tri-specific NK-cell engager (TriKE) (e.g., not having an Fc) or bi-specific antibody (e.g., having an Fc) against an NK cell activating receptor, e.g., CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp80), Fc receptor FcγR (which mediates antibody-dependent cell cytotoxicity), SLAM family receptors (e.g., 2B4, SLAM6 and SLAM7), killer cell immunoglobulin-like receptors (KIR) (KIR-2DS and KIR-3DS), DNAM-1 and CD137 (41BB). Illustrative anti-CD16 bi-specific antibodies, BiKEs or TriKEs that can be co-administered include AFM26 (BCMA/CD16A) and AFM-13 (CD16/CD30). As appropriate, the anti-CD16 binding bi-specific molecules may or may not have an Fc. Illustrative bi-specific NK-cell engagers that can be co-administered target CD16 and one or more tumor-associated antigens as described herein, including, e.g., CD19, CD20, CD22, CD30, CD33, CD123, EGFR, EpCAM, ganglioside GD2, HER2/neu, HLA Class II and FOLR1. BiKEs and TriKEs are described, e.g., in Felices, et al., *Methods Mol Biol*. (2016) 1441:333-346; Fang, et al., *Semin Immunol*. (2017) 31:37-54.

MCL1 Apoptosis Regulator, BCL2 Family Member (MCL1) Inhibitors

In some embodiments the antibody and/or fusion protein provided herein is administered with an inhibitor of MCL1 apoptosis regulator, BCL2 family member (MCL1, TM;

EAT; MCL1L; MCL1S; Mcl-1; BCL2L3; MCL1-ES; bcl2-L-3; mcl1/EAT; NCBI Gene ID: 4170). Examples of MCL1 inhibitors include AMG-176, AMG-397, S-64315, AZD-5991, 483-LM, A-1210477, UMI-77, JKY-5-037, GS-9716, and those described in WO2018183418, WO2016033486, and WO2017147410.

SHP2 Inhibitors

In some embodiments antibody and/or fusion protein provided herein (e.g., 7-B16) is administered with an inhibitor of protein tyrosine phosphatase non-receptor type 11 (PTPN11; BPTP3, CFC, JMML, METCDS, NS1, PTP-1D, PTP2C, SH-PTP2, SH-PTP3, SHP2; NCBI Gene ID: 5781). Examples of SHP2 inhibitors include TNO155 (SHP-099), RMC-4550, JAB-3068, RMC-4630, and those described in WO2018172984 and WO2017211303.

Hematopoietic Progenitor Kinase 1 (HPK1) Inhibitors

In some embodiments, the antibody and/or fusion protein provided herein (e.g., 7-B16) is administered with an inhibitor of mitogen-activated protein kinase kinase kinase kinase 1 (MAP4K1, HPK1; NCBI Gene ID: 11184). Examples of Hematopoietic Progenitor Kinase 1 (HPK1) inhibitors include without limitation, those described in WO2020092621, WO2018183956, WO2018183964, WO2018167147, WO2018183964, WO2016205942, WO2018049214, WO2018049200, WO2018049191, WO2018102366, WO2018049152, and WO2016090300.

Apoptosis Signal-Regulating Kinase (ASK) Inhibitors

In some embodiments the antibody and/or fusion protein provided herein (e.g., 7-B16) is administered with an inhibitor of an ASK inhibitor, e.g., mitogen-activated protein kinase kinase kinase 5 (MAP3K5; ASK1, MAPKKK5, MEKK5; NCBI Gene ID: 4217). Examples of ASK1 inhibitors include those described in WO2011008709 (Gilead Sciences) and WO 2013112741 (Gilead Sciences).

Bruton Tyrosine Kinase (BTK) Inhibitors

In some embodiments the antibody and/or fusion protein provided herein (e.g., 7-B16) is administered with an inhibitor of Bruton tyrosine kinase (BTK, AGMX1, AT, ATK, BPK, IGHD3, IMD1, PSCTK1, XLA; NCBI Gene ID: 695). Examples of BTK inhibitors include (S)-6-amino-9-(1-(but-2-ynoyl)pyrrolidin-3-yl)-7-(4-phenoxyphenyl)-7H-purin-8 (9H)-one, acalabrutinib (ACP-196), BGB-3111, CB988, HM71224, ibrutinib, M-2951 (evobrutinib), M7583, tirabrutinib (ONO-4059), PRN-1008, spebrutinib (CC-292), TAK-020, vecabrutinib, ARQ-531, SHR-1459, DTRMWXHS-12, and TAS-5315.

Cluster of Differentiation 47 (CD47) Inhibitors

In some embodiments the antibody and/or fusion protein provided herein (e.g., 7-B16) is administered with an inhibitor of CD47 (IAP, MER6, OA3; NCBI Gene ID: 961). Examples of CD47 inhibitors include anti-CD47 mAbs (Vx-1004), anti-human CD47 mAbs (CNTO-7108), CC-90002, CC-90002-ST-001, humanized anti-CD47 antibody or a CD47-blocking agent (Hu5F9-G4), NI-1701, NI-1801, RCT-1938, and TTI-621. In some embodiments the CD47 inhibitor is magrolimab.

SIRPα Targeting Agents

In some embodiments the antibody and/or fusion protein provided herein (e.g., 7-B16) is administered with a SIRPα targeting agent (NCBI Gene ID: 140885; UniProt P78324). Examples of SIRPα targeting agents include SIRPα inhibitors, such as AL-008, RRx-001, and CTX-5861, and anti-SIRPα antibodies, such as FSI-189 (GS-0189), ES-004, BI765063, ADU1805, and CC-95251. Additional SIRPα-targeting agents of use are described, for example, in WO200140307, WO2002092784, WO2007133811, WO2009046541, WO2010083253, WO2011076781, WO2013056352, WO2015138600, WO2016179399, WO2016205042, WO2017178653, WO2018026600, WO2018057669, WO2018107058, WO2018190719, WO2018210793, WO2019023347, WO2019042470, WO2019175218, WO2019183266, WO2020013170 and WO2020068752.

Cyclin-Dependent Kinase (CDK) Inhibitors

In some embodiments the antibody and/or fusion protein provided herein (e.g., 7-B16) is administered with an inhibitor of cyclin dependent kinase 1 (CDK1, CDC2; CDC28A; P34CDC2; NCBI Gene ID: 983); cyclin dependent kinase 2 (CDK2, CDKN2; p33(CDK2); NCBI Gene ID: 1017); cyclin dependent kinase 3 (CDK3; NCBI Gene ID: 1018); cyclin dependent kinase 4 (CDK4, CMM3; PSK-J3; NCBI Gene ID: 1019); cyclin dependent kinase 6 (CDK6, MCPH12; PLSTIRE; NCBI Gene ID: 1021); cyclin dependent kinase 7 (CDK7, CAK; CAK1; HCAK; MO15; STK1; CDKN7; p39MO15; NCBI Gene ID: 1022), or cyclin dependent kinase 9 (CDK9, TAK; C-2k; CTK1; CDC2L4; PITALRE; NCBI Gene ID: 1025). Inhibitors of CDK 1, 2, 3, 4, 6, 7 and/or 9, include abemaciclib, alvocidib (HMR-1275, flavopiridol), AT-7519, dinaciclib, ibrance, FLX-925, LEE001, palbociclib, ribociclib, rigosertib, selinexor, UCN-01, SY1365, CT-7001, SY-1365, G1T38, milciclib, trilaciclib, and TG-02.

Discoidin Domain Receptor (DDR) Inhibitors

In some embodiments the antibody and/or fusion protein provided herein (e.g., 7-B16) is combined with an inhibitor of discoidin domain receptor tyrosine kinase 1 (DDR1, CAK, CD167, DDR, EDDR1, HGK2, MCK10, NEP, NTRK4, PTK3, PTK3A, RTK6, TRKE; NCBI Gene ID: 780); and/or discoidin domain receptor tyrosine kinase 2 (DDR2, MIG20a, NTRKR3, TKT, TYRO10, WRCN; NCBI Gene ID: 4921). Examples of DDR inhibitors include dasatinib and those disclosed in WO2014/047624 (Gilead Sciences), US 2009-0142345 (Takeda Pharmaceutical), US 2011-0287011 (Oncomed Pharmaceuticals), WO 2013/027802 (Chugai Pharmaceutical), and WO2013/034933 (Imperial Innovations).

Targeted E3 Ligase Ligand Conjugates

In some embodiments the antibody and/or fusion protein provided herein (e.g., 7-B16) is administered with a targeted E3 ligase ligand conjugate. Such conjugates have a target protein binding moiety and an E3 ligase binding moiety (e.g., an inhibitor of apoptosis protein (IAP) (e.g., XIAP, c-IAP1, c-IAP2, NIL-IAP, Bruce, and surviving) E3 ubiquitin ligase binding moiety, Von Hippel-Lindau E3 ubiquitin ligase (VHL) binding moiety, a cereblon E3 ubiquitin ligase binding moiety, mouse double minute 2 homolog (MDM2) E3 ubiquitin ligase binding moiety), and can be used to promote or increase the degradation of targeted proteins, e.g., via the ubiquitin pathway. In some embodiments the targeted E3 ligase ligand conjugates comprise a targeting or binding moiety that targets or binds a protein described herein, and an E3 ligase ligand or binding moiety. In some embodiments the targeted E3 ligase ligand conjugates comprise a targeting or binding moiety that targets or binds a protein selected from Cbl proto-oncogene B (CBLB; Cbl-b, Nbla00127, RNF56; NCBI Gene ID: 868) and hypoxia inducible factor 1 subunit alpha (HIF1A; NCBI Gene ID: 3091). In some embodiments the targeted E3 ligase ligand conjugates comprise a kinase inhibitor (e.g., a small molecule kinase inhibitor, e.g., of BTK and an E3 ligase ligand or binding moiety. See, e.g., WO2018098280. In some embodiments the targeted E3 ligase ligand conjugates comprise a binding moiety targeting or binding to Interleukin-1 (IL-1) Receptor-Associated Kinase-4 (IRAK-4); Rapidly Accelerated Fibrosarcoma (RAF, such as c-RAF, A-RAF and/or B-RAF), c-Met/p38, or a BRD protein; and an E3 ligase ligand or binding moiety. See, e.g., WO2019099926, WO2018226542, WO2018119448, WO2018223909, WO2019079701. Additional targeted E3 ligase ligand conjugates that can be co-administered are described, e.g., in WO2018237026, WO2019084026, WO2019084030, WO2019067733, WO2019043217, WO2019043208, and WO2018144649.

Histone Deacetylase (HDAC) Inhibitors

In some embodiments the antibody and/or fusion protein provided herein (e.g., 7-B16) is administered with an inhibitor of a histone deacetylase, e.g., histone deacetylase 9 (HDAC9, HD7, HD7b, HD9, HDAC, HDAC7, HDAC7B, HDAC9B, HDAC9FL, HDRP, MITR; Gene ID: 9734). Examples of HDAC inhibitors include abexinostat, ACY-241, AR-42, BEBT-908, belinostat, CKD-581, CS-055 (HBI-8000), CUDC-907 (fimepinostat), entinostat, givinostat, mocetinostat, panobinostat, pracinostat, quisinostat (JNJ-26481585), resminostat, ricolinostat, SHP-141, valproic acid (VAL-001), vorinostat, tinostamustine, remetinostat, and entinostat.

Indoleamine-Pyrrole-2,3-Dioxygenase (IDO1) Inhibitors

In some embodiments the antibody and/or fusion protein provided herein is administered with an inhibitor of indoleamine 2,3-dioxygenase 1 (IDO1; NCBI Gene ID: 3620). Examples of IDO1 inhibitors include BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, BMS-986205, and shIDO-ST, EOS-200271, KHK-2455, and LY-3381916.

Janus Kinase (JAK) Inhibitors

In some embodiments, the antibody and/or fusion protein provided herein (e.g., 7-B16) is administered with an inhibitor of Janus kinase 1 (JAK1, JAK1A, JAK1B, JTK3; NCBI Gene ID: 3716); Janus kinase 2 (JAK2, JTK10, THCYT3; NCBI Gene ID: 3717); and/or Janus kinase 3 (JAK3, JAK-3, JAK3_HUMAN, JAKL, L-JAK, LJAK; NCBI Gene ID: 3718). Examples of JAK inhibitors include AT9283, AZD1480, baricitinib, BMS-911543, fedratinib, filgotinib (GLPG0634), gandotinib (LY2784544), INCB039110 (itacitinib), lestaurtinib, momelotinib (CYT0387), NS-018, pacritinib (SB1518), peficitinib (ASP015K), ruxolitinib, tofacitinib (formerly tasocitinib), INCB052793, and XL019.

Lysyl Oxidase-Like Protein (LOXL) Inhibitors

In some embodiments the antibody and/or fusion protein provided herein (e.g., 7-B16) is administered with an inhibitor of a LOXL protein, e.g., LOXL1 (NCBI Gene ID: 4016), LOXL2 (NCBI Gene ID: 4017), LOXL3 (NCBI Gene ID: 84695), LOXL4 (NCBI Gene ID: 84171), and/or LOX (NCBI Gene ID: 4015). Examples of LOXL2 inhibitors include the antibodies described in WO 2009017833 (Arresto Biosciences), WO 2009035791 (Arresto Biosciences), and WO 2011097513 (Gilead Biologics).

Matrix Metalloprotease (AIP) Inhibitors

In some embodiments the antibody and/or fusion protein provided herein (e.g., 7-B16) is administered with an inhibitor of a matrix metallopeptidase (MMP), e.g., an inhibitor of MMP1 (NCBI Gene ID: 4312), MMP2 (NCBI Gene ID: 4313), MMP3 (NCBI Gene ID: 4314), MMP7 (NCBI Gene ID: 4316), MMP8 (NCBI Gene ID: 4317), MMP9 (NCBI Gene ID: 4318); MMP10 (NCBI Gene ID: 4319); MMP11 (NCBI Gene ID: 4320); MMP12 (NCBI Gene ID: 4321), MMP13 (NCBI Gene ID: 4322), MMP14 (NCBI Gene ID: 4323), MMP15 (NCBI Gene ID: 4324), MMP16 (NCBI Gene ID: 4325), MMP17 (NCBI Gene ID: 4326), MMP19 (NCBI Gene ID: 4327), MMP20 (NCBI Gene ID: 9313), MMP21 (NCBI Gene ID: 118856), MMP24 (NCBI Gene ID: 10893), MMP25 (NCBI Gene ID: 64386), MMP26 (NCBI Gene ID: 56547), MMP27 (NCBI Gene ID: 64066) and/or MMP28 (NCBI Gene ID: 79148). Examples of MMP9 inhibitors include marimastat (BB-2516), cipemastat (Ro 32-3555), GS-5745 (andecaliximab), and those described in WO 2012027721 (Gilead Biologics).

RAS and RAS Pathway Inhibitors

In some embodiments the antibody and/or fusion protein provided herein (e.g., 7-B16) is administered with an inhibitor of KRAS proto-oncogene, GTPase (KRAS; a.k.a., NS; NS3; CFC2; RALD; K-Ras; KRAS1; KRAS2; RASK2; KI-RAS; C-K-RAS; K-RAS2A; K-RAS2B; K-RAS4A; K-RAS4B; c-Ki-ras2; NCBI Gene ID: 3845); NRAS proto-oncogene, GTPase (NRAS; a.k.a., NS6; CMNS; NCMS; ALPS4; N-ras; NRAS1; NCBI Gene ID: 4893) or HRAS proto-oncogene, GTPase (HRAS; a.k.a., CTLO; KRAS; HAMSV; HRAS1; KRAS2; RASH1; RASK2; Ki-Ras; p21ras; C-H-RAS; c-K-ras; H-RASIDX; c-Ki-ras; C-BAS/HAS; C-HA-RAS1; NCBI Gene ID: 3265). The Ras inhibitors can inhibit Ras at either the polynucleotide (e.g., transcriptional inhibitor) or polypeptide (e.g., GTPase enzyme inhibitor) level. In some embodiments, the inhibitors target one or more proteins in the Ras pathway, e.g., inhibit one or more of EGFR, Ras, Raf (A-Raf, B-Raf, C-Raf), MEK (MEK1, MEK2), ERK, PI3K, AKT and mTOR. Illustrative K-Ras inhibitors that can be co-administered include ARS-1620 (G12C), SML-8-73-1 (G12C), Compound 3144 (G12D), Kobe0065/2602 (Ras GTP), RT11, MRTX-849 (G12C) and K-Ras(G12D)-selective inhibitory peptides, including KRpep-2 (Ac-RRCPLYISYDPVCRR-NH$_2$) (SEQ ID NO: 126) and KRpep-2d (Ac-RRRRCPLYI-SYDPVCRRRR-NH$_2$) (SEQ ID NO: 127). Illustrative KRAS mRNA inhibitors include anti-KRAS U1 adaptor, AZD-4785, siG12D-LODER™, and siG12D exosomes. Illustrative MEK inhibitors that can be co-administered include binimetinib, cobimetinib, PD-0325901, pimasertib, RG-7304, selumetinib, trametinib, and those described below and herein. Illustrative Raf dimer inhibitors that can be co-administered include BGB-283, HM-95573, LXH-254, LY-3009120, RG7304 and TAK-580. Illustrative ERK inhibitors that can be co-administered include LTT-462, LY-3214996, MK-8353, ravoxertinib and ulixertinib. Illustrative Ras GTPase inhibitors that can be co-administered include rigosertib. Illustrative PI3K inhibitors that can be co-administered include idelalisib (Zydelig®), alpelisib, buparlisib, and pictilisib. Illustrative PI3K/mTOR inhibitors that can be co-administered include dactolisib, omipalisib and voxtalisib. In some embodiments, Ras-driven cancers (e.g., NSCLC) having CDKN2A mutations can be inhibited by co-administration of the MEK inhibitor selumetinib and the CDK4/6 inhibitor palbociclib. See, e.g., Zhou, et al., Cancer Lett. 2017 Nov. 1; 408:130-137. Also, K-RAS and mutant N-RAS can be reduced by the irreversible ERBB1/2/4 inhibitor neratinib. See, e.g., Booth, et al., Cancer Biol Ther. 2018 Feb. 1; 19(2):132-137.

Mitogen-activated Protein Kinase (MEK) Inhibitors

In some embodiments the antibody and/or fusion protein provided herein (e.g., 7-B16) is administered with an inhibitor of mitogen-activated protein kinase kinase 7 (MAP2K7, JNKK2, MAPKK7, MEK, MEK 7, MKK7, PRKMK7, SAPKK-4, SAPKK4; NCBI Gene ID: 5609). Examples of MEK inhibitors include antroquinonol, binimetinib, cobimetinib (GDC-0973, XL-518), MT-144, selumetinib (AZD6244), sorafenib, trametinib (GSK1120212), uprosertib+trametinib, PD-0325901, pimasertib, LTT462, AS703988, CC-90003, and refametinib.

Phosphatidylinositol 3-Kinase (PI3K) Inhibitors

In some embodiments antibody and/or fusion protein provided herein (e.g., 7-B16) is administered with an inhibitor of a phosphatidylinositol-4,5-bisphosphate 3-kinase catalytic subunit, e.g., phosphatidylinositol-4,5-bisphosphate 3-kinase catalytic subunit alpha (PIK3CA, CLAPO, CLOVE, CWS5, MCAP, MCM, MCMTC, PI3K, PI3K-alpha, p110-alpha; NCBI Gene ID: 5290); phosphatidylinositol-4,5-bisphosphate 3-kinase catalytic subunit beta (PIK3CB, P110BETA, PI3K, PI3KBETA, PIK3C1; NCBI Gene ID: 5291); phosphatidylinositol-4,5-bisphosphate 3-kinase catalytic subunit gamma (PIK3CG, PI3CG, PI3K, PI3Kgamma, PIK3, p110gamma, p120-PI3K; Gene ID: 5494); and/or phosphatidylinositol-4,5-bisphosphate 3-kinase catalytic subunit delta (PIK3CD, APDS, IMD14, P110DELTA, PI3K, p110D, NCBI Gene ID: 5293). In some embodiments the PI3K inhibitor is a pan-PI3K inhibitor. Examples of PI3K inhibitors include ACP-319, AEZA-129, AMG-319, AS252424, AZD8186, BAY 10824391, BEZ235, buparlisib (BKM120), BYL719 (alpelisib), CH5132799, copanlisib (BAY 80-6946), duvelisib, GDC-0032, GDC-0077, GDC-0941, GDC-0980, GSK2636771, GSK2269557, idelalisib (Zydelig®), INCB50465, IPI-145, IPI-443, IPI-549, KAR4141, LY294002, LY3023414, MLN1117, OXY111A, PA799, PX-866, RG7604, rigosertib, RP5090, RP6530, SRX3177, taselisib, TG100115, TGR-1202 (umbralisib), TGX221, WX-037, X-339, X-414, XL147 (SAR245408), XL499, XL756, wortmannin, ZSTK474, and the compounds described in WO2005113556 (ICOS), WO 2013/052699 (Gilead Calistoga), WO2013116562 (Gilead Calistoga), WO2014100765 (Gilead Calistoga), WO2014100767 (Gilead Calistoga), and WO2014201409 (Gilead Sciences).

Spleen Tyrosine Kinase (SYK) Inhibitors

In some embodiments the antibody and/or fusion protein provided herein (e.g., 7-B16) is administered with an inhibitor of spleen associated tyrosine kinase (SYK, p72-Syk, Gene ID: 6850). Examples of SYK inhibitors include 6-(1H-indazol-6-yl)-N-(4-morpholinophenyl)imidazo[1,2-a]pyrazin-8-amine, BAY-61-3606, cerdulatinib (PRT-062607), entospletinib, fostamatinib (R788), HMPL-523, NVP-QAB 205 AA, R112, R343, tamatinib (R406), and those described in U.S. Pat. No. 8,450,321 (Gilead Connecticut) and US20150175616.

Toll-Like Receptor (TLR) Agonists

In some embodiments antibody and/or fusion protein provided herein (e.g., 7-B16) is administered with an agonist of a toll-like receptor (TLR), e.g., an agonist of TLR1 (NCBI Gene ID: 7096), TLR2 (NCBI Gene ID: 7097), TLR3 (NCBI Gene ID: 7098), TLR4 (NCBI Gene ID: 7099), TLR5 (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793). Example TLR7 agonists that can be co-administered include DS-0509, GS-9620 (vesatolimod), vesatolimod analogs, LHC-165, TMX-101 (imiquimod), GSK-2245035, resiquimod, DSR-6434, DSP-3025, IMO-4200, MCT-465, MEDI-9197, 3M-051, SB-9922, 3M-052, Limtop, TMX-30X, TMX-202, RG-7863, RG-7795, and the compounds disclosed in US20100143301 (Gilead Sciences), US20110098248 (Gilead Sciences), and US20090047249 (Gilead Sciences), US20140045849 (Janssen), US20140073642 (Janssen), WO2014056953 (Janssen), WO2014076221 (Janssen), WO2014128189 (Janssen), US20140350031 (Janssen), WO2014023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). An TLR7/TLR8 agonist that can be co-administered is NKTR-262. Example TLR8 agonists that can be co-administered include E-6887, IMO-4200, IMO-8400, IMO-9200, MCT-465, MEDI-9197, motolimod, resiquimod, GS-9688, VTX-1463, VTX-763, 3M-051, 3M-052, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). Example TLR9 agonists that can be co-administered include AST-008, CMP-001, IMO-2055, IMO-2125, litenimod, MGN-1601, BB-001, BB-006, IMO-3100, IMO-8400, IR-103, IMO-9200, agatolimod, DIMS-9054, DV-1079, DV-1179, AZD-1419, leftolimod (MGN-1703), CYT-003, CYT-003-QbG10 and PUL-042. Examples of TLR3 agonist include rintatolimod, poly-ICLC, RIBOXXON®, Apoxxim, RIBOXXIM®, IPH-33, MCT-465, MCT-475, and ND-1.1.

Tyrosine-Kinase Inhibitors (TKIs)

In some embodiments the antibody and/or fusion protein provided herein (e.g., 7-B16) is administered with a tyrosine kinase inhibitor (TKI). TKIs may target epidermal growth factor receptors (EGFRs) and receptors for fibroblast growth factor (FGF), platelet-derived growth factor (PDGF), and vascular endothelial growth factor (VEGF). Examples of TKIs include without limitation, afatinib, ARQ-087 (derazantinib), asp5878, AZD3759, AZD4547, bosutinib, brigatinib, cabozantinib, cediranib, crenolanib, dacomitinib, dasatinib, dovitinib, E-6201, erdafitinib, erlotinib, gefitinib, gilteritinib (ASP-2215), FP-1039, HM61713, icotinib, imatinib, KX2-391 (Src), lapatinib, lestaurtinib, lenvatinib, midostaurin, nintedanib, ODM-203, osimertinib (AZD-9291), ponatinib, poziotinib, quizartinib, radotinib, rociletinib, sulfatinib (HMPL-012), sunitinib, famitinib L-malate, (MAC-4), tivoanib, TH-4000, and MEDI-575 (anti-PDGFR antibody).

Chemotherapeutic Agents

In some embodiments the antibody and/or fusion protein provided herein (e.g., 7-B16) is administered with a chemotherapeutic agent or anti-neoplastic agent.

As used herein, the term "chemotherapeutic agent" or "chemotherapeutic" (or "chemotherapy" in the case of treatment with a chemotherapeutic agent) is meant to encompass any non-proteinaceous (e.g., non-peptidic) chemical compound useful in the treatment of cancer. Examples of chemotherapeutic agents include but not limited to: alkylating agents such as thiotepa and cyclophosphamide (CYTOXAN®); alkyl sulfonates such as busulfan, improsulfan, and piposulfan; aziridines such as benzodepa, carboquone, meturedepa, and uredepa; ethylenimines and methylamelamines including altretamine, triethylenemelamine, triethylenephosphoramide, triethylenethiophosphoramide, and trimemylolomelamine; acetogenins, e.g., bullatacin and bullatacinone; a camptothecin, including synthetic analog topotecan; bryostatin, callystatin; CC-1065, including its adozelesin, carzelesin, and bizelesin synthetic analogs; cryptophycins, particularly cryptophycin 1 and cryptophycin 8; dolastatin; duocarmycin, including the synthetic analogs KW-2189 and CBI-TMI; eleutherobin; 5-azacytidine; pancratistatin; a sarcodictyin; spongistatin; nitrogen mustards such as chlorambucil, chlornaphazine, cyclophosphamide, glufosfamide, evofosfamide, bendamustine, estramustine, ifosfamide, mechlorethamine, mechlorethamine oxide hydrochloride, melphalan, novembichin, phenesterine, prednimustine, trofosfamide, and uracil mustard; nitrosoureas such as carmustine, chlorozotocin, foremustine, lomustine, nimustine, and ranimustine; antibiotics such as the enediyne antibiotics (e.g., calicheamicin, especially calicheamicin gammaII and calicheamicin phiI1), dynemicin including dynemicin A, bisphosphonates such as clodronate, an esperamicin, neocarzinostatin chromophore and related chromoprotein enediyne antibiotic chromomophores, aclacinomycins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; anti-metabolites such as methotrexate and 5-fluorouracil (5-FU); folic acid analogs such as demopterin, methotrexate, pteropterin, and trimetrexate; purine analogs such as cladribine, pentostatin, fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replinishers such as frolinic acid; radiotherapeutic agents such as Radium-223; trichothecenes, especially T-2 toxin, verracurin A, roridin A, and anguidine; taxoids such as paclitaxel (TAXOL®), abraxane, docetaxel (TAXOTERE®), cabazitaxel, BIND-014, tesetaxel; platinum analogs such as cisplatin and carboplatin, NC-6004 nanoplatin; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; polysaccharide-K (PSK); razoxane; rhizoxin; sizofiran; spirogermanium; tenuazonic acid; trabectedin, triaziquone; 2,2',2"-trichlorotriemylamine; urethane; vindesine; dacarbazine; mannomustine; mitobronitol; mitolactol; pipobroman; gacytosine; arabinoside ("Ara-C"); cyclophosphamide; thiopeta; chlorambucil; gemcitabine (GEMZAR®); 6-thioguanine; mercaptopurine; methotrexate; vinblastine; platinum; etoposide (VP-16); ifosfamide; mitroxantrone; vancristine; vinorelbine (NAVELBINE®); novantrone; teniposide; edatrexate; daunomycin; aminopterin; xeoloda; ibandronate; CPT-11; topoisomerase inhibitor RFS 2000; difluoromethylornithine (DFMO); retinoids such as retinoic acid; capecitabine; NUC-1031; FOLFOX (folinic acid, 5-fluorouracil, oxaliplatin); FOLFIRI (folinic acid, 5-fluorouracil, irinotecan); FOLFOXIRI (folinic acid, 5-fluorouracil, oxaliplatin, irinotecan), FOLFIRINOX (folinic acid, 5-fluorouracil, irinotecan, oxaliplatin), and pharmaceutically acceptable salts, acids, or derivatives of any of the above. Such agents can be conjugated onto an antibody or any targeting agent described herein to create an antibody-drug conjugate (ADC) or targeted drug conjugate.

Anti-Hormonal Agents

Also included in the definition of "chemotherapeutic agent" are anti-hormonal agents such as anti-estrogens and selective estrogen receptor modulators (SERMs), inhibitors of the enzyme aromatase, anti-androgens, and pharmaceutically acceptable salts, acids or derivatives of any of the above that act to regulate or inhibit hormone action on tumors.

Examples of anti-estrogens and SERMs include tamoxifen (including NOLVADEX™), raloxifene, droloxifene, 4-hydroxytamoxifen, trioxifene, keoxifene, LY117018, onapristone, and toremifene (FARESTON®).

Inhibitors of the enzyme aromatase regulate estrogen production in the adrenal glands. Examples include 4(5)-imidazoles, aminoglutethimide, megestrol acetate (MEGACE®), exemestane, formestane, fadrozole, vorozole (RIVISOR®), letrozole (FEMARA®), and anastrozole (ARIMIDEX®).

Examples of anti-androgens include apalutamide, abiraterone, enzalutamide, flutamide, galeterone, nilutamide, bicalutamide, leuprolide, goserelin, ODM-201, APC-100, ODM-204.

An example progesterone receptor antagonist includes onapristone.

Anti-Angiogenic Agents

In some embodiments the antibody and/or fusion protein provided herein (e.g., 7-B16) is administered with an anti-angiogenic agent. Anti-angiogenic agents that can be co-administered include retinoid acid and derivatives thereof, 2-methoxyestradiol, ANGIOSTATIN®, ENDOSTATIN®, regorafenib, necuparanib, suramin, squalamine, tissue inhibitor of metalloproteinase-1, tissue inhibitor of metalloproteinase-2, plasminogen activator inhibitor-1, plasminogen activator inhibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism including proline analogs such as 1-azetidine-2-carboxylic acid (LACA), cishydroxyproline, d,I-3,4-dehydroproline, thiaproline, α,α'-dipyridyl, beta-aminopropionitrile fumarate, 4-propyl-5-(4-pyridinyl)-2(3h)-oxazolone, methotrexate, mitoxantrone, heparin, interferons, 2 macroglobulin-serum, chicken inhibitor of metalloproteinase-3 (ChIMP-3), chymostatin, beta-cyclodextrin tetradecasulfate, eponemycin, fumagillin, gold sodium thiomalate, d-penicillamine, beta-1-anticollagenase-serum, alpha-2-antiplasmin, bisantrene, lobenzarit disodium, n-2-carboxyphenyl-4-chloroanthronilic acid disodium or "CCA", thalidomide, angiostatic steroid, carboxy aminoimidazole, metalloproteinase inhibitors such as BB-94, inhibitors of S100A9 such as tasquinimod. Other anti-angiogenesis agents include antibodies, preferably monoclonal antibodies against these angiogenic growth factors: beta-FGF, alpha-FGF, FGF-5, VEGF isoforms, VEGF-C, HGF/SF, and Ang-1/Ang-2.

Anti-Fibrotic Agents

In some embodiments the antibody and/or fusion protein provided herein is administered with an anti-fibrotic agent. Anti-fibrotic agents that can be co-administered include (e.g., 7-B16) the compounds such as beta-aminoproprionitrile (BAPN), as well as the compounds disclosed in U.S. Pat. No. 4,965,288 relating to inhibitors of lysyl oxidase and their use in the treatment of diseases and conditions associated with the abnormal deposition of collagen and U.S. Pat. No. 4,997,854 relating to compounds which inhibit LOX for the treatment of various pathological fibrotic states, which are herein incorporated by reference. Further exemplary inhibitors are described in U.S. Pat. No. 4,943,593 relating to compounds such as 2-isobutyl-3-fluoro-, chloro-, or bromo-allylamine, U.S. Pat. Nos. 5,021,456, 5,059,714, 5,120,764, 5,182,297, 5,252,608 relating to 2-(1-naphthyloxymemyl)-3-fluoroallylamine, and US 20040248871, which are herein incorporated by reference.

Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives; semicarbazide and urea derivatives; aminonitriles such as BAPN or 2-nitroethylamine; unsaturated or saturated haloamines such as 2-bromo-ethylamine, 2-chloroethylamine, 2-trifluoroethylamine, 3-bromopropylamine, and p-halobenzylamines; and selenohomocysteine lactone.

Other anti-fibrotic agents are copper chelating agents penetrating or not penetrating the cells. Exemplary compounds include indirect inhibitors which block the aldehyde derivatives originating from the oxidative deamination of the lysyl and hydroxylysyl residues by the lysyl oxidases. Examples include the thiolamines, particularly D-penicillamine, and its analogs such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, and sodium-4-mercaptobutanesulphinate trihydrate.

Anti-Inflammatory Agents

In some embodiments the antibody and/or fusion protein provided herein (e.g., 7-B16) is administered with an anti-inflammatory agent. Example anti-inflammatory agents include without limitation inhibitors of one or more of arginase (ARG1 (NCBI Gene ID: 383), ARG2 (NCBI Gene ID: 384)), carbonic anhydrase (CA1 (NCBI Gene ID: 759), CA2 (NCBI Gene ID: 760), CA3 (NCBI Gene ID: 761), CA4 (NCBI Gene ID: 762), CA5A (NCBI Gene ID: 763), CA5B (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)), prostaglandin-endoperoxide synthase 1 (PTGS1, COX-1; NCBI Gene ID: 5742), prostaglandin-endoperoxide synthase 2 (PTGS2, COX-2; NCBI Gene ID: 5743), secreted phospholipase A2, prostaglandin E synthase (PTGES, PGES; Gene ID: 9536), arachidonate 5-lipoxygenase (ALOX5, 5-LOX; NCBI Gene ID: 240), soluble epoxide hydrolase 2 (EPHX2, SEH; NCBI Gene ID: 2053) and/or mitogen-activated protein kinase kinase kinase 8 (MAP3K8, TPL2; NCBI Gene ID: 1326). In some embodiments, the inhibitor is a dual inhibitor, e.g., a dual inhibitor of COX-2/COX-1, COX-2/SEH, COX-2/CA, COX-2/5-LOX.

Examples of inhibitors of prostaglandin-endoperoxide synthase 1 (PTGS1, COX-1; NCBI Gene ID: 5742) that can be co-administered include mofezolac, GLY-230, and TRK-700.

Examples of inhibitors of prostaglandin-endoperoxide synthase 2 (PTGS2, COX-2; NCBI Gene ID: 5743) that can be co-administered include diclofenac, meloxicam, parecoxib, etoricoxib, AP-101, celecoxib, AXS-06, diclofenac potassium, DRGT-46, AAT-076, meisuoshuli, lumiracoxib, meloxicam, valdecoxib, zaltoprofen, nimesulide, Anitrazafen, Apricoxib, Cimicoxib, Deracoxib, Flumizole, Firocoxib, Mavacoxib, NS-398, Pamicogrel, Parecoxib, Robenacoxib, Rofecoxib, Rutecarpine, Tilmacoxib, and Zaltoprofen. Examples of dual COX1/COX2 inhibitors that can be co-administered include HP-5000, lornoxicam, ketorolac tromethamine, bromfenac sodium, ATB-346, HP-5000. Examples of dual COX-2/carbonic anhydrase (CA) inhibitors that can be co-administered include polmacoxib and imrecoxib.

Examples of inhibitors of secreted phospholipase A2, prostaglandin E synthase (PTGES, PGES; Gene ID: 9536) that can be co-administered include LY3023703, GRC 27864, and compounds described in WO2015158204, WO2013024898, WO2006063466, WO2007059610, WO2007124589, WO2010100249, WO2010034796, WO2010034797, WO2012022793, WO2012076673, WO2012076672, WO2010034798, WO2010034799, WO2012022792, WO2009103778, WO2011048004, WO2012087771, WO2012161965, WO2013118071, WO2013072825, WO2014167444, WO2009138376, WO2011023812, WO2012110860, WO2013153535, WO2009130242, WO2009146696, WO2013186692, WO2015059618, WO2016069376, WO2016069374, WO2009117985, WO2009064250, WO2009064251, WO2009082347, WO2009117987, and WO2008071173. Metformin has further been found to repress the COX2/PGE2/STAT3 axis, and can be co-administered. See, e.g., Tong, et al., *Cancer Lett.* (2017) 389:23-32; and Liu, et al., *Oncotarget.* (2016) 7(19):28235-46.

Examples of inhibitors of carbonic anhydrase (e.g., one or more of CA1 (NCBI Gene ID: 759), CA2 (NCBI Gene ID: 760), CA3 (NCBI Gene ID: 761), CA4 (NCBI Gene ID: 762), CA5A (NCBI Gene ID: 763), CA5B (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)) that can be co-administered include acetazolamide, methazolamide, dorzolamide, zonisamide, brinzolamide and dichlorphenamide. A dual COX-2/CA1/CA2 inhibitor that can be co-administered includes CG100649.

Examples of inhibitors of arachidonate 5-lipoxygenase (ALOX5, 5-LOX; NCBI Gene ID: 240) that can be co-administered include meclofenamate sodium, zileuton.

Examples of inhibitors of soluble epoxide hydrolase 2 (EPHX2, SEH; NCBI Gene ID: 2053) that can be co-administered include compounds described in WO2015148954. Dual inhibitors of COX-2/SEH that can be co-administered include compounds described in WO2012082647. Dual inhibitors of SEH and fatty acid amide hydrolase (FAAH; NCBI Gene ID: 2166) that can be co-administered include compounds described in WO2017160861.

Examples of inhibitors of mitogen-activated protein kinase kinase kinase 8 (MAP3K8, tumor progression loci-2, TPL2; NCBI Gene ID: 1326) that can be co-administered include GS-4875, GS-5290, BHM-078 and those described in WO2006124944, WO2006124692, WO2014064215, WO2018005435, Teli, et al., *J Enzyme Inhib Med Chem.* (2012) 27(4):558-70; Gangwall, et al., *Curr Top Med Chem.* (2013) 13(9):1015-35; Wu, et al., *Bioorg Med Chem Lett.* (2009) 19(13):3485-8; Kaila, et al., *Bioorg Med Chem.* (2007) 15(19):6425-42; and Hu, et al., *Bioorg Med Chem Lett.* (2011) 21(16):4758-61.

Tumor Oxygenation Agents

In some embodiments the antibody and/or fusion protein provided herein (e.g., 7-B16) is administered with an agent that promotes or increases tumor oxygenation or reoxygenation, or prevents or reduces tumor hypoxia. Illustrative agents that can be co-administered include, e.g., Hypoxia inducible factor-1 alpha (HIF-1α) inhibitors, such as PT-2977, PT-2385; VEGF inhibitors, such as bevasizumab, IMC-3C5, GNR-011, tanibirumab, LYN-00101, ABT-165; and/or an oxygen carrier protein (e.g., a heme nitric oxide and/or oxygen binding protein (HNOX)), such as OMX-302 and HNOX proteins described in WO2007137767, WO2007139791, WO2014107171, and WO2016149562.

Immunotherapeutic Agents

In some embodiments the antibody and/or fusion protein provided herein (e.g., 7-B16) is administered with an immunotherapeutic agent. Example immunotherapeutic agents that can be co-administered include abagovomab, AB308, ABP-980, adecatumumab, afutuzumab, alemtuzumab, altumomab, amatuximab, anatumomab, arcitumomab, atezolizumab, bavituximab, bectumomab, bevacizumab, bivatuzumab, blinatumomab, brentuximab, cantuzumab, catumaxomab, CC49, cetuximab, citatuzumab, cixutumumab, clivatuzumab, conatumumab, dacetuzumab, dalotuzumab, daratumumab, detumomab, dinutuximab, domvanalimab, drozitumab, duligotumab, dusigitumab, ecromeximab, elotuzumab, emibetuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab (YERVOY®, MDX-010, BMS-734016, and MDX-101), iratumumab, labetuzumab, lexatumumab, lintuzumab, lorvotuzumab, lucatumumab, mapatumumab, matuzumab, milatuzumab, minretumomab, mitumomab, mogamulizumab, moxetumomab, naptumomab, narnatumab, necitumumab, nimotuzumab, nofetumomab, OBI-833, obinutuzumab, ocaratuzumab, ofatumumab, olaratumab, onartuzumab, oportuzumab, oregovomab, panitumumab, parsatuzumab, pasudotox, patritumab, pemtumomab, pertuzumab, pintumomab, pritumumab, racotumomab, radretumab, ramucirumab (Cyramza®), rilotumumab, rituximab, robatumumab, samalizumab, satumomab, sibrotuzumab, siltuximab, solitomab, simtuzumab, tacatuzumab, taplitumomab, tenatumomab, teprotumumab, tigatuzumab, tositumomab, trastuzumab, tucotuzumab, ubilituximab, veltuzumab, vorsetuzumab, votumumab, zalutumumab, and 3F8. Rituximab can be used for treating indolent B-cell cancers, including marginal-zone lymphoma, WM, CLL, and small lymphocytic lymphoma. A combination of rituximab and chemotherapy agents is especially effective.

The exemplified therapeutic antibodies can be further labeled or combined with a radioisotope particle such as indium-111, yttrium-90 (90Y-clivatuzumab), or iodine-131.

In some embodiments, the immunotherapeutic agent is an antibody-drug conjugate (ADC). Illustrative ADCs that can be co-administered include without limitation drug-conjugated antibodies, fragments thereof, or antibody mimetics targeting the proteins or antigens listed above and herein. Example ADCs that can be co-administered include gemtuzumab, brentuximab, trastuzumab, inotuzumab, glembatumumab, anetumab, mirvetuximab, depatuxizumab, rovalpituzumab, vadastuximab, labetuzumab, sacituzumab (e.g., sacituzumab govitecan), lifastuzumab, indusatumab, polatzumab, pinatuzumab, coltuximab, indatuximab, milatuzumab, rovalpituzumab, ABBV-399, AGS-16C3F, ASG-22ME, AGS67E, AMG172, AMG575, BAY1129980, BAY1187982, BAY94-9343, GSK2857916, Humax-TF-ADC, IMGN289, IMGN529, IMGN853, LOP628, PCA062, MDX-1203 (BMS936561), MEDI-547, PF-06263507, PF-06647020, PF-06647263, PF-06664178, RG7450, RG7458, RG7598, SAR566658, SGN-CD19A, SGN-CD33A, SGN-CD70A, SGN-LIV1A and SYD985. ADCs that can be co-administered are described, e.g., in Lambert, et al., *Adv Ther* (2017) 34:1015-1035 and in de Goeij, *Current Opinion in Immunology* (2016) 40:14-23. In some embodiments, the antibody and/or fusion protein provided herein is administered with sacituzumab govitecan.

Illustrative therapeutic agents (e.g., anticancer or antineoplastic agents) that can be conjugated to the drug-conjugated antibodies, fragments thereof, or antibody mimetics include without limitation monomethyl auristatin E (MMAE), monomethyl auristatin F (MMAF), a calicheamicin, ansamitocin, maytansine or an analog thereof (e.g., mertansine/emtansine (DM1), ravtansine/soravtansine (DM4)), an anthracyline (e.g., doxorubicin, daunorubicin, epirubicin, idarubicin), pyrrolobenzodiazepine (PBD) DNA cross-linking agent SC-DR002 (D6.5), duocarmycin, a microtubule inhibitors (MTI) (e.g., a taxane, a *vinca* alkaloid, an epothilone), a pyrrolobenzodiazepine (PBD) or dimer thereof, a duocarmycin (A, B1, B2, C1, C2, D, SA, CC-1065), and other anticancer or anti-neoplastic agents described herein. In some embodiments, the therapeutic agent conjugated to the drug-conjugated antibody is a topoisomerase I inhibitor (e.g., a camptothecin analog, such as irinotecan or its active metabolite SN38). In some embodiments, the therapeutic agents (e.g., anticancer or antineoplastic agents) that can be conjugated to the drug-conjugated antibodies, fragments thereof, or antibody mimetics include an immune checkpoint inhibitor. In some embodiments the conjugated immune checkpoint inhibitor is a conjugated small molecule inhibitor of CD274 (PDL1, PD-L1), programmed cell death 1 (PDCD1, PD1, PD-1) or CTLA4. In some embodiments the conjugated small molecule inhibitor of CD274 or PDCD1 is selected from the group consisting of GS-4224, GS-4416, INCB086550 and MAX10181. In some embodiments the conjugated small molecule inhibitor of CTLA4 comprises BPI-002.

Cancer Gene Therapy and Cell Therapy

In some embodiments the antibody and/or fusion protein provided herein (e.g., 7-B16) is administered with a cancer gene therapy and cell therapy. Cancer gene therapies and cell therapies include the insertion of a normal gene into cancer cells to replace a mutated or altered gene; genetic modification to silence a mutated gene; genetic approaches to directly kill the cancer cells; including the infusion of immune cells designed to replace most of the patient's own immune system to enhance the immune response to cancer cells, or activate the patient's own immune system (T cells or Natural Killer cells) to kill cancer cells, or find and kill the cancer cells; genetic approaches to modify cellular activity to further alter endogenous immune responsiveness against cancer.

Cellular Therapies

In some embodiments the antibody and/or fusion protein provided herein (e.g., 7-B16) is administered with one or more cellular therapies. Illustrative cellular therapies include without limitation co-administration of one or more of a population of natural killer (NK) cells, NK-T cells, T cells, cytokine-induced killer (CIK) cells, macrophage (MAC) cells, tumor infiltrating lymphocytes (TILs) and/or dendritic cells (DCs). In some embodiments, the cellular therapy entails a T cell therapy, e.g., co-administering a population of alpha/beta TCR T cells, gamma/delta TCR T cells, regulatory T (Treg) cells and/or TRuC™ T cells. In some embodiments, the cellular therapy entails a NK cell therapy, e.g., co-administering NK-92 cells. As appropriate, a cellular therapy can entail the co-administration of cells that are autologous, syngeneic or allogeneic to the subject.

In some embodiments the cellular therapy entails co-administering cells comprising chimeric antigen receptors (CARs). In such therapies, a population of immune effector cells engineered to express a CAR, wherein the CAR comprises a tumor antigen-binding domain. In T cell therapies, the T cell receptors (TCRs) are engineered to target tumor derived peptides presented on the surface of tumor cells.

With respect to the structure of a CAR, in some embodiments, the CAR comprises an antigen binding domain, a transmembrane domain, and an intracellular signaling domain. In some embodiments, the intracellular domain comprises a primary signaling domain, a costimulatory domain, or both of a primary signaling domain and a costimulatory domain. In some embodiments, the primary signaling domain comprises a functional signaling domain of one or more proteins selected from the group consisting of CD3 zeta, CD3 gamma, CD3 delta, CD3 epsilon, common FcR gamma (FCERIG), FcR beta (Fc Epsilon Rlb), CD79a, CD79b, Fcgamma RIIa, DAP10, and DAP12.

In some embodiments, the costimulatory domain comprises a functional domain of one or more proteins selected from the group consisting of CD27, CD28, 4-1BB(CD137), OX40, CD30, CD40, PD-1, ICOS, CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRFI), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, ITGAE, CD103, ITGAL, CD1A (NCBI Gene ID: 909), CD1B (NCBI Gene ID: 910), CD1C (NCBI Gene ID: 911), CD1D (NCBI Gene ID: 912), CD1E (NCBI Gene ID: 913), ITGAM, ITGAX, ITGB1, CD29, ITGB2 (CD18, LFA-1), ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D.

In some embodiments, the transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, ICOS (CD278), 4-1BB(CD137), GITR, CD40, BAFFR, HVEM (LIGHTR), SLAMF7, NKp80 (KLRF1), CD160, CD19, IL2R beta, IL2R gamma, IL7R, ITGA1, VLA1, CD49a, ITGA4, IA4, CD49D, ITGA6, VLA-6, CD49f, ITGAD, CD1A, CD1B, CD1C, CD1D, CD1E, ITGAE, CD103, ITGAL, ITGAM, ITGAX, ITGB1, CD29, ITGB2 (LFA-1, CD18), ITGB7, TNFR2, DNAM1 (CD226), SLAMF4 (CD244, 2B4), CD84, CD96 (TACTILE), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and NKG2C.

In some embodiments, the TCR or CAR antigen binding domain or the immunotherapeutic agent described herein (e.g., monospecific or multi-specific antibody or antigen-binding fragment thereof or antibody mimetic) binds a tumor-associated antigen (TAA). In some embodiments, the tumor-associated antigen is selected from the group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECLI); CD33; epidermal growth factor receptor variant III (EGFRvIII); ganglioside G2 (GD2); ganglioside GD3 (αNeuSAc(2-8)αNeuSAc(2-3)βDGaip(1-4)bDGIcp(1-1) Cer); ganglioside GM3 (αNeuSAc(2-3)βDGalp(1-4) βDGlcp(1-1)Cer); TNF receptor superfamily member 17 (TNFRSF17, BCMA); Tn antigen ((Tn Ag) or (GaINAcu-Ser/Thr)); prostate-specific membrane antigen (PSMA); receptor tyrosine kinase-like orphan receptor 1 (RORI); tumor-associated glycoprotein 72 (TAG72); CD38; CD44v6; Carcinoembryonic antigen (CEA); epithelial cell adhesion molecule (EPCAM); B7H3 (CD276); KIT (CD117); interleukin-13 receptor subunit alpha-2 (IL-13Ra2 or CD213A2); Mesothelin; interleukin 11 receptor alpha (IL-11Ra); prostate stem cell antigen (PSCA); protease serine 21 (Testisin or PRSS21); vascular endothelial growth factor receptor 2 (VEGFR2); Lewis(Y) antigen; CD24; platelet-derived growth factor receptor beta (PDGFR-beta); stage-specific embryonic antigen-4 (SSEA-4); CD20; delta like 3 (DLL3); folate receptor alpha; receptor tyrosine-protein kinase, ERBB2 (Her2/neu); mucin 1, cell surface associated (MUC1); epidermal growth factor receptor (EGFR); neural cell adhesion molecule (NCAM); prostase; prostatic acid phosphatase (PAP); elongation factor 2 mutated (ELF2M); ephrin B2; fibroblast activation protein alpha (FAP); insulin-like growth factor 1 receptor (IGF-I receptor), carbonic anhydrase IX (CAIX); proteasome (Prosome, Macropain) subunit, beta type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); fucosyl GM1; sialyl Lewis adhesion molecule (sLe); transglutaminase 5 (TGS5); high molecular weight-melanomaassociatedantigen (HMW-MAA); o-acetyl-GD2 ganglioside (OAcGD2); folate receptor beta; tumor endothelial marker 1 (TEM1/CD248); tumor endothelial marker 7-related (TEM7R); six transmembrane epithelial antigen of the prostate I (STEAP1); claudin 6 (CLDN6); thyroid stimulating hormone receptor (TSHR); G protein-coupled receptor class C group 5, member D (GPRCSD); chromosome X open reading frame 61 (CX-ORF61); CD97; CD179a; anaplastic lymphoma kinase (ALK); polysialic acid; placenta-specific 1 (PLAC1); hexa-saccharide portion of globoH glycoceramide (GloboH); mammary gland differentiation antigen (NY-BR-1); uroplakin 2 (UPK2); hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); olfactory receptor 51E2 (ORS IE2); TCR Gamma Alternate Reading Frame Protein (TARP); Wilms tumor protein (WT1); cancer/testis antigen 1 (NY-ESO-1); cancer/testis antigen 2 (LAGE-la); melanoma associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MADCT-1); melanoma cancer testis antigen-2 (MAD-CT-2); fos-related antigen 1; tumor protein p53, (p53); p53 mutant; prostein; survivin; telomerase; prostate carcinoma tumor antigen-1 (PCTA-1 or Galectin 8), melanoma antigen recognized by T cells 1 (MelanA or MART1); rat sarcoma (Ras) mutant; human telomerase reverse transcriptase (hTERT); sarcoma translocation breakpoints; melanoma inhibitor of apoptosis (ML-IAP); ERG (transmembrane protease, serine 2 (TM-PRSS2) ETS fusion gene); N-Acetyl glucosaminyl-transferase V (NA17); paired box protein Pax-3 (PAX3); androgen receptor; cyclin B1; v-myc avian myelocytomatosis viral oncogene neuroblastoma derived homolog (MYCN); ras homolog family member C (RhoC); tyrosinase-related protein 2 (TRP-2); cytochrome P450 1B1(CYP IBI); CCCTC-Binding Factor (Zinc Finger Protein)-Like (BORIS or Brother of the Regulator of Imprinted Sites), squamous cell carcinoma antigen recognized by T-cells 3 (SART3); paired box protein Pax-5 (PAX5); proacrosin binding protein sp32 (OY-TES I); lymphocyte-specific protein tyrosine kinase (LCK); A kinase anchor protein 4 (AKAP-4); synovial sarcoma, X breakpoint 2 (SSX2); receptor for advanced glycation endproducts (RAGE-I); renal ubiquitous 1 (RUI); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; leukocyte-associated immunoglobulin-like receptor 1 (LAIRI); Fc fragment of IgA receptor (FCAR or CD89); leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1). In some embodiments, the target is an epitope of the tumor associated antigen presented in an MHC.

In some embodiments, the tumor antigen is selected from CD150, 5T4, ActRIIA, B7, TNF receptor superfamily member 17 (TNFRSF17, BCMA), CA-125, CCNA1, CD123, CD126, CD138, CD14, CD148, CD15, CD19, CD20, CD200, CD21, CD22, CD23, CD24, CD25, CD26, CD261, CD262, CD30, CD33, CD362, CD37, CD38, CD4, CD40, CD40L, CD44, CD46, CD5, CD52, CD53, CD54, CD56, CD66a-d, CD74, CD8, CD80, CD92, CE7, CS-1, CSPG4, ED-B fibronectin, EGFR, EGFRvIII, EGP-2, EGP-4, EPHa2, ErbB2, ErbB3, ErbB4, FBP, HER1-HER2 in combination, HER2-HER3 in combination, HERV-K, HIV-1 envelope glycoprotein gp120, HIV-1 envelope glycoprotein gp41, HLA-DR, HM1.24, HMW-MAA, Her2, Her2/neu, IGF-1R, IL-11Ralpha, IL-13R-alpha2, IL-2, IL-22R-alpha, IL-6, IL-6R, Ia, Ii, L1-CAM, L1-cell adhesion molecule, Lewis Y, L1-CAM, MAGE A3, MAGE-A1, MART-1, MUC1, NKG2C ligands, NKG2D Ligands, NYESO-1, OEPHa2, PIGF, PSCA, PSMA, ROR1, T101, TAC, TAG72, TIM-3, TRAIL-R1, TRAIL-R1 (DR4), TRAIL-R2 (DR5), VEGF, VEGFR2, WT-I, a G-protein coupled receptor, alphafetoprotein (AFP), an angiogenesis factor, an exogenous cognate binding molecule (ExoCBM), oncogene product, anti-folate receptor, c-Met, carcinoembryonic antigen (CEA), cyclin (D 1), ephrinB2, epithelial tumor antigen, estrogen receptor, fetal acetylcholine e receptor, folate binding protein, gp100, hepatitis B surface antigen, kappa chain, kappa light chain, kdr, lambda chain, livin, melanoma-associated antigen, mesothelin, mouse double minute 2 homolog (MDM2), mucin 16 (MUC16), mutated p53, mutated ras, necrosis antigens, oncofetal antigen, ROR2, progesterone receptor, prostate specific antigen, tEGFR, tenascin, P2-Microgiobuiin, Fc Receptor-like 5 (FcRL5).

In some embodiments, the antigen binding domain binds to an epitope of a target or tumor associated antigen (TAA) presented in a major histocompatibility complex (MHC) molecule. In some embodiments, the TAA is a cancer testis antigen. In some embodiments, the cancer testis antigen is selected from the group consisting of acrosin binding protein (ACRBP; CT23, OY-TES-1, SP32; NCBI Gene ID: 84519), alpha fetoprotein (AFP; AFPD, FETA, HPAFP; NCBI Gene ID: 174); A-kinase anchoring protein 4 (AKAP4; AKAP 82, AKAP-4, AKAP82, CT99, FSC1, HI, PRKA4, hAKAP82, p82; NCBI Gene ID: 8852), ATPase family AAA domain containing 2 (ATAD2; ANCCA, CT137, PR02000; NCBI Gene ID: 29028), kinetochore scaffold 1 (KNL1; AF15Q14, CASC5, CT29, D40, MCPH4, PPP1R55, Spc7, hKNL-1, hSpc105; NCBI Gene ID: 57082), centrosomal protein 55 (CEP55; C10orf3, CT111, MARCH, URCC6; NCBI Gene ID: 55165), cancer/testis antigen 1A (CTAG1A; ESO1; CT6.1; LAGE-2; LAGE2A; NY-ESO-1; NCBI Gene ID: 246100), cancer/testis antigen 1B (CTAG1B; CT6.1, CTAG, CTAG1, ESO1, LAGE-2, LAGE2B, NY-ESO-1; NCBI Gene ID: 1485), cancer/testis antigen 2 (CTAG2; CAMEL, CT2, CT6.2, CT6.2a, CT6.2b, ESO2, LAGE-1, LAGE2B; NCBI Gene ID: 30848), CCCTC-binding factor like (CTCFL; BORIS, CT27, CTCF-T, HMGB1L1, dJ579F20.2; NCBI Gene ID: 140690), catenin alpha 2 (CTNNA2; CAP-R, CAPR, CDCBM9, CT114, CTNR; NCBI Gene ID: 1496), cancer/testis antigen 83 (CT83; CXorf61, KK-LC-1, KKLC1; NCBI Gene ID: 203413), cyclin A1 (CCNA1; CT146; NCBI Gene ID: 8900), DEAD-box helicase 43 (DDX43; CT13, HAGE; NCBI Gene ID: 55510), developmental pluripotency associated 2 (DPPA2; CT100, ECAT15-2, PESCRG1; NCBI Gene ID: 151871), fetal and adult testis expressed 1 (FATE1; CT43, FATE; NCBI Gene ID: 89885), FMR1 neighbor (FMR1NB; CT37, NY-SAR-35, NYSAR35; NCBI Gene ID: 158521), HORMA domain containing 1 (HORMAD1; CT46, NOHMA; NCBI Gene ID: 84072), insulin like growth factor 2 mRNA binding protein 3 (IGF2BP3; CT98, IMP-3, IMP3, KOC, KOC1, VICKZ3; NCBI Gene ID: 10643), leucine zipper protein 4 (LUZP4; CT-28, CT-8, CT28, HOM-TES-85; NCBI Gene ID: 51213), lymphocyte antigen 6 family member K (LY6K; CT97, HSJ001348, URLC10, ly-6K; NCBI Gene ID: 54742), maelstrom spermatogenic transposon silencer (MAEL; CT128, SPATA35; NCBI Gene ID: 84944), MAGE family member A1 (MAGEA1; CT1.1, MAGE1; NCBI Gene ID: 4100); MAGE family member A3 (MAGEA3; CT1.3, HIP8, HYPD, MAGE3, MAGEA6; NCBI Gene ID: 4102); MAGE family member A4 (MAGEA4; CT1.4, MAGE-41, MAGE-X2, MAGE4, MAGE4A, MAGE4B; NCBI Gene ID: 4103); MAGE family member A11 (MAGEA11; CT1.11, MAGE-11, MAGE11, MAGEA-11; NCBI Gene ID: 4110); MAGE family member C1 (MAGEC1; CT7, CT7.1; NCBI Gene ID: 9947); MAGE family member C2 (MAGEC2; CT10, HCA587, MAGEE1; NCBI Gene ID: 51438); MAGE family member D1 (MAGED1; DLXIN-1, NRAGE; NCBI Gene ID: 9500); MAGE family member D2 (MAGED2; 11B6, BARTS5, BCG-1, BCG1, HCA10, MAGE-D2; NCBI Gene ID: 10916), kinesin family member 20B (KIF20B; CT90, KRMP1, MPHOSPH1, MPP-1, MPP1; NCBI Gene ID: 9585), NUF2 component of NDC80 kinetochore complex (NUF2; CDCA1, CT106, NUF2R;

NCBI Gene ID: 83540), nuclear RNA export factor 2 (NXF2; CT39, TAPL-2, TCP11X2; NCBI Gene ID: 56001), PAS domain containing repressor 1 (PASD1; CT63, CT64, OXTES1; NCBI Gene ID: 139135), PDZ binding kinase (PBK; CT84, HEL164, Nori-3, SPK, TOPK; NCBI Gene ID: 55872), piwi like RNA-mediated gene silencing 2 (PIWIL2; CT80, HILI, PIWIL1L, mili; NCBI Gene ID: 55124), preferentially expressed antigen in melanoma (PRAME; CT130, MAPE, OIP-4, OIP4; NCBI Gene ID: 23532), sperm associated antigen 9 (SPAG9; CT89, HLC-6, HLC4, HLC6, JIP-4, JIP4, JLP, PHET, PIG6; NCBI Gene ID: 9043), sperm protein associated with the nucleus, X-linked, family member A1 (SPANXA1; CT11.1, CT11.3, NAP-X, SPAN-X, SPAN-Xa, SPAN-Xb, SPANX, SPANX-A; NCBI Gene ID: 30014), SPANX family member A2 (SPANXA2; CT11.1, CT11.3, SPANX, SPANX-A, SPANX-C, SPANXA, SPANXC; NCBI Gene ID: 728712), SPANX family member C (SPANXC; CT11.3, CTp11, SPANX-C, SPANX-E, SPANXE; NCBI Gene ID: 64663), SPANX family member D (SPANXD; CT11.3, CT11.4, SPANX-C, SPANX-D, SPANX-E, SPANXC, SPANXE, dJ171K16.1; NCBI Gene ID: 64648), SSX family member 1 (SSX1; CT5.1, SSRC; NCBI Gene ID: 6756), SSX family member 2 (SSX2; CT5.2, CT5.2A, HD21, HOM-MEL-40, SSX; NCBI Gene ID: 6757), synaptonemal complex protein 3 (SYCP3; COR1, RPRGL4, SCP3, SPGF4; NCBI Gene ID: 50511), testis expressed 14, intercellular bridge forming factor (TEX14; CT113, SPGF23; NCBI Gene ID: 56155), transcription factor Dp family member 3 (TFDP3; CT30, DP4, HCA661; NCBI Gene ID: 51270), serine protease 50 (PRSS50; CT20, TSP50; NCBI Gene ID: 29122), TTK protein kinase (TTK; CT96, ESK, MPH1, MPS1, MPS1L1, PYT; NCBI Gene ID: 7272) and zinc finger protein 165 (ZNF165; CT53, LD65, ZSCAN7; NCBI Gene ID: 7718). T cell receptors (TCRs) and TCR-like antibodies that bind to an epitope of a cancer testis antigen presented in a major histocompatibility complex (MHC) molecule are known in the art and can be used in the herein described heterodimers. Cancer testis antigens associated with neoplasia are summarized, e.g., in Gibbs, et al., *Trends Cancer* 2018 October; 4(10):701-712 and the CT database website at cta.lncc.br/index.php. Illustrative TCRs and TCR-like antibodies that bind to an epitope of NY-ESO-1 presented in an MHC are described, e.g., in Stewart-Jones, et al., *Proc Natl Acad Sci USA*. 2009 Apr. 7; 106(14):5784-8; WO2005113595, WO2006031221, WO2010106431, WO2016177339, WO2016210365, WO2017044661, WO2017076308, WO2017109496, WO2018132739, WO2019084538, WO2019162043, WO2020086158 and WO2020086647. Illustrative TCRs and TCR-like antibodies that bind to an epitope of PRAME presented in an MHC are described, e.g., in WO2011062634, WO2016142783, WO2016191246, WO2018172533, WO2018234319 and WO2019109821. Illustrative TCRs and TCR-like antibodies that bind to an epitope of a MAGE variant presented in an MHC are described, e.g., in WO2007032255, WO2012054825, WO2013039889, WO2013041865, WO2014118236, WO2016055785, WO2017174822, WO2017174823, WO2017174824, WO2017175006, WO2018097951, WO2018170338, WO2018225732 and WO2019204683. Illustrative TCRs and TCR-like antibodies that bind to an epitope of alpha fetoprotein (AFP) presented in an MHC are described, e.g., in WO2015011450. Illustrative TCRs and TCR-like antibodies that bind to an epitope of SSX2 presented in an MHC are described, e.g., in WO2020063488. Illustrative TCRs and TCR-like antibodies that bind to an epitope of KK-LC-1 (CT83) presented in an MHC are described, e.g., in WO2017189254.

Examples of cell therapies include: Algenpantucel-L, Sipuleucel-T, (BPX-501) rivogenlecleucel U.S. Pat. No. 9,089,520, WO2016100236, AU-105, ACTR-087, activated allogeneic natural killer cells CNDO-109-AANK, MG-4101, AU-101, BPX-601, FATE-NK100, LFU-835 hematopoietic stem cells, Imilecleucel-T, baltaleucel-T, PNK-007, UCARTCS1, ET-1504, ET-1501, ET-1502, ET-190, CD19-ARTEMIS, ProHema, FT-1050-treated bone marrow stem cell therapy, CD4CARNK-92 cells, CryoStim, AlloStim, lentiviral transduced huCART-meso cells, CART-22 cells, EGFRt/19-28z/4-1BBL CAR T cells, autologous 4H111-28z/fIL-12/EFGRt T cell, CCR5-SBC-728-HSPC, CAR4-1BBZ, CH-296, dnTGFbRII-NY-ESOc259T, Ad-RTS-IL-12, IMA-101, IMA-201, CARMA-0508, TT-18, CMD-501, CMD-503, CMD-504, CMD-502, CMD-601, CMD-602, and CSG-005.

In some embodiments the one or more additional co-administered therapeutic agents can be categorized by their mechanism of action, e.g., into the following groups:
  agents targeting adenosine deaminase, such as pentostatin or cladribine;
  agents targeting AKT1, such as GSK2141795;
  agents targeting ATM, such as AZD1390;
  agents targeting MET, such as savolitinib, capmatinib, tepotinib, ABT-700, AG213, JNJ-38877618 (OMO-1), merestinib, HQP-8361, BMS-817378, or TAS-115;
  agents targeting mitogen-activated protein kinase, such as antroquinonol, binimetinib, cobimetinib, selumetinib, trametinib, uprosertib, mirdametinib (PD-0325901), pimasertib, refametinib, or compounds disclosed in WO2011008709, WO2013112741, WO2006124944, WO2006124692, WO2014064215, WO2018005435, Zhou, et al., Cancer Lett. 2017 Nov. 1, 408:130-137, Teli, et al., J Enzyme Inhib Med Chem. (2012) 27(4): 558-70; Gangwall, et al., Curr Top Med Chem. (2013) 13(9):1015-35; Wu, et al., Bioorg Med Chem Lett. (2009) 19(13):3485-8; Kaila, et al., Bioorg Med Chem. (2007) 15(19):6425-42, or Hu, et al., Bioorg Med Chem Lett. (2011) 21(16):4758-61;
  agents targeting MAP4K1, such as compounds disclosed in WO2018183956, WO2018183964, WO2018167147, WO2018183964, WO2016205942, WO2018049214, WO2018049200, WO2018049191, WO2018102366, WO2018049152, WO2020092528, WO2020092621, or WO2016090300;
  agents targeting thymidine kinase, such as aglatimagene besadenovec (ProstAtak, PancAtak, GliAtak, GMCI, or AdV-tk);
  agents targeting androgen receptor, such as enobosarm (GTX-024) or darolutamide;
  agents targeting CD47, such as RRx-001, DSP-107, VT-1021, IM-02, SGN-CD47M, SIRPa-Fc-CD40L (SL-172154), or magrolimab;
  agents targeting targeting an interleukin pathway, such as Pegilodecakin (AM-0010) (pegylated IL10), CA-4948 (IRAK4);
  agents targeting cluster of differentiation markers, such as A6, AD-IL24, neratinib, tucatinib (ONT 380), mobocertinib (TAK-788), tesevatinib, trastuzumab (HERCEPTIN®), trastuzumab biosimimar (HLX-02), margetuximab, BAT-8001, pertuzumab (Perjeta), pegfilgrastim, RG6264, zanidatamab (ZW25), cavatak, AIC-100, tagraxofusp (SL-401), HLA-A2402/HLA-A0201 restricted epitope peptide vaccine, dasatinib, imatinib, nilotinib, sorafenib, lenvatinib mesylate, ofranergene obadenovec, cabozantinib malate, AL-8326, ZLJ-33, KBP-7018, sunitinib malate, pazopanib derivatives, AGX-73, rebastinib, NMS-088, lucitanib hydrochloride, midostaurin, cediranib, dovitinib, sitravatinib, tivozanib, masitinib, regorafenib, olverembatinib dimesylate (HQP-1351), cabozantinib, ponatinib, and famitinib L-malate, CX-2029 (ABBV-2029), SCB-313, CA-170, COM-701, CDX-301, GS-3583, asunercept (APG-101), APO-010, or compounds disclosed in WO2016196388, WO2016033570, WO2015157386, WO199203459, WO199221766, WO2004080462, WO2005020921, WO2006009755, WO2007078034, WO2007092403, WO2007127317, WO2008005877, WO2012154480, WO2014100620, WO2014039714, WO2015134536, WO2017167182, WO2018112136, WO2018112140, WO2019155067, WO2020076105, PCT/US2019/063091, WO19173692, WO2016179517, WO2017096179, WO2017096182, WO2017096281, WO2018089628, WO2017096179, WO2018089628, WO2018195321, WO2020014643, WO2019160882, WO2018195321, WO200140307, WO2002092784, WO2007133811, WO2009046541, WO2010083253, WO2011076781, WO2013056352, WO2015138600, WO2016179399, WO2016205042, WO2017178653, WO2018026600, WO2018057669, WO2018107058, WO2018190719, WO2018210793, WO2019023347, WO2019042470, WO2019175218, WO2019183266, WO2020013170, WO2020068752, Cancer Discov. 2019 Jan. 9(1):8; or Gariepy J., et al. 106th Annu Meet Am Assoc Immunologists (AAI) (May 9-13, San Diego, 2019, Abst 71.5);

agents targeting cytochrome P450 family members, such as letrozole, anastrozole, aminoglutethimide, megestrol acetate (MEGACE®), exemestane, formestane, fadrozole, vorozole (RIVISOR®), letrozole (FEMARA®), or anastrozole (ARIMIDEX®);

agents targeting DKK3, such as MTG-201;

agents targeting EEF1A2, such as plitidepsin;

agents targeting EIF4A1, such as rohinitib;

agents targeting endoglin, such as TRC105 (carotuximab);

agents targeting EGFR, such as neratinib, tucatinib (ONT-380), tesevatinib, mobocertinib (TAK-788), DZD-9008, varlitinib, abivertinib (ACEA-0010), EGF816 (nazartinib), olmutinib (BI-1482694), osimertinib (AZD-9291), AMG-596, lifirafenib (BGB-283), vectibix, or compounds disclosed in Booth, et al., Cancer Biol Ther. 2018 Feb. 1; 19(2):132-137;

agents targeting exportin-1, such as eltanexor;

agents targeting fatty acid amide hydrolase, such as compounds disclosed in WO2017160861;

agents targeting heat shock protein 90 beta family member 1, such as anlotinib;

agents targeting interleukin, such as SAR441000;

agents targeting lactotransferrin, such as ruxotemitide (LTX-315);

agents targeting lysyl oxidase, such as compounds disclosed in U.S. Pat. Nos. 4,965,288, 4,997,854, 4,943,593, 5,021,456, 5,059,714, 5,120,764, 5,182,297, 5,252,608, or US20040248871;

agents targeting MAGE family members, such as KITE-718, MAGE-A10C796T, or MAGE-A10 TCR;

agents targeting matrix metallopeptidase 9, such as compounds disclosed in WO2012027721;

agents targeting MCL1, such as tapotoclax (AMG-176), AMG-397, S-64315, AZD-5991, 483-LM, A-1210477, UMI-77, or compounds disclosed in WO2018183418, WO2016033486, or WO2017147410;

agents targeting MDM2, such as ALRN-6924, CMG-097, milademetan monotosylate monohydrate (DS-3032b), or AMG-232;

agents targeting MDM4, such as ALRN-6924;

agents targeting melan-A, such as MART-1 F5 TCR engineered PBMCs;

agents targeting mesothelin, such as CSG-MESO or TC-210;

agents targeting METAP2, such as M8891 or APL-1202;

agents targeting NLRP3, such as BMS-986299;

agents targeting oxoglutarate dehydrogenase, such as devimistat (CPI-613);

agents targeting placenta growth factor, such as aflibercept;

agents targeting progesterone receptor, such as TRI-CYCLEN LO (norethindrone+ethinyl estradiol);

agents targeting prostaglandin E synthase, such as GRC 27864 or compounds disclosed in WO2015158204, WO2013024898, WO2006063466, WO2007059610, WO2007124589, WO2010100249, WO2010034796, WO2010034797, WO2012022793, WO2012076673, WO2012076672, WO2010034798, WO2010034799, WO2012022792, WO2009103778, WO2011048004, WO2012087771, WO2012161965, WO2013118071, WO2013072825, WO2014167444, WO2009138376, WO2011023812, WO2012110860, WO2013153535, WO2009130242, WO2009146696, WO2013186692, WO2015059618, WO2016069376, WO2016069374, WO2009117985, WO2009064250, WO2009064251, WO2009082347, WO2009117987, WO2008071173, or Tong, et al., Cancer Lett. (2017) 389:23-32; Liu, et al., Oncotarget. (2016) 7(19):28235-46;

agents targeting signal regulatory protein alpha, such as CC-95251, GS-0189 (FSI-189), ES-004, BI765063, ADU1805, AL-008, BAT-6030, APX-700, CTX-5861, or RRx-001;

agents targeting SLC10A3, such as compounds disclosed in WO2015148954, WO2012082647, or WO2017160861;

agents targeting transforming growth factor alpha, such as compounds disclosed in WO2019103203;

agents targeting tumor protein p53, such as kevetrin (stimulator);

agents targeting vascular endothelial growth factor A, such as aflibercept;

agents targeting vascular endothelial growth factor receptor, such as fruquintinib or MP0250;

agents targeting VISTA, such as CA-170, or HMBD-002;

agents targeting WEE1, such as adavosertib (AZD-1775);

small molecule inhibitors targeting ABL1, such as imatinib, rebastinib, asciminib, or ponatinib (ICLUSIG®);

small molecule antagonists targeting adenosine receptor, such as CPI-444, AZD-4635, preladenant, or PBF-509;

small molecule antagonists targeting androgen receptor, such as apalutamide, enzalutamide, flutamide, galeterone, nilutamide, bicalutamide, leuprolide, goserelin, ODM-201, APC-100, or ODM-204;

small molecule inhibitors targeting arachidonate 5-lipoxygenase, such as meclofenamate sodium or zileuton;

small molecule inhibitors targeting ATR serine/threonine kinase, such as BAY-937, ceralasertib (AZD6738), AZD6783, VX-803, or VX-970 (berzosertib);

small molecule inhibitors targeting AXL receptor tyrosine kinase, such as bemcentinib (BGB-324), SLC-0211, or gilteritinib (Axl/Flt3);

small molecule inhibitors targeting Bruton's tyrosine kinase (BTK), such as (S)-6-amino-9-(1-(but-2-ynoyl) pyrrolidin-3-yl)-7-(4-phenoxyphenyl)-7H-purin-8 (9H)-one, acalabrutinib (ACP-196), zanubrutinib (BGB-3111), CB988, poseltinib (HM71224), ibrutinib (Imbruvica), M-2951 (evobrutinib), tirabrutinib (ONO-4059), rilzabrutinib (PRN-1008), spebrutinib (CC-292), vecabrutinib, ARQ-531 (MK-1026), SHR-1459, DTRMWXHS-12, or TAS-5315;

small molecule inhibitors targeting neurotrophic receptor tyrosine kinase such as larotrectinib, entrectinib, or selitrectinib (LOXO-195);

small molecule inhibitors targeting ROS proto-oncogene 1, receptor tyrosine kinase, such as entrectinib, repotrectinib (TPX-0005), or lorlatinib;

small molecule inhibitors targeting spleen associated tyrosine kinase, such as gusacitinib (ASN-002), 6-(1H-indazol-6-yl)-N-(4-morpholinophenyl)imidazo[1,2-a] pyrazin-8-amine, cerdulatinib, entospletinib, fostamatinib disodium (R788, R406), HMPL-523, NVP-QAB 205 AA, R112, or compounds disclosed in U.S. Pat. No. 8,450,321, or US20150175616;

small molecule inhibitors targeting SRC proto-oncogene, non-receptor tyrosine kinase, such as VAL-201, tirbanibulin (KX2-391), or ilginatinib maleate (NS-018);

small molecule inhibitors targeting B-cell lymphoma 2, such as navitoclax (ABT-263), venetoclax (ABT-199, RG-7601), or AT-101 (gossypol);

small molecule inhibitors targeting breakpoint cluster region, such as RG-7304;

small molecule inhibitors targeting bromodomain and external domain (BET) bromodomain containing protein, such as ABBV-744, INCB-054329, INCB057643, AZD-5153, ABT-767, BMS-986158, CC-90010, NHWD-870, ODM-207, ZBC246, ZEN3694, CC-95775 (FT-1101), mivebresib, BI-894999, PLX-2853, PLX-51107, CPI-0610, or GS-5829;

small molecule inhibitors targeting carbohydrate sulfotransferase 15, such as STNM-01;

small molecule inhibitors targeting carbonic anhydrase, such as polmacoxib, acetazolamide, or methazolamide;

small molecule inhibitors targeting catenin beta 1, such as CWP-291, or PRI-724;

small molecule antagonists targeting a C-C motif chemokine receptor, such as CCX-872, BMS-813160 (CCR2/CCR5), or MK-7690 (vicriviroc);

small molecule inhibitors targeting cell division cycle 7, such as simurosertib hydrate (TAK931);

small molecule inhibitors targeting cereblon, such as avadomide (CC-122), CC-92480, CC-90009, or iberdomide;

small molecule inhibitors targeting checkpoint kinase 1, such as SRA737;

small molecule inhibitors targeting cluster of differentiation markers, such as PBF-1662, BLZ-945, pemigatinib (INCB-054828), BAY-1163877 (rogaratinib), AZD4547, FGF-401 (roblitinib), quizartinib dihydrochloride, SX-682, AZD-5069, PLX-9486, avapritinib (BLU-285), ripretinib (DCC-2618), imatinib mesylate, JSP-191, BLU-263, CD117-ADC, AZD3229, telatinib, vorolanib, GO-203-2C, AB-680, PSB-12379, PSB-12441, PSB-12425, CB-708, HM-30181A, motixafortide (BL-8040), LY2510924, burixafor (TG-0054), X4P-002, mavorixafor (X4P-001-IO), Plerixafor, CTX-5861, or REGN-5678 (PSMA/CD28);

small molecule inhibitors targeting a complement component, such as Imprime PGG (Biothera Pharmaceuticals);

small molecule inhibitor targeting a C-X-C motif chemokine ligand (e.g., CXCL12), such as olaptesed pegol (NOX-A12);

small molecule inhibitors targeting cyclin dependent kinase, such as palbociclib;

small molecule inhibitors targeting cytochrome P450 family, such as ODM-209, LAE-201, seviteronel (VT-464), CFG920, abiraterone, or abiraterone acetate;

small molecule inhibitors targeting DEAD-box helicase 5, such as supinoxin (RX-5902);

small molecule inhibitors targeting diablo IAP-binding mitochondrial protein, such as BI-891065;

small molecule inhibitors targeting dihydrofolate reductase, such as pralatrexate or pemetrexed disodium;

small molecule inhibitors targeting DNA dependent protein kinase, such as MSC2490484A (nedisertib), VX-984, AsiDNA (DT-01), LXS-196, or sotrastaurin;

small molecule inhibitors targeting mitogen-activated protein kinase, such as ralimetinib, RG-7304, GS-4875, or GS-5290;

small molecule inhibitors targeting MARCKS, such as BIO-11006;

small molecule inhibitors targeting RIPK1, such as GSK-3145094;

small molecule inhibitors targeting Rho associated coiled-coil containing protein kinase, such as AT13148 or KD025;

small molecule inhibitors targeting DNA topoisomerase, such as irinotecan, firtecan pegol, or amrubicin;

small molecule inhibitors targeting dopamine receptor D2, such as ONC-201;

small molecule inhibitors targeting DOT1 like histone lysine methyltransferase, such as pinometostat (EPZ-5676);

small molecule inhibitors targeting EZH2, such as tazemetostat, CPI-1205, or PF-06821497;

small molecule inhibitors targeting fatty acid synthase, such as TVB-2640 (Sagimet Biosciences);

small molecule inhibitors targeting fibroblast growth factor, such as bemarituzumab (FPA144);

small molecule inhibitors targeting focal adhesion kinase 2, such as VS-4718, defactinib, or GSK2256098;

small molecule inhibitors targeting folate receptor 1, such as pralatrexate;

small molecule inhibitors targeting FOXM1, such as thiostrepton;

small molecule inhibitors targeting galectin 3, such as belapectin (GR-MD-02);

small molecule antagonists targeting glucocorticoid receptor, such as relacorilant (CORT-125134);

small molecule inhibitors targeting glutaminase include without limitation CB-839 (telaglenastat), or bis-2-(5-phenylacetamido-1,3,4-thiadiazol-2-yl)ethyl sulfide (BPTES);

small molecule inhibitors targeting GNRHR, such as elagolix, relugolix, or degarelix;

small molecule inhibitors targeting EPAS1, such as belzutifan (PT-2977 (Merck & Co.));

small molecule inhibitors targeting IDO, such as epacadostat, linrodostat (F-001287), PF-06840003, resminostat, linrodostat (BMS-986205), EOS-200271, or KHK-2455;

small molecule inhibitors targeting isocitrate dehydrogenase (NADP(+)), such as limitation ivosidenib (AG-120), vorasidenib (AG-881) (IDH1 and IDH2), IDH-305, or enasidenib (AG-221);

small molecule inhibitors targeting Janus kinase, such as ZD-1480, baricitinib, filgotinib (GLPG0634), itacitinib (INCB039110), momelotinib (CYT0387), peficitinib (ASP015K), ruxolitinib, tofacitinib, INCB052793, ZD-1480, baricitinib, fedratinib, gandotinib (LY2784544), lestaurtinib (FLT3/JAK2/TRKA), momelotinib (CYT0387), ilginatinib maleate (NS-018), pacritinib (SB1518) (JAK2/IRAK-1/CSF1R/Flt3), or ruxolitinib;

small molecule inhibitors targeting KRAS, such as sotorasib (AMG-510), COTI-219, ARS-3248, WDB-178, BI-3406, BI-1701963, SML-8-73-1 (G12C), Compound 3144 (G12D), Kobe0065, Kobe/2602, (Ras GTP), RT11, or adagrasib (MRTX-849);

small molecule inhibitors targeting lysine demethylase 1A, such as CC-90011;

small molecule inhibitors targeting MAPK interacting serine/threonine kinase, such as tomivosertib (eFT-508);

small molecule inhibitors targeting mechanistic target of rapamycin kinase (mTOR), such as dactolisib, omipalisib, voxtalisib, gedatolisib, GSK2141795, inavolisib (RG6114), sapanisertib, ME-344, sirolimus (oral nano-amorphous formulation, cancer), racemetyrosine (TYME-88 (mTOR/cytochrome P450 3A4)), sirolimus, temsirolimus (TORISEL®, CCI-779), CC-115, onatasertib (CC-223), SF-1126, PQR-309 (bimiralisib), voxtalisib, or GSK-2126458;

small molecule inhibitors targeting notch receptor, such as AL-101 (BMS-906024);

small molecule inhibitors targeting phosphatidylinositol-4,5-bisphosphate 3-kinase catalytic subunit, such as ASN-003, inavolisib (RG6114), alpelisib, pictilisib, or idelalisib (Zydelig®);

small molecule inhibitors targeting polo like kinase 1, such as volasertib or onvansertib;

small molecule inhibitors targeting poly(ADP-ribose) polymerase, such as olaparib (MK7339), rucaparib, veliparib, talazoparib, ABT-767, pamiparib (BGB-290), fluazolepali (SHR-3162), niraparib (JNJ-64091742), stenoparib (2X-121 (e-7499)), simmiparib, IMP-4297, SC-10914, IDX-1197, HWH-340, or CK-102;

small molecule inhibitors targeting polycomb protein EED, such as MAK683;

small molecule inhibitors targeting porcupine O-acyltransferase, such as WNT-974;

small molecule antagonists targeting progesterone receptor, such as onapristone;

small molecule inhibitors targeting prostaglandin-endoperoxide synthase, such as HP-5000, lornoxicam, ketorolac tromethamine, bromfenac sodium, otenaproxesul (ATB-346), mofezolac, GLY-230, TRK-700, diclofenac, meloxicam, parecoxib, etoricoxib, celecoxib, AXS-06, diclofenac potassium, reformulated celecoxib (DRGT-46), AAT-076, meisuoshuli, lumiracoxib, meloxicam, valdecoxib, zaltoprofen, nimesulide, anitrazafen, apricoxib, cimicoxib, deracoxib, flumizole, firocoxib, mavacoxib, pamicogrel, parecoxib, robenacoxib, rofecoxib, rutecarpine, tilmacoxib, zaltoprofen, or imrecoxib;

small molecule inhibitors targeting protein arginine N methyltransferase, such as MS203, PF-06939999, GSK3368715, or GSK3326595;

small molecule inhibitors targeting PTPN11, such as TNO155 (SHP-099), RMC-4550, JAB-3068, RMC-4630 (SAR442720), or compounds disclosed in WO2018172984 or WO2017211303;

small molecule inhibitors targeting Raf-1 proto-oncogene, serine/threonine kinase, such as RG-7304;

small molecule antagonist targeting retinoic acid receptor, such as tamibarotene (SY-1425);

small molecule inhibitors targeting ribosomal protein S6 kinase B1, such as MSC2363318A;

small molecule inhibitors targeting S100 calcium binding protein A9, such as tasquinimod;

small molecule inhibitors targeting selectin E, such as uproleselan sodium (GMI-1271);

small molecule inhibitors targeting SF3B1, such as H3B-8800;

small molecule inhibitors targeting Sirtuin-3, such as YC8-02;

small molecule inhibitors targeting SMO, such as sonidegib (Odomzo®, formerly LDE-225), vismodegib (GDC-0449), glasdegib (PF-04449913), itraconazole, or patidegib, taladegib;

small molecule antagonists targeting somatostatin receptor, such as OPS-201;

small molecule inhibitors targeting sphingosine kinase 2, such as opaganib (Yeliva®, ABC294640);

small molecule inhibitors targeting STAT3, such as napabucasin (BBI-608);

small molecule inhibitors targeting tankyrase, such as G007-LK or stenoparib (2X-121 (e-7499));

small molecule inhibitors targeting TFGBR1, such as galunisertib, PF-06952229;

small molecule inhibitors targeting thymidylate synthase, such as idetrexed (ONX-0801);

small molecule inhibitors targeting tumor protein p53, such as CMG-097;

small molecule inhibitors targeting valosin-containing protein, such as CB-5083;

small molecule inhibitors targeting WT1, such as ombipepimut-S(DSP-7888);

small molecule agonists targeting adenosine receptor, such as AB928, or namodenoson (CF102);

small molecule agonist(s) targeting asparaginase, such as crisantaspase (Erwinase®), GRASPA (ERY-001, ERY-ASP), calaspargase pegol, or pegaspargase;

small molecule agonists targeting CCAAT enhancer binding protein alpha, such as MTL-501;

small molecule agonists targeting cluster of differentiation markers, such as interleukin 2 receptor subunit gamma, eltrombopag, rintatolimod, poly-ICLC (NSC-301463), Riboxxon, Apoxxim, RIBOXXIM®, MCT-465, MCT-475, G100, PEPA-10, eftozanermin alfa (ABBV-621), E-6887, motolimod, resiquimod, selgantolimod (GS-9688), VTX-1463, NKTR-262, AST-008, CMP-001, cobitolimod, tilsotolimod, litenimod, MGN-1601, BB-006, IMO-8400, IMO-9200, agatolimod, DIMS-9054, DV-1079, lefitolimod (MGN-1703), CYT-003, or PUL-042;

small molecule agonists targeting cytochrome P450 family, such as mitotane;

small molecule agonists targeting DExD/H-box helicase 58, such as RGT-100;
small molecule agonists targeting GNRHR, such as leuprorelin acetate, leuprorelin acetate sustained release depot (ATRIGEL), triptorelin pamoate, or goserelin acetate;
small molecule agonists targeting GRB2, such as prexigebersen (BP1001);
small molecule agonists targeting NFE2L2, such as omaveloxolone (RTA-408);
small molecule agonists targeting NOD2, such as mifamurtide (liposomal);
small molecule agonists targeting PD-L1, such as CA-170, GS-4224, GS-4416, lazertinib (GNS-1480; PD-L1/EGFR);
small molecule agonists targeting progesterone receptor, such as norgestimate+ethinylestradiol (Tri-Cyclen) or levonorgestrel;
small molecule agonists targeting RAR-related orphan receptor gamma, such as cintirorgon (LYC-55716);
small molecule agonists targeting retinoic acid receptor, such as tretinoin;
small molecule agonists targeting STING1, such as ADU-S100 (MIW-815), SB-11285, MK-1454, SR-8291, AdVCA0848, GSK-532, SYN-STING, MSA-1, SR-8291, cyclic-GAMP (cGAMP), or cyclic-di-AMP;
small molecule agonists targeting thyroid hormone receptor beta, such as levothyroxine sodium;
small molecule agonists targeting TLR7, such as BDB-001, DSP-0509, versatolimod (GS-9620), LHC-165, imiquimod (TMX-101), resiquimod, MCT-465, RG-7854, NKTR-262, or compounds disclosed in US20100143301, US20110098248, US20090047249, US20140045849, US20140073642, WO2014056953, WO2014076221, WO2014128189, US20140350031, WO2014023813, US20080234251, US20080306050, US20100029585, US20110092485, US20110118235, US20120082658, US20120219615, US20140066432, US20140088085, US20140275167, or US20130251673;
small molecule agonists targeting tumor necrosis factor, such as tasonermin;
inhibitory peptides targeting KRAS, such as KRpep-2 (Ac-RRCPLYISYDPVCRR-NH2) or KRpep-2d (Ac-RRRRCPLYISYDPVCRRRR-NH2);
antisense agents targeting AKT1, such as RX-0201;
antisense agents targeting androgen receptor, such as IONIS-AR-2.5Rx;
antisense agents targeting baculoviral IAP repeat containing 5, such as EZN-3042;
antisense agents targeting GRB2, such as prexigebersen;
antisense agents targeting heat shock protein 27, such as apatorsen;
antisense agents targeting KRAS, such as anti-KRAS U1 adaptor, siG12D-LODER™, or siG12D exosomes;
antisense agents targeting STAT3, such as danvatirsen (IONIS-STAT3-2.5Rx);
gene therapies targeting a C-C motif chemokine receptor, such as SB-728-T;
gene therapies targeting an interleukin, such as EGENE-001, tavokinogene telseplasmid, nogapendekin alfa (ALT-803), NKTR-255, NIZ-985 (hetIL-15), or MDNA-55;
antibodies targeting CD47, such as CC-90002, magrolimab (Hu5F9-G4), AO-176 (Vx-1004), IBI-188, lemzoparlimab (TJC-4), SHR-1603, HLX-24, LQ-001, IMC-002, ZL-1201, IMM-01, B6H12, GenSci-059, TAY-018, PT-240, 1F8-GMCSF, SY-102, KD-015, ALX-148, AK-117, TTI-621, TTI-622, or compounds disclosed in WO199727873, WO199940940, WO2002092784, WO2005044857, WO2009046541, WO2010070047, WO2011143624, WO2012170250, WO2013109752, WO2013119714, WO2014087248, WO2015191861, WO2016022971, WO2016023040, WO2016024021, WO2016081423, WO2016109415, WO2016141328, WO2016188449, WO2017027422, WO2017049251, WO2017053423, WO2017121771, WO2017194634, WO2017196793, WO2017215585, WO2018075857, WO2018075960, WO2018089508, WO2018095428, WO2018137705, WO2018233575, WO2019027903, WO2019034895, WO2019042119, WO2019042285, WO2019042470, WO2019086573, WO2019108733, WO2019138367, WO2019144895, WO2019157843, WO2019179366, WO2019184912, WO2019185717, WO2019201236, WO2019238012, WO2019241732, WO2020019135, WO2020036977, WO2020043188, WO2020009725;
antibodies targeting claudin 18, such as claudiximab;
antibodies targeting cluster of differentiation markers, such as tafasitamab (MOR208; MorphoSys AG), Inebilizumab (MEDI-551), obinutuzumab, IGN-002, rituximab biosimilar (PF-05280586), varlilumab (CDX-1127), AFM-13 (CD16/CD30), AMG330, otlertuzumab (TRU-016), isatuximab, felzartamab (MOR-202), TAK-079, TAK573, daratumumab (DARZALEX®), TTX-030, selicrelumab (RG7876), APX-005M, ABBV-428, ABBV-927, mitazalimab (JNJ-64457107), lenziluma, alemtuzuma, emactuzumab, AMG-820, FPA-008 (cabiralizumab), PRS-343 (CD-137/Her2), AFM-13 (CD16/CD30), belantamab mafodotin (GSK-2857916), AFM26 (BCMA/CD16A), simlukafusp alfa (RG7461), urelumab, utomilumab (PF-05082566), AGEN2373, ADG-106, BT-7480, PRS-343 (CD-137/HER2), FAP-4-IBBL (4-1BB/FAP), ramucirumab, CDX-0158, CDX-0159 and FSI-174, relatlimab (ONO-4482), LAG-525, MK-4280, fianlimab (REGN-3767), INCAGN2385, encelimab (TSR-033), atipotuzumab, BrevaRex (MabAR-20.5), MEDI-9447 (oleclumab), CPX-006, IPH-53, BMS-986179, NZV-930, CPI-006, PAT-SC1, lirilumab (IPH-2102), lacutamab (IPH-4102), monalizumab, BAY-1834942, NEO-201 (CEACAM 5/6), Iodine (131I) apamistamab (131I-BC8 (lomab-B)), MEDI0562 (tavolixizumab), GSK-3174998, INCAGN1949, BMS-986178, GBR-8383, ABBV-368, denosumab, BION-1301, MK-4166, INCAGN-1876, TRX-518, BMS-986156, MK-1248, GWN-323, CTB-006, INBRX-109, GEN-1029, pepinemab (VX-15), vopratelimab (JTX-2011), GSK3359609, cobolimab (TSR-022), MBG-453, INCAGN-2390, or compounds disclosed in WO 2017096179, WO2017096276, WO2017096189, or WO2018089628;
antibodies targeting clusterin, such as AB-16B5;
antibodies targeting a complement component, such as ravulizumab (ALXN-1210);
antibodies targeting CTLA4, such as ipilimumab, tremelimumab, BMS-986218, AGEN1181, zalifrelimab (AGEN1884), BMS-986249, MK-1308, REGN-4659, ADU-1604, ipilimumab biosimilar (CS-1002), BCD-145, APL-509, JS-007, BA-3071, ONC-392, KN-044, CG-0161, BPI-002, or HBM-4003;
antibodies targeting a C-X-C motif chemokine ligand, such as BMS-986253 (HuMax-Inflam);

antibodies targeting delta like canonical Notch ligand 4, such as demcizumab;

antibodies targeting EPH receptor A3, such as fibatuzumab (KB-004);

antibodies targeting epidermal growth factor receptor, such as modotuximab, cetuximab sarotalocan (RM-1929), seribantumab, necitumumab, depatuxizumab mafodotin (ABT-414), tomuzotuximab, depatuxizumab (ABT-806), or cetuximab;

antibodies targeting epithelial cell adhesion molecule, such as oportuzumab monatox (VB4-845);

antibodies targeting fibroblast growth factor, such as GAL-F2, B-701 (vofatamab);

antibodies targeting hepatocyte growth factor, such as MP-0250;

antibodies targeting an interleukin, such as canakinumab (ACZ885), gevokizumab (VPM087), CJM-112, guselkumab, talacotuzumab (JNJ-56022473), siltuximab, or tocilizumab;

antibodies targeting LRRC15, such as ABBV-085 or cusatuzumab (ARGX-110);

antibodies targeting mesothelin, such as BMS-986148, SEL-403, or anti-MSLN-MMAE;

antibodies targeting MET, such as telisotuzumab vedotin (ABBV-399);

antibodies targeting myostatin, such as landogrozumab;

antibodies targeting notch receptor, such as tarextumab;

antibodies targeting PD-1, such as pembrolizumab, nivolumab, cemiplimab, pidilizumab, AMG-404, MEDI0680 (AMP-514), atezolizumab, durvalumab, cosibelimab (CK-301), sasanlimab (PF-06801591), BGB-A317 (tislelizumab), zimberelimab (GLS-010 (WBP-3055)), AK-103 (HX-008), AK-105, CS-1003, HLX-10, retifanlimab (MGA-012), BI-754091, balstilimab (AGEN-2034), JS-001 (toripalimab), cetrelimab (JNJ-63723283), genolimzumab (CBT-501), LZM-009, prolgolimab (BCD-100), lodapolimab (LY-3300054), SHR-1201, SHR-1210 (camrelizumab), Sym-021, budigalimab (ABBV-181), BAT-1306, avelumab (MSB0010718C), CX-072, CBT-502, TSR-042 (dostarlimab), MSB-2311, JTX-4014, BGB-A333, SHR-1316, CS-1001 (WBP-3155), envafolimab (KN-035), IBI-308 (sintilimab), HLX-20, KL-A167, STI-A1014, STI-A1015 (IMC-001), BCD-135, FAZ-053, TQB-2450, MDX1105-01, INCB086550, MAX10181, spartalizumab (PDR-001), or compounds disclosed in WO2018195321, WO2020014643, WO2019160882, or WO2018195321;

antibodies targeting TGFB1, such as SAR439459, ABBV-151, NIS793, XOMA 089, or compounds disclosed in WO2019103203;

antibodies for targeting vascular endothelial growth factor A, such as bevacizumab, vanucizumab, or faricimab;

bispecific antibodies targeting CD47, such as IBI-322 (CD47/PD-L1), IMM-0306 (CD47/CD20), TJ-L1C4 (CD47/PD-L1), HX-009 (CD47/PD-1), PMC-122 (CD47/PD-L1), PT-217, (CD47/DLL3), IMM-26011 (CD47/FLT3), IMM-0207 (CD47/VEGF), IMM-2902 (CD47/HER2), BH29xx (CD47/PD-L1), IMM-03 (CD47/CD20), IMM-2502 (CD47/PD-L1), HMBD-004B (CD47/BCMA), HMBD-004A (CD47/CD33), TG-1801 (NI-1701), or NI-1801;

bispecific antibodies targeting PD-1, such as PF-06936308 (PD-1/CTLA4), MGD-013 (PD-1/LAG-3), RO-7247669 (PD-1/LAG-3), MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), RG7769 (PD-1/TIM-3), or TAK-252 (PD-1/OX40L);

bispecific antibodies targeting PD-L1, such as FS-118 (LAG-3/PD-L1), FPT-155 (CTLA4/PD-L1/CD28), GEN-1046 (PD-L1/4-1BB), bintrafusp alfa (M7824 (PD-L1/TGFβ-EC domain)), CDX-527 (CD27/PD-L1), or INBRX-105 (4-1BB/PDL1);

T-cell engagers (targeting CD3), such as AMG-160 (PSMA/CD3), AMG-212 (PSMA/CD3), AMG-330 (CD33/CD3), AMG-420 (BCMA/CD3), AMG-427 (FLT3/CD3), AMG-562 (CD19/CD3), AMG-596 (EGFRvIII/CD3), AMG-673 (CD33/CD3), AMG-701 (BCMA/CD3), AMG-757 (DLL3/CD3), AMG-211 (CEA/CD3), BLINCYTO® (CD19/CD3), RG7802 (CEA/CD3), ERY-974 (CD3/GPC3), huGD2-BsAb (CD3/GD2), PF-06671008 (Cadherins/CD3), APV0436 (CD123/CD3), ERY974, flotetuzumab (CD123/CD3), GEM333 (CD3/CD33), GEMoab (CD3/PSCA), REGN-1979 (CD20/CD3), MCLA-117 (CD3/CLEC12A), JNJ-0819, JNJ-7564 (CD3/heme), JNJ-63709178 (CD123/CD3), MGD-007 (CD3/gpA33), MGD-009 (CD3/B7H3), IMCgp100 (CD3/gp100), XmAb-14045 (CD123/CD3), XmAb-13676 (CD3/CD20), catumaxomab (CD3/EpCAM), REGN-4018 (MUC16/CD3), RG6026, RG6076, RG6194, RG-7828 (CD20/CD3), CC-93269 (CD3/BCMA), REGN-5458 (CD3/BCMA), GRB-1302 (CD3/Erbb2), GRB-1342 (CD38/CD3), GEM-333 (CD3/CD33), PF-06863135 (BCMA/CD3), SAR440234 (CD3/CDw123), JNJ-9383 (MGD-015), blinatumomab (CD19/CD3), odronextamab (REGN-1979 (CD20xCD3)), plamotamab (XmAb-13676 (CD3/CD20)), mosunetuzumab (RG-7828 (CD20/CD3)), AMG-424 (CD38/CD3), tidutamab (XmAb-18087 (SSTR2/CD3)), or duvortuxizumab (JNJ-64052781) (CD19/CD3);

vaccines targeting fms related receptor tyrosine kinase, such as HLA-A2402/HLA-A0201 restricted epitope peptide vaccine;

vaccines targeting heat shock protein 27, such as PSV-AML (PhosphoSynVax);

vaccines targeting PD-L1, such as IO-120+IO-103 (PD-L1/PD-L2 vaccines) or IO-103;

vaccines targeting tumor protein p53, such as MVA-p53;

vaccines targeting WT1, such as WT-1 analog peptide vaccine (WT1-CTL);

cell therapies targeting baculoviral IAP repeat containing 5, such as tumor lysate/MUC1/survivin PepTivator-loaded dendritic cell vaccine;

cell therapies targeting carbonic anhydrase, such as DC-Ad-GMCAIX;

cell therapies targeting C-C motif chemokine receptor, such as CCR5-SBC-728-HSPC;

cell therapies for targeting cluster of differentiation markers include without limitation CD19-ARTEMIS, TBI-1501, CTL-119 huCART-19 T cells, 1 iso-cel, lisocabtagene maraleucel (JCAR-017), axicabtagene ciloleucel (KTE-C19, Yescarta®), axicabtagene ciloleucel (KTE-X19), U.S. Pat. Nos. 7,741,465, 6,319,494, UCART-19, tabelecleucel (EBV-CTL), T tisagenlecleucel-T (CTL019), CD19CAR-CD28-CD3zeta-EGFRt-expressing T cells, CD19/4-1BBL armored CAR T cell therapy, C-CAR-011, CIK-CAR.CD19, CD19CAR-28-zeta T cells, PCAR-019, MatchCART, DSCAR-01, IM19 CAR-T, TC-110, anti-CD19 CAR T-cell therapy (B-cell acute lymphoblastic leukemia, Universiti Kebangsaan Malaysia), anti-CD19 CAR T-cell therapy (acute lymphoblastic leukemia/Non-Hodgkin's lymphoma, University Hospital Heidelberg), anti-CD19 CAR T-cell therapy (silenced IL-6 expression, cancer, Shanghai Unicar-Therapy Biomedicine Technology), MB-CART2019.1 (CD19/CD20), GC-197 (CD19/CD7), CLIC-1901, ET-019003, anti-CD19-STAR-T cells, AVA-001, BCMA-CD19 cCAR (CD19/APRIL), ICG-134, ICG-132 (CD19/CD20), CTA-101, WZTL-002, dual anti-CD19/anti-CD20 CAR T-cells (chronic lymphocytic leukemia/B-cell lymphomas), HY-001, ET-019002, YTB-323, GC-012 (CD19/APRIL), GC-022 (CD19/CD22), CD19CAR-CD28-CD3zeta-EGFRt-expressing Tn/mem, UCAR-011, ICTCAR-014, GC-007F, PTG-01, CC-97540, GC-007G, TC-310, GC-197, tisagenlecleucel-T, CART-19, tisagenlecleucel (CTL-019)), anti-CD20 CAR T-cell therapy (non-Hodgkin's lymphoma), MB-CART2019.1 (CD19/CD20), WZTL-002 dual anti-CD19/anti-CD20 CAR-T cells, ICG-132 (CD19/CD20), ACTR707 ATTCK-20, PBCAR-20A, LB-1905, CIK-CAR.CD33, CD33CART, dual anti-BCMA/anti-CD38 CAR T-cell therapy, CART-ddBCMA, MB-102, IM-23, JEZ-567, UCART-123, PD-1 knockout T cell therapy (esophageal cancer/NSCLC), ICTCAR-052, Tn MUC-1 CAR-T, ICTCAR-053, PD-1 knockout T cell therapy (esophageal cancer/NSCLC), AUTO-2, anti-BCMA CAR T-cell therapy, Descartes-011, anti-BCMA/anti-CD38 CAR T-cell therapy, CART-ddBCMA, BCMA-CS1 cCAR, CYAD-01 (NKG2D LIGAND MODULATOR), KD-045, PD-L1 t-haNK, BCMA-CS1 cCAR, MEDI5083, anti-CD276 CART, or therapies disclosed in WO2012079000 or WO2017049166;

cell therapies targeting folate hydrolase 1, such as CIK-CAR.PSMA or CART-PSMA-TGFβRDN;

cell therapies targeting GSTP1, such as CPG3-CAR (GLYCAR);

cell therapies targeting HLA-A, such as FH-MCVA2TCR or NeoTCR-P1;

cell therapies targeting an interleukin, such as CST-101;

cell therapies targeting KRAS, such as anti-KRAS G12D mTCR PBL;

cell therapies targeting MET, such as anti-cMet RNA CAR T;

cell therapies targeting MUC16, such as JCAR-020;

cell therapies targeting PD-1, such as PD-1 knockout T cell therapy (esophageal cancer/NSCLC);

cell therapies targeting PRAME, such as BPX-701;

cell therapies targeting transforming protein E7, such as KITE-439;

cell therapies targeting WT1, such as WT1-CTL, ASP-7517, or JTCR-016;

Exemplified Combination Therapies

Lymphoma or Leukemia Combination Therapy

Some chemotherapy agents are suitable for treating lymphoma or leukemia. These agents include aldesleukin, alvocidib, amifostine trihydrate, aminocamptothecin, antineoplaston A10, antineoplaston AS2-1, anti-thymocyte globulin, arsenic trioxide, Bcl-2 family protein inhibitor ABT-263, beta alethine, BMS-345541, bortezomib (VELCADE®), bortezomib (VELCADE®, PS-341), bryostatin 1, bulsulfan, campath-1H, carboplatin, carfilzomib (Kyprolis®), carmustine, caspofungin acetate, CC-5103, chlorambucil, CHOP (cyclophosphamide, doxorubicin, vincristine, and prednisone), cisplatin, cladribine, clofarabine, curcumin, CVP (cyclophosphamide, vincristine, and prednisone), cyclophosphamide, cyclosporine, cytarabine, denileukin diftitox, dexamethasone, docetaxel, dolastatin 10, doxorubicin, doxorubicin hydrochloride, DT-PACE (dexamethasone, thalidomide, cisplatin, doxorubicin, cyclophosphamide, and etoposide), enzastaurin, epoetin alfa, etoposide, everolimus (RAD001), FCM (fludarabine, cyclophosphamide, and mitoxantrone), FCR (fludarabine, cyclophosphamide, and rituximab), fenretinide, filgrastim, flavopiridol, fludarabine, FR (fludarabine and rituximab), geldanamycin (17 AAG), hyperCVAD (hyperfractionated cyclophosphamide, vincristine, doxorubicin, dexamethasone, methotrexate, and cytarabine), ICE (iphosphamide, carboplatin, and etoposide), ifosfamide, irinotecan hydrochloride, interferon alpha-2b, ixabepilone, lenalidomide (REVLIMID®, CC-5013), lymphokine-activated killer cells, MCP (mitoxantrone, chlorambucil, and prednisolone), melphalan, mesna, methotrexate, mitoxantrone hydrochloride, motexafin gadolinium, mycophenolate mofetil, nelarabine, obatoclax (GX15-070), oblimersen, octreotide acetate, omega-3 fatty acids, Omr-IgG-am (WNIG, Omrix), oxaliplatin, paclitaxel, palbociclib (PD0332991), pegfilgrastim, PEGylated liposomal doxorubicin hydrochloride, perifosin, prednisolone, prednisone, recombinant flt3 ligand, recombinant human thrombopoietin, recombinant interferon alfa, recombinant interleukin-11, recombinant interleukin-12, rituximab, R-CHOP (rituximab and CHOP), R-CVP (rituximab and CVP), R-FCM (rituximab and FCM), R-ICE (rituximab and ICE), and R MCP (rituximab and MCP), R-roscovitine (seliciclib, CYC202), sargramostim, sildenafil citrate, simvastatin, sirolimus, styryl sulphones, tacrolimus, tanespimycin, temsirolimus (CCI-779), thalidomide, therapeutic allogeneic lymphocytes, thiotepa, tipifarnib, vincristine, vincristine sulfate, vinorelbine ditartrate, SAHA (suberanilohydroxamic acid, or suberoyl, anilide, and hydroxamic acid), vemurafenib (Zelboraf®), venetoclax (ABT-199).

One modified approach is radioimmunotherapy, wherein a monoclonal antibody is combined with a radioisotope particle, such as indium-111, yttrium-90, and iodine-131. Examples of combination therapies include, but are not limited to, iodine-131 tositumomab (BEXXAR®), yttrium-90 ibritumomab tiuxetan (ZEVALIN®), and BEXXAR® with CHOP.

The abovementioned therapies can be supplemented or combined with stem cell transplantation or treatment. Therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, low-LET cobalt-60 gamma ray therapy, bleomycin, conventional surgery, radiation therapy, and nonmyeloablative allogeneic hematopoietic stem cell transplantation.

Non-Hodgkin's Lymphomas Combination Therapy

Treatment of non-Hodgkin's lymphomas (NHL), especially those of B cell origin, includes using monoclonal antibodies, standard chemotherapy approaches (e.g., CHOP (cyclophosphamide, doxorubicin, vincristine, and prednisone), CVP (cyclophosphamide, vincristine, and prednisone), FCM (fludarabine, cyclophosphamide, and mitoxantrone), MCP (Mitoxantrone, Chlorambucil, Prednisolone), all optionally including rituximab (R) and the like), radioimmunotherapy, and combinations thereof, especially integration of an antibody therapy with chemotherapy.

Examples of unconjugated monoclonal antibodies for the treatment of NHL/B-cell cancers include rituximab, alemtuzumab, human or humanized anti-CD20 antibodies, lumiliximab, anti-TNF-related apoptosis-inducing ligand (anti-TRAIL), bevacizumab, galiximab, epratuzumab, SGN-40, and anti-CD74.

Examples of experimental antibody agents used in treatment of NHL/B-cell cancers include ofatumumab, ha20, PRO131921, alemtuzumab, galiximab, SGN-40, CHIR-12.12, epratuzumab, lumiliximab, apolizumab, milatuzumab, and bevacizumab.

Examples of standard regimens of chemotherapy for NHL/B-cell cancers include CHOP, FCM, CVP, MCP, R-CHOP (rituximab, cyclophosphamide, doxorubicin, vincristine, and prednisone), R-FCM, R-CVP, and R MCP.

Examples of radioimmunotherapy for NHL/B-cell cancers include yttrium-90 ibritumomab tiuxetan (ZEVALIN®) and iodine-131 tositumomab (BEXXAR®).

Mantle Cell Lymphoma Combination Therapy

Therapeutic treatments for mantle cell lymphoma (MCL) include combination chemotherapies such as CHOP, hyper-CVAD, and FCM. These regimens can also be supplemented with the monoclonal antibody rituximab to form combination therapies R-CHOP, hyperCVAD-R, and R-FCM. Any of the abovementioned therapies may be combined with stem cell transplantation or ICE in order to treat MCL.

An alternative approach to treating MCL is immunotherapy. One immunotherapy uses monoclonal antibodies like rituximab. Another uses cancer vaccines, such as GTOP-99, which are based on the genetic makeup of an individual patient's tumor.

A modified approach to treat MCL is radioimmunotherapy, wherein a monoclonal antibody is combined with a radioisotope particle, such as iodine-131 tositumomab (BEXXAR®) and yttrium-90 ibritumomab tiuxetan (ZEVALIN®). In another example, BEXXAR® is used in sequential treatment with CHOP.

Other approaches to treating MCL include autologous stem cell transplantation coupled with high-dose chemotherapy, administering proteasome inhibitors such as bortezomib (VELCADE® or PS-341), or administering antiangiogenesis agents such as thalidomide, especially in combination with rituximab.

Another treatment approach is administering drugs that lead to the degradation of Bcl-2 protein and increase cancer cell sensitivity to chemotherapy, such as oblimersen, in combination with other chemotherapeutic agents.

A further treatment approach includes administering mTOR inhibitors, which can lead to inhibition of cell growth and even cell death. Non-limiting examples are sirolimus, temsirolimus (TORISEL®, CCI-779), CC-115, CC-223, SF-1126, PQR-309 (bimiralisib), voxtalisib, GSK-2126458, and temsirolimus in combination with RITUXAN®, VELCADE®, or other chemotherapeutic agents.

Other recent therapies for MCL have been disclosed. Such examples include flavopiridol, palbociclib (PD0332991), R-roscovitine (selicicilib, CYC202), styryl sulphones, obatoclax (GX15-070), TRAIL, Anti-TRAIL death receptors DR4 and DR5 antibodies, temsirolimus (TORISEL®, CCI-779), everolimus (RAD001), BMS-345541, curcumin, SAHA, thalidomide, lenalidomide (REVLIMID®, CC-5013), and geldanamycin (17 AAG).

Waldenstrom's Macroglobulinemia Combination Therapy

Therapeutic agents used to treat Waldenstrom's Macroglobulinemia (WM) include aldesleukin, alemtuzumab, alvocidib, amifostine trihydrate, aminocamptothecin, antineoplaston A10, antineoplaston AS2-1, anti-thymocyte globulin, arsenic trioxide, autologous human tumor-derived HSPPC-96, Bcl-2 family protein inhibitor ABT-263, beta alethine, bortezomib (VELCADE®), bryostatin 1, busulfan, campath-1H, carboplatin, carmustine, caspofungin acetate, CC-5103, cisplatin, clofarabine, cyclophosphamide, cyclosporine, cytarabine, denileukin diftitox, dexamethasone, docetaxel, dolastatin 10, doxorubicin hydrochloride, DT-PACE, enzastaurin, epoetin alfa, epratuzumab (hLL2-anti-CD22 humanized antibody), etoposide, everolimus, fenretinide, filgrastim, fludarabine, ibrutinib, ifosfamide, indium-111 monoclonal antibody MN-14, iodine-131 tositumomab, irinotecan hydrochloride, ixabepilone, lymphokine-activated killer cells, melphalan, mesna, methotrexate, mitoxantrone hydrochloride, monoclonal antibody CD19 (such as tisagenlecleucel-T, CART-19, CTL-019), monoclonal antibody CD20, motexafin gadolinium, mycophenolate mofetil, nelarabine, oblimersen, octreotide acetate, omega-3 fatty acids, oxaliplatin, paclitaxel, pegfilgrastim, PEGylated liposomal doxorubicin hydrochloride, pentostatin, perifosine, prednisone, recombinant flt3 ligand, recombinant human thrombopoietin, recombinant interferon alfa, recombinant interleukin-11, recombinant interleukin-12, rituximab, sargramostim, sildenafil citrate (VIAGRA®), simvastatin, sirolimus, tacrolimus, tanespimycin, thalidomide, therapeutic allogeneic lymphocytes, thiotepa, tipifarnib, tositumomab, ulocuplumab, veltuzumab, vincristine sulfate, vinorelbine ditartrate, vorinostat, WT1 126-134 peptide vaccine, WT-1 analog peptide vaccine, yttrium-90 ibritumomab tiuxetan, yttrium-90 humanized epratuzumab, and any combination thereof.

Examples of therapeutic procedures used to treat WM include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme techniques, low-LET cobalt-60 gamma ray therapy, bleomycin, conventional surgery, radiation therapy, and nonmyeloablative allogeneic hematopoietic stem cell transplantation.

Diffuse Large B-Cell Lymphoma Combination Therapy

Therapeutic agents used to treat diffuse large B-cell lymphoma (DLBCL) include cyclophosphamide, doxorubicin, vincristine, prednisone, anti-CD20 monoclonal antibodies, etoposide, bleomycin, many of the agents listed for WM, and any combination thereof, such as ICE and RICE.

Chronic Lymphocytic Leukemia Combination Therapy

Examples of therapeutic agents used to treat chronic lymphocytic leukemia (CLL) include chlorambucil, cyclophosphamide, fludarabine, pentostatin, cladribine, doxorubicin, vincristine, prednisone, prednisolone, alemtuzumab, many of the agents listed for WM, and combination chemotherapy and chemoimmunotherapy, including the following common combination regimens: CVP, R-CVP, ICE, R-ICE, FCR, and FR.

Breast Cancer Combination Therapy

Therapeutic agents used to treat breast cancer include albumin-bound paclitaxel, anastrozole, atezolizumab, capecitabine, carboplatin, cisplatin, cyclophosphamide, docetaxel, doxorubicin, epirubicin, everolimus, exemestane, fluorouracil, fulvestrant, gemcitabine, Ixabepilone, lapatinib, letrozole, methotrexate, mitoxantrone, paclitaxel, pegylated liposomal doxorubicin, pertuzumab, tamoxifen, toremifene, trastuzumab, vinorelbine, and any combinations thereof.

Triple Negative Breast Cancer Combination Therapy

Therapeutic agents used to treat triple negative breast cancer include atezolizumab, cyclophosphamide, docetaxel, doxorubicin, epirubicin, fluorouracil, paclitaxel, and combinations thereof.

Colorectal Cancer Combination Therapy

Therapeutic agents used to treat colorectal cancer include bevacizumab, capecitabine, cetuximab, fluorouracil, irinotecan, leucovorin, oxaliplatin, panitumumab, ziv-aflibercept, and any combinations thereof.

Esophageal and Esophagogastric Junction Cancer Combination Therapy

Therapeutic agents used to treat esophageal and esophagogastric junction cancer include capecitabine, carboplatin, cisplatin, docetaxel, epirubicin, fluoropyrimidine, fluorouracil, irinotecan, leucovorin, oxaliplatin, paclitaxel, ramucirumab, trastuzumab, and any combinations thereof.

Gastric Cancer Combination Therapy

Therapeutic agents used to treat gastric cancer include capecitabine, carboplatin, cisplatin, docetaxel, epirubicin, fluoropyrimidine, fluorouracil, Irinotecan, leucovorin, mitomycin, oxaliplatin, paclitaxel, ramucirumab, trastuzumab, and any combinations thereof.

Head and Neck Cancer Combination Therapy

Therapeutic agents used to treat head & neck cancer include afatinib, bleomycin, capecitabine, carboplatin, cetuximab, cisplatin, docetaxel, fluorouracil, gemcitabine, hydroxyurea, methotrexate, nivolumab, paclitaxel, pembrolizumab, vinorelbine, and any combinations thereof.

Non-Small Cell Lung Cancer Combination Therapy

Therapeutic agents used to treat non-small cell lung cancer (NSCLC) include afatinib, albumin-bound paclitaxel, alectinib, atezolizumab, bevacizumab, bevacizumab, cabozantinib, carboplatin, cisplatin, crizotinib, dabrafenib, docetaxel, erlotinib, etoposide, gemcitabine, nivolumab, paclitaxel, pembrolizumab, pemetrexed, ramucirumab, trametinib, trastuzumab, vandetanib, vemurafenib, vinblastine, vinorelbine, and any combinations thereof.

Small Cell Lung Cancer Combination Therapy

Therapeutic agents used to treat small cell lung cancer (SCLC) include atezolizumab, bendamustime, carboplatin, cisplatin, cyclophosphamide, docetaxel, doxorubicin, etoposide, gemcitabine, ipillimumab, irinotecan, nivolumab, paclitaxel, temozolomide, topotecan, vincristine, vinorelbine, and any combinations thereof.

Ovarian Cancer Combination Therapy

Therapeutic agents used to treat ovarian cancer include 5-flourouracil, albumin bound paclitaxel, altretamine, anastrozole, bevacizumab, capecitabine, carboplatin, cisplatin, cyclophosphamide, docetaxel, doxorubicin, etoposide, exemestane, gemcitabine, ifosfamide, irinotecan, letrozole, leuprolide acetate, liposomal doxorubicin, megestrol acetate, melphalan, olaparib, oxaliplatin, paclitaxel, Pazopanib, pemetrexed, tamoxifen, topotecan, vinorelbine, and any combinations thereof.

Additional Exemplified Combination Therapies

In some embodiments the antibody and/or fusion protein provided herein (e.g., 7-B16) is administered with one or more therapeutic agents selected from a Trop-2 binding agent, CD47 antagonist, a SIRPα antagonist, a FLT3R agonist, a PD-1 antagonist, a PD-L1 antagonist, an MCL1 inhibitor, a CCR8 binding agent, an HPK1 antagonist, a DGKa inhibitor, a CD73 inhibitor, an adenosine receptor antagonist, a TIGIT antagonist, a TREM1 binding agent, a TREM2 binding agent, a TGFβ (e.g., TGFβ1 or TGFβ3) binding agent, and a CAR-T cell therapy.

In some embodiments the antibody and/or fusion protein provided herein (e.g., 7-B16) is administered with one or more therapeutic agents selected from an anti-Trop-2 antibody (e.g., sacituzumab govitecan, SKB-264, JS-108 (DAC-002), datopotamab deruxtecan, BAT-8003), an anti-CD47 antibody or a CD47-blocking agent (e.g., magrolimab, DSP-107, AO-176, ALX-148, IBI-188, lemzoparlimab, TTI-621, TTI-622), an anti-SIRPα antibody (e.g., GS-0189), a FLT3L-Fc fusion protein (e.g., GS-3583), an anti-PD-1 antibody (pembrolizumab, nivolumab, zimberelimab), a small molecule PD-L1 inhibitor (e.g., GS-4224), an anti-PD-L1 antibody (e.g., atezolizumab), a small molecule MCL1 inhibitor (e.g., GS-9716), a small molecule HPK1 inhibitor (e.g., GS-6451), a HPK1 degrader (PROTAC; e.g., ARV-766), a small molecule DGKa inhibitor, a small molecule CD73 inhibitor (e.g., AB680), an anti-CD73 antibody (e.g., oleclumab), a dual $A_{2a}/A_{2b}$ adenosine receptor antagonist (e.g., etrumadenant (AB928)), an anti-TIGIT antibody (e.g., tiragolumab, vibostolimab, domvanalimab, AB308), an anti-TREM1 antibody (e.g., PY159), an anti-TREM2 antibody (e.g., PY314), a TGFβ-trap (e.g., bintrafusp alpha, AGEN-1423), an anti-TGFβ1 antibody (e.g., SRK-181), and a CAR-T cell therapy (e.g., axicabtagene ciloleucel, brexucabtagene autoleucel, tisagenlecleucel).

In some embodiments the antibody and/or fusion protein provided herein (e.g., 7-B16) is administered with an anti-PD-1 antibody and a small molecule PD-L1 inhibitor or anti-PD-L1 antibody (e.g., atezolizumab), and an anti-TIGIT antibody.

In some embodiments the antibody and/or fusion protein provided herein (e.g., 7-B16) is administered with an anti-PD-1 antibody and a dual $A_{2a}/A_{2b}$ adenosine receptor antagonist. In some embodiments the antibody and/or fusion protein provided herein (e.g., 7-B16) is administered with an anti-PD-1 antibody, a small molecule CD73 inhibitor, and a dual $A_{2a}/A_{2b}$ adenosine receptor antagonist.

In some embodiments the antibody and/or fusion protein provided herein (e.g., 7-B16) is administered with one or more therapeutic agents selected from sacituzumab govitecan-hziy, magrolimab, GS-0189, GS-3583, zimberelimab, GS-4224, GS-9716, GS-6451, AB680, etrumadenant (AB928), domvanalimab, AB308, PY159, PY314, SRK-181, axicabtagene ciloleucel and brexucabtagene autoleucel.

In some embodiments the antibody and/or fusion protein provided herein (e.g., 7-B16) is administered with sacituzumab govitecan-hziy.

In some embodiments the antibody and/or fusion protein provided herein (e.g., 7-B16) is administered with magrolimab.

In some embodiments the antibody and/or fusion protein provided herein (e.g., 7-B16) is administered with zimberelimab.

In some embodiments the antibody and/or fusion protein provided herein (e.g., 7-B16) is administered with zimberelimab and domvanalimab.

In some embodiments the antibody and/or fusion protein provided herein (e.g., 7-B16) is administered with zimberelimab and etrumadenant (AB928).

In some embodiments the antibody and/or fusion protein provided herein (e.g., 7-B16) is administered with one or more therapeutic agents selected from zimberelimab, AB680, and etrumadenant (AB928).

In some embodiments the antibody and/or fusion protein provided herein (e.g., 7-B16) is administered with axicabtagene ciloleucel or brexucabtagene autoleucel.

In some embodiments the antibody and/or fusion protein provided herein (e.g., 7-B16) is administered with a FLT3R agonist. In some embodiments, the antibody and/or fusion protein provided herein (e.g., 7-B16) is administered with a FLT3 ligand. In some embodiments, the antibody and/or fusion protein provided herein (e.g., 7-B16) is administered with a FLT3L-Fc fusion protein, e.g., as described in WO2020263830. In some embodiments the antibody and/or fusion protein provided herein (e.g., 7-B16) is administered with GS-3583 or CDX-301. In some embodiments the antibody and/or fusion protein provided herein (e.g., 7-B16) is administered with GS-3583.

Diagnostic Uses

Provided herein are methods of using the antibody and/or fusion protein (e.g., 7-B16, 1-K17, etc.), polypeptides and polynucleotides for detection, diagnosis and monitoring of a disease, disorder or condition associated with CCR8 expression (either increased or decreased relative to a normal sample, and/or inappropriate expression, such as presence of expression in tissues(s) and/or cell(s) that normally lack the epitope expression). Provided herein are methods of determining whether a patient will respond to treatment with an antibody and/or fusion protein provided herein.

In some embodiments, the method comprises detecting whether the patient has cells that express CCR8 using an anti-CCR8 antibody. In some embodiments, the method of detection comprises contacting the sample with an antibody, polypeptide, or polynucleotide and determining whether the level of binding differs from that of a reference or comparison sample (such as a control). In some embodiments, the method may be useful to determine whether the antibodies or polypeptides described herein are an appropriate treatment for the subject.

In some embodiments, the cells or cell/tissue lysate are contacted with an anti-CCR8 antibody and the binding between the antibody and the cell is determined. When the test cells show binding activity as compared to a reference cell of the same tissue type, it may indicate that the subject would benefit from treatment with an antibody and/or fusion protein provided herein. In some embodiments, the test cells are from human tissues. In some embodiments, the test cells are from human blood.

Various methods known in the art for detecting specific antibody-antigen binding can be used. Exemplary immunoassays which can be conducted include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). An indicator moiety, or label group, can be attached to the subject antibodies and is selected so as to meet the needs of various uses of the method which are often dictated by the availability of assay equipment and compatible immunoassay procedures. Appropriate labels include, without limitation, radionuclides (for example $^{125}$I, $^{131}$I, $^{35}$S, $^{3}$H, or $^{32}$P), enzymes (for example, alkaline phosphatase, horseradish peroxidase, luciferase, or β-galactosidase), fluorescent moieties or proteins (for example, fluorescein, rhodamine, phycoerythrin, GFP, or BFP), or luminescent moieties (for example, Qdot™ nanoparticles supplied by the Quantum Dot Corporation, Palo Alto, Calif.). General techniques to be used in performing the various immunoassays noted above are known to those of ordinary skill in the art.

For purposes of diagnosis, the polypeptide including antibodies can be labeled with a detectable moiety including but not limited to radioisotopes, fluorescent labels, and various enzyme-substrate labels know in the art. Methods of conjugating labels to an antibody are known in the art.

In some embodiments, the anti-CCR8 antibodies need not be labeled, and the presence thereof can be detected using a second labeled antibody which binds to the first anti-CCR8 antibody.

In some embodiments, the anti-CCR8 antibody can be employed in any known assay method, such as competitive binding assays, direct and indirect sandwich assays, and immunoprecipitation assays. Zola, Monoclonal Antibodies: A Manual of Techniques, pp. 147-158 (CRC Press, Inc. 1987).

The anti-CCR8 antibodies and polypeptides can also be used for in vivo diagnostic assays, such as in vivo imaging. Generally, the antibody or the polypeptide is labeled with a radionuclide (such as $^{111}$In, $^{99}$Tc, $^{14}$C, $^{131}$I, $^{125}$I, $^{3}$H, or any other radionuclide label, including those outlined herein) so that the cells or tissue of interest can be localized using immunoscintigraphy.

The antibody may also be used as staining reagent in pathology using techniques well known in the art.

In some embodiments, a first antibody is used for a diagnostic and a second antibody is used as a therapeutic. In some embodiments, the first and second antibodies are different. In some embodiments, the first antibody is from a non-human, while the therapeutic is from a human. In some embodiments, the first and second antibodies can both bind to the antigen at the same time, by binding to separate epitopes.

VII. Kits/Articles of Manufacture

Provided herein are also kits, medicines, compositions, and unit dosage forms for use in any of the methods described herein.

Kits can include one or more containers comprising an antibody and/or fusion protein provided herein (e.g., 7-B16, 1-K17, etc.) or unit dosage forms and/or articles of manufacture. In some embodiments, a unit dosage is provided wherein the unit dosage contains a predetermined amount of a composition comprising an antibody and/or fusion protein provided herein, with or without one or more additional agents. In some embodiments, such a unit dosage is supplied in single-use prefilled syringe for injection. In some embodiments, the composition contained in the unit dosage can comprise saline, sucrose, or the like; a buffer, such as phosphate, or the like; and/or be formulated within a stable and effective pH range. In some embodiments, the composition can be provided as a lyophilized powder that may be reconstituted upon addition of an appropriate liquid, for example, sterile water. In some embodiments, the composition comprises one or more substances that inhibit protein aggregation, including, but not limited to, sucrose and arginine. In some embodiments, a composition comprises heparin and/or a proteoglycan.

In some embodiments, the amount of the antibody and/or fusion protein used in the unit dose can be any of the amounts provided herein for the various methods and/or compositions described.

In some embodiments, kits further comprise instructions for use in the treatment of cancer in accordance with any of the methods described herein. The kit may further comprise a description of selection an individual suitable or treatment. Instructions supplied in the kits are typically written instructions on a label or package insert (for example, a paper sheet included in the kit), but machine-readable instructions (for example, instructions carried on a magnetic or optical storage disk) are also acceptable. In some embodiments, the kit further comprises another therapeutic agent.

The kits are in suitable packaging. Suitable packaging includes, but is not limited to, vials, bottles, jars, flexible packaging (for example, sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: Evaluation of CCR8 mRNA Expression in Human Tumors

The expression of CCR8 mRNA in a variety of human tumors was determined using data publicly available in Gene Expression Omnibus database under series accession number GSE13204, and accessed through Bloodspot (See Bagger et al., *Nucleic Acids Research* 44(D1):D917-924 (2016); Haferlach, Torsten, et al. *Journal of Clinical Oncology* 28:2529-37 (2010); and Kohlmann, A. et al. *British Journal of Haematology* 142, 802-807 (2008)). It was found that 10% of patients with T-cell acute lymphoblastic leukemia (T-ALL) had CCR8 mRNA levels above the maximum value observed in healthy bone marrow (FIG. 1).

Figure 2:
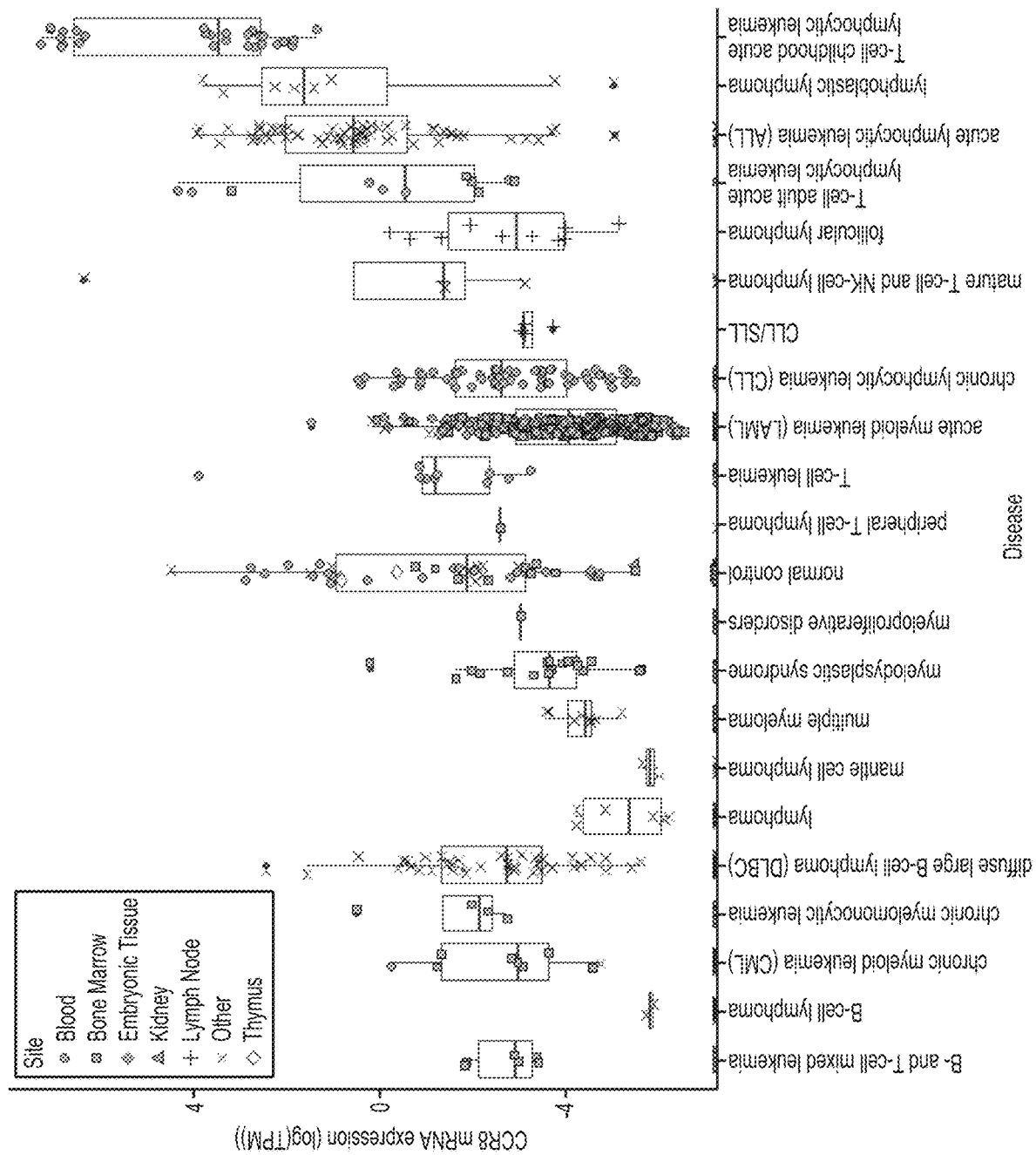
FIG. 2 shows a box and whisker plot showing CCR8 mRNA expression levels determined by RNA sequencing. On the y-axis is CCR8 gene expression as measured by log-transformed transcripts per million (TPM). On the x-axis are lymphoma subtypes, leukemia subtypes, or healthy blood or tissue.

CCR8 mRNA expression levels were also determined from RNA sequencing data obtained from OmicSoft OncoL- and Hematology, a collection of data sets of blood related cancers from multiple studies, including Gene Expression Omnibus database and Multiple Myeloma Genomics Portal (MMGP). Data was generated from primary patient samples, xenografts, or cell lines. Expression of CCR8 in these samples suggests that certain hematological malignancies in this database have elevated levels of expression compared to normal controls, including T-cell childhood acute lymphocytic leukemia, lymphoblastic lymphoma, acute lymphocytic leukemia, and others (FIG. 2).

Example 2: CCR8 Expression is Specific to Tregs in Solid Tumors

Expression of CCR8 on tumor-infiltrating Treg and conventional T cells (Tconv) was determined by flow cytometry, as follows. Human tumor biopsies were dissociated mechanically with a cell strainer to obtain single cell suspension. Anti-human CCR8 antibody (BD Biosciences, clone #433H) or an isotype-matched control was used for flow cytometry analysis. The density of CCR8 expression on the cell surface of tumor-infiltrating Treg and Tconv cells was determined by quantitative flow cytometry using beads from bangs Laboratories, Inc (Quantum Simply Cellular anti IgG) and following manufacturer's instruction.

Figure 3A:
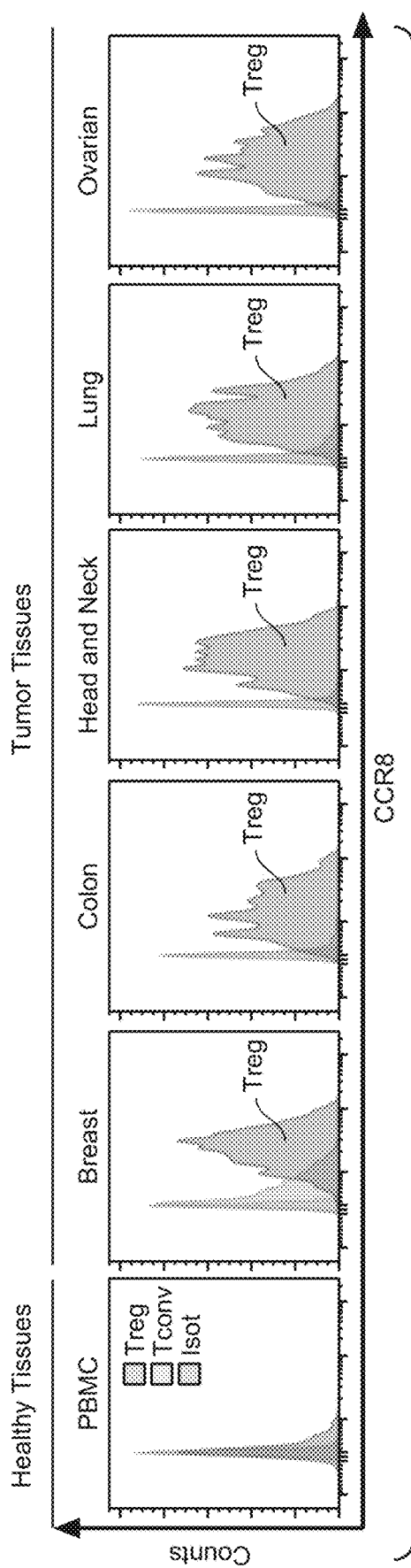
FIGS. 3A and 3B show that human tumor-infiltrating (TIL) Tregs preferentially express CCR8 but at a low receptor number on a per cell basis. Illustrative flow cytometry plots (gated on Tumor T CD4+ cells) (A) and quantitative plots (B) are shown.
Figure 3B:
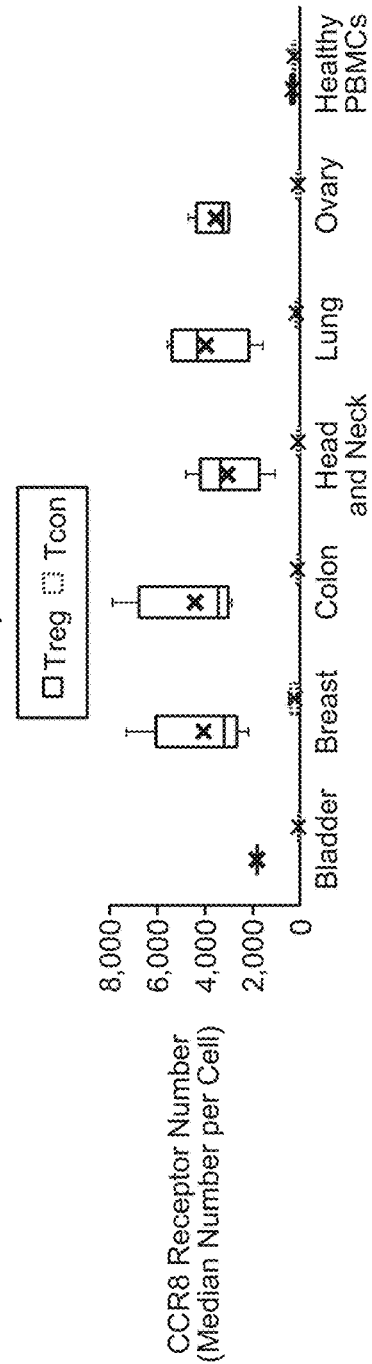

As shown in FIG. 3A, CCR8 was preferentially expressed on tumor-infiltrating Treg cells in tumors from breast, colon, head and neck, lung, and ovarian cancers. As shown in FIG. 3B, the density of CCR8 on the cell surface was higher in tumor-infiltrating Treg cells compared to Tconv cells, although was low, in the range of 2,000-8,000 CCR8 receptors per cell.

Example 3: Generation of Mouse Anti-huCCR8 Antibodies

Anti-CCR8 monoclonal antibodies were generated by immunizing the BALB/C, CD1, B6/129, B6/SJL, NZB/NZW, JIL-E strains of inbred mice with one or more of the following antigens: 1) plasmid DNA encoding human CCR8, or 2) a 3T12 cell line that expresses human CCR8.

Plasmid DNA immunization was by hydrodynamic tail vein injection. Cellular immunization was performed by intraperitoneal (i.p.) injection of mitomycin C-treated human CCR8 overexpressing 3T12 cells. A cohort of animals was immunized with CCR8 overexpressing cell line followed by DNA boosting, as follows. Mice were injected with 200 μl of the prepared antigens into the peritoneal cavity or subcutaneous or foot pad every two to fourteen days. Animals that developed anti-CCR8 titers were given an intravenous injection of $10 \times 10^6$ CCR8 overexpressing 3T12 cells. Lymph nodes and/or spleens were harvested, and the isolated lymph node cells and/or splenocytes were used for hybridoma preparation.

To select an animal that produced CCR8-binding antibodies, sera from immunized animals was tested by flow cytometry to determine binding to human CCR8-overexpressing CHO-S cell line, but not to parental CHO-S cell line. Briefly, the binding of polyclonal sera was assessed by incubating human CCR8-expressing CHO-S cells with the serial diluted (1:4) serum samples. The cells were then washed, and binding was detected with a phycoerythrin (PE)-labeled species-specific anti-Fc IgG antibody. Flow cytometric analyses were performed using a BD Fortessa flow cytometer (Becton Dickinson, San Jose, Calif.). Mice that developed the highest titers of anti-CCR8 antibodies were used for fusions. Fusions were performed as described below. Hybridoma supernatants were tested for anti-CCR8 activity by flow cytometry.

The splenocytes and/or lymphocytes isolated from mice were fused with a mouse myeloma cell line by electrofusion. Briefly, single cell suspensions of splenocytes from immunized mice were fused to an equal number of IgG non-secreting mouse myeloma cells. Cells were plated at approximately $2 \times 10^4$/well in 384-well flat bottom microtiter plates, followed by about two weeks incubation in selective medium containing 1×hypoxanthine-aminopterin-thymidine (HAT) medium. After one to two weeks, cells were cultured in medium in which the HAT was replaced with hypoxanthine and thymidine (HT) medium. Approximately 10-14 days after cell plating, supernatants from individual wells were screened first for whether they contained mouse IgG. The supernatants that were scored positive for mouse IgG antibodies were then subsequently screened by flow cytometry for anti-CCR8 IgG antibodies. The anti-CCR8 antibody-secreting hybridomas were then undergone subcloning process by limiting dilution. The stable subclones were cultured in vitro to determine binding to human CCR8 by flow cytometry. The confirmed positive clones were scaled up to generate small amounts of antibody in tissue culture medium for further characterization. The monoclonal antibodies from hybridoma supernatants were purified by protein A column chromatography.

Example 4: Anti-CCR8 Antibody Screening for Binding to Human CCR8 and Human CCR4

Figure 4A:
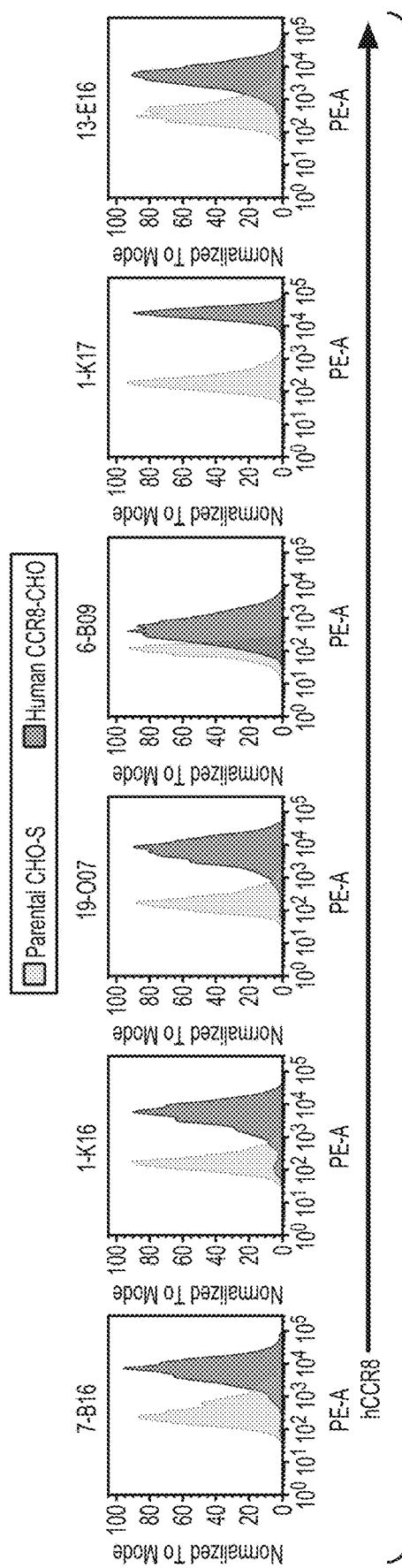
FIGS. 4A-4B show binding of anti-CCR8 monoclonal antibodies to human CCR8-expressing CHO-S cells (A) and CCR4-expressing CHO-S cells (B).
Figure 4B:
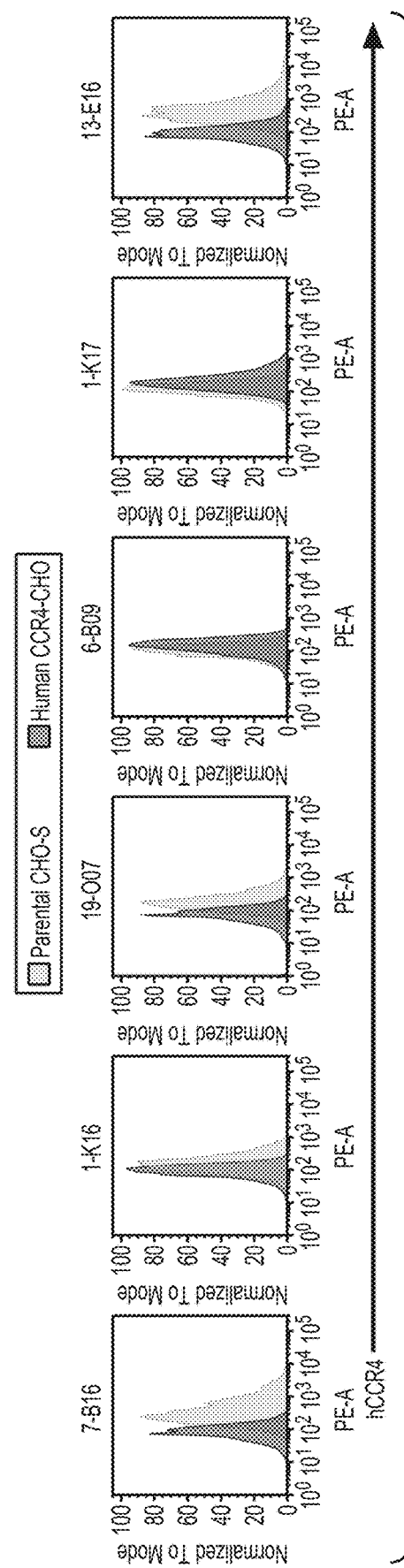

Antibodies were screened for specific binding to human CCR8 by flow cytometry using human CCR8-overexpressing and parental CHO-S cell line. Antibodies specifically binding to human CCR8 were also tested for binding to CCR4 by flow cytometry. As shown in FIGS. 4A-4B, antibodies 1-K16, 1-K17, 6-B09, 7-B16, 13-E16 and 19-O07 bound CHO-S cells expressing human CCR8 (4A), but did not bind CHO-S cells expressing human CCR4 (4B), or untransfected CHO-S cells.

Antibodies 1-K16, 1-K17, 6-B09, 7-B16, 13-E16 and 19-O07, were sequenced and reformatted to human IgG1 backbone for further characterization.

Binding to CCR8 and not CCR4 was confirmed for chimeric and humanized antibodies as well.

Example 5: Screening for CCL1 Blocking by Anti-CCR8 Chimeric Antibodies

Binding of CCL1 to surface-expressed CCR8 induces downstream signaling, and blocking CCR8 with anti-CCR8 antibody may inhibit this signaling pathway. Anti-CCR8 antibodies in a chimeric format were therefore screened for the ability to inhibit ligand-receptor interactions in a cell-based assay, DiscoverX Bioassay (Eurofins), to identify the antagonists of CCR8 signal transduction.

Briefly, 5000 PathHunter eXpress β-Arrestin GPCR cells from PathHunter® β-Arrestin eXpress GPCR Assay kit (Eurofins) were plated in each well of 96-well assay plate and cultured in 37° C., 5% $CO_2$. After 48 hours of incubation, each chimeric antibody was serially diluted and added to the designated rows of the assay plate and incubate for 30 minutes at 37° C. 13.7 nM of human CCL1 was then added and incubated for 90 minutes at 37° C. Working Detection Solution was then added to all wells of the assay plate, and the assay plate was incubate for 1 hour at room temperature in the dark. The assay plates were read on a standard luminescence plate reader at 0.1 to 1 second/well for photomultiplier tube readers or 5 to 10 seconds for imagers. Data was plotted using GraphPad Prism software to obtain IC50 values and summarized in FIG. 5 and Table 2.

TABLE 2

| IC50s of chimeric anti-CCR8 antibodies | |
|---|---|
| mAb clone | IC50 (μg/mL) |
| 7-B16 | 0.090 |
| 1-K16 | 4.551 |
| 13-E16 | 12.590 |
| 6-B09 | 182020.00 |
| 19-O07 | 995.10 |
| 1-K17 | 0.071 |

Figure 5:
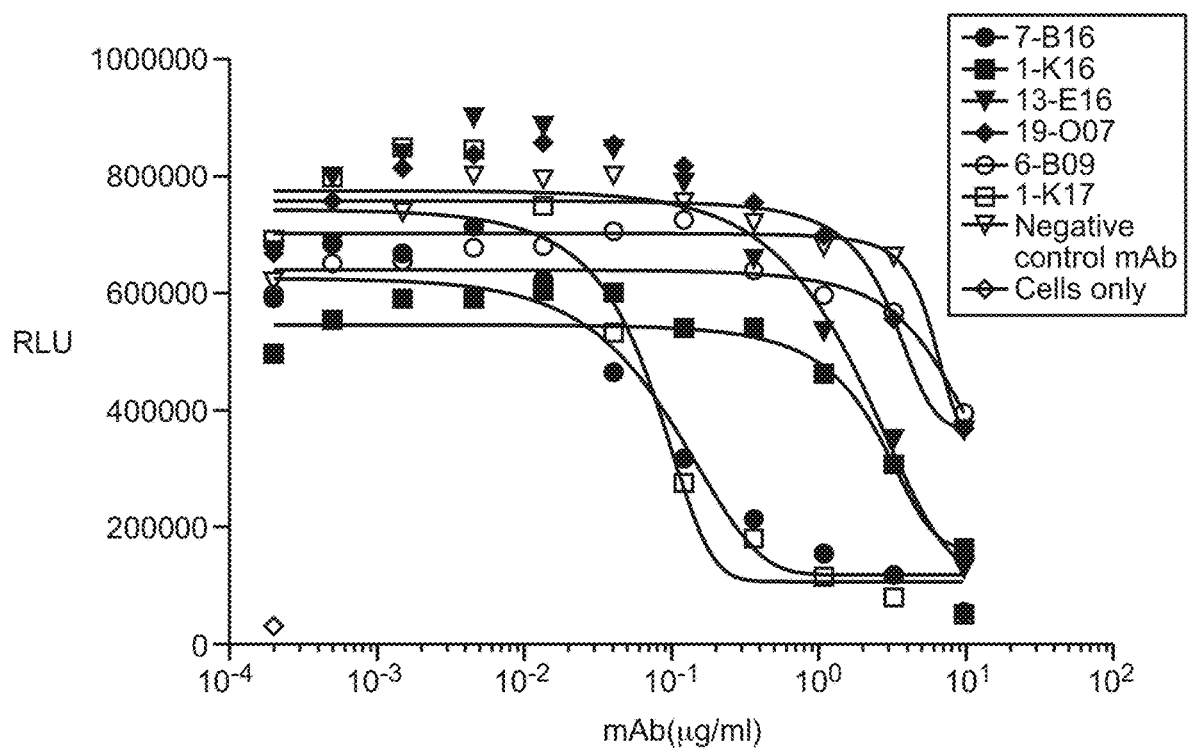
FIG. 5 shows antagonist activity of anti-CCR8 chimeric antibodies using DiscoverX assay (Eurofins).

As shown in FIG. 5 an Table 2, the antibodies showed varying levels of antagonism. Antibodies 1-K17 and 7-B16 were the most potent antagonists in the DiscoverX assay.

Example 6. Epitope Binning of Anti-CCR8 Antibodies by Flow Cytometry and ELISA A subset of antibodies against human CCR8 were epitope binned using flow cytometry method in tandem format. Briefly, one set of antibodies was biotinylated. Human CCR8-overexpressing cells were incubated at 4° C. with the non-biotinylated antibodies at 10 μg/mL for 1 hour, then without washing the biotinylated antibodies were added at 10 μg/mL. After a further 1-hour incubation, cells were washed three times and then stained with streptavidin-phycoerythrin (PE-strep) secondary antibody for 30 minutes. Binding competition was determined by detecting PE by flow cytometry. The response values were normalized as the % of the maximum binding of the individual antibody. The binning results are shown in Table 3A, and were confirmed by sequential format ELISA method using human CCR8-overexpression lipoparticles (Table 3B).

TABLE 3A

| Epitope binning by FACS analysis | | | | | |
|---|---|---|---|---|---|
| FACS | 7-B16 | 1-K16 | 1-K17 | 19-O07 | 6-B09 |
| 7-B16 | 41 | 14 | 18 | 148 | 175 |
| 1-K16 | 88 | 31 | 32 | 149 | 167 |
| 1-K17 | 14 | 12 | 11 | 28 | 102 |
| 19-O07 | 108 | 109 | 91 | 54 | 39 |
| 6-B09 | 89 | 102 | 94 | 32 | 44 |

TABLE 3B

| Epitope binning by ELISA analysis | | | | | |
|---|---|---|---|---|---|
| ELISA | 7-B16 | 1-K16 | 1-K17 | 19-O07 | 6-B09 |
| 7-B16 | 0.655 | 0.101 | 0.771 | 0.437 | 1.045 |
| 1-K16 | 0.758 | 0.264 | 0.794 | 1.493 | 0.964 |
| 1-K17 | 0.047 | 0.036 | 0.124 | 0.268 | 0.651 |
| 19-O07 | 1.023 | 0.882 | 0.784 | 0.817 | 0.679 |
| 6-B09 | 0.776 | 0.800 | 0.820 | 0.577 | 0.512 |

As shown in Tables 3A and 3B, 7-B16, 1-K16 and 1-K17 are in the same epitope bin and 19-O07 and 6-B09 are in the same epitope bin. 7-B16 and 1-K16 show unidirectional binding.

Example 7. Screening of Anti-CCR8 Chimeric Antibodies for ADCC Function

The ADCC reporter Bioassay kit from Promega was used to determine the effector function of human IgG1 chimera and humanized versions of anti-CCR8. Briefly, human CCR8-expressing CHO-S cells was resuspended in pre-warmed assay buffer (37° C.) at $10^6$ cells/mL concentration. 25,000 cells were mixed with serially diluted anti-CCR8 antibodies in 96-well flat, clear-bottom plate, and then incubated for 1 hour at 37° C., 5% $CO_2$. Promega BioAssay effector cells were added to individual well at varied ratios to target cells and further incubated for 6 hours at 37° C. 5% $CO_2$. After incubation, assay plates were equilibrated to room temperature for 15 min under foil on the benchtop. Pre-mixed Bio-Glo Luciferase Assay Substrate was added to each well and incubated at room temperature for 5 min. The assay plates were read on Bio-Tek plate reader within 30 min of substrate addition. Data was plotted using GraphPad Prism software to generate EC50 value for individual antibodies.

Figure 6:
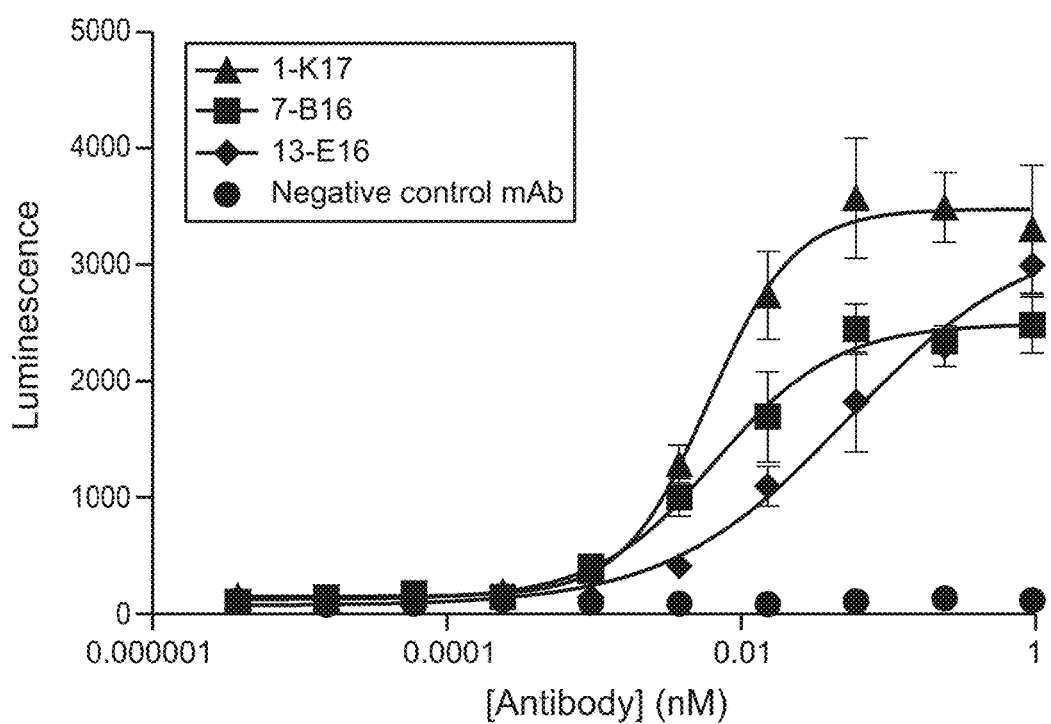
FIG. 6 shows antibody-dependent cellular cytotoxicity (ADCC) of certain anti-CCR8 chimeric antibodies using an ADCC reporter bioassay (Promega).

The results are shown in FIG. 6 and Table 4, which shows the EC50 values for ADCC function for each antibody tested. Human IgG1 chimeric 1-K17 and 7-B16 showed potent ADCC activity.

TABLE 4

EC50 values of ADCC function of chimeric anti-CCR8 antibodies

| mAb clone | EC50 (ng/mL) |
|---|---|
| 1-K17 | 6.182 |
| 7-B16 | 6.912 |
| 13-E16 | 54.880 |

Example 8. Affinity Characterization of Antibodies 1-K17 and 7-B16

Affinity of chimeric antibodies 1-K17 and 7-B16 was determined by the Kinetic Exclusion Assay (KinExA) at Sapidyne Instruments Inc. To determine the equilibrium dissociation constant (Kd), human CCR8-expressing CHO-S Cells were titrated in a background of 1-K17 or 7-B16 or negative control mAb. Samples were gently rocked for 2.5 hours at 37° C. to achieve equilibrium. After incubation, cells were centrifuged and the free fraction of 1-K17 or 7-B16 or negative control mAb was removed without disturbing the cell pellet; PMMA beads coated with biotinylated goat anti-human IgG were used to capture a portion of free 1-K17 or 7-B16 or negative control mAb from an equilibrated sample of 1-K17 or 7-B16 or negative control mAb and human CCR8-expressing CHO-S cells. Captured 1-K17 or 7-B16 or negative control mAb was detected with a fluorescently labeled detection antibody. The fluorescent signal was converted to a voltage signal that is directly proportional to the amount of free 1-K17 or 7-B16 or negative control mAb in the equilibrated sample.

To determine the rate of association (kon), the same immobilized biotinylated goat anti-human IgG-PMMA column was used as the capture reagent for kinetic experiments. The amount of free 1-K17 or 7-B16 or negative control mAb in the sample was measured pre-equilibrium, yielding data points that monitored the decrease in free 1-K17 or 7-B16 or negative control mAb as the sample moves toward equilibrium.

Data analysis was performed using KinExA Pro software at Sapidyne Instruments Inc to generate Kd and kon. The rate of dissociation (koff) was calculated based on the equation below.

$koff = Kd \times kon$

Both antibodies showed high affinity ranged from 18 to 220 pM, as shown in Table 5.

TABLE 5

Anti-CCR8 antibody on-cell affinity determined by KinExA

| Antibody Reference | Ka [1/(M·s)] | Kd [1/s] | $K_D$ [M] |
|---|---|---|---|
| 1-K17.hG1 Chimera | $7.81 \times 10^6$ | $1.44 \times 10^{-4}$ | $0.18 \times 10^{-10}$ |
| 7-B16.hG1 Chimera | $6.08 \times 10^6$ | $1.34 \times 10^{-3}$ | $2.20 \times 10^{-10}$ |

Example 9: Humanization and Hotspots-Correction of Antibodies 1-K17 and 7-B16

Antibodies 1-K17 and 7-B16 were humanized by grafting the CDRs of lead antibodies into selected human IgG germline frameworks. Human germline IGHV, IGKV, IGHJ and IGKJ were selected based on sequence similarity within both frameworks (FR). Parental antibodies and selected germlines are summarized in Table 6. To maintain canonical loop structure and chain interface, certain residues in human germline frameworks were back mutated to corresponding mouse residues (bold in Table 6).

In silico prediction implied high risk sequence liabilities in CDRs of both 1-K17 and 7-B16. For example, there is an NG motif in CDR-H2 region of humanized 1-K17. Three liability mutations at the N55 position in the heavy chain were evaluated to see if the potential deamidation site in the VH could be removed without affecting activity. The residue substitution N55Q was selected to eliminate the potential deamidation site (N55) in the heavy chain and incorporated into the humanized sequence. In the CDR-L1 region of 1-K17, there are NG and NT motifs that may be susceptible to deamidation. The residue substitutions G34A and N35Q were selected to eliminate the potential deamidation sites (N33 and N35) in the light chain and incorporated into the humanized sequence. The same mutation designs as humanized 1-K17 light chain were tested to remove potential deamidation liability in 7-B16 CDR-L1, in addition to M56L mutation to remove oxidation liability in CDR-L2. Sequences are summarized in Table 6.

TABLE 6

Humanization and Hotspots Correction of 1-K17 and 7-B16

| Antibody | Chain | Parental | Germline HV | Germline HJ | Humanized with hotspot correction |
|---|---|---|---|---|---|
| 1-K17.015 | VH | QVQLQQPGAELVKPGASVKMSCKA SGYTFTSYNMHWVKQTPGQGLEWI GAIYPGNGDTSYNQKFKGKATLTAD KSSSTAYMHLSSLTSEDSAVYYCARK GGTPFAYWGQGTLLTVSA (SEQ ID NO: 56) | IGHV1-3*01 | IGHJ04*1 | EVQLVQSGAEVKKPGASVKVSCKAS GYTFTSYNMHWVRQAPGQRLEWIG AIYPGQGDTSYNQKFKGRATLTADKS ASTAYMELSSLRSEDTAVYYCARKGG TPFAYWGQGTLVTVSS (SEQ ID NO: 68) |
| | VL | DVVMTQTPLSLPVSLGDQASISCRSS QSLVHSNGNTYLYWYLQKPGQSPKL LIYKVSNRFSGVPDRFSGSGSGTDFT LKISRVEAEDLGVYFCSQSTHVPYTF GGGTKLEIK (SEQ ID NO: 57) | IGKV2-30*01 | IGKJ02*01 | DVVMTQSPLSLPVTLGQPASISCRSSQ SLVHSNAQTYLYWYQQRPGQSPRLLI YKVSNRFSGVPDRFSGSGSGTDFTLKI SRVEAEDVGVYFCSQSTHVPYTFGQG TKLEIK (SEQ ID NO: 69) |

TABLE 6-continued

Humanization and Hotspots Correction of 1-K17 and 7-B16

| Antibody | Chain | Parental | Germline HV | Germline HJ | Humanized with hotspot correction |
|---|---|---|---|---|---|
| 1-K17.044 | VH | QVQLQQPGAELVKPGASVKMSCKA SGYTFTSYNMHWVKQTPGQGLEWI GAIYPGNGDTSYNQKFKGKATLTAD KSSSTAYMHLSSLTSEDSAVYYCARK GGTPFAYWGQGTLLTVSA (SEQ ID NO: 56) | IGHV1-46*01 | IGHJ04*1 | EVQLVQSGAEVKKPGASVKVSCKAS GYTFTSYNMHWVRQAPGQGLEWIG AIYPG<u>A</u>GDTSYNQKFKGRATLTADKS TSTAYMELSSLRSEDTAVYYCARKGG TPFAYWGQGTLVTVSS (SEQ ID NO: 74) |
| | VL | DVVMTQTPLSLPVSLGDQASISCRSS QSLVHSNGNTYLYWYLQKPGQSPKL LIYKVSNRFSGVPDRFSGSGSGTDFT LKISRVEAEDLGVYFCSQSTHVPYTF GGGTKLEIK (SEQ ID NO: 57) | IGKV2-30*01 | IGKJ02*01 | DVVMTQSPLSLPVTLGQPASISCRSSQ SLVHSN<u>AA</u>TYLYWYQQRPGQSPRLLI YKVSNRFSGVPDRFSGSGSGTDFTLKI SRVEAEDVGVYFCSQSTHVPYTFGQG TKLEIK (SEQ ID NO: 75) |
| 7-B16.001 | VH | EVQLVESGGGLVQPKGSLKLSCAAS GFTFNTYAMNWVRQAPGKGLEWVA RIRSKSNNYATYYADSVKDRFTISRD DSQSMLYLQMNNLKTEDTAMYYCV RGLLRYRFFDVWGAGTTVTVSS (SEQ ID NO: 80) | IGHV3-73*01 | IGHJ06*1 | EVQLVESGGGLVQPGGSLKLSCAASG FTFNTYAMNWVRQASGKGLEWVGRI RSKSNNYATYYADSVKDRFTISRDDS KNTAYLQMNSLKTEDTAVYYCVRGL LRYRFFDVWGQGTTVTVSS (SEQ ID NO: 92) |
| | VL | DIVMTQAEPSVPVTPGESISISCRSSK SLLHSNGNTYLYWFLQRPGQSPQLLI YRMSNLASGVPDRFSGSGSGTAFTL RISRVEAEDVGVYYCMQHLEYPFTF GGGTKLEIK (SEQ ID NO: 81) | IGKV2-18*01 | IGKJ04*01 | DIVMTQSPLSLPVTPGEPASISCRSSKS LLHSNGNTYLYWFLQKPGQSPQLLIY RMSNLASGVPDRFSGSGSGTDFTLKI SRVEAEDVGVYYCMQHLEYPFTFGG GTKVEIK (SEQ ID NO: 93) |
| 7-B16.033 | VH | EVQLVESGGGLVQPKGSLKLSCAAS GFTFNTYAMNWVRQAPGKGLEWVA RIRSKSNNYATYYADSVKDRFTISRD DSQSMLYLQMNNLKTEDTAMYYCV RGLLRYRFFDVWGAGTTVTVSS (SEQ ID NO: 80) | IGHV3-49*01 | IGHJ06*1 | EVQLVESGGGLVQPGRSLRLSCTASG FTFATYAMNWVRQAPGKGLEWVARI RSKSNNYATYYADSVKDRFTISRDDS KSILYLQMNSLKTEDTAVYYCVRGLL RYRFFDVWGQGTTVTVSS (SEQ ID NO: 96) |
| | VL | DIVMTQAEPSVPVTPGESISISCRSSK SLLHSNGNTYLYWFLQRPGQSPQLLI YRMSNLASGVPDRFSGSGSGTAFTL RISRVEAEDVGVYYCMQHLEYPFTF GGGTKLEIK (SEQ ID NO: 81) | IGKV2-18*01 | IGKJ04*01 | DIVMTQSPLSLPVTPGEPASISCRSSKS LLHSNGNTYLYWFLQKPGQSPQLLIY RMSNLASGVPDRFSGSGSGTDFTLKI SRVEAEDVGVYYCMQHLEYPFTFGG GTKVEIK (SEQ ID NO: 97) |

All optimized antibodies were confirmed to bind to human CCR8-expressing CHO-S. The affinity constants for the humanized versions of antibodies 1-K17 and 7-B16 are shown in Table 7.

TABLE 7

Anti-CCR8 antibody on-cell affinity determined by KinExA assay

| Antibody Reference | Kon ($M^{-1}s^{-1}$) | Koff ($s^{-1}$) | $K_D$ [M] |
|---|---|---|---|
| Humanized 1-K17.015 | $9.78 \times 10^6$ | $1.42 \times 10^{-4}$ | $14.5 \times 10^{-12}$ |
| Humanized 1-K17.044 | $8.29 \times 10^6$ | $6.67 \times 10^{-5}$ | $8.05 \times 10^{-12}$ |
| Humanized 7-B16.001 | $4.99 \times 10^6$ | $7.93 \times 10^{-5}$ | $15.9 \times 10^{-12}$ |
| Humanized 7-B16.033 | $5.25 \times 10^6$ | $3.91 \times 10^{-4}$ | $74.6 \times 10^{-12}$ |

Example 10: Analysis of Antibody Afucosylation

ADCC reporter activity was evaluated for human IgG1 and afucosylated human IgG1 versions of anti-human CCR8 clone 1K17 using the Promega ADCC reporter Bioassay kit following manufacturer recommendations. Chinese Hamster ovarian (CHO) cells overexpressing 300,000 or 10,000 human CCR8 molecules on the cell surface were used as target cells at a 3:1 effector cell to target cell ratio.

Figure 7A:
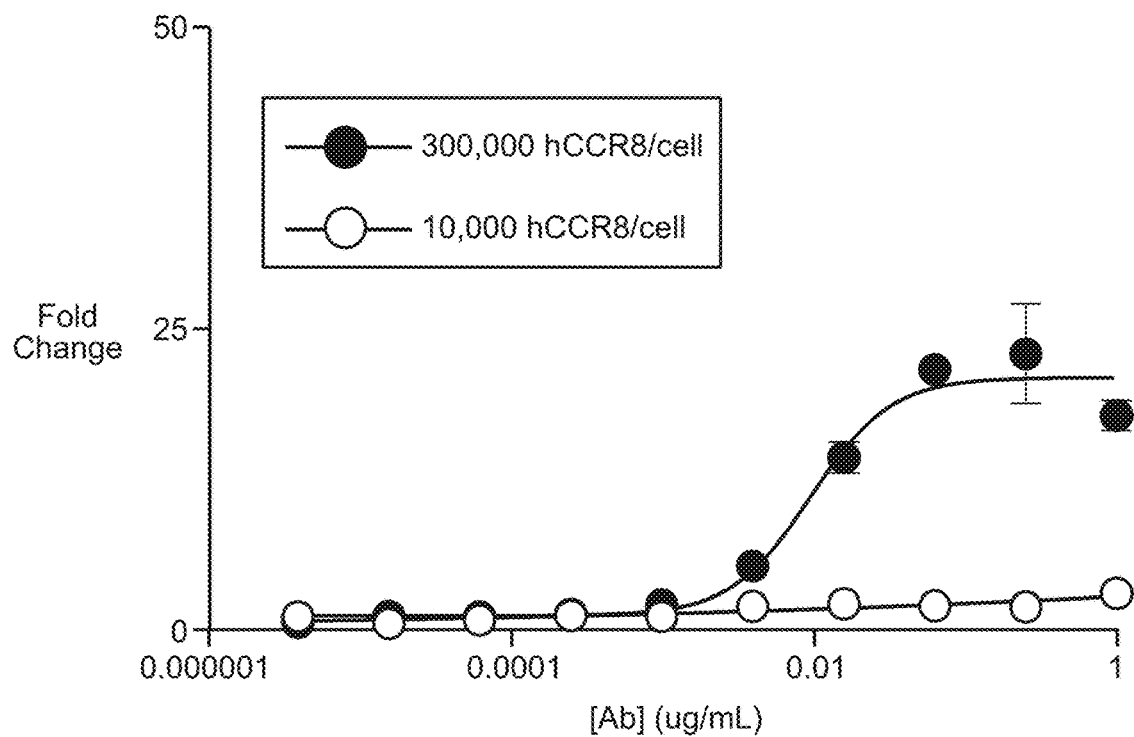
FIGS. 7A-7B show that afucosylation of human IgG1 anti-CCR8 antibodies is required for killing of target cells that express low levels of CCR8. Fold change in ADCC reporter activity of titrated human IgG1 (A) and afucosylated human IgG1 (B) versions of anti-human CCR8 clone 1K17. CHO target cells expressed 300,000 (black filled circle) or 10,000 (white filled circle) cell surface human CCR8 molecules per cell.
Figure 7B:
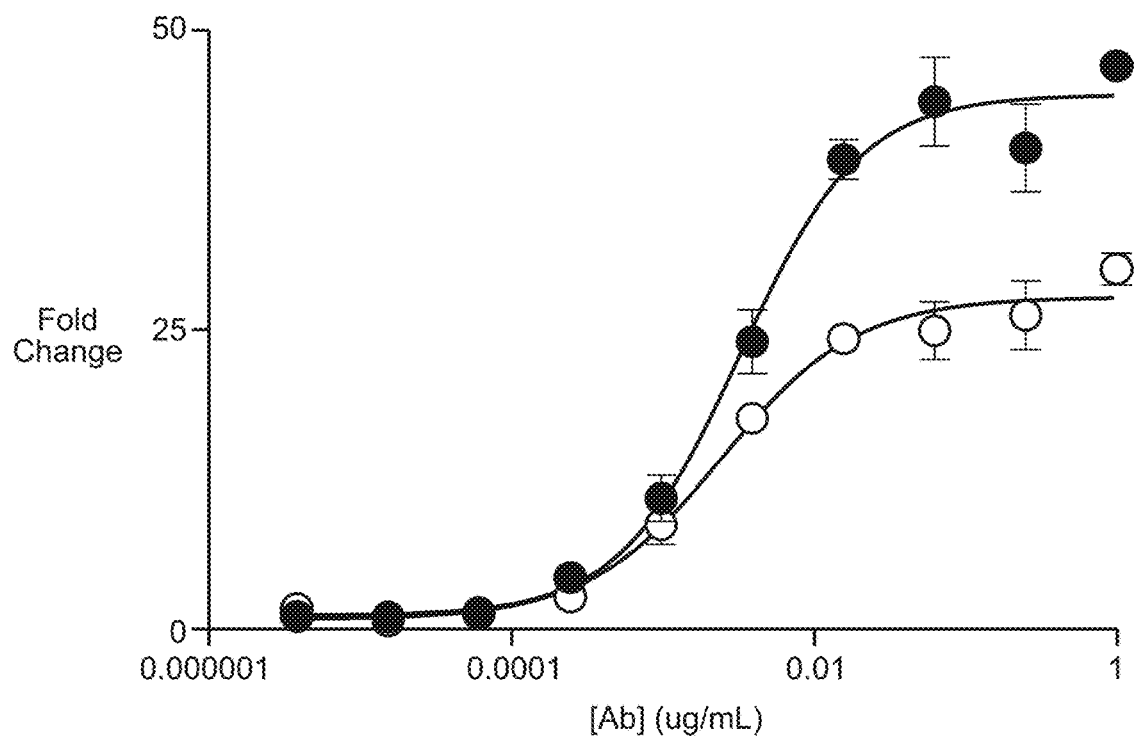

The IK17 hIgG1 antibody did not trigger ADCC of cells expressed a low density of CCR8 (FIG. 7A). In contrast, treatment with the IK17 hIgG1 afucosylated antibody produced greater Fc-mediated ADCC in cells expressing both high and low levels of CCR8 (FIG. 7B). Thus, afucosylation of anti-human CCR8 IgG1 antibody improves ADCC activity against cells expressing low levels of CCR8. As discussed herein, it was found that tumor-infiltrating Tregs express low levels of CCR8, and accordingly, afucosylated anti-CCR8 antibodies may provide effective ADCC activity against CCR8-expressing tumor-infiltrating Tregs where non-afucosylated antibodies do not.

Example 11: In Vivo Analysis of Antibodies

Anti-CCR8 mIgG2a and mIgG1 antibodies were evaluated in a tumor model compared to mIgG2a isotype control. 57B16 mice were inoculated with 2.5×10e5 MC38 cells. Each treatment group included 4 animals with already established tumors (100 $mm^3$) at day 0. Animals were injected once intraperitoneally (i.p) on day 0 with 200 µg of anti-mouse CCR8 or isotype control antibodies described above (i.e., anti-mouse CCR8 mIgG2a or anti-mouse CCR8 mIgG1 or mouse IgG2a isotype control), and tumors were collected three days later for flow cytometry analysis.

Figure 8A:
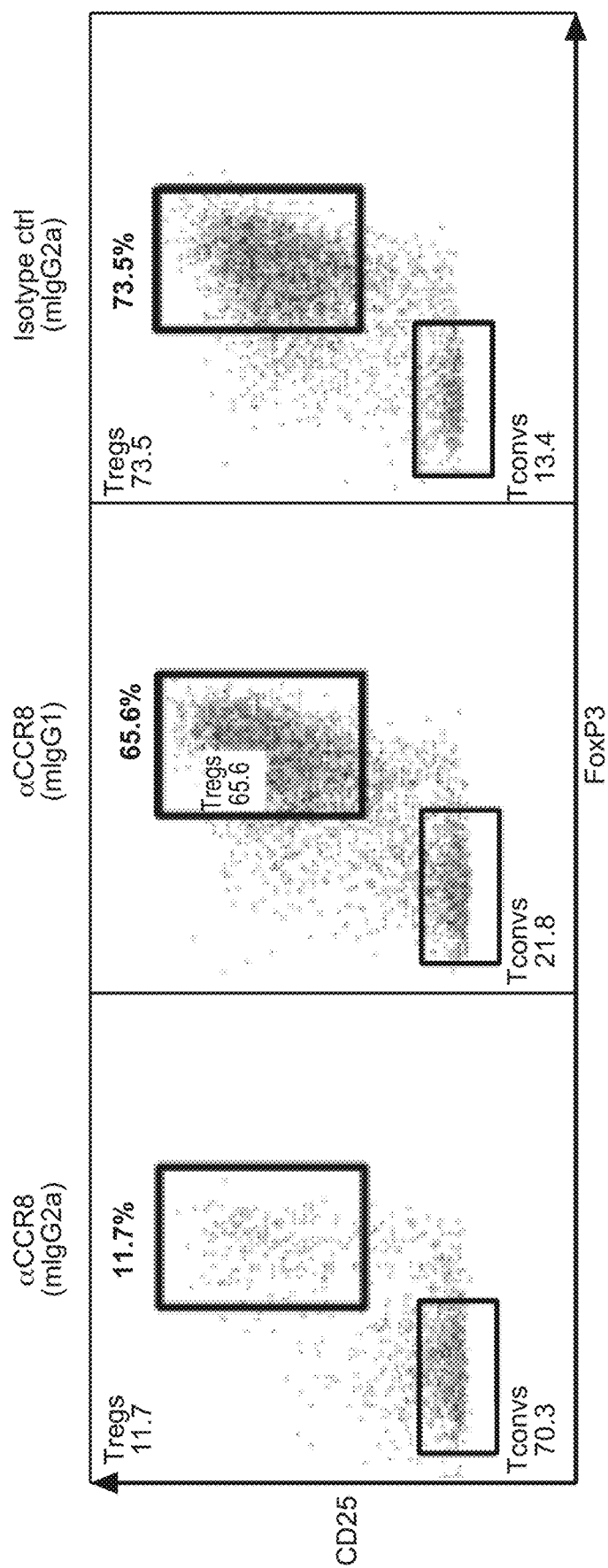
FIGS. 8A-8C show that Fc effector function of anti-mouse CCR8 mAb are required for efficient in vivo killing of tumor-infiltrating (TIL) Tregs. Fc-competent (mouse IgG2a, white full circle) anti-mouse CCR8 mIgG2a antibody enabled depletion of TIL Tregs in vivo in MC38 syngeneic model in mice, while Fc incompetent (mouse IgG1, black full circle) anti-mouse CCR8 mIgG1 antibody did not. Illustrative flow cytometry plots (gated on tumor T CD4+ cells) (A) and quantitative plots (B and C) show the frequencies of TIL Tregs three days post injection of 200 g of indicated antibodies (n=4).
Figure 8B:
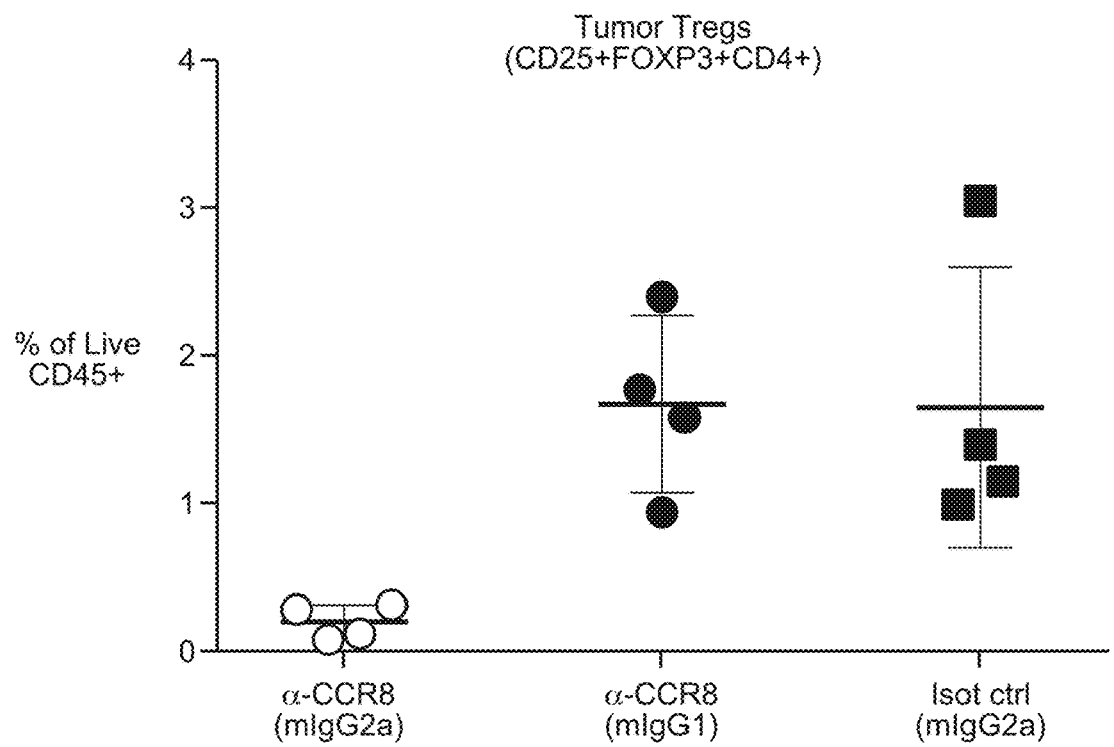
Figure 8C:
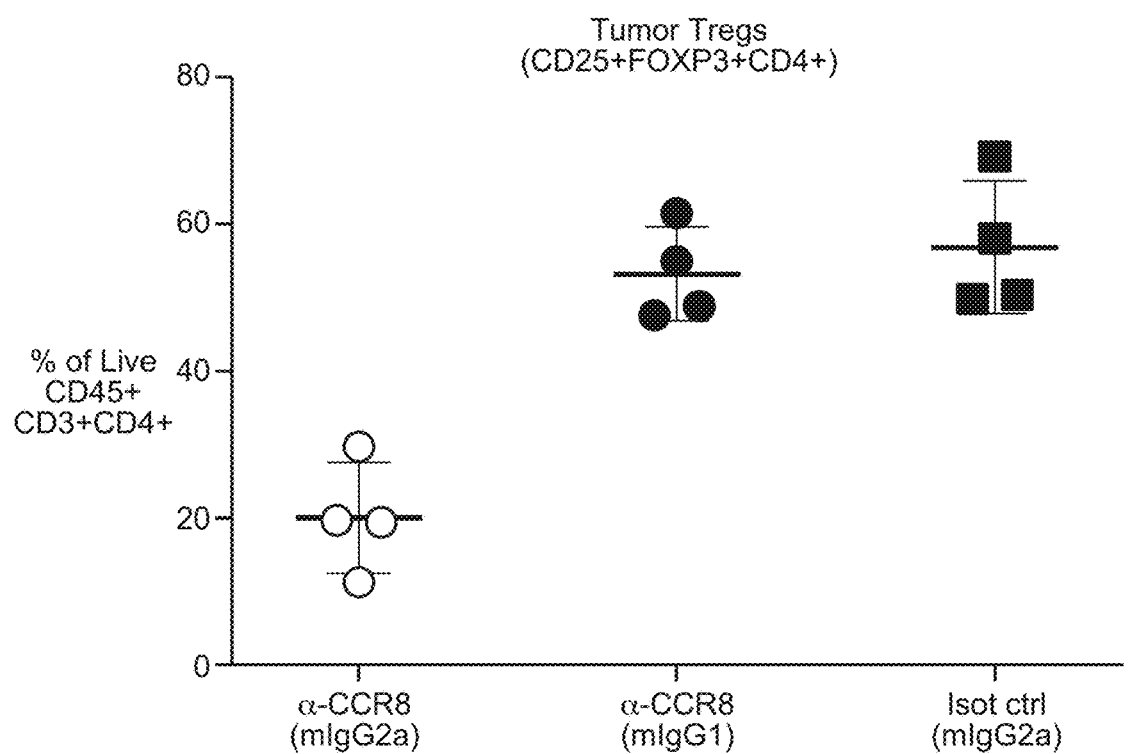

As shown in FIGS. 8A-8C, the proportion of tumor-infiltrating Tregs decreased in the anti-CCR8 mIgG2a group, but not in the other groups.

The therapeutic efficacy of antibodies was also assessed. Mice with established tumors (100 $mm^3$) at day 0 were injected intraperitoneally (i.p) with 200 µg of anti-mouse CCR8 or isotype control antibodies described above (i.e., anti-mouse CCR8 mIgG2a or anti-mouse CCR8 mIgG1 or mouse IgG2a isotype control) twice per week, one days 0, 3, 7, 10, 14, and 17. Each treatment group included 10-15 animals, and tumor growth was measured with a Caliper instrument.

Figure 9A:
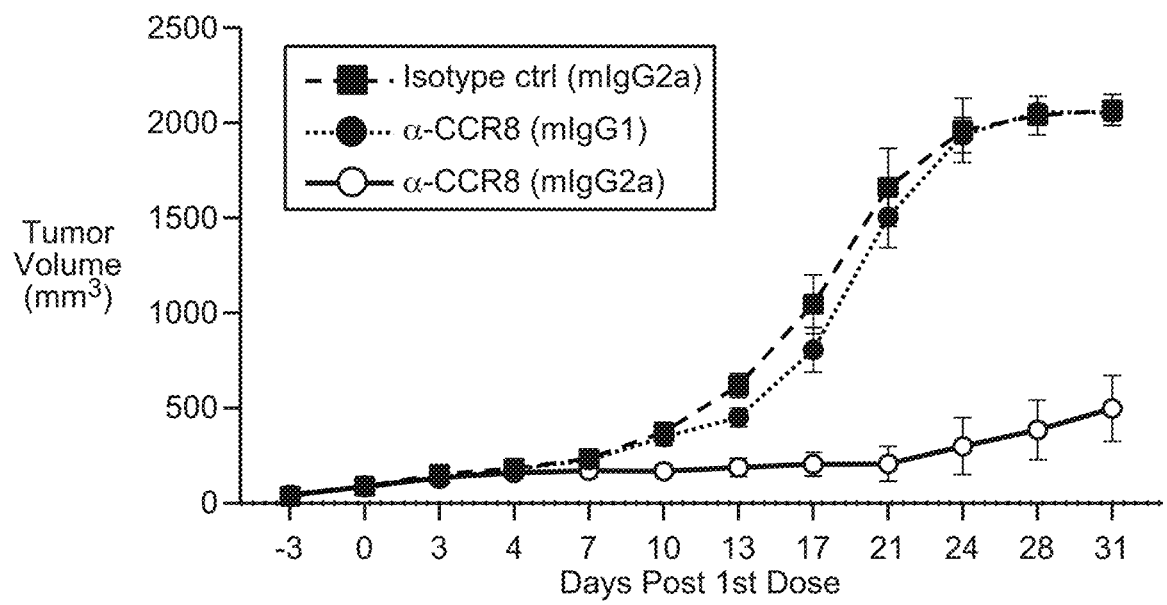
FIGS. 9A-9B show that Fc-competent (mouse IgG2a, white full circle) anti-mouse CCR8 mIgG2a antibody reduces tumor growth (A) and increases survival (B) in MC38 syngeneic mouse model, while Fc incompetent (mouse IgG1, black full circle) anti-mouse CCR8 mIgG1 antibody did not. Tumor growth curves (A) and survival curves of MC38 mice (B) are shown after therapeutic treatment with isotype control, Fc-competent (mouse IgG2a) or Fc-incompetent (mouse IgG1) anti-mouse CCR8 antibody (n=10-15).
Figure 9B:
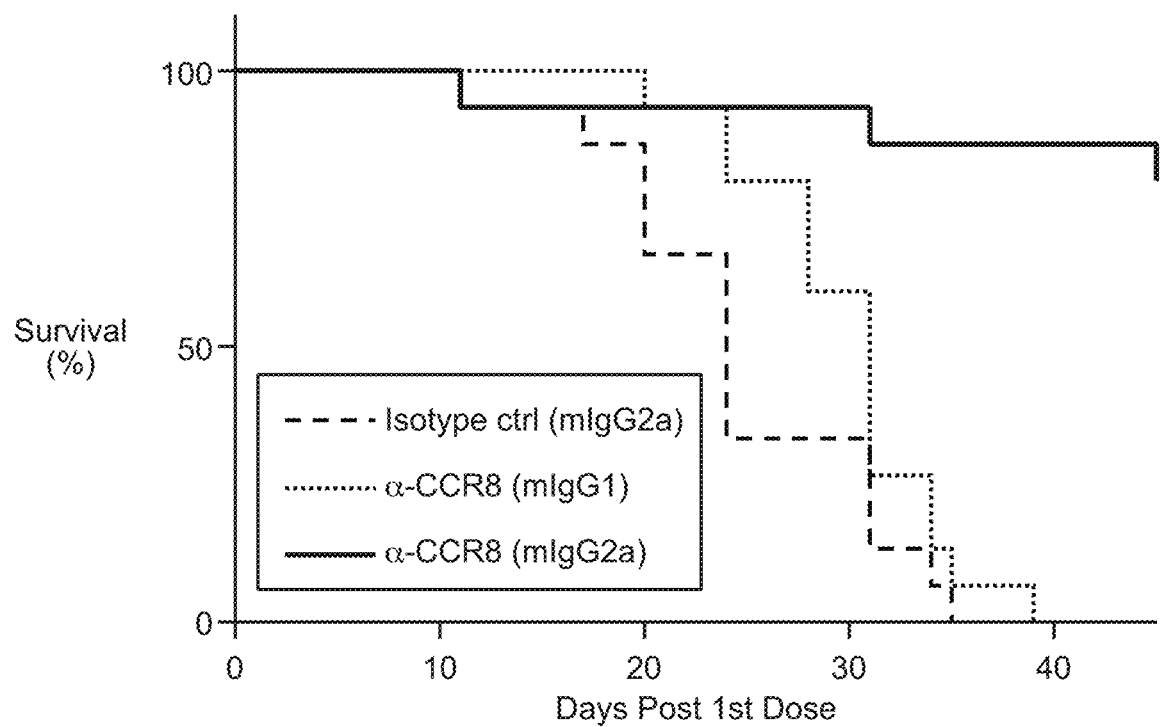

FIGS. 9A-9B show that the Fc effector function of anti-mouse CCR8 monoclonal antibodies drives therapeutic efficacy. An Fc-competent (mouse IgG2a) but not Fc-incompetent (mouse IgG1) anti-mouse CCR8 antibody reduced tumor growth and promoted survival of the mice in this MC38 syngeneic model.

Example 12: CCR8 mRNA Expression in Hematological Cancers

A database of whole transcriptome sequencing ('RNAseq') studies was constructed to explore CCR8 expression across multiple studies directed towards leukemia and lymphoma. Datasets were selected for keywords "leukemia" and "lymphoma" and downloaded from recount2 (Collado-Torres et al., Nature biotechnology 35.4 (2017): 319-321). The database comprised 2,679 samples from 98 studies across 22 cancer types. The dataset included samples from primary patient samples, cell lines, and xenografts. Sources included bone marrow, peripheral blood, and other tissue sources. mRNA expression levels were converted into Transcripts Per Million (TPM), quantile normalized across samples to adjust for gross expression differences across studies and samples, and log 2 transformed. Datasets with a high number of non-expressed genes or those with incomplete metadata were omitted. CCR8 was evaluated across cancer types, and in log fold change compared to normal healthy blood.

Figure 10:
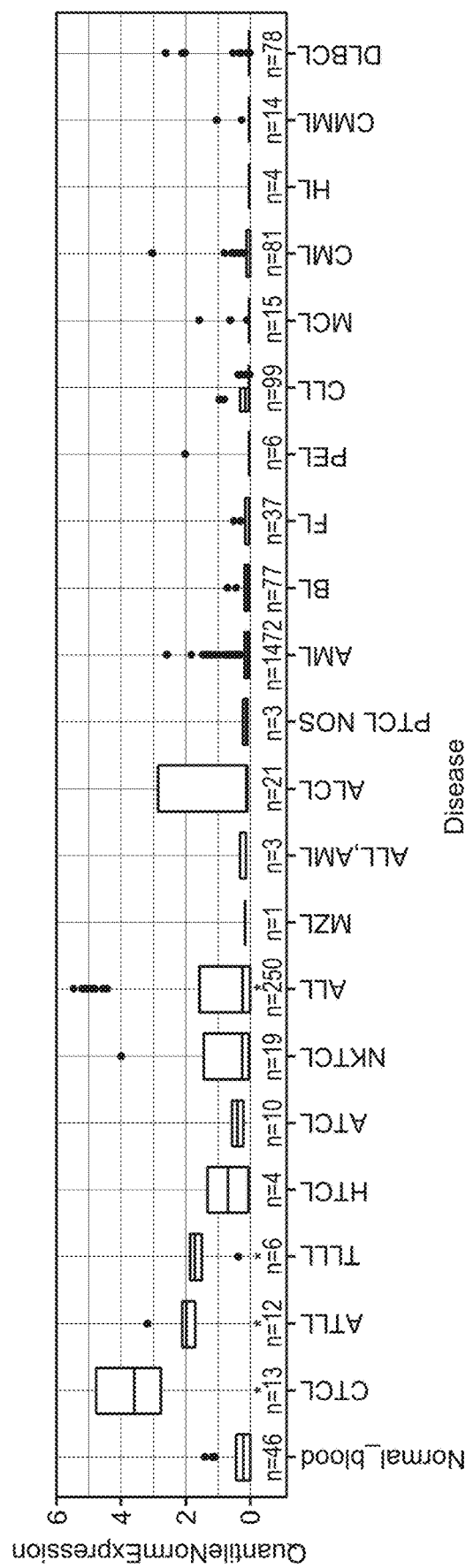
FIG. 10 shows CCR8 mRNA expression in various hematological malignancies compared to normal healthy blood. *indicates cancer types with FDR-adjusted p value<0.05. N indicate the number of samples in the cancer type. The cancers shown include acute lymphocytic leukemia (ALL), acute myeloid leukemia (AML), chronic lymphocytic leukemia (CLL), diffuse large B cell lymphoma (DLBCL), chronic myeloid leukemia (CML), mantle cell lymphoma (MCL), angioimmunoblastic T cell lymphoma (ATCL), hepatosplenic T cell lymphoma (HTCL), peripheral T cell lymphoma not otherwise specified (PTCL NOS), Burkitt lymphoma (BL), adult T cell leukemia/lymphoma (ATLL), anaplastic large cell lymphoma (ALCL), chronic myelomonocytic leukemia (CMML), follicular lymphoma (FL), T cell lymphoblastic leukemia/lymphoma (TLLL), extranodal NK/T cell lymphoma (NKTCL), primary effusion lymphoma (PEL), acute lymphocytic leukemia/acute myeloid leukemia (ALL, AML), histiocytic lymphoma (HL), cutaneous T cell lymphoma (CTCL), and marginal zone lymphoma (MZL).

As shown in FIG. 10, the following indications had significant upregulation of CCR8 compared to normal blood in one-sided t-test when corrected for false discovery rate (adjusted p value<0.05): Cutaneous T Cell Lymphoma (CTCL), Adult T cell Leukemia/Lymphoma (ATLL), T cell Lymphoblastic Leukemia/Lymphoma (TLLL), and T Acute Lymphocytic Leukemia (TALL). Anaplastic Large Cell Lymphoma (ALCL) was significant by a nominal p value but not significant after FDR correction.

Example 13: Screening Variants of 7-B16

Different categories of variants of 7-B16 were generated and screened to establish binding affinity and activity. The first category comprised a single substitution mutation in the CDR H3 of 7-B16. The second category comprised two or three substitution mutations in the CDR H3 of 7-B16. The third category comprised variants in which the CDR H1, H2, L1, L2, or L3 of 7-B16 is swapped with a corresponding CDR from one of the other antibodies disclosed herein.

The first category of variant (single substitution mutation in the CDR H3) included variants in which each amino acid residue of the heavy chain CDR 3 (i.e., CDR H3) was iteratively substituted with an alanine residue. These mutants were assessed for ADCC activity (both EC50 and fold induction), octet response, and CCR8 binding.

ADCC activity was assessed according to the same methods used in Example 7 above. Briefly, the ADCC reporter Bioassay kit from Promega was used to determine the effector function of human IgG1 chimera and humanized versions of anti-CCR8. Human CCR8-expressing CHO-S cells were resuspended in prewarmed assay buffer (37° C.) at $10^6$ cells/mL concentration. 25,000 cells were mixed with serially diluted anti-CCR8 antibodies in 96-well flat, clear-bottom plate, and then incubated for 1 hour at 37° C., 5% $CO_2$. Promega BioAssay effector cells were added to individual well at varied ratios to target cells and further incubated for 6 hours at 37° C. 5% $CO_2$. After incubation, assay plates were equilibrated to room temperature for 15 min under foil on the benchtop. Pre-mixed Bio-Glo Luciferase Assay Substrate was added to each well and incubated at room temperature for 5 min. The assay plates were read on Bio-Tek plate reader within 30 min of substrate addition.

CCR8 binding was determined using flow cytometry according to the same methods used in Example 4. Briefly, antibodies were screened for specific binding to human CCR8 by flow cytometry using human CCR8-overexpressing and parental CHO-S cell line. Antibodies specifically binding to human CCR8 were also tested for binding to CCR4 by flow cytometry.

Finally, to understand the paratope of 7-B16, CDR-H3 alanine scan variants were generated. Binding of CDR-H3 alanine scan variants of 7-B16 to CCR8 was determined by ForteBio Octet using N-terminus peptide (aa 1-35) fused with maltose binding protein (CCR8-NT.MBP, the full sequence of which is provided as SEQ ID NO: 128). Amino acids 406-440 of SEQ ID NO: 128 (i.e., CCR8-NT.MBP) represent amino acids 1-35 of the CCR8 protein, and within this sequence, all of the tyrosine residues, which are shown in bold italics, could be sulfated: MDYTLD-LSVTTVTDYYYPDIFSSPCDAELIQTNGK (amino acids 406-440 of SEQ ID NO: 128). Amino acids 1-364 of SEQ ID NO: 128 represent the maltose binding protein.

For this assessment, 10 μg/ml of alanine scan variants of 7-B16 were captured on AHC biosensors. 300 nM CCR8-NT.MBP was used as analyte to determine the binding of variants to CCR8. The binding of variants to CCR8-NT.MBP was recorded as the Octet response (nM shift).

Figure 11:
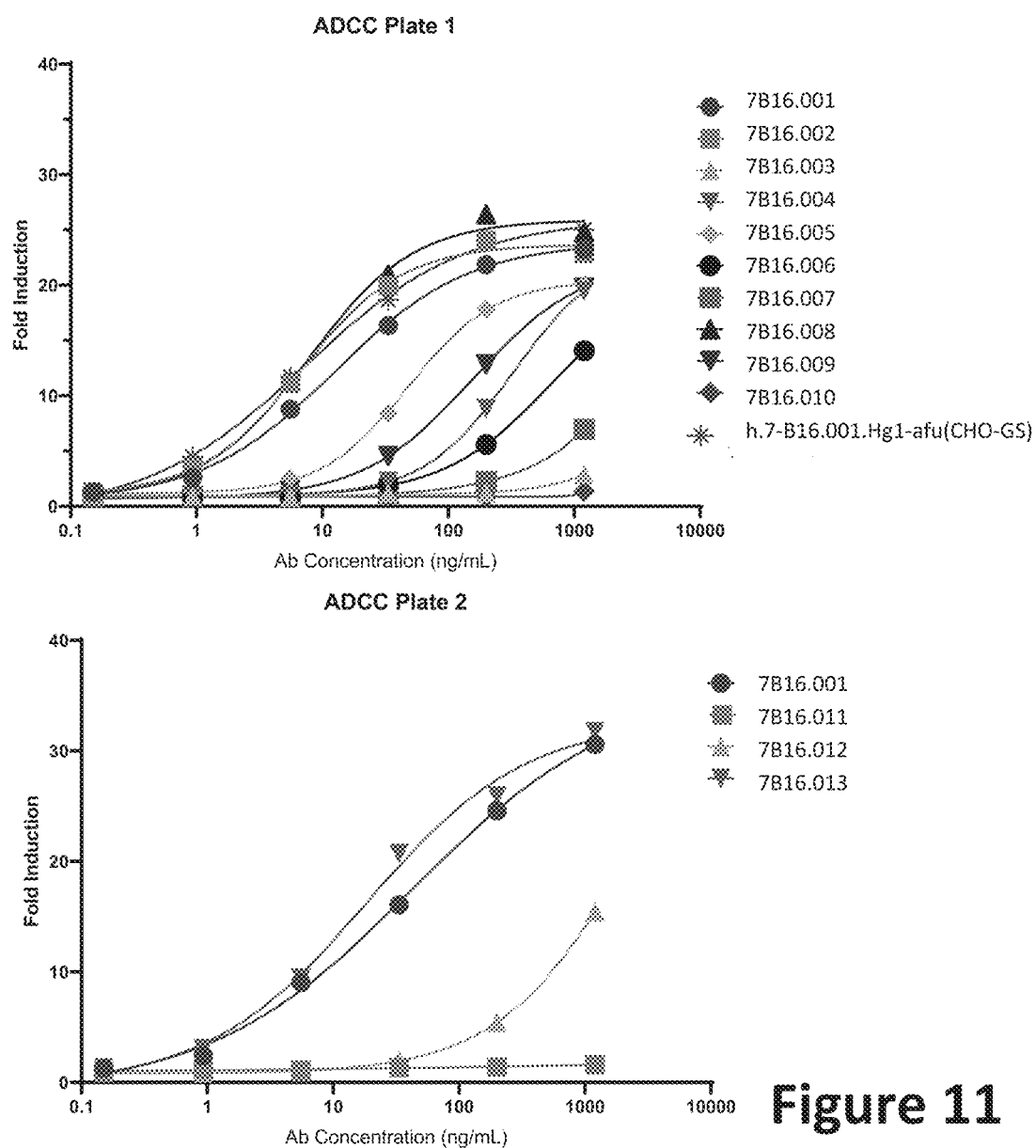
FIG. 11 shows antibody-dependent cellular cytotoxicity (ADCC) of CDR H3 variants of the anti-CCR8 chimeric antibody 7-B16 using an ADCC reporter bioassay (Promega).

The results of these assays are summarized in Table 8 below and FIG. 11.

TABLE 8

Assessment of CDR H3 variants of 7-B16

| Antibody | ADCC (EC50) | ADCC (Fold Induction) | Octet (nm shift) | Flow (fold over parent) | CDR mutations | SEQ ID NO: |
|---|---|---|---|---|---|---|
| 7-B16 | 12.51 | 23.25801 | 0.4367 | 10 | VRGLLRYRFFDV | 86 |
| 7B16.002 | 6.805 | 22.88078 | 0.4693 | 8 | ARGLLRYRFFDV | 104 |
| 7B16.003 | No Fit | 2.873665 | 0.0844 | 5 | VAGLLRYRFFDV | 105 |
| 7B16.004 | 326.4 | 19.45374 | 0.2205 | 6 | VRALLRYRFFDV | 106 |

TABLE 8-continued

Assessment of CDR H3 variants of 7-B16

| Antibody | ADCC (EC50) | ADCC (Fold Induction) | Octet (nm shift) | Flow (fold over parent) | CDR mutations | SEQ ID NO: |
|---|---|---|---|---|---|---|
| 7B16.005 | 48.03 | 20.03381 | 0.2963 | 9 | VRGALRYRFFDV | 107 |
| 7B16.006 | 678.2 | 14.0694 | 0.22 | 8 | VRGLARYRFFDV | 108 |
| 7B16.007 | No Fit | 6.959075 | 0.1727 | 7 | VRGLLAYRFFDV | 109 |
| 7B16.008 | 7.795 | 24.79537 | 0.4357 | 9 | VRGLLRARFFDV | 110 |
| 7B16.009 | 155.6 | 19.7669 | 0.3027 | 10 | VRGLLRYAFFDV | 111 |
| 7B16.010 | No Fit | 1.36121 | 0.155 | 4 | VRGLLRYRAFDV | 112 |
| 7B16.011 | No Fit | 1.61039 | 0.1733 | 6 | VRGLLRYRFADV | 113 |
| 7B16.012 | No Fit | 15.42857 | 0.0954 | 2 | VRGLLRYRFFAV | 114 |
| 7B16.013 | 18.37 | 25.91342 | 0.3826 | 9 | VRGLLRYRFFDA | 115 |

Variants 7B16.002, 7B16.008, and 7B16.013 were selected for combination variants, which are discussed in more detail below.

The second and third category (two or three substitution mutations in the CDR H3 or CDR swapped, respectively) variants are shown in Table 9 below.

The further variants of 7-B16 that are shown in Table 9 were assessed for octet response and CCR8 binding according to the same methods described for the CDR H3 single substitution variants disclosed in Table 8. The results are shown below. Specifically, Table 10 shows Octet Response and binding to CHO CCR8, as determined by flow cytometry.

TABLE 9

Further variants of 7-B16 Antibody

| Category | | Antibody | CDR mutations | Wild type 7-B16 |
|---|---|---|---|---|
| Combo mutant | | 7B16-H3C1.001 | ARGLLARFFDV (SEQ ID NO: 116) | VRGLLRYRFFDV (SEQ ID NO: 86) |
| | | 7B16-H3C2.001 | ARGLLRYRFFDA (SEQ ID NO: 117) | VRGLLRYRFFDV (SEQ ID NO: 86) |
| | | 7B16-H3C3.001 | VRGLLARFFDA (SEQ ID NO: 118) | VRGLLRYRFFDV (SEQ ID NO: 86) |
| | | 7B16-H3C4.001 | ARGLLARFFDA (SEQ ID NO: 119) | VRGLLRYRFFDV (SEQ ID NO: 86) |
| CDR swapped mutant | L1 | 7B16-L1.001 | RSSQSLLHSNGYNYLD (SEQ ID NO: 120) | RSSKSLLHSNGNTYLY (SEQ ID NO: 15) |
| | L2 | 7B16-L2.001 | LGSNRAS (SEQ ID NO: 121) | RMSNLAS (SEQ ID NO: 16) |
| | L3 | 7B16-L3.001 | MQALQTPFV (SEQ ID NO: 122) | MQHLEYPFT (SEQ ID NO: 17) |
| | H1 | 7B16-H1.001 | GFTFSGSAMH (SEQ ID NO: 123) | GFTFNTYAMN (SEQ ID NO: 84) |
| | H2 | 7B16-H2.001 | RIRSKANSYATAYAASVKD (SEQ ID NO: 124) | RIRSKSNNYATYYADSVKD (SEQ ID NO: 85) |
| | H3 | 7B16-H3.001 | TRYYYYYGMDV (SEQ ID NO: 125) | VRGLLRYRFFDV (SEQ ID NO: 86) |

TABLE 10

Assessment of Further Variants of 7B16

| Category | | Antibody | Octet Response (nm) | Binding to CHO CCR8 OCL by Flow cytometry (EC50) |
|---|---|---|---|---|
| Wild-Type | | 7B16 | 0.3024 | 0.017 |
| Combo mutant | | 7B16-H3C1.001 | 0.4308 | 0.024 |
| | | 7B16-H3C2.001 | 0.3569 | 0.023 |
| | | 7B16-H3C3.001 | 0.3759 | 0.025 |
| | | 7B16-H3C4.001 | 0.4043 | 0.024 |
| CDR swapped mutant | L1 | 7B16-L1.001 | 0.0039 | N/A |
| | L2 | 7B16-L2.001 | 0.2054 | 0.017 |
| | L3 | 7B16-L3.001 | 0.0463 | N/A |
| | H1 | 7B16-H1.001 | 0.0922 | N/A |
| | H2 | 7B16-H2.001 | 0.2991 | 0.021 |
| | H3 | 7B16-H3.001 | 0.0093 | N/A |

As shown in Table 10, there was no significant change in Octet response for any of the alanine combo mutants. There was, however, a loss in binding in CDR swapped variants H1, H3, L1, and L3, and there was a modest reduction in binding for CDR swapped variant L1.

The further variants of 7B16 that are shown in Table 9 will also be assessed for ADCC activity (both EC50 and fold induction), according to the same methods described for the CDR H3 single substitution variants disclosed in Table 8. It is expected that these variants will also possess similar ADCC activity.

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

TABLE of Certain Sequences

| Description | Sequence | SEQ ID NO |
|---|---|---|
| Human CCL1.hFc1 Full length sequence (mature sequence amino acids 24-316) | MQIITTALVCLLLAGMWPEDVDSKSMQVPFSRCCFSFAEQEI PLRAILCYRNTSSICSNEGLIFKLKRGKEACALDTVGWVQR HRKMLRHCPSKRKSGGSGGGSGDKTHTCPPCPAPELLGGPS VFLFPPKPKDTLMISRTPEVTCVVVDVSHEDPEVKFNWYVD GVEVHNAKTKPREEQYNSTYRVVSVLTVLHQDWLNGKEY KCKVSNKALPAPIEKTISKAKGQPREPQVYTLPPSREEMTKN QVSLTCLVKGFYPSDIAVEWESNGQPENNYKTTPPVLDSDGS FFLYSKLTVDKSRWQQGNVFSCSVMHEALHNHYTQKSLSLS PGKGSGEPEA | 1 |
| Human CCL1 sequence (mature sequence amino acids 24-96) | MQIITTALVCLLLAGMWPEDVDSKSMQVPFSRCCFSFAEQEI PLRAILCYRNTSSICSNEGLIFKLKRGKEACALDTVGWVQR HRKMLRHCPSKRK | 2 |
| Human CCL1.hFc1 Linker sequence | SGGSGGGSG | 3 |
| hFc1 sequence | DKTHTCPPCPAPELLGGPSVFLFPPKPKDTLMISRTPEVTCVV VDVSHEDPEVKFNWYVDGVEVHNAKTKPREEQYNSTYRV VSVLTVLHQDWLNGKEYKCKVSNKALPAPIEKTISKAKGQP REPQVYTLPPSREEMTKNQVSLTCLVKGFYPSDIAVEWESNG QPENNYKTTPPVLDSDGSFFLYSKLTVDKSRWQQGNVFSCS VMHEALHNHYTQKSLSLSPGKGSGEPEA | 4 |
| MC148.hFc1 Full length sequence | LARRKCCLNPTNRPIPNPLLQDLSRVDYQAIGHDCGREAFRV TLQDGRQGCVSVGNKSLLDWLRGHKDLCPQIWSGCESLGG GSGGGSDKTHTCPPCPAPELLGGPSVFLFPPKPKDTLMISRTP EVTCVVVDVSHEDPEVKFNWYVDGVEVHNAKTKPREEQY NSTYRVVSVLTVLHQDWLNGKEYKCKVSNKALPAPIEKTIS KAKGQPREPQVYTLPPSREEMTKNQVSLTCLVKGFYPSDIAV EWESNGQPENNYKTTPPVLDSDGSFFLYSKLTVDKSRWQQG NVFSCSVMHEALHNHYTQKSLSLSPGKGSGEPEA | 5 |
| MC148 sequence | LARRKCCLNPTNRPIPNPLLQDLSRVDYQAIGHDCGREAFRV TLQDGRQGCVSVGNKSLLDWLRGHKDLCPQIWSGCESL | 6 |
| MC148.hFc1 Linker sequence | GGGSGGGS | 7 |
| 1-K16 VH | EVQLVETGGGLVQPKGSLKLSCAASGFTFNINAMNWVRQA PGKGLEWVARIRSKSNNYATYYADSVKDRFTISRDDSQSML YLQMNNLKTEDTAMYYCVRGGYGSSPYDMDYWGQGTSV TVSS | 8 |

TABLE of-continued

Certain Sequences

| Description | Sequence | SEQ ID NO |
|---|---|---|
| 1-K16 VL | DIVMTQAAPSVPVTPGESVSISCRSSKSLLHSNGNTYLYWFL QRPGQSPQLLIYRMSNLASGVPDRFSGSGSGTAFTLRISRVE AEDVGVYYCMQHLEYPFTFGAGTKLELK | 9 |
| 1-K16 HC | EVQLVETGGGLVQPKGSLKLSCAASGFTFNINAMNWVRQA PGKGLEWVARIRSKSNNYATYYADSVKDRFTISRDDSQSML YLQMNNLKTEDTAMYYCVRGGYGSSPYDMDYWGQGTSV TVSSAKTTPPSVYPLAPGSAAQTNSMVTLGCLVKGYFPEPV TVTWNSGSLSSGVHTFPAVLESDLYTLSSSVTVPSSPRPSETV TCNVAHPASSTKVDKKIVPRDCGCKPCICTVPEVSSVFIFPPK PKDVLTITLTPKVTCVVVDISKDDPEVQFSWFVDDVEVHTA QTQPREEQFNSTFRSVSELPIMHQDWLNGKEFKCRVNSAAF PAPIEKTISKTKGRPKAPQVYTIPPPKEQMAKDKVSLTCMIT DFFPEDITVEWQWNGQPAENYKNTQPIMNTNGSYFVYSKL NVQKSNWEAGNTFTCSVLHEGLHNHHTEKSLSHSPG | 10 |
| 1-K16 LC | DIVMTQAAPSVPVTPGESVSISCRSSKSLLHSNGNTYLYWFL QRPGQSPQLLIYRMSNLASGVPDRFSGSGSGTAFTLRISRVE AEDVGVYYCMQHLEYPFTFGAGTKLELKRADAAPTVSIFPP SSEQLTSGGASVVCFLNNFYPKDINVKWKIDGSERQNGVLN SWTDQDSKDSTYSMSSTLTLTKDEYERHNSYTCEATHKTST SPIVKSFNRNEC | 11 |
| 1-K16 CDR-H1 | GFTFNINAMN | 12 |
| 1-K16 CDR-H2 | RIRSKSNNYATYYADSV | 13 |
| 1-K16 CDR-H3 | VRGGYGSSPYDMDY | 14 |
| 1-K16 CDR-L1 | RSSKSLLHSNGNTYLY | 15 |
| 1-K16 CDR-L2 | RMSNLAS | 16 |
| 1-K16 chimera CDR-L3 | MQHLEYPFT | 17 |
| 1-K16 chimera HC | EVQLVETGGGLVQPKGSLKLSCAASGFTFNINAMNWVRQA PGKGLEWVARIRSKSNNYATYYADSVKDRFTISRDDSQSML YLQMNNLKTEDTAMYYCVRGGYGSSPYDMDYWGQGTSV TVSSASTKGPSVFPLAPSSKSTSGGTAALGCLVKDYFPEPVT VSWNSGALTSGVHTFPAVLQSSGLYSLSSWTVPSSSLGTQT YICNVNHKPSNTKVDKKVEPKSCDKTHTCPPCPAPELLGGP SVFLFPPKPKDTLMISRTPEVTCVVVDVSHEDPEVKFNWYV DGVEVHNAKTKPREEQYNSTYRVVSVLTVLHQDWLNGKE YKCKVSNKALPAPIEKTISKAKGQPREPQVYTLPPSREEMTK NQVSLTCLVKGFYPSDIAVEWESNGQPENNYKTTPPVLDSD GSFFLYSKLTVDKSRWQQGNVFSCSVMHEALHNHYTQKSL SLSPG | 18 |
| 1-K16 chimera LC | DIVMTQAAPSVPVTPGESVSISCRSSKSLLHSNGNTYLYWFL QRPGQSPQLLIYRMSNLASGVPDRFSGSGSGTAFTLRISRVE AEDVGVYYCMQHLEYPFTFGAGTKLELKRTVAAPSVFIFPP SDEQLKSGTASVVCLLNNFYPREAKVQWKVDNALQSGNSQ ESVTEQDSKDSTYSLSSTLTLSKADYEKHKVYACEVTHQGL SSPVTKSFNRGEC | 19 |
| 6-B09 VH | QVQLKESGPGLVAPSQSLSITCTVSGFSLARYDISWIRQPPGK GLEWLGVIWTGGGTNYNSAFMSRLSISKDNSKSQVFLKMN GLQTDDTAIYYCVSIRYDETYWGQGTLVTVSA | 20 |
| 6-B09 VL | QIVLTQSPAIMSASPGEKVTITCSASSSVIYMHWFQQKPGTSP KLWIYATSNLASGVPARFSGSGSGTSYSLTISRMEAEDAATY YCQQRSSYPLTFGAGTKLELK | 21 |
| 6-B09 HC | QVQLKESGPGLVAPSQSLSITCTVSGFSLARYDISWIRQPPGK GLEWLGVIWTGGGTNYNSAFMSRLSISKDNSKSQVFLKMN GLQTDDTAIYYCVSIRYDETYWGQGTLVTVSAAKTTAPSVY PLAPVCGDTTGSSVTLGCLVKGYFPEPVTLTWNSGSLSSGV HTFPAVLQSDLYTLSSSVTVTSSTWPSQSITCNVAHPASSTKV | 22 |

TABLE of-continued
Certain Sequences

| Description | Sequence | SEQ ID NO |
|---|---|---|
| | DKKIEPRGPTIKPCPPCKCPAPNLLGGPSVFIFPPKIKDVLMIS<br>LSPIVTCVVVDVSEDDPDVQISWFVNNVEVHTAQTQTHRED<br>YNSTLRVVSALPIQHQDWMSGKEFKCKVNNKDLPAPIERTIS<br>KPKGSVRAPQVYVLPPPEEEMTKKQVTLTCMVTDFMPEDIY<br>VEWTNNGKTELNYKNTEPVLDSDGSYFMYSKLRVEKKNW<br>VERNSYSCSVVHEGLHNHHTTKSFSRTPG | |
| 6-B09 LC | QIVLTQSPAIMSASPGEKVTITCSASSSVIYMHWFQQKPGTSP<br>KLWIYATSNLASGVPARFSGSGSGTSYSLTISRMEAEDAATY<br>YCQQRSSYPLTFGAGTKLELKRADAAPTVSIFPPSSEQLTSG<br>GASVVCFLNNFYPKDINVKWKIDGSERQNGVLNSWTDQDS<br>KDSTYSMSSTLTLTKDEYERHNSYTCEATHKTSTSPIVKSFN<br>RNEC | 23 |
| 6-B09<br>CDR-H1 | GFSLARYDIS | 24 |
| 6-B09<br>CDR-H2 | GGTNYNSAFMSRLSIS | 25 |
| 6-B09<br>CDR-H3 | VSIRYDETY | 26 |
| 6-B09<br>CDR-L1 | SASSSVIYMH | 27 |
| 6-B09<br>CDR-L2 | TSNLASG | 28 |
| 6-B09<br>CDR-L3 | QQRSSYPLT | 29 |
| 6-B09<br>chimera HC | QVQLKESGPGLVAPSQSLSITCTVSGFSLARYDISWIRQPPGK<br>GLEWLGVIWTGGGTNYNSAFMSRLSISKDNSKSQVFLKMN<br>GLQTDDTAIYYCVSIRYDETYWGQGTLVTVSAASTKGPSVF<br>PLAPSSKSTSGGTAALGCLVKDYFPEPVTVSWNSGALTSGV<br>HTFPAVLQSSGLYSLSSVVTVPSSSLGTQTYICNVNHKPSNTK<br>VDKKVEPKSCDKTHTCPPCPAPELLGGPSVFLFPPKPKDTLM<br>ISRTPEVTCVVVDVSHEDPEVKFNWYVDGVEVHNAKTKPR<br>EEQYNSTYRVVSVLTVLHQDWLNGKEYKCKVSNKALPAPIE<br>KTISKAKGQPREPQVYTLPPSREEMTKNQVSLTCLVKGFYPS<br>DIAVEWESNGQPENNYKTTPPVLDSDGSFFLYSKLTVDKSR<br>WQQGNVFSCSVMHEALHNHYTQKSLSLSPG | 30 |
| 6-B09<br>chimera LC | QIVLTQSPAIMSASPGEKVTITCSASSSVIYMHWFQQKPGTSP<br>KLWIYATSNLASGVPARFSGSGSGTSYSLTISRMEAEDAATY<br>YCQQRSSYPLTFGAGTKLELKRTVAAPSVFIFPPSDEQLKSGT<br>ASVVCLLNNFYPREAKVQWKVDNALQSGNSQESVTEQDSK<br>DSTYSLSSTLTLSKADYEKHKVYACEVTHQGLSSPVTKSFNR<br>GEC | 31 |
| 13-E16 VH | EVQLVETGGGLVQPKGSLKLSCAASGFTFSTNAMNWVRQA<br>PGKGLEWIARIRSKSNNYATHYADSVKDRFTISRDDSQSILH<br>LQMNNLKNEDTAMYYCVRDSHYYVSTYVGLAWFAYWGQ<br>GTLVTVSA | 32 |
| 13-E16 VL | QIVLTQSPAIMSASPGEKVTITCSASSSVSYMHWFQQKPGTS<br>PKLWIYSTSNLASGVPARFSGSGSGTSYFLTISRMEAEDAAT<br>YYCQQRSSYPYTFGGGTKLERK | 33 |
| 13-E16 HC | EVQLVETGGGLVQPKGSLKLSCAASGFTFSTNAMNWVRQA<br>PGKGLEWIARIRSKSNNYATHYADSVKDRFTISRDDSQSILH<br>LQMNNLKNEDTAMYYCVRDSHYYVSTYVGLAWFAYWGQ<br>GTLVTVSAAKTTAPSVYPLAPVCGDTTGSSVTLGCLVKGYF<br>PEPVTLTWNSGSLSSGVHTFPAVLQSDLYTLSSSVTVTSSTW<br>PSQSITCNVAHPASSTKVDKKIEPRGPTIKPCPPCKCPAPNLL<br>GGPSVFIFPPKIKDVLMISLSPIVTCVVVDVSEDDPDVQISWF<br>VNNVEVHTAQTQTHREDYNSTLRVVSALPIQHQDWMSGKE<br>FKCKVNNKDLPAPIERTISKPKGSVRAPQVYVLPPPEEEMTK<br>KQVTLTCMVTDFMPEDIYVEWTNNGKTELNYKNTEPVLDS<br>DGSYFMYSKLRVEKKNWVERNSYSCSVVHEGLHNHHTTKS<br>FSRTPG | 34 |
| 13-E16 LC | QIVLTQSPAIMSASPGEKVTITCSASSSVSYMHWFQQKPGTS<br>PKLWIYSTSNLASGVPARFSGSGSGTSYFLTISRMEAEDAAT<br>YYCQQRSSYPYTFGGGTKLERKRADAAPTVSIFPPSSEQLTS | 35 |

TABLE of-continued

Certain Sequences

| Description | Sequence | SEQ ID NO |
|---|---|---|
| | GGASVVCFLNNFYPKDINVKWKIDGSERQNGVLNSWTDQD SKDSTYSMSSTLTLTKDEYERHNSYTCEATHKTSTSPIVKSF NRNEC | |
| 13-E16 CDR-H1 | GFTFSTNAMN | 36 |
| 13-E16 CDR-H2 | RIRSKSNNYATHYADSV | 37 |
| 13-E16 CDR-H3 | VRDSHYYVSTYVGLA | 38 |
| 13-E16 CDR-L1 | SASSSVSYMH | 39 |
| 13-E16 CDR-L2 | TSNLAS | 40 |
| 13-E16 CDR-L3 | QQRSSYPYT | 41 |
| 13-E16 chimera HC | EVQLVETGGGLVQPKGSLKLSCAASGFTFSTNAMNWVRQA PGKGLEWIARIRSKSNNYATHYADSVKDRFTISRDDSQSILH LQMNNLKNEDTAMYYCVRDSHYYVSTYVGLAWFAYWGQ GTLVTVSAASTKGPSVFPLAPSSKSTSGGTAALGCLVKDYFP EPVTVSWNSGALTSGVHTFPAVLQSSGLYSLSSVVTVPSSSL GTQTYICNVNHKPSNTKVDKKVEPKSCDKTHTCPPCPAPEL LGGPSVFLFPPKPKDTLMISRTPEVTCVVVDVSHEDPEVKFN WYVDGVEVHNAKTKPREEQYNSTYRVVSVLTVLHQDWLN GKEYKCKVSNKALPAPIEKTISKAKGQPREPQVYTLPPSREE MTKNQVSLTCLVKGFYPSDIAVEWESNGQPENNYKTTPPVL DSDGSFFLYSKLTVDKSRWQQGNVFSCSVMHEALHNHYTQ KSLSLSPG | 42 |
| 13-E16 chimera LC | QIVLTQSPAIMSASPGEKVTITCSASSSVSYMHWFQQKPGTS PKLWIYSTSNLASGVPARFSGSGSGTSYFLTISRMEAEDAAT YYCQQRSSYPYTFGGGTKLERKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC | 43 |
| 19-007 VH | EVQLQQSVAELVRPGASVKLSCTASGFNIKNTQMHWVKQR PEQGLEWIGRIDPANGNTKYAPKFQGKATITGDTSSNTAYLQ LSSSLTSEDTAIYYCARFDYYYGSGDYAMDWGQGTSVTSS | 44 |
| 19-007 VL | DVVMTQTPLTLSVTIGQPASISCKSSQSLLYSNGKTYLNWLL QRPGQSPKRLIYLVSKLDSGVPDRFTGSGSGTDFTLKISRVE AEDLGVYYCVQGTRFPWTFGGGTNLEIK | 45 |
| 19-007 HC | EVQLQQSVAELVRPGASVKLSCTASGFNIKNTQMHWVKQR PEQGLEWIGRIDPANGNTKYAPKFQGKATITGDTSSNTAYLQ LSSSLTSEDTAIYYCARFDYYYGSGDYAMDWGQGTSVTSS TTTAPSVYPLVPGCSDTSGSSVTLGCLVKGYFPEPVTVKWN YGALSSGVRTVSSVLQSGFYSLSSLVTVPSSTWPSQTVICNV AHPASKTELIKRIEPRIPKPSTPPGSSCPPGNILGGPSVFIFPPK PKDALMISLTPKVTCVVVDVSEDDPDVHVSWFVDNKEVHT AWTQPREAQYNSTFRVVSALPIQHQDWMRGKEFKCKVNN KALPAPIERTISKPKGRAQTPQVYTIPPPREQMSKKKVSLTCL VTNFFSEAISVEWERNGELEQDYKNTPPILDSDGTYFLYSKL TVDTDSWLQGEIFTCSVVHEALHNHHTQKNLSRSPELELNE TCAEAQDGELDGLWTTITIFISLFLLSVCYSASVTLFKVKWIF SSVVQVKQTAIPDYRNMIGQGA | 46 |
| 19-007 LC | DVVMTQTPLTLSVTIGQPASISCKSSQSLLYSNGKTYLNWLL QRPGQSPKRLIYLVSKLDSGVPDRFTGSGSGTDFTLKISRVE AEDLGVYYCVQGTRFPWTFGGGTNLEIKRADAAPTVSIFPP SSEQLTSGGASVVCFLNNFYPKDINVKWKIDGSERQNGVLN SWTDQDSKDSTYSMSSTLTLTKDEYERHNSYTCEATHKTST SPIVKSFNRNEC | 47 |
| 19-007 CDR-H1 | GFNIKNTQMH | 48 |
| 19-007 CDR-H2 | RIDPANGNTKYAP | 49 |

TABLE of-continued

Certain Sequences

| Description | Sequence | SEQ ID NO |
|---|---|---|
| 19-007 CDR-H3 | ARFDYYYGSGDYAMDY | 50 |
| 19-007 CDR-L1 | KSSQSLLYSNGKTYLN | 51 |
| 19-007 CDR-L2 | LVSKLDS | 52 |
| 19-007 CDR-L3 | VQGTRFPWT | 53 |
| 19-007 chimera HC | EVQLQQSVAELVRPGASVKLSCTASGFNIKNTQMHWVKQR PEQGLEWIGRIDPANGNTKYAPKFQGKATITGDTSSNTAYLQ LSSLTSEDTAIYYCARFDYYYGSGDYAMDYWGQGTSVTSS ASTKGPSVFPLAPSSKSTSGGTAALGCLVKDYFPEPVTVSWN SGALTSGVHTFPAVLQSSGLYSLSSWTVPSSSLGTQTYICNV NHKPSNTKVDKKVEPKSCDKTHTCPPCPAPELLGGPSVFLFP PKPKDTLMISRTPEVTCVVVDVSHEDPEVKFNWYVDGVEV HNAKTKPREEQYNSTYRVVSVLTVLHQDWLNGKEYKCKVS NKALPAPIEKTISKAKGQPREPQVYTLPPSREEMTKNQVSLT CLVKGFYPSDIAVEWESNGQPENNYKTTPPVLDSDGSFFLYS KLTVDKSRWQQGNVFSCSVMHEALHNHYTQKSLSLSPG | 54 |
| 19-007 chimera LC | DVVMTQTPLTLSVTIGQPASISCKSSQSLLYSNGKTYLNWLL QRPGQSPKRLIYLVSKLDSGVPDRFTGSGSGTDFTLKISRVE AEDLGVYYCVQGTRFPWTFGGGTNLEIKRTVAAPSVFIFPPS DEQLKSGTASVVCLLNNFYPREAKVQWKVDNALQSGNSQE SVTEQDSKDSTYSLSSTLTLSKADYEKHKVYACEVTHQGLS SPVTKSFNRGEC | 55 |
| 1-K17 VH | QVQLQQPGAELVKPGASVKMSCKASGYTFTSYNMHWVKQ TPGQGLEWIGAIYPGNGDTSYNQKFKGKATLTADKSSSTAY MHLSSLTSEDSAVYYCARKGGTPFAYWGQGTLLTVSA | 56 |
| 1-K17 VL | DVVMTQTPLSLPVSLGDQASISCRSSQSLVHSNGNTYLYWY LQKPGQSPKLLIYKVSNRFSGVPDRFSGSGSGTDFTLKISRVE AEDLGVYFCSQSTHVPYTFGGGTKLEIK | 57 |
| 1-K17 HC | QVQLQQPGAELVKPGASVKMSCKASGYTFTSYNMHWVKQ TPGQGLEWIGAIYPGNGDTSYNQKFKGKATLTADKSSSTAY MHLSSLTSEDSAVYYCARKGGTPFAYWGQGTLLTVSAAKTT PPSVYPLAPGSAAQTNSMVTLGCLVKGYFPEPVTVTWNSGS LSSGVHTFPAVLESDLYTLSSSVTVPSSPRPSETVTCNVAHPA SSTKVDKKIVPRDCGCKPCICTVPEVSSVFIFPPKPKDVLTITL TPKVTCVVVDISKDDPEVQFSWFVDDVEVHTAQTQPREEQF NSTFRSVSELPIMHQDWLNGKEFKCRVNSAAFPAPIEKTISK TKGRPKAPQVYTIPPPKEQMAKDKVSLTCMITDFFPEDITVE WQWNGQPAENYKNTQPIMNTNGSYFVYSKLNVQKSNWEA GNTFTCSVLHEGLHNHHTEKSLSHSPG | 58 |
| 1-K17 LC | DVVMTQTPLSLPVSLGDQASISCRSSQSLVHSNGNTYLYWY LQKPGQSPKLLIYKVSNRFSGVPDRFSGSGSGTDFTLKISRVE AEDLGVYFCSQSTHVPYTFGGGTKLEIKRADAAPTVSIFPPS SEQLTSGGASVVCFLNNFYPKDINVKWKIDGSERQNGVLNS WTDQDSKDSTYSMSSTLTLTKDEYERHNSYTCEATHKTSTS PIVKSFNRNEC | 59 |
| 1-K17, 1-K17.015 CDR-H1, 1-K17.044 CDR-H1 | GYTFTSYNMH | 60 |
| 1-K17 CDR-H2 | AIYPGNGDTSYNQ | 61 |
| 1-K17, 1-K17.015 CDR-H1, 1-K17.044 CDR-H3 | ARKGGTPFAY | 62 |
| 1-K17 CDR-L1 | RSSQSLVHSNGNTYLY | 63 |

TABLE of-continued

Certain Sequences

| Description | Sequence | SEQ ID NO |
|---|---|---|
| 1-K17, 1-K17.015 CDR-H1, 1-K17.044 CDR-L2 | KVSNRFS | 64 |
| 1-K17, 1-K17.015 CDR-H1, 1-K17.044 CDR-L3 | SQSTHVPYT | 65 |
| 1-K17 chimera HC | QVQLQQPGAELVKPGASVKMSCKASGYTFTSYNMHWVKQ TPGQGLEWIGAIYPGNGDTSYNQKFKGKATLTADKSSSTAY MHLSSLTSEDSAVYYCARKGGTPFAYWGQGTLLTVSAASTK GPSVFPLAPSSKSTSGGTAALGCLVKDYFPEPVTVSWNSGAL TSGVHTFPAVLQSSGLYSLSSVVTVPSSSLGTQTYICNVNHKP SNTKVDKKVEPKSCDKTHTCPPCPAPELLGGPSVFLFPPKPK DTLMISRTPEVTCVVVDVSHEDPEVKFNWYVDGVEVHNAK TKPREEQYNSTYRVVSVLTVLHQDWLNGKEYKCKVSNKAL PAPIEKTISKAKGQPREPQVYTLPPSREEMTKNQVSLTCLVK GFYPSDIAVEWESNGQPENNYKTTPPVLDSDGSFFLYSKLTV DKSRWQQGNVFSCSVMHEALHNHYTQKSLSLSPG | 66 |
| 1-K17 chimera LC | DVVMTQTPLSLPVSLGDQASISCRSSQSLVHSNGNTYLYWY LQKPGQSPKLLIYKVSNRFSGVPDRFSGSGSGTDFTLKISRVE AEDLGVYFCSQSTHVPYTFGGGTKLEIKRTVAAPSVFIFPPSD EQLKSGTASVVCLLNNFYPREAKVQWKVDNALQSGNSQES VTEQDSKDSTYSLSSTLTLSKADYEKHKVYACEVTHQGLSS PVTKSFNRGEC | 67 |
| 1-K17.015 VH | EVQLVQSGAEVKKPGASVKVSCKASGYTFTSYNMHWVRQ APGQRLEWIGAIYPGQGDTSYNQKFKGRATLTADKSASTAY MELSSLRSEDTAVYYCARKGGTPFAYWGQGTLVTVSS | 68 |
| 1-K17.015 VL | DVVMTQSPLSLPVTLGQPASISCRSSQSLVHSNAQTYLYWY QQRPGQSPRLLIYKVSNRFSGVPDRFSGSGSGTDFTLKISRVE AEDVGVYFCSQSTHVPYTFGQGTKLEIK | 69 |
| 1-K17.015 HC | EVQLVQSGAEVKKPGASVKVSCKASGYTFTSYNMHWVRQ APGQRLEWIGAIYPGQGDTSYNQKFKGRATLTADKSASTAY MELSSLRSEDTAVYYCARKGGTPFAYWGQGTLVTVSSASTK GPSVFPLAPSSKSTSGGTAALGCLVKDYFPEPVTVSWNSGAL TSGVHTFPAVLQSSGLYSLSSWTVPSSSLGTQTYICNVNHKP SNTKVDKKVEPKSCDKTHTCPPCPAPELLGGPSVFLFPPKPK DTLMISRTPEVTCVVVDVSHEDPEVKFNWYVDGVEVHNAK TKPREEQYNSTYRVVSVLTVLHQDWLNGKEYKCKVSNKAL PAPIEKTISKAKGQPREPQVYTLPPSREEMTKNQVSLTCLVK GFYPSDIAVEWESNGQPENNYKTTPPVLDSDGSFFLYSKLTV DKSRWQQGNVFSCSVMHEALHNHYTQKSLSLSPG | 70 |
| 1-K17.015 LC | DVVMTQSPLSLPVTLGQPASISCRSSQSLVHSNAQTYLYWY QQRPGQSPRLLIYKVSNRFSGVPDRFSGSGSGTDFTLKISRVE AEDVGVYFCSQSTHVPYTFGQGTKLEIKRTVAAPSVFIFPPS DEQLKSGTASVVCLLNNFYPREAKVQWKVDNALQSGNSQE SVTEQDSKDSTYSLSSTLTLSKADYEKHKVYACEVTHQGLS SPVTKSFNRGEC | 71 |
| 1-K17.015 CDR-H2 | AIYPGQGDTSYNQ | 72 |
| 1-K17.015 CDR-L1 | RSSQSLVHSNAQTYLY | 73 |
| 1-K17.044 VH | EVQLVQSGAEVKKPGASVKVSCKASGYTFTSYNMHWVRQ APGQGLEWIGAIYPGAGDTSYNQKFKGRATLTADKSTSTAY MELSSLRSEDTAVYYCARKGGTPFAYWGQGTLVTVSS | 74 |
| 1-K17.044 VL | DVVMTQSPLSLPVTLGQPASISCRSSQSLVHSNAATYLYWYQ QRPGQSPRLLIYKVSNRFSGVPDRFSGSGSGTDFTLKISRVEA EDVGVYFCSQSTHVPYTFGQGTKLEIK | 75 |
| 1-K17.044 HC | EVQLVQSGAEVKKPGASVKVSCKASGYTFTSYNMHWVRQ APGQGLEWIGAIYPGAGDTSYNQKFKGRATLTADKSTSTAY MELSSLRSEDTAVYYCARKGGTPFAYWGQGTLVTVSSASTK | 76 |

TABLE of-continued

Certain Sequences

| Description | Sequence | SEQ ID NO |
|---|---|---|
| | GPSVFPLAPSSKSTSGGTAALGCLVKDYFPEPVTVSWNSGAL TSGVHTFPAVLQSSGLYSLSSVVTVPSSSLGTQTYICNVNHKP SNTKVDKKVEPKSCDKTHTCPPCPAPELLGGPSVFLFPPKPK DTLMISRTPEVTCVVVDVSHEDPEVKFNWYVDGVEVHNAK TKPREEQYNSTYRVVSVLTVLHQDWLNGKEYKCKVSNKAL PAPIEKTISKAKGQPREPQVYTLPPSREEMTKNQVSLTCLVK GFYPSDIAVEWESNGQPENNYKTTPPVLDSDGSFFLYSKLTV DKSRWQQGNVFSCSVMHEALHNHYTQKSLSLSPG | |
| 1-K17.044 LC | DVVMTQSPLSLPVTLGQPASISCRSSQSLVHSNAATYLYWYQ QRPGQSPRLLIYKVSNRFSGVPDRFSGSGSGTDFTLKISRVEA EDVGVYFCSQSTHVPYTFGQGTKLEIKRTVAAPSVFIFPPSDE QLKSGTASVVCLLNNFYPREAKVQWKVDNALQSGNSQESV TEQDSKDSTYSLSSTLTLSKADYEKHKVYACEVTHQGLSSP VTKSFNRGEC | 77 |
| 1-K17.044 CDR-H2 | AIYPGAGDTSYNQ | 78 |
| 1-K17.044 CDR-L1 | RSSQSLVHSNAATYLY | 79 |
| 7-B16 VH | EVQLVESGGGLVQPKGSLKLSCAASGFTFNTYAMNWVRQA PGKGLEWVARIRSKSNNYATYYADSVKDRFTISRDDSQSML YLQMNNLKTEDTAMYYCVRGLLRYRFFDVWGAGTTVTVS S | 80 |
| 7-B16 VL | DIVMTQAEPSVPVTPGESISISCRSSKSLLHSNGNTYLYWFLQ RPGQSPQLLIYRMSNLASGVPDRFSGSGSGTAFTLRISRVEAE DVGVYYCMQHLEYPFTFGGGTKLEIK | 81 |
| 7-B16 HC | EVQLVESGGGLVQPKGSLKLSCAASGFTFNTYAMNWVRQA PGKGLEWVARIRSKSNNYATYYADSVKDRFTISRDDSQSML YLQMNNLKTEDTAMYYCVRGLLRYRFFDVWGAGTTVTVS SAKTTPPSVYPLAPGSAAQTNSMVTLGCLVKGYFPEPVTVT WNSGSLSSGVHTFPAVLESDLYTLSSSVTVPSSPRPSETVTCN VAHPASSTKVDKKIVPRDCGCKPCICTVPEVSSVFIFPPKPKD VLTITLTPKVTCVVVDISKDDPEVQFSWFVDDVEVHTAQTQ PREEQFNSTFRSVSELPIMHQDWLNGKEFKCRVNSAAFPAPI EKTISKTKGRPKAPQVYTIPPPKEQMAKDKVSLTCMITDFFP EDITVEWQWNGQPAENYKNTQPIMNTNGSYFVYSKLNVQK SNWEAGNTFTCSVLHEGLHNHHTEKSLSHSPG | 82 |
| 7-B16 LC | DIVMTQAEPSVPVTPGESISISCRSSKSLLHSNGNTYLYWFLQ RPGQSPQLLIYRMSNLASGVPDRFSGSGSGTAFTLRISRVEAE DVGVYYCMQHLEYPFTFGGGTKLEIKRADAAPTVSIFPPSSE QLTSGGASVVCFLNNFYPKDINVKWKIDGSERQNGVLNSW TDQDSKDSTYSMSSTLTLTKDEYERHNSYTCEATHKTSTSPI VKSFNRNEC | 83 |
| 7-B16, 7-B16.001 CDR-H1 | GFTFNTYAMN | 84 |
| 7-B16, 7-B16.001, 7-B16.033 CDR-H2 | RIRSKSNNYATYYADSVKD | 85 |
| 7-B16, 7-B16.001, 7-B16.033 CDR-H3 | VRGLLRYRFFDV | 86 |
| 7-B16, 7-B16.001, 7-B16.033 CDR-L1 | RSSKSLLHSNGNTYLY | 87 |
| 7-B16, 7-B16.001, 7-B16.033 CDR-L2 | RMSNLAS | 88 |

TABLE of-continued

Certain Sequences

| Description | Sequence | SEQ ID NO |
|---|---|---|
| 7-B16, 7-B16.001, 7-B16.033 CDR-L3 | MQHLEYPFT | 89 |
| 7-B16 chimera HC | EVQLVESGGGLVQPKGSLKLSCAASGFTFNTYAMNWVRQA PGKGLEWVARIRSKSNNYATYYADSVKDRFTISRDDSQSML YLQMNNLKTEDTAMYYCVRGLLRYRFFDVWGAGTTVTVS SASTKGPSVFPLAPSSKSTSGGTAALGCLVKDYFPEPVTVSW NSGALTSGVHTFPAVLQSSGLYSLSSVVTVPSSSLGTQTYICN VNHKPSNTKVDKKVEPKSCDKTHTCPPCPAPELLGGPSVFL FPPKPKDTLMISRTPEVTCVVVDVSHEDPEVKFNWYVDGVE VHNAKTKPREEQYNSTYRVVSVLTVLHQDWLNGKEYKCK VSNKALPAPIEKTISKAKGQPREPQVYTLPPSREEMTKNQVS LTCLVKGFYPSDIAVEWESNGQPENNYKTTPPVLDSDGSFFL YSKLTVDKSRWQQGNVFSCSVMHEALHNHYTQKSLSLSPG | 90 |
| 7-B16 chimera LC | DIVMTQAEPSVPVTPGESISISCRSSKSLLHSNGNTYLYWFLQ RPGQSPQLLIYRMSNLASGVPDRFSGSGSGTAFTLRISRVEAE DVGVYYCMQHLEYPFTFGGGTKLEIKRTVAAPSVFIFPPSDE QLKSGTASVVCLLNNFYPREAKVQWKVDNALQSGNSQESV TEQDSKDSTYSLSSTLTLSKADYEKHKVYACEVTHQGLSSP VTKSFNRGEC | 91 |
| 7-B16.001 VH | EVQLVESGGGLVQPGGSLKLSCAASGFTFNTYAMNWVRQA SGKGLEWVGRIRSKSNNYATYYADSVKDRFTISRDDSKNTA YLQMNSLKTEDTAVYYCVRGLLRYRFFDVWGQGTTVTVSS | 92 |
| 7-B16.001 VL | DIVMTQSPLSLPVTPGEPASISCRSSKSLLHSNGNTYLYWFLQ KPGQSPQLLIYRMSNLASGVPDRFSGSGSGTDFTLKISRVEA EDVGVYYCMQHLEYPFTFGGGTKVEIK | 93 |
| 7-B16.001 HC | EVQLVESGGGLVQPGGSLKLSCAASGFTFNTYAMNWVRQA SGKGLEWVGRIRSKSNNYATYYADSVKDRFTISRDDSKNTA YLQMNSLKTEDTAVYYCVRGLLRYRFFDVWGQGTTVTVSS ASTKGPSVFPLAPSSKSTSGGTAALGCLVKDYFPEPVTVSWN SGALTSGVHTFPAVLQSSGLYSLSSWTVPSSSLGTQTYICNV NHKPSNTKVDKKVEPKSCDKTHTCPPCPAPELLGGPSVFLFP PKPKDTLMISRTPEVTCVVVDVSHEDPEVKFNWYVDGVEV HNAKTKPREEQYNSTYRVVSVLTVLHQDWLNGKEYKCKVS NKALPAPIEKTISKAKGQPREPQVYTLPPSREEMTKNQVSLT CLVKGFYPSDIAVEWESNGQPENNYKTTPPVLDSDGSFFLYS KLTVDKSRWQQGNVFSCSVMHEALHNHYTQKSLSLSPG | 94 |
| 7-B16.001 LC | DIVMTQSPLSLPVTPGEPASISCRSSKSLLHSNGNTYLYWFLQ KPGQSPQLLIYRMSNLASGVPDRFSGSGSGTDFTLKISRVEA EDVGVYYCMQHLEYPFTFGGGTKVEIKRTVAAPSVFIFPPSD EQLKSGTASVVCLLNNFYPREAKVQWKVDNALQSGNSQES VTEQDSKDSTYSLSSTLTLSKADYEKHKVYACEVTHQGLSS PVTKSFNRGEC | 95 |
| 7-B16.033 VH | EVQLVESGGGLVQPGRSLRLSCTASGFTFATYAMNWVRQAP GKGLEWVARIRSKSNNYATYYADSVKDRFTISRDDSKSILYL QMNSLKTEDTAVYYCVRGLLRYRFFDVWGQGTTVTVSS | 96 |
| 7-B16.033 VL | DIVMTQSPLSLPVTPGEPASISCRSSKSLLHSNGNTYLYWFLQ KPGQSPQLLIYRMSNLASGVPDRFSGSGSGTDFTLKISRVEA EDVGVYYCMQHLEYPFTFGGGTKVEIK | 97 |
| 7-B16.033 HC | EVQLVESGGGLVQPGRSLRLSCTASGFTFATYAMNWVRQAP GKGLEWVARIRSKSNNYATYYADSVKDRFTISRDDSKSILYL QMNSLKTEDTAVYYCVRGLLRYRFFDVWGQGTTVTVSSAS TKGPSVFPLAPSSKSTSGGTAALGCLVKDYFPEPVTVSWNSG ALTSGVHTFPAVLQSSGLYSLSSWTVPSSSLGTQTYICNVNH KPSNTKVDKKVEPKSCDKTHTCPPCPAPELLGGPSVFLFPPK PKDTLMISRTPEVTCVVVDVSHEDPEVKFNWYVDGVEVHN AKTKPREEQYNSTYRVVSVLTVLHQDWLNGKEYKCKVSNK ALPAPIEKTISKAKGQPREPQVYTLPPSREEMTKNQVSLTCL VKGFYPSDIAVEWESNGQPENNYKTTPPVLDSDGSFFLYSKL TVDKSRWQQGNVFSCSVMHEALHNHYTQKSLSLSPG | 98 |

TABLE of-continued

Certain Sequences

| Description | Sequence | SEQ ID NO |
|---|---|---|
| 7-B16.033 LC | DIVMTQSPLSLPVTPGEPASISCRSSKSLLHSNGNTYLYWFLQ KPGQSPQLLIYRMSNLASGVPDRFSGSGSGTDFTLKISRVEA EDVGVYYCMQHLEYPFTFGGGTKVEIKRTVAAPSVFIFPPSD EQLKSGTASVVCLLNNFYPREAKVQWKVDNALQSGNSQES VTEQDSKDSTYSLSSTLTLSKADYEKHKVYACEVTHQGLSS PVTKSFNRGEC | 99 |
| 7-B16.033 CDR-H1 | GFTFATYAMN | 100 |
| Human CCR8 | MDYTLDLSVTTVTDYYYPDIFSSPCDAELIQTNGKLLLAVFY CLLFVFSLLGNSLVILVLVVCKKLRSITDVYLLNLALSDLLFV FSFPFQTYYLLDQWVFGTVMCKWSGFYYIGFYSSMFFITL MSVDRYLAVVHAVYALKVRTIRMGTTLCLAVWLTAIMATIP LLVFYQVASEDGVLQCYSFYNQQTLKWKIFTNFKMNILGLL IPFTIFMFCYIKILHQLKRCQNHNKTKAIRLVLIVVIASLLFW VPFNVVLFLTSLHSMHILDGCSISQQLTYATHVTEIISFTHCCV NPVIYAFVGEKFKKHLSEIFQKSCSQIFNYLGRQMPRESCEK SSSCQQHSSRSSSVDYIL | 101 |
| Mouse CCR8 | MDYTMEPNVTMTDYYPDFFTAPCDAEFLLRGSMLYLAILYC VLFVLGLLGNSLVILVLVGCKKLRSITDIYLLNLAASDLLFVL SIPFQTHNLLDQWVFGTAMCKVVSGLYYIGFFSSMFFITLMS VDRYLAIVHAVYAIKVRTASVGTALSLTVWLAAVTATIPLMV FYQVASEDGMLQCFQFYEEQSLRWKLFTHFEINALGLLLPFA ILLFCYVRILQQLRGCLNHNRTRAIKLVLTVVIVSLLFWVPFN VALFLTSLHDLHILDGCATRQRLALAIHVTEVISFTHCCVNPV IYAFIGEKFKKHLMDVFQKSCSHIFLYLGRQMPVGALERQLS SNQRSSHSSTLDDIL | 102 |
| Cynomolgus monkey CCR8 | MDYTLDPSMTTMTDYYYPDSLSSPCDGELIQRNDKLLLAVF YCLLFVFSLLGNSLVILVLVVCKKLRNITDIYLLNLALSDLLF VFSFPFQTYYQLDQWVFGTVMCKVVSGFYYIGFYSSMFFIT LMSVDRYLAVVHAVYAIKVRTIRMGTTLSLVVWLTAIMATIP LLVFYQVASEDGVLQCYSFYNQQTLKWKIFTNFEMNILGLLI PFTIFMFCYIKILHQLKRCQNHNKTKAIRLVLIVVIASLLFWV PFNVVLFLTSLHSMHILDGCSISQQLNYATHVTEIISFTHCCV NPVIYAFVGEKFKKHLSEIFQKSCSHIFIYLGRQMPRESCEKS SSCQQHSFRSSSIDYIL | 103 |
| 7B16.002 CDRH3 | ARGLLRYRFFDV | 104 |
| 7B16.003 CDRH3 | VAGLLRYRFFDV | 105 |
| 7B16.004 CDRH3 | VRALLRYRFFDV | 106 |
| 7B16.005 CDRH3 | VRGALRYRFFDV | 107 |
| 7B16.006 CDRH3 | VRGLARYRFFDV | 108 |
| 7B16.007 CDRH3 | VRGLLAYRFFDV | 109 |
| 7B16.008 CDRH3 | VRGLLRARFFDV | 110 |
| 7B16.009 CDRH3 | VRGLLRYAFFDV | 111 |
| 7B16.010 CDRH3 | VRGLLRYRAFDV | 112 |
| 7B16.011 CDRH3 | VRGLLRYRFADV | 113 |
| 7B16.012 CDRH3 | VRGLLRYRFFAV | 114 |
| 7B16.013 CDRH3 | VRGLLRYRFFDA | 115 |

TABLE of-continued

Certain Sequences

| Description | Sequence | SEQ ID NO |
|---|---|---|
| 7B16-H3C1.001 CDRH3 | ARGLLRARFFDV | 116 |
| 7B16-H3C2.001 CDRH3 | ARGLLRYRFFDA | 117 |
| 7B16-H3C3.001 CDRH3 | VRGLLRARFFDA | 118 |
| 7B16-H3C4.001 CDRH3 | ARGLLRARFFDA | 119 |
| 7B16-L1.001 CDRL1 | RSSQSLLHSNGYNYLD | 120 |
| 7B16-L2.001 CDRL2 | LGSNRAS | 121 |
| 7B16-L3.001 CDRL3 | MQALQTPFV | 122 |
| 7B16-H1.001 CDRH1 | GFTFSGSAMH | 123 |
| 7B16-H2.001 CDRH2 | RIRSKANSYATAYAASVKD | 124 |
| 7B16-H3.001 CDRH3 | TRYYYYYGMDV | 125 |
| KRpep-2 | RRCPLYISYDPVCRR | 126 |
| KRpep-2d | RRRRCPLYISYDPVCRRRR | 127 |
| CCR8-NT.MBP | EEGKLVIWINGDKGYNGLAEVGKKFEKDTGIKVTVEHPDKL EEKFPQVAATGDGPDIIFWAHDRFGGYAQSGLLAEITPDKAF QDKLYPFTWDAVRYNGKLIAYPIAVEALSLIYNKDLLPNPPK TWEEIPALDKELKAKGKSALMFNLQEPYFTWPLIAADGGYA FKYENGKYDIKDVGVDNAGAKAGLTFLIDLIKNKHMNADT DYSIAEAAFNKGETAMTINGPWAWSNIDTSKVNYGVTVLPT FKGQPSKPFVGVLSAGINAASPNKELAKEFLENYLLTDEGLE AVNKDKPLGAVALKSYEEELAKDPRIAATMENAQKGEIMPN IPQMSAFWYAVRTAVINAASGRQTVDEALKDAQTSGGGSGG GSGGGSGGGSHHHHHGGGSGGGGSGGENLYFQGMDYTL DLSVTTVTDYYYPDIFSSPCDAELIQTNGK | 128 |

The invention claimed is:

1. An isolated antibody that binds human CCR8, wherein the antibody comprises a heavy chain complementarity determining region 1 (HCDR1) comprising the amino acid sequence of SEQ ID NO: 84 or 100, an HCDR2 comprising the amino acid sequence of SEQ ID NO: 85, an HCDR3 comprising the amino acid sequence of SEQ ID NO: 86, a light chain complementarity determining region 1 (LCDR1) comprising the amino acid sequence of SEQ ID NO: 87, an LCDR2 comprising the amino acid sequence of SEQ ID NO: 88, and an LCDR3 comprising the amino acid sequence of SEQ ID NO: 89.

2. The isolated antibody of claim 1, wherein the antibody is a monoclonal antibody.

3. The isolated antibody of claim 1, wherein the antibody is a humanized antibody.

4. The isolated antibody of claim 1, wherein the antibody is a full-length antibody.

5. The isolated antibody of claim 1, wherein the antibody is an IgG1 or IgG3 antibody.

6. The isolated antibody of claim 1, wherein the antibody comprises at least one modification that enhances cell killing.

7. The isolated antibody of claim 6, wherein the enhanced cell killing is enhanced antibody-dependent cellular cytotoxicity (ADCC) and/or complement-dependent cytotoxicity (CDC).

8. The isolated antibody of claim 6, wherein the at least one modification is afucosylation.

9. The isolated antibody of claim 6, wherein the at least one modification is one or more heavy chain constant regions mutations at one or more positions selected from L234, L235, G236, S239, F243, H268, D270, R292, S298, Y300, V305, K326, A330, I332, E333, K334, and P396.

10. The isolated antibody of claim 9, wherein the one or more heavy chain constant A region mutations are one or more mutations selected from S239D, S239M, F243L, H268D, D270E, R292P, S298A, Y300L, V305I, K326D, A330L, A330M, I332E, E333A, K334A, K334E, and P396L.

11. The isolated antibody of claim 9, wherein the one or more heavy chain constant region mutations are selected from: F243L/R292P/Y300L/V305I/P396L, S239D/I332E, S239D/I332E, S239D/I332E/A330L, S298A/E333A/K334A, 234Y/L235Q/G236W/S239M/H268D/D270E/S298 A, and D270E/K326D/A330M/K334E.

12. The isolated antibody of claim 6, wherein the at least one modification is galactosylation.

13. The isolated antibody of claim 1, wherein the antibody binds human CCR8 with an affinity ($K_D$) of less than 10 nM, but at least 15.9 pM.

14. The isolated antibody of claim 1, wherein the antibody binds human CCR8 with an on-cell affinity ($K_D$) of less than 10 nM, but at least 15.9 pM.

15. The isolated antibody of claim 14, wherein the on-cell affinity ($K_D$) is determined by Kinetic Exclusion Assay (KinExA).

16. The isolated antibody of claim 1, wherein the antibody comprises a heavy chain variable region (VH) comprising an amino acid sequence that is at least 90% identical to the amino acid sequence of SEQ ID NO: 92, and a light chain variable region (VL) comprising an amino acid sequence that is at least 90% identical to the amino acid sequence of SEQ ID NO: 93.

17. The isolated antibody of claim 1, wherein the antibody comprises a VH comprising an amino acid sequence that is at least 90% identical to the amino acid sequence of SEQ ID NO: 96, and a VL comprising an amino acid sequence that is at least 90% identical to the amino acid sequence of SEQ ID NO: 97.

18. The isolated antibody of claim 1, wherein the antibody comprises a VH comprising the amino acid sequence of SEQ ID NO: 92, and a VL comprising the amino acid sequence of SEQ ID NO: 93.

19. The isolated antibody of claim 1, wherein the antibody comprises a VH comprising the amino acid sequence of SEQ ID NO: 96, and a VL comprising the amino acid sequence of SEQ ID NO: 97.

20. The isolated antibody of claim 1, wherein the antibody comprises a heavy chain comprising an amino acid sequence that is at least 90% identical to the amino acid sequence of SEQ ID NO: 94, and a light chain comprising an amino acid sequence that is at least 90% identical to the amino acid sequence of SEQ ID NO: 95.

21. The isolated antibody of claim 1, wherein the antibody comprises a heavy chain comprising an amino acid sequence that is at least 90% identical to the amino acid sequence of SEQ ID NO: 98, and a light chain comprising an amino acid sequence that is at least 90% identical to the amino acid sequence of SEQ ID NO: 99.

22. The isolated antibody of claim 1, wherein the antibody comprises a heavy chain comprising the amino acid sequence of SEQ ID NO: 94, and a light chain comprising the amino acid sequence of SEQ ID NO: 95.

23. The isolated antibody of claim 1, wherein the antibody comprises a heavy chain comprising the amino acid sequence of SEQ ID NO: 98, and a light chain comprising the amino acid sequence of SEQ ID NO: 99.

24. The isolated antibody of claim 1, wherein the HCDR1 comprises the amino acid sequence of SEQ ID NO: 84, and wherein the antibody is afucosylated.

25. The isolated antibody of claim 1, wherein the HCDR1 comprises the amino acid sequence of SEQ ID NO: 100, and wherein the antibody is afucosylated.

26. The isolated antibody of claim 1, wherein the antibody comprises a VH comprising the amino acid sequence of SEQ ID NO: 92, and a VL comprising the amino acid sequence of SEQ ID NO: 93, and wherein the antibody is afucosylated.

27. The isolated antibody of claim 1, wherein the antibody comprises a VH comprising the amino acid sequence of SEQ ID NO: 96, and a VL comprising the amino acid sequence of SEQ ID NO: 97, and wherein the antibody is afucosylated.

28. The isolated antibody of claim 1, wherein the antibody comprises a heavy chain comprising the amino acid sequence of SEQ ID NO: 94, and a light chain comprising the amino acid sequence of SEQ ID NO: 95, and wherein the antibody is afucosylated.

29. The isolated antibody of claim 1, wherein the antibody comprises a heavy chain comprising the amino acid sequence of SEQ ID NO: 98, and a light chain comprising the amino acid sequence of SEQ ID NO: 99, and wherein the antibody is afucosylated.

* * * * *